(12) United States Patent
Mitchell et al.

(10) Patent No.: US 8,450,321 B2
(45) Date of Patent: *May 28, 2013

(54) 6-(1H-INDAZOL-6-YL)-N-[4-(MORPHOLIN-4-YL)PHENYL]IMIDAZO-[1,2-A]PYRAZIN-8-AMINE, OR A PHARMACEUTICALLY ACCEPTABLE SALT THEREOF, AS A SYK INHIBITOR

(75) Inventors: Scott A. Mitchell, East Haven, CT (US); Kevin S. Currie, North Branford, CT (US)

(73) Assignee: Gilead Connecticut, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/441,441

(22) Filed: Apr. 6, 2012

(65) Prior Publication Data

US 2012/0220582 A1    Aug. 30, 2012

Related U.S. Application Data

(63) Continuation-in-part of application No. 12/632,140, filed on Dec. 7, 2009.

(60) Provisional application No. 61/240,979, filed on Sep. 9, 2009, provisional application No. 61/140,514, filed on Dec. 23, 2008, provisional application No. 61/120,587, filed on Dec. 8, 2008.

(51) Int. Cl.
*A61K 31/495*    (2006.01)

(52) U.S. Cl.
USPC .......... 514/249; 544/117; 544/350; 348/361.1

(58) Field of Classification Search
USPC ............... 514/249; 544/117, 350; 548/361.1
See application file for complete search history.

(56) References Cited

U.S. PATENT DOCUMENTS

| | | | |
|---|---|---|---|
| 5,593,997 | A | 1/1997 | Dow et al. |
| 5,658,857 | A | 8/1997 | Andree et al. |
| 5,783,576 | A | 7/1998 | Roos et al. |
| 5,846,514 | A | 12/1998 | Foster et al. |
| 6,334,997 | B1 | 1/2002 | Foster et al. |
| 6,919,340 | B2 | 7/2005 | Currie et al. |
| 6,919,341 | B2 | 7/2005 | Paruch et al. |
| 7,160,885 | B2 | 1/2007 | Currie et al. |
| 7,189,723 | B2 | 3/2007 | Mitchell et al. |
| 7,259,164 | B2 | 8/2007 | Mitchell et al. |
| 7,312,341 | B2 | 12/2007 | DeSimone et al. |
| 7,405,295 | B2 | 7/2008 | Currie et al. |
| 2003/0212073 | A1 | 11/2003 | Currie et al. |
| 2004/0063715 | A1 | 4/2004 | Paruch et al. |
| 2004/0067951 | A1 | 4/2004 | DeSimone et al. |
| 2004/0072835 | A1 | 4/2004 | Paruch et al. |
| 2004/0220189 | A1 | 11/2004 | Sun et al. |
| 2005/0009832 | A1 | 1/2005 | Sun et al. |
| 2005/0054648 | A1 | 3/2005 | Mitchell et al. |
| 2005/0054649 | A1 | 3/2005 | Currie et al. |
| 2005/0085484 | A1 | 4/2005 | Mitchell et al. |
| 2005/0090499 | A1 | 4/2005 | Currie et al. |
| 2005/0101604 | A1 | 5/2005 | Currie et al. |
| 2005/0288295 | A1 | 12/2005 | Currie et al. |
| 2006/0069084 | A1 | 3/2006 | Burns et al. |
| 2006/0084650 | A1 | 4/2006 | Dong et al. |
| 2006/0183746 | A1 | 8/2006 | Currie et al. |
| 2007/0117804 | A1 | 5/2007 | Zhao et al. |
| 2009/0221612 | A1 | 9/2009 | Mitchell et al. |
| 2010/0152159 | A1 | 6/2010 | Mitchell et al. |
| 2010/0222323 | A1 | 9/2010 | Mitchell et al. |

FOREIGN PATENT DOCUMENTS

| | | |
|---|---|---|
| CA | 2175837 A1 | 5/1995 |
| DE | 04337609 A1 | 5/1995 |
| EP | 0 480 713 A1 | 4/1992 |
| WO | WO-88/04298 A1 | 6/1988 |
| WO | WO-95/12594 A1 | 5/1995 |
| WO | WO-96/04298 A1 | 2/1996 |

(Continued)

OTHER PUBLICATIONS

Extended European Search Report mailed on Jul. 27, 2012, for EP 09 83 2228.2, filed on Jun. 21, 2011, 12 pages.
Extended European Search Report mailed on Apr. 26, 2012, for EP 09 83 2229.0, filed on Jun. 21, 2011, 6 pages.
Final Office Action mailed on May 25, 2012, for U.S. Appl. No. 12/632,140, filed Dec. 7, 2009, 9 pages.
Non-Final Office Action mailed on May 17, 2012, for U.S. Appl. No. 12/632,151, filed Dec. 7, 2009, 15 pages.
Al-Dabbagh, S.G. et al. (1984). "Species Differences in Oxidative Drug Metabolism: Some Basic Considerations." *Archives of Toxicology. Supplement. Archive fur Toxikologie. Supplement*, 7:219-231.
Bundgaard, H., (1985). *Design of Prodrugs*, Elsevier Science Publishers, B.V., The Netherlands, p. 1.
Dean, D.C. "Recent Advances in the Synthesis and Applications of Radiolabeled Compounds for Drug Discovery and Development," (2000). *Curr. Pharm Des.* 6(10):110.

(Continued)

*Primary Examiner* — Douglas M Willis
(74) *Attorney, Agent, or Firm* — Morrison & Foerster LLP

(57) ABSTRACT

An imidazopyrazine having the structure

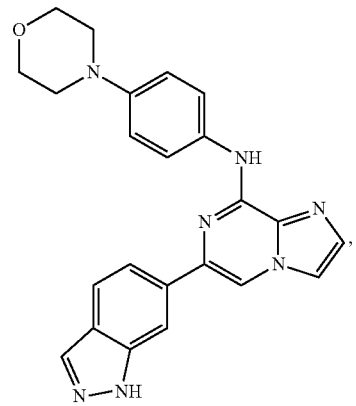

or a pharmaceutically acceptable salt thereof, and pharmaceutical compositions thereof are provided herein. Methods of treating patients suffering from certain diseases and disorders responsive to the inhibition of Syk activity, which comprises administering to such patients an amount of at least one chemical entity effective to reduce signs or symptoms of the disease or disorder are provided. Also provided are methods for determining the presence or absence of Syk kinase in a sample.

2 Claims, No Drawings

FOREIGN PATENT DOCUMENTS

| | | |
|---|---|---|
| WO | WO-96/34866 A1 | 11/1996 |
| WO | WO-99/28322 A1 | 6/1999 |
| WO | WO-01/27119 A2 | 4/2001 |
| WO | WO-01/27119 A3 | 4/2001 |
| WO | WO-02/10170 A1 | 2/2002 |
| WO | WO-02/30428 A1 | 4/2002 |
| WO | WO-02/060492 A1 | 8/2002 |
| WO | WO-02/066481 A1 | 8/2002 |
| WO | WO-02/076985 A1 | 10/2002 |
| WO | WO-03/070732 A1 | 8/2003 |
| WO | WO-03/089434 A2 | 10/2003 |
| WO | WO-03/089434 A3 | 10/2003 |
| WO | WO-2004/022562 A1 | 3/2004 |
| WO | WO-2004/026310 A1 | 4/2004 |
| WO | WO-2004/026310 C1 | 4/2004 |
| WO | WO-2004/026877 A1 | 4/2004 |
| WO | WO-2004/072080 A1 | 8/2004 |
| WO | WO-2004/072081 A1 | 8/2004 |
| WO | WO-2005/005429 A1 | 1/2005 |
| WO | WO-2005/014599 A1 | 2/2005 |
| WO | WO-2005/019220 A2 | 3/2005 |
| WO | WO-2005/019220 A3 | 3/2005 |
| WO | WO-2005/019220 C1 | 3/2005 |
| WO | WO-2005/047290 A2 | 5/2005 |
| WO | WO-2005/047290 A3 | 5/2005 |
| WO | WO-2005/085252 A1 | 9/2005 |
| WO | WO-2006/044687 A2 | 4/2006 |
| WO | WO-2006/044687 A3 | 4/2006 |
| WO | WO-2008/025821 A1 | 3/2008 |
| WO | WO-2009/077334 A1 | 6/2009 |
| WO | WO-2009/102468 A1 | 8/2009 |
| WO | WO-2010/006947 A1 | 1/2010 |
| WO | WO-2010/027500 A1 | 3/2010 |
| WO | WO-2010/068257 A1 | 6/2010 |
| WO | WO-2010/068258 A1 | 6/2010 |

OTHER PUBLICATIONS

Ding, S. et al. (2002) "A Combinatorial Scaffold Approach Toward Kinase-Directed Heterocycle Libraries," *J. Am Chem Soc.*, 124(8):1594-1596.

Evans, E.A. "Synthesis of Radiolabeled Compounds," (1981). *J. Radioanal. Chem.* 64(1-2):9-32.

Final Office Action mailed on Jan. 27, 2012, for U.S. Appl. No. 12/632,151, filed Dec. 7, 2009, 15 pages.

Final Office Action mailed on Sep. 15, 2011, for U.S. Appl. No. 12/632,140, filed Dec. 7, 2009, 15 pages.

GenBank Accession No. AY050647.1, created on Oct. 7, 2001, located at <http://www.ncbi.nlm.nih.gov/nuccore/AY050647.1>, last visited on Dec. 28, 2011, 1 page.

International Preliminary Examination Report mailed on Aug. 5, 2004, for PCT Application No. PCT/US2003/12222, filed Apr. 21, 2003, 11 pages.

International Preliminary Examination Report mailed on Oct. 27, 2004, for PCT Application No. PCT/US2003/28329, filed on Sep. 9, 2003, 5 pages.

International Preliminary Report on Patentability mailed on May 12, 2009, for PCT Application No. PCT/US2009/000919, filed on Feb. 12, 2009, 8 pages.

International Preliminary Report on Patentability mailed on Jan. 5, 2011, for PCT Application No. PCT/US2009/006445, filed on Dec. 7, 2009, 6 pages.

International Preliminary Report on Patentability mailed on Jun. 8, 2011, for PCT Application No. PCT/US/2009/006446, filed on Dec. 7, 2009, 6 pages.

International Search Report mailed Oct. 22, 2003, for PCT Application No. PCT/US2003/12222, filed on Apr. 21, 2003, 6 pages.

International Search Report mailed Feb. 9, 2004, for PCT Application No. PCT/US2003/28329, filed on Sep. 9, 2003, 4 pages.

International Search Report and Written Opinion mailed on Jul. 7, 2004, for PCT Application No. PCT/US2004/003922, filed on Feb. 10, 2004, 12 pages.

International Search Report and Written Opinion mailed on Jul. 7, 2004, for PCT Application No. PCT/US2004/003923, filed on Feb. 10, 2004, 12 pages.

International Search Report and Written Opinion mailed on Dec. 8, 2004, for PCT Application No. PCT/US2004/021150, filed on Jun. 30, 2004, 10 pages.

International Search Report and Written Opinion mailed on Dec. 30, 2004, for PCT Application No. PCT/US2004/018227, filed on Jun. 4, 2004, 10 pages.

International Search Report and Written Opinion mailed on Feb. 1, 2005 for PCT Application No. PCT/US2004/025884, filed on Aug. 11, 2004, 8 pages.

International Search Report and Written Opinion mailed on Jun. 23, 2005, for PCT Application No. PCT/US2004/037433, filed on Nov. 10, 2004, 15 pages.

International Search Report mailed on May 12, 2009, for PCT Application No. PCT/US2009/000919, filed on Feb. 12, 2009, 5 pages.

International Search Report mailed on Feb. 12, 2010, for PCT Application No. PCT/US2009/006445, filed on Dec. 7, 2009, 3 pages.

International Search Report mailed on Feb. 12, 2010, for PCT Application No. PCT/US/2009/006446, filed on Dec. 7, 2009, 3 pages.

Invitation to Pay Additional Fees with Partial International Search Report mailed May 3, 2005, for PCT Application No. PCT/US2004/037433, filed on Nov. 10, 2004, 9 pages.

Jeffrey,T.K. et al. (1998). "Phosphodiesterase III and V Inhibitors on Pulmonary Artery from Pulmonary Hypertensive Rats: Differences Between Early and established Pulmonary Hypertension", *J. Cardiovascular Pharmacology*, 32(2): 213-219.

Kabalka, G.W. et al. "The Synthesis of Radiolabeled Compounds via Organometallic Intermediates," (1989). *Tetrahedron* 45(21):6601-21.

Kuhnz, W. et al. (Jun. 11, 1998). "Predicting the Oral Bioavailability of 19-Nortestosterone Progestins In Vivo From Their Metabolic Stability in Human Liver Microsomal Preparation In Vitro," *The American Society for Pharmacology and Experimental Therapeutics* 26(11)1120-1127.

Lumma, Jr., W.C. et al. (1983) "Piperazinylimidazo [1,2-a]pyrazines with Selective affinity for in Vitro a-Adrenergic Receptor Subtypes," *J. Med. Chem.* 26(3):357-363.

Non-Final Office Action mailed on Feb. 17, 2012 for U.S. Appl. No. 12/632,140, filed Dec. 7, 2009, 11 pages.

Non-Final Office Action mailed on May 10, 2011 for U.S. Appl. No. 12/632,140, filed Dec. 7, 2009, 17 pages.

Non-Final Office Action mailed on Apr. 3, 2006, for U.S. Appl. No. 10/776,002, filed Feb. 10, 2004, 13 pages.

Non-Final Office Action mailed on May 24, 2006, for U.S. Appl. No. 10/776,631, filed Feb. 10, 2004, 10 pages.

Non-Final Office Action mailed on Sep. 26, 2006, for U.S. Appl. No. 10/658,121, filed Sep. 9, 2003, 7 pages.

Non-Final Office Action mailed on Jan. 8, 2007, for U.S. Appl. No. 10/915,696, filed Aug. 11, 2004, 8 pages.

Non-Final Office Action mailed on Apr. 13, 2011 for U.S. Appl. No. 12/370,103, filed Feb. 12, 2009, 11 pages.

Non-Final Office Action mailed on Jun. 29, 2011, for U.S. Appl. No. 12/632,151, filed Dec. 7, 2009, 17 pages.

Notice of Allowance mailed Aug. 11, 2006, for U.S. Appl. No. 10/776,002, filed Feb. 10, 2004, 10 pages.

Notice of Allowance mailed Sep. 7, 2006, for U.S. Appl. No. 10/776,631, filed Feb. 10, 2004, 7 pages.

Notice of Allowance mailed Mar. 6, 2007, for U.S. Appl. No. 10/658,121, filed Sep. 9, 2003, 6 pages.

Notice of Allowance mailed Apr. 20, 2007, for U.S. Appl. No. 10/915,696, filed Aug. 11, 2004, 7 pages.

Notice of Allowance mailed Aug. 8, 2007, for U.S. Appl. No. 10/658,121, filed Sep. 9, 2003, 4 pages.

Oravcova, J. et al. (1996). "Drug-Protein Binding Studies New Trends in Analytical and Experimental Methodology," *J Chromatogr B* 677:1-28.

Restriction Requirement mailed Oct. 20, 2004, for U.S. Appl. No. 10/419,682, filed Apr. 21, 2003, 9 pages.

Restriction Requirement mailed Jan. 4, 2006, for U.S. Appl. No. 10/776,002, filed Feb. 10, 2004, 7 pages.

Restriction Requirement mailed Jan. 27, 2006, for U.S. Appl. No. 10/776,631, filed Feb. 10, 2004, 6 pages.

Restriction Requirement mailed Jan. 30, 2006, for U.S. Appl. No. 10/658,121, filed Sep. 9, 2003, 5 pages.

Restriction Requirement mailed May 18, 2006, for U.S. Appl. No. 10/658,121, filed Sep. 9, 2003, 5 pages.
Restriction Requirement mailed Oct. 13, 2006, for U.S. Appl. No. 10/915,696, filed Aug. 11, 2004, 5 pages.
Restriction Requirement mailed Dec. 8, 2010, for U.S. Appl. No. 12/632,140, filed Dec. 7, 2009, 10 pages.
Restriction Requirement mailed on Dec. 8, 2010, for U.S. Appl. No. 12/632,151, filed Dec. 7, 2009, 10 pages.
Restriction Requirement mailed on Feb. 17, 2011, for U.S. Appl. No. 12/370,103, filed Feb. 12, 2009, 10 pages.
Second Written Opinion mailed on Apr. 13, 2004, for PCT Application No. PCT/US2003/12222, filed Apr. 21, 2003, 7 pages.
Silverman, R.B. (1992), *The Organic Chemistry of Drug Design and Drug Action*, Academic Press, Inc., San Diego, CA, pp. 352-400.
Stenberg, K.A.E. et al., (2000). "KinMutBase, a Database of Human Disease-Causing Protein Kinase Mutations," *Nucleic Acids Research* 28(1):369-371.
Taylor, R. et al., (1984). "Hydrogen-Bond Geometry in Organic Crystals", *Acc. Chem Res.* 17(320-326).
Vitse, O. et al. (1999). "New Imidazo [1,2-a]pyrazine Derivatives with Bronchodilatory and Cyclic Nucleotide Phosphodiesterase Inhibitory Activities," *Bioorganic and Medicinal Chemistry* 7:1059-1065.
Written Opinion mailed Dec. 5, 2003, for PCT Application No. PCT/US2003/12222, filed Apr. 21, 2003, 6 pages.
Written Opinion mailed Jul. 6, 2004, for PCT Application No. PCT/US2003/28329, filed on Sep. 9, 2003, 5 pages.
Written Opinion mailed on May 12, 2009, for PCT Application No. PCT/US2009/000919, filed on Feb. 12, 2009, 7 pages.
Written Opinion mailed on Feb. 12, 2010, for PCT Application No. PCT/US2009/006445, filed on Dec. 7, 2009, 4 pages.
Written Opinion mailed on Feb. 12, 2010, for PCT Application No. PCT/US/2009/006446, filed on Dec. 7, 2009, 4 pages.
European Communication mailed on Oct. 24, 2012, for European Patent Application No. 09710901.1, filed on Feb. 12, 2009, five pages.
Final Office Action mailed on Oct. 30, 2012, for U.S. Appl. No. 12/632,140, filed Dec. 7, 2009, 9 pages.
Final Office Action mailed on Sep. 5, 2012, for U.S. Appl. No. 12/632,151, filed Dec. 7, 2009, 11 pages.
International Search Report mailed Apr. 26, 2011, for Application No. PCT/US2011/028194, filed on Mar. 11, 2011, 5 pages.
Restriction Requirement mailed on Nov. 27, 2012, for U.S. Appl. No. 13/343,624, filed Jan. 4, 2012, 10 pages.
Written Opinion mailed Apr. 26, 2011, for Application No. PCT/US2011/028194, filed on Mar. 11, 2011, 6 pages.
U.S. Appl. No. 13/343,624, filed Jan. 4, 2012, Mitchell et al.
U.S. Appl. No. 13/609,068, internationally filed on Mar. 11, 2011, Blomgren et al.

6-(1H-INDAZOL-6-YL)-N-[4-(MORPHOLIN-4-YL)PHENYL]IMIDAZO-[1,2-A]PYRAZIN-8-AMINE, OR A PHARMACEUTICALLY ACCEPTABLE SALT THEREOF, AS A SYK INHIBITOR

CROSS-REFERENCE TO RELATED APPLICATIONS

This application is a Continuation-in-Part of U.S. patent application Ser. No. 12/632,140, filed Dec. 7, 2009, which claims the benefit of provisional U.S. Patent Application 61/120,587, filed Dec. 8, 2008, provisional U.S. Patent Application No. 61/140,514, filed Dec. 23, 2008, and provisional U.S. Patent Application No. 61/240,979, filed Sep. 9, 2009. The contents of the above patent applications are incorporated by reference herein in their entirety.

FIELD

Provided herein are certain imidazopyrazines, compositions, and methods of their manufacture and use.

BACKGROUND

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

Syk is a non-receptor tyrosine kinase that plays critical roles in immunoreceptor- and integrin-mediated signaling in a variety of cell types, including B cells, macrophages, monocytes, mast cells, eosinophils, basophils, neutrophils, dendritic cells, T cells, natural killer cells, platelets, and osteoclasts. Immunoreceptors as described here include classical immunoreceptors and immunoreceptor-like molecules. Classical immunoreceptors include B-cell and T-cell antigen receptors as well as various immunoglobulin receptors (Fc receptors). Immunoreceptor-like molecules are either structurally related to immunoreceptors or participate in similar signal transduction pathways and are primarily involved in non-adaptive immune functions, including neutrophil activation, natural killer cell recognition, and osteoclast activity. Integrins are cell surface receptors that play key roles in the control of leukocyte adhesion and activation in both innate and adaptive immunity.

Ligand binding leads to activation of both immunoreceptors and integrins, which results in Src family kinases being activated, and phosphorylation of immunoreceptor tyrosine-based activation motifs (ITAMs) in the cytoplasmic face of receptor-associated transmembrane adaptors. Syk binds to the phosphorylated ITAM motifs of the adaptors, leading to activation of Syk and subsequent phosphorylation and activation of downstream signaling pathways.

Syk is essential for B-cell activation through B-cell receptor (BCR) signaling. SYK becomes activated upon binding to phosphoryated BCR and thus initiates the early signaling events following BCR activation. B-cell signaling through BCR can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mice lacking Syk show impaired maturation of B-cells, diminished immunoglobulin production, compromised T-cell-independent immune responses and marked attenuation of the sustained calcium sign upon BCR stimulation.

A large body of evidence supports the role of B-cells and the humoral immune system in the pathogenesis of autoimmune and/or inflammatory diseases. Protein-based therapeutics (such as Rituxan) developed to deplete B-cells represent an approach to the treatment of a number of autoimmune and inflammatory diseases. Auto-antibodies and their resulting immune complexes are known to play pathogenic roles in autoimmune disease and/or inflammatory disease. The pathogenic response to these antibodies is dependent on signaling through Fc Receptors, which is, in turn, dependent upon Syk. Because of Syk's role in B-cell activation, as well as FcR dependent signaling, inhibitors of Syk can be useful as inhibitors of B-cell mediated pathogenic activity, including autoantibody production. Therefore, inhibition of Syk enzymatic activity in cells is proposed as a treatment for autoimmune disease through its effects on autoantibody production.

Syk also plays a key role in FCεRI mediated mast cell degranulation and eosinophil activation. Thus, Syk is implicated in allergic disorders including asthma. Syk binds to the phosphorylated gamma chain of FCεRI via its SH2 domains and is essential for downstream signaling. Syk deficient mast cells demonstrate defective degranulation, arachidonic acid and cytokine secretion. This also has been shown for pharmacologic agents that inhibit Syk activity in mast cells. Treatment with Syk antisense oligonucleotides inhibits antigen-induced infiltration of eosinophils and neutrophils in an animal model of asthma. Syk deficient eosinophils also show impaired activation in response to FCεRI stimulation. Therefore, small molecule inhibitors of Syk will be useful for treatment of allergy-induced inflammatory diseases including asthma.

Syk is also expressed in mast cells and monocytes and has been shown to be important for the function of these cells. For example, Syk deficiency in mice is associated with impaired IgE-mediated mast cell activation, which is marked diminution of TNF-alpha and other inflammatory cytokine release. Syk kinase inhibitors have also been shown to inhibit mast cell degranulation in cell based assays. Additionally, a Syk inhibitors have been shown to inhibit antigen-induced passive cutaneous anaphylaxsis, bronchoconstriction and bronchial edema in rats.

Thus, the inhibition of Syk activity can be useful for the treatment of allergic disorders, autoimmune diseases and inflammatory diseases such as: SLE, rheumatoid arthritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may be useful in treating certain types of cancer, including B-cell lymphoma and leukemia.

BRIEF SUMMARY

Provided is at least one chemical entity chosen from compounds of Formula I:

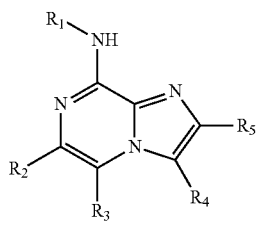

and pharmaceutically acceptable salts thereof, wherein
$R_1$ is phenyl substituted with one or two groups chosen from
  halo,
  hydroxy,
  carboxy,
  cyano,
  cycloalkyl optionally substituted with one or two groups chosen from hydroxy, lower alkoxy, and lower alkyl,
  cycloalkyloxy optionally substituted with one or two groups chosen from hydroxy, lower alkoxy, and lower alkyl,
  heterocycloalkyl optionally substituted with one or two groups chosen from acyl, halo, optionally substituted amino, hydroxy, lower alkoxy, lower alkyl, lower alkyl substituted with hydroxy, lower alkyl substituted with lower alkoxy, lower alkyl substituted with one, two, or three halo groups, optionally substituted amino, optionally substituted heterocycloalkyl, and oxo,
  heterocycloalkyloxy optionally substituted with one or two groups chosen from halo, optionally substituted amino, hydroxy, lower alkoxy, lower alkyl, lower alkyl substituted with hydroxy, lower alkyl substituted with lower alkoxy, lower alkyl substituted with one, two, or three halo groups, optionally substituted amino, optionally substituted heterocycloalkyl, and oxo,
  heteroaryl,
  amino optionally substituted with one or two groups chosen from lower alkyl, lower alkyl substituted with halo, lower alkyl substituted with hydroxy, and lower alkyl substituted with lower alkoxy,
  —C(O)NR$_6$R$_7$ wherein $R_6$ and $R_7$ are independently selected from hydrogen, lower alkyl, lower alkyl substituted with hydroxy, lower alkyl substituted with optionally substituted amino, cycloalkyl, aryl, heteroaryl, and heterocycloalkyl, or $R_6$ and $R_7$ together with the nitrogen to which they are bound form a 3- to 7-membered heterocycloalkyl ring optionally substituted with one or two groups chosen from hydroxy, lower alkyl, and lower alkyl substituted with hydroxy,
  —S(O)$_2$NR$_6$R$_7$ wherein $R_6$ and $R_7$ are independently selected from hydrogen, lower alkyl, lower alkyl substituted with hydroxy, lower alkyl substituted optionally substituted amino, cycloalkyl, aryl, heteroaryl, and heterocycloalkyl, or $R_6$ and $R_7$ together with the nitrogen to which they are bound form a 3- to 7-membered heterocycloalkyl ring optionally substituted with one or two groups chosen from hydroxy, lower alkyl, and lower alkyl substituted with hydroxy, provided that at least one of $R_6$ and $R_7$ is not hydrogen,
  lower alkoxy optionally substituted with one or two groups chosen from hydroxy, lower alkoxy, optionally substituted aminocarbonyl, optionally substituted amino, carboxy, aminocarbonyl, and heterocycloalkyl,
  heteroaryloxy, and
  lower alkyl optionally substituted with one or two groups chosen from hydroxy, lower alkoxy, halo, trifluoromethyl, optionally substituted amino, and heterocycloalkyl optionally substituted with lower alkyl; or
$R_1$ is

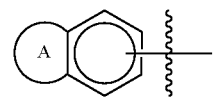

wherein A is chosen from aryl, cycloalkyl and heterocycloalkyl groups, each of which groups having from 5 to 7 ring atoms including the atoms shared with the 6 membered aromatic ring and each of which groups being optionally substituted;
$R_2$ is chosen from optionally substituted aryl and optionally substituted heteroaryl;
$R_3$ is chosen from hydrogen, lower alkyl, and halo;
$R_4$ is chosen from hydrogen and lower alkyl; and
$R_5$ is hydrogen,
provided that
if $R_3$ and $R_4$ are hydrogen and $R_1$ is 3-methoxy-4-(morpholin-4-ylcarbonyl)phenyl, 4-(morpholin-4-yl)phenyl, 3,4-diethoxyphenyl, 3-fluoro-4-methoxyphenyl, 4-(4-ethylpiperazin-1-1)phenyl, 4-(3-oxopiperazin-1-yl)phenyl, 4-(morpholin-4-yl)phenyl, 3-methoxy-4-(morpholin-4-yl)phenyl, 3-methoxy-4-methylphenyl, 4-methoxy-3-methylphenyl, 2-(dimethylamino)ethoxy-3-methoxyphenyl, 3-ethoxy-4-methoxyphenyl, or 4-ethoxy-3-methoxyphenyl, then $R_2$ is not phenyl substituted with —(CO)NHR$_6$ where $R_6$ is optionally substituted aryl;
if $R_3$ and $R_4$ are hydrogen and $R_1$ is 3,4-dimethoxyphenyl, then $R_2$ is not phenyl substituted with
  —(CO)NR$_8$R$_9$ where $R_8$ and $R_9$ taken together form an heterocycloalkyl or optionally substituted heteroaryl or where $R_8$ is hydrogen, methyl or ethyl and $R_9$ is hydrogen, optionally substituted aryl, optionally substituted cycloalkyl, optionally substituted heterocycloalkyl, optionally substituted alkyl, or optionally substituted heteroaryl wherein said phenyl is further optionally substituted with a group chosen from methyl, methoxy, and halo, or
  —(SO$_2$)NHR$_{10}$ where R$_{10}$ is optionally substituted phenyl;
if $R_3$ and $R_4$ are hydrogen and $R_1$ is 4-(morpholin-4-yl)phenyl, then $R_2$ is not pyridinyl, 2-fluorophenyl, benzo[d][1,3]dioxolyl, 2-methoxyphenyl, 2,6-dimethoxyphenyl, 3-acetamidophenyl, 3-carboxyphenyl, 2-(hydroxymethyl)phenyl, furanyl, or 3-(hydroxyethylcarbamoyl)phenyl;
if $R_3$ and $R_4$ are hydrogen and $R_1$ is chlorophenyl, then $R_2$ is not phenyl substituted with piperidin-1-yl-carbonyl or NH(CO)NHR$_{12}$ where R$_{12}$ is phenyl substituted with trifluoromethyl or one or more halogens;
if $R_3$ and $R_4$ are hydrogen and $R_1$ is phenyl substituted with optionally substituted piperazinyl then $R_2$ is not 3-aminophenyl;
if $R_3$ and $R_4$ are hydrogen and $R_1$ is 4-chlorophenyl, then $R_2$ is not 4-carboxyphenyl, 3-(2-(dimethylamino)ethylcarbamoyl)phenyl, or 4-(2-(dimethylamino)ethylcarbamoyl)phenyl; and if R₃ and R₄ are hydrogen and R₁ is 4-(2-hydroxy-ethyl)phenyl or 4-(hydroxyethyl)phenyl, then R₂ is not 2-methoxyphenyl or 2-fluorophenyl;

if R₃ and R₄ are hydrogen and R₁ is 4-[(4-ethylpiperazin-1-yl)methyl]phenyl or 4-(2-hydroxypropan-2-yl)phenyl, then R₂ is not phenyl substituted with —(CO)NR₈R₉ where R₈ is hydrogen and R₉ is hydrogen, methyl or optionally substituted aryl wherein said phenyl is optionally further substituted with a group chosen from methyl;

if R₃ and R₄ are hydrogen and R₂ is 4-carbamoylphenyl, then R₁ is not 4-(hydroxymethyl)phenyl, 3-(1-hydroxyethyl)phenyl, 4-(1H-imidazol-2-yl)-3-methylphenyl, 3-methoxy-4-(piperidin-4-yloxy)phenyl, 3-methoxy-4-(2-methoxyethoxy)phenyl, 4[2-(dimethylamino)ethoxy]-3-methoxyphenyl, 4-(2-hydroxyethoxy)-3-methoxyphenyl, 3-methoxy-4-(propan-2-yloxy)phenyl, 3-methoxy-4-propoxyphenyl, 4-(propylcarbamoyl)phenyl, 4-ethoxy-3-methoxyphenyl, 4-(1H-imidazol-2-yl)phenyl, 3-methoxy-4-(1H-pyrazol-5-yl)phenyl, if R₃ and R₄ are hydrogen and R₂ is pyridin-3-yl substituted with carbamoyl, then R₁ is not 3,4-dimethoxyphenyl, if R₃ and R₄ are hydrogen and R₁ is 4-ethoxy-3-methoxyphenyl, then R₂ is not phenyl substituted with methyl and further substituted with —(CO)NR₈R₉ where R₈ is hydrogen and R₉ is 4-(methylcarbamoyl)phenyl, and further provided that R₂ is not phenyl substituted with —NHC(O)R₁₁ where R₁₁ is optionally substituted aryl.

Also provided is at least one chemical entity chosen from compounds of Formula I:

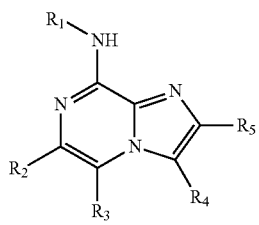

(I)

and pharmaceutically acceptable salts thereof, wherein

R₁ is phenyl substituted with one or two groups chosen from
halo,
hydroxy,
carboxy,
cycloalkyl optionally substituted with one or two groups chosen from hydroxy, lower alkoxy, and lower alkyl,
heterocycloalkyl optionally substituted with one or two groups chosen from hydroxy, lower alkoxy, lower alkyl, lower alkyl substituted with hydroxy, optionally substituted amino, and oxo,
heteroaryl,
amino optionally substituted with one or two groups chosen from lower alkyl, lower alkyl substituted with halo, lower alkyl substituted with hydroxy, and lower alkyl substituted with lower alkoxy,
—C(O)NR₆R₇ wherein R₆ and R₇ are independently selected from hydrogen, lower alkyl, lower alkyl substituted with hydroxy, lower alkyl substituted with optionally substituted amino, cycloalkyl, aryl, heteroaryl, and heterocycloalkyl, or R₆ and R₇ together with the nitrogen to which they are bound form a 3- to 7-membered heterocycloalkyl ring optionally substituted with one or two groups chosen from hydroxy, lower alkyl, and lower alkyl substituted with hydroxy,
—S(O)₂NR₆R₇ wherein R₆ and R₇ are independently selected from hydrogen, lower alkyl, lower alkyl substituted with hydroxy, lower alkyl substituted with optionally substituted amino, cycloalkyl, aryl, heteroaryl, and heterocycloalkyl, or R₆ and R₇ together with the nitrogen to which they are bound form a 3- to 7-membered heterocycloalkyl ring optionally substituted with one or two groups chosen from hydroxy, lower alkyl, and lower alkyl substituted with hydroxy, provided that at least one of R₆ and R₇ is not hydrogen,
lower alkoxy optionally substituted with one or two groups chosen from hydroxy, lower alkoxy, optionally substituted amino, carboxy, aminocarbonyl, and heterocycloalkyl,
heteroaryloxy, and
lower alkyl optionally substituted with one or two groups chosen from hydroxy, lower alkoxy, halo, trifluoromethyl, optionally substituted amino, and heterocycloalkyl optionally substituted with lower alkyl; or R₁ is

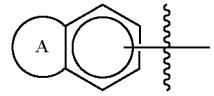

wherein A is chosen from aryl, cycloalkyl and heterocycloalkyl groups, each of which groups having from 5 to 7 ring atoms including the atoms shared with the 6 membered aromatic ring and each of which groups being optionally substituted;

R₂ is chosen from optionally substituted aryl and optionally substituted heteroaryl;

R₃ is hydrogen;

R₄ is hydrogen; and

R₅ is hydrogen, provided that if R₁ is 3-methoxy-4-methylphenyl, 4-methoxy-3-methylphenyl, 2-(dimethylamino)ethoxy-3-methoxyphenyl, 3-ethoxy-4-methoxyphenyl, or 4-ethoxy-3-methoxyphenyl, then R₂ is not phenyl substituted with —(CO)NHR₆ where R₆ is optionally substituted aryl;

if R₁ is 3,4-dimethoxyphenyl, then R₂ is not phenyl substituted with

—(CO)NR₈R₉ where R₈ and R₉ taken together form an optionally substituted heterocycloalkyl or optionally substituted heteroaryl or where R₈ is hydrogen and R₉ is optionally substituted aryl, optionally substituted cycloalkyl, optionally substituted heterocycloalkyl, optionally substituted alkyl, or optionally substituted heteroaryl, or —(SO₂)NHR₁₀ where R₁₀ is optionally substituted phenyl;

if R₁ is 4-(morpholin-4-yl)phenyl, then R₂ is not pyridinyl, 2-fluorophenyl, benzo[d][1,3]dioxolyl, 2-methoxyphenyl, 2,6-dimethoxyphenyl, 3-acetamidophenyl, 3-carboxyphenyl, 2-(hydroxymethyl)phenyl, furanyl, or 3-(hyroxyethylcarbamoyl)phenyl;

if R₁ is chlorophenyl, then R₂ is not phenyl substituted with piperidin-1-yl-carbonyl or NH(CO)NR₁₂ where R₁₂ is phenyl substituted with trifluoromethyl or one or more halogens;

if R₁ is optionally substituted piperazinyl then R₂ is not 3-aminophenyl;

if R₁ is 4-chlorophenyl, then R₂ is not 4-carboxyphenyl, 3-(2-(dimethylamino)ethylcarbamoyl)phenyl, or 4-(2-(dimethylamino)ethylcarbamoyl)phenyl; and if $R_1$ is 4-(2-hydroxy-ethyl)phenyl or 4-(hydroxyethyl)phenyl, then $R_2$ is not 2-methoxyphenyl or 2-fluorophenyl; and further provided that $R_2$ is not phenyl substituted with —NHC(O)$R_{11}$ where $R_{11}$ is optionally substituted aryl.

Also provided is at least one chemical entity chosen from compounds of Formula I:

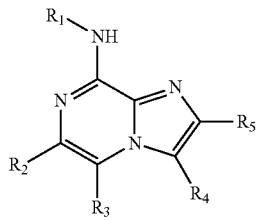

and pharmaceutically acceptable salts thereof, wherein $R_1$ is phenyl substituted with one or two groups chosen from
halo,
hydroxy,
cycloalkyl optionally substituted with one or two groups chosen from hydroxy, lower alkoxy, and lower alkyl,
heterocycloalkyl optionally substituted with one or two groups chosen from hydroxy, lower alkoxy, and lower alkyl,
amino optionally substituted with one or two groups chosen from lower alkyl,
lower alkyl substituted with halo, lower alkyl substituted with hydroxy, and lower alkyl substituted with lower alkoxy,
lower alkoxy optionally substituted with one or two groups chosen from hydroxy, lower alkoxy, and optionally substituted amino, and
lower alkyl optionally substituted with one or two groups chosen from hydroxy, lower alkoxy, halo, trifluoromethyl, and optionally substituted amino; or
$R_1$ is

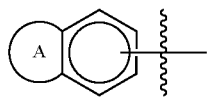

wherein A is chosen from aryl, cycloalkyl and heterocycloalkyl groups, each of which groups having from 5 to 7 ring atoms including the atoms shared with the 6 membered aromatic ring and each of which groups being optionally substituted;
$R_2$ is chosen from optionally substituted aryl and optionally substituted heteroaryl;
$R_3$ is hydrogen;
$R_4$ is hydrogen; and
$R_5$ is hydrogen,
provided that
if $R_1$ is 3-methoxy-4-methylphenyl, 4-methoxy-3-methylphenyl, 2-(dimethylamino)ethoxy-3-methoxyphenyl, 3-ethoxy-4-methoxyphenyl, or 4-ethoxy-3-methoxyphenyl, then $R_2$ is not phenyl substituted with —(CO)NH$R_6$ where $R_6$ is optionally substituted aryl;
if $R_1$ is 3,4-dimethoxyphenyl, then $R_2$ is not phenyl substituted with
—(CO)N$R_8R_9$ where $R_8$ and $R_9$ taken together form an optionally substituted heterocycloalkyl or optionally substituted heteroaryl or where $R_8$ is hydrogen and $R_9$ is optionally substituted aryl, optionally substituted cycloalkyl, optionally substituted heterocycloalkyl, optionally substituted alkyl, or optionally substituted heteroaryl, or
—(SO$_2$)NH$R_{10}$ where $R_{10}$ is optionally substituted phenyl;
if $R_1$ is 4-(morpholin-4-yl)phenyl, then $R_2$ is not pyridinyl, 2-fluorophenyl, benzo[d][1,3]dioxolyl, 2-methoxyphenyl, 2,6-dimethoxyphenyl, 3-acetamidophenyl, 3-carboxyphenyl, 2-(hydroxymethyl)phenyl, furanyl, or 3-(hydroxyethylcarbamoyl)phenyl;
if $R_1$ is chlorophenyl, then $R_2$ is not phenyl substituted with piperidin-1-yl-carbonyl or NH(CO)N$R_{12}$ where $R_{12}$ is phenyl substituted with trifluoromethyl or one or more halogens;
if $R_1$ is optionally substituted piperazinyl then $R_2$ is not 3-aminophenyl;
if $R_1$ is 4-chlorophenyl, then $R_2$ is not 4-carboxyphenyl, 3-(2-(dimethylamino)ethylcarbamoyl)phenyl, or 4-(2-(dimethylamino)ethylcarbamoyl)phenyl; and
if $R_1$ is 4-(2-hydroxy-ethyl)phenyl or 4-(hydroxyethyl)phenyl, then $R_2$ is not 2-methoxyphenyl or 2-fluorophenyl; and further provided that $R_2$ is not phenyl substituted with —NHC(O)$R_{11}$ where $R_{11}$ is optionally substituted aryl.

Also provided is a pharmaceutical composition, comprising at least one chemical entity described herein, together with at least one pharmaceutically acceptable vehicle chosen from carriers, adjuvants, and excipients.

Also provided is a method for treating a patient having a disease responsive to inhibition of Syk activity, comprising administering to the patient an effective amount of at least one chemical entity described herein.

Also provided is a method for treating a patient having a disease chosen from cancer, autoimmune diseases, inflammatory diseases, acute inflammatory reactions, and allergic disorders comprising administering to the patient an effective amount of at least one chemical entity described herein. Also provided is a method for treating a patient having polycystic kidney disease comprising administering to the patient an effective amount of at least one chemical entity described herein.

Also provided is a method for increasing sensitivity of cancer cells to chemotherapy, comprising administering to a patient undergoing chemotherapy with a chemotherapeutic agent an amount of at least one chemical entity described herein, sufficient to increase the sensitivity of cancer cells to the chemotherapeutic agent.

Also provided is a method for inhibiting ATP hydrolysis, the method comprising contacting cells expressing Syk with at least one chemical entity described herein in an amount sufficient to detectably decrease the level of ATP hydrolysis in vitro.

Also provided is a method for determining the presence of Syk in a sample, comprising contacting the sample with at least one chemical entity described herein under conditions that permit detection of Syk activity, detecting a level of Syk activity in the sample, and therefrom determining the presence or absence of Syk in the sample.

Also provided is a method for inhibiting B-cell activity comprising contacting cells expressing Syk with at least one chemical entity described herein in an amount sufficient to detectably decrease B-cell activity in vitro.

DETAILED DESCRIPTION

As used herein, when any variable occurs more than one time in a chemical formula, its definition on each occurrence is independent of its definition at every other occurrence. In accordance with the usual meaning of "a" and "the" in patents, reference, for example, to "a" kinase or "the" kinase is inclusive of one or more kinases.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_o$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Alkenyl" indicates an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In some embodiments, an alkenyl group has from 2 to 20 carbon atoms and in other embodiments, from 2 to 6 carbon atoms.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aminocarbonyl" encompasses a group of the formula —(C=O)NR$_a$R$_b$ where R$_a$ and R$_b$ are independently chosen from hydrogen and the optional substituents for "substituted amino" described below.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula CH$_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —NH$_2$.

"Aryl" encompasses:

5- and 6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "halo" includes fluoro, chloro, bromo, and iodo, and the term "halogen" includes fluorine, chlorine, bromine, and iodine.

"Heteroaryl" encompasses:

5- to 7-membered aromatic, monocyclic rings containing one or more, for example, from 1 to 4, or In some embodiments, from 1 to 3, heteroatoms chosen from N, O, and S, with the remaining ring atoms being carbon; and bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O⁻) substituents, such as pyridinyl N-oxides.

The term "heteroaryloxy" refers to the group —O-heteroaryl.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein neither of the rings is aromatic and wherein at least one of the rings in the bicyclic ring system contains at least 2 carbon atoms in addition to 1-3 heteroatoms independently chosen from oxygen, sulfur, and nitrogen.

The term "heterocycloalkyloxy" refers to the group —O-heterocylcoalkyl.

The term "nitro" refers to the group —NO$_2$.

The term "phosphono" refers to the group —PO$_3$H$_2$.

"Thiocarbonyl" refers to the group —C(=O)SH.

The term "optionally substituted thiocarbonyl" includes the following groups: —C(=O)S-(optionally substituted (C$_1$-C$_6$)alkyl), —C(=O)S-(optionally substituted aryl), —C(=O)S-(optionally substituted heteroaryl), and C(=O)S-(optionally substituted heterocycloalkyl).

The term "sulfanyl" includes the groups: —S-(optionally substituted (C$_1$-C$_6$)alkyl), —S-(optionally substituted aryl), —S-(optionally substituted heteroaryl), and —S-(optionally substituted heterocycloalkyl). Hence, sulfanyl includes the group C$_1$-C$_6$ alkylsulfanyl.

The term "sulfinyl" includes the groups: —S(O)—H, —S(O)-(optionally substituted (C$_1$-C$_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)—H, —S(O$_2$)-(optionally substituted (C$_1$-C$_6$)alkyl), —S(O$_2$)-optionally substituted aryl), —S(O$_2$)-optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocycyloxy); and —S(O$_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl (including without limitation dihydrobenzoxazinyl, dihydroquinoxalinyl, dihydrobenzodiazolyl, dihydroindolyl, pyrimidinyl, quinolinyl, indazolyl, indolyl, benzoimidazolyl, benzothiozolyl, benzotriazolyl, quinoxalinyl, quinazolinyl, morpholinyl, azetidinyl, pyrrolidinyl, oxanyl, pyridinyl, oxazolyl, piperazinyl, and pyradazinyl group), unless otherwise expressly defined, refer respectively to alkyl, cycloalkyl, aryl, heterocycloalkyl, and heteroaryl (including without limitation dihydrobenzoxazinyl, dihydroquinoxalinyl, dihydrobenzodiazolyl, dihydroindolyl, pyrimidinyl, quinolinyl, indazolyl, indolyl, benzoimidazolyl, benzothiozolyl, benzotriazolyl, quinoxalinyl, quinazolinyl, morpholinyl, azetidinyl, pyrrolidinyl, oxanyl, pyridinyl, oxazolyl, piperazinyl, and pyradazinyl group) wherein one or more (such as up to 5, for example, up to 3) hydrogen atoms are replaced by a substituent independently chosen from:

—R$^a$, —OR$^b$, —O(C$_1$-C$_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, oxo (as a substituent for heterocycloalkyl), nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted cycloalkyl, optionally substituted aryl, optionally substituted heterocycloalkyl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein "substituted alkyl" is as described herein.

The term "substituted aryloxy" refers to aryloxy wherein the aryl constituent is substituted (i.e., —O-(substituted aryl)) wherein "substituted aryl" is as described herein.

The term "substituted heteroaryloxy" refers to heteroaryloxy wherein the aryl constituent is substituted (i.e., —O-(substituted heteroaryl)) wherein "substituted heteroaryl" is as described herein.

The term "substituted cycloalkyloxy" refers to cycloalkyloxy wherein the cycloalkyl constituent is substituted (i.e., —O-(substituted cycloalkyl)) wherein "substituted cycloalkyl" is as described herein.

The term "substituted heterocycloalkyloxy" refers to heterocycloalkyloxy wherein the alkyl constituent is substituted (i.e., —O-(substituted heterocycloalkyl)) wherein "substituted heterocycloalkyl" is as described herein.

The term "substituted amino" refers to the group —$NHR^d$ or —$NR^dR^d$ where each $R^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, alkoxycarbonyl, sulfinyl and sulfonyl, provided that only one $R^d$ may be hydroxyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl); and wherein optionally substituted acyl, aminocarbonyl, alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, chemical entities include all tautomeric forms of the compound. Such compounds also include crystal forms including polymorphs and clathrates.

Compounds of Formula I also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. Compounds of Formula I also include pharmaceutically acceptable forms of the recited compounds, including chelates, non-covalent complexes, prodrugs, and mixtures thereof.

Chemical entities include, but are not limited to compounds described herein and all pharmaceutically acceptable forms thereof. Hence, the terms "chemical entity" and "chemical entities" also encompass pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COON where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of compounds of Formula I. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, especially an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-cancer therapeutic.

The term "therapeutically effective amount" of a chemical entity described herein means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of Syk activity. In some embodiments, a therapeutically effective amount is an amount sufficient to reduce cancer symptoms, the symptoms of an allergic disorder, the symptoms of an autoimmune and/or inflammatory disease, or the symptoms of an acute inflammatory reaction. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor. In some circumstances a patient suffering from cancer may not present symptoms of being affected. In some embodiments, a therapeutically effective amount of a chemical entity is an amount sufficient to prevent a significant increase or significantly reduce the detectable level of cancerous cells or cancer markers in the patient's blood, serum, or tissues. In methods described herein for treating allergic disorders and/or autoimmune and/or inflammatory diseases and/or acute inflammatory reactions, a therapeutically effective amount may also be an amount sufficient, when administered to a patient, to detectably slow progression of the disease, or prevent the patient to whom the chemical entity is given from presenting symptoms of the allergic disorders and/or autoimmune and/or inflammatory disease, and/or acute inflammatory response. In some methods described herein for treating allergic disorders and/or autoimmune and/or inflammatory diseases and/or acute inflammatory reactions, a therapeutically effective amount may also be an amount sufficient to produce a detectable decrease in the amount of a marker protein or cell type in the patient's blood or serum. For example, in some embodiments a therapeutically effective amount is an amount of a chemical entity described herein sufficient to significantly decrease the activity of B-cells. In another example, in some embodiments a therapeutically effective amount is an amount of a chemical entity described herein sufficient to significantly decrease the number of B-cells. In another example, in some embodiments a therapeutically effective amount is an amount of a chemical entity described herein sufficient to decrease the level of anti-acetylcholine receptor antibody in a patient's blood with the disease myasthenia gravis.

The term "inhibition" indicates a significant decrease in the baseline activity of a biological activity or process. "Inhibition of Syk activity" refers to a decrease in Syk activity as a direct or indirect response to the presence of at least one chemical entity described herein, relative to the activity of Syk in the absence of the at least one chemical entity. The decrease in activity may be due to the direct interaction of the compound with Syk, or due to the interaction of the chemical entity(ies) described herein with one or more other factors that in turn affect Syk activity. For example, the presence of the chemical entity(ies) may decrease Syk activity by directly binding to the Syk, by causing (directly or indirectly) another factor to decrease Syk activity, or by (directly or indirectly) decreasing the amount of Syk present in the cell or organism.

Inhibition of Syk activity also refers to observable inhibition of Syk activity in a standard biochemical assay for Syk activity, such as the ATP hydrolysis assay described below. In some embodiments, the chemical entity described herein has an $IC_{50}$ value less than or equal to 1 micromolar. In some embodiments, the chemical entity has an $IC_{50}$ value less than or equal to less than 100 nanomolar. In some embodiments, the chemical entity has an $IC_{50}$ value less than or equal to 10 nanomolar.

"Inhibition of B-cell activity" refers to a decrease in B-cell activity as a direct or indirect response to the presence of at least one chemical entity described herein, relative to the activity of B-cells in the absence of the at least one chemical entity. The decrease in activity may be due to the direct interaction of the compound with Syk or with one or more other factors that in turn affect B-cell activity.

Inhibition of B-cell activity also refers to observable inhibition of CD86 expression in a standard assay such as the assay described below. In some embodiments, the chemical entity described herein has an $IC_{50}$ value less than or equal to 10 micromolar. In some embodiments, the chemical entity has an $IC_{50}$ value less than or equal to less than 1 micromolar. In some embodiments, the chemical entity has an $IC_{50}$ value less than or equal to 500 nanomolar.

"B cell activity" also includes activation, redistribution, reorganization, or capping of one or more various B cell membrane receptors, or membrane-bound immunoglobulins, e.g., IgM, IgG, and IgD. Most B cells also have membrane receptors for Fc portion of IgG in the form of either antigen-antibody complexes or aggregated IgG. B cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also consist of IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus an inhibition of B-cell proliferation in vitro would be any significant decrease in the number of B-cells in an in vitro sample contacted with at least one chemical entity described herein as compared to a matched sample not contacted with the chemical entity(ies).

Inhibition of B-cell proliferation also refers to observable inhibition of B-cell proliferation in a standard thymidine incorporation assay for B-cell proliferation, such as the assay described herein. In some embodiments, the chemical entity has an $IC_{50}$ value less than or equal to 10 micromolar. In some embodiments, the chemical entity has an $IC_{50}$ value less than or equal to less than 1 micromolar. In some embodiments, the chemical entity has an $IC_{50}$ value less than or equal to 500 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where p<0.05.

A "disease responsive to inhibition of Syk activity" is a disease in which inhibiting Syk kinase provides a therapeutic benefit such as an amelioration of symptoms, decrease in disease progression, prevention or delay of disease onset, or inhibition of aberrant activity of certain cell-types (monocytes, B-cells, and mast cells).

"Treatment or treating means any treatment of a disease in a patient, including:
  a) preventing the disease, that is, causing the clinical symptoms of the disease not to develop;
  b) inhibiting the disease;
  c) slowing or arresting the development of clinical symptoms; and/or
  d) relieving the disease, that is, causing the regression of clinical symptoms.

"Patient" refers to an animal, such as a mammal, that has been or will be the object of treatment, observation or experiment. The methods described herein may be useful in both human therapy and veterinary applications. In some embodiments, the patient is a mammal; in some embodiments the patient is human; and in some embodiments the patient is chosen from cats and dogs.

Provided is at least one chemical entity chosen from compounds of Formula I:

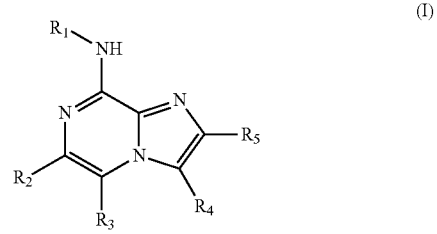

and pharmaceutically acceptable salts thereof, wherein $R_1$ is phenyl substituted with one or two groups chosen from
halo,
hydroxy,
carboxy,
cyano,
cycloalkyl optionally substituted with one or two groups chosen from hydroxy, lower alkoxy, and lower alkyl,
cycloalkyloxy optionally substituted with one or two groups chosen from hydroxy, lower alkoxy, and lower alkyl,
heterocycloalkyl optionally substituted with one or two groups chosen from acyl, halo, optionally substituted amino, hydroxy, lower alkoxy, lower alkyl, lower alkyl substituted with hydroxy, lower alkyl substituted with lower alkoxy, lower alkyl substituted with one, two, or three halo groups, optionally substituted amino, optionally substituted heterocycloalkyl, and oxo,
heterocycloalkyloxy optionally substituted with one or two groups chosen from halo, optionally substituted amino, hydroxy, lower alkoxy, lower alkyl, lower alkyl substituted with hydroxy, lower alkyl substituted with lower alkoxy, lower alkyl substituted with one, two, or three halo groups, optionally substituted amino, optionally substituted heterocycloalkyl, and oxo,
heteroaryl,
amino optionally substituted with one or two groups chosen from lower alkyl, lower alkyl substituted with halo, lower alkyl substituted with hydroxy, and lower alkyl substituted with lower alkoxy,
—C(O)NR$_6$R$_7$ wherein R$_6$ and R$_7$ are independently selected from hydrogen, lower alkyl, lower alkyl substituted with hydroxy, lower alkyl substituted with optionally substituted amino, cycloalkyl, aryl, heteroaryl, and heterocycloalkyl, or R$_6$ and R$_7$ together with the nitrogen to which they are bound form a 3- to 7-membered heterocycloalkyl ring optionally substituted with one or two groups chosen from hydroxy, lower alkyl, and lower alkyl substituted with hydroxy,
—S(O)$_2$NR$_6$R$_7$ wherein R$_6$ and R$_7$ are independently selected from hydrogen, lower alkyl, lower alkyl substituted with hydroxy, lower alkyl substituted with optionally substituted amino, cycloalkyl, aryl, heteroaryl, and heterocycloalkyl, or R$_6$ and R$_7$ together with the nitrogen to which they are bound form a 3- to 7-membered heterocycloalkyl ring optionally substituted with one or two groups chosen from hydroxy, lower alkyl, and lower alkyl substituted with hydroxy, provided that at least one of R$_6$ and R$_7$ is not hydrogen,
lower alkoxy optionally substituted with one or two groups chosen from hydroxy, lower alkoxy, optionally substituted aminocarbonyl, optionally substituted amino, carboxy, aminocarbonyl, and heterocycloalkyl,
heteroaryloxy, and
lower alkyl optionally substituted with one or two groups chosen from hydroxy, lower alkoxy, halo, trifluoromethyl, optionally substituted amino, and heterocycloalkyl optionally substituted with lower alkyl; or
$R_1$ is

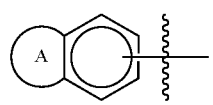

wherein A is chosen from aryl, cycloalkyl and heterocycloalkyl groups, each of which groups having from 5 to 7 ring atoms including the atoms shared with the 6 membered aromatic ring and each of which groups being optionally substituted;
$R_2$ is chosen from optionally substituted aryl and optionally substituted heteroaryl;
$R_3$ is chosen from hydrogen, lower alkyl, and halo;
$R_4$ is chosen from hydrogen and lower alkyl; and
$R_5$ is hydrogen,
provided that
if $R_3$ and $R_4$ are hydrogen and $R_1$ is 3-methoxy-4-(morpholin-4-ylcarbonyl)phenyl, 4-(morpholin-4-yl)phenyl, 3,4-diethoxyphenyl, 3-fluoro-4-methoxyphenyl, 4-(4-ethylpiperazin-1-yl)phenyl, 4-(3-oxopiperazin-1-yl)phenyl, 4-(morpholin-4-yl)phenyl, 3-methoxy-4-(morpholin-4-yl)phenyl, 3-methoxy-4-methylphenyl, 4-methoxy-3-methylphenyl, 2-(dimethylamino)ethoxy-3-methoxyphenyl, 3-ethoxy-4-methoxyphenyl, or 4-ethoxy-3-methoxyphenyl, then $R_2$ is not phenyl substituted with —(CO)NH R$_6$ where R$_6$ is optionally substituted aryl;
if $R_3$ and $R_4$ are hydrogen and $R_1$ is 3,4-dimethoxyphenyl, then $R_2$ is not phenyl substituted with
—(CO)NR$_8$R$_9$ where R$_8$ and R$_9$ taken together form an optionally substituted heterocycloalkyl or optionally substituted heteroaryl or where R$_8$ is hydrogen, methyl or ethyl and R$_9$ is hydrogen, optionally substituted aryl, optionally substituted cycloalkyl, optionally substituted heterocycloalkyl, optionally substituted alkyl, or optionally substituted heteroaryl wherein said phenyl is further optionally substituted with a group chosen from methyl, methoxy, and halo, or
—(SO$_2$)NHR$_{10}$ where R$_{10}$ is optionally substituted phenyl;
if $R_3$ and $R_4$ are hydrogen and $R_1$ is 4-(morpholin-4-yl)phenyl, then $R_2$ is not pyridinyl, 2-fluorophenyl, benzo[d][1,3]dioxolyl, 2-methoxyphenyl, 2,6-dimethoxyphenyl, 3-acetamidophenyl, 3-carboxyphenyl, 2-(hydroxymethyl) phenyl, furanyl, or 3-(hydroxyethylcarbamoyl)phenyl;
if $R_3$ and $R_4$ are hydrogen and $R_1$ is chlorophenyl, then $R_2$ is not phenyl substituted with piperidin-1-yl-carbonyl or NH(CO)NHR$_{12}$ where R$_{12}$ is phenyl substituted with trifluoromethyl or one or more halogens;
if $R_3$ and $R_4$ are hydrogen and $R_1$ is phenyl substituted with optionally substituted piperazinyl then $R_2$ is not 3-aminophenyl;
if $R_3$ and $R_4$ are hydrogen and $R_1$ is 4-chlorophenyl, then $R_2$ is not 4-carboxyphenyl, 3-(2-(dimethylamino)ethylcarbamoyl)phenyl, or 4-(2-(dimethylamino)ethylcarbamoyl)phenyl; and
if $R_3$ and $R_4$ are hydrogen and $R_1$ is 4-(2-hydroxy-ethyl) phenyl or 4-(hydroxyethyl)phenyl, then $R_2$ is not 2-methoxyphenyl or 2-fluorophenyl;
if $R_3$ and $R_4$ are hydrogen and $R_1$ is 4-[(4-ethylpiperazin-1-yl)methyl]phenyl or 4-(2-hydroxypropan-2-yl)phenyl, then $R_2$ is not phenyl substituted with —(CO)NR$_8$R$_9$ where R$_8$ is hydrogen and R$_9$ is hydrogen, methyl or optionally substituted aryl wherein said phenyl is optionally further substituted with a group chosen from methyl;
if $R_3$ and $R_4$ are hydrogen and $R_2$ is 4-carbamoylphenyl, then $R_1$ is not 4-(hydroxymethyl)phenyl, 3-(1-hydroxyethyl) phenyl, 4-(1H-imidazol-2-yl)-3-methylphenyl, 3-methoxy-4-(piperidin-4-yloxy)phenyl, 3-methoxy-4-(2-methoxyethoxy)phenyl, 4-[2-(dimethylamino)ethoxy]-3-methoxyphenyl, 4-(2-hydroxyethoxy)-3-methoxyphenyl, 3-methoxy-4-(propan-2-yloxy)phenyl, 3-methoxy-4-propoxyphenyl, 4-(propylcarbamoyl)phenyl, 4-ethoxy-3-methoxyphenyl, 4-(1H-imidazol-2-yl)phenyl, 3-methoxy-4-(1H-pyrazol-5-yl)phenyl, if R₃ and R₄ are hydrogen and R₂ is pyridin-3-yl substituted with carbamoyl, then R₁ is not 3,4-dimethoxyphenyl, if R₃ and R₄ are hydrogen and R₁ is 4-ethoxy-3-methoxyphenyl, then R₂ is not phenyl substituted with methyl and further substituted with —(CO)NR₈R₉ where R₈ is hydrogen and R₉ is 4-(methylcarbamoyl)phenyl, and further provided that R₂ is not phenyl substituted with —NHC(O)R₁₁ where R₁₁ is optionally substituted aryl.

In some embodiments, R₃ is chosen from hydrogen, methyl, ethyl, and chloro. In some embodiments, R₃ is hydrogen.

In some embodiments, R₄ is chosen from hydrogen and methyl. In some embodiments, R₄ is hydrogen.

Also provided is at least one chemical entity chosen from compounds of Formula I:

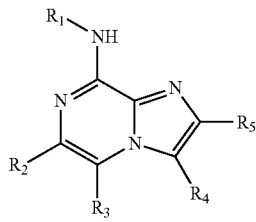

(I)

and pharmaceutically acceptable salts thereof, wherein

R₁ is phenyl substituted with one or two groups chosen from
halo,
hydroxy,
carboxy,
cycloalkyl optionally substituted with one or two groups chosen from hydroxy, lower alkoxy, and lower alkyl,
heterocycloalkyl optionally substituted with one or two groups chosen from hydroxy, lower alkoxy, lower alkyl, lower alkyl substituted with hydroxy, optionally substituted amino, and oxo,
heteroaryl,
amino optionally substituted with one or two groups chosen from lower alkyl, lower alkyl substituted with halo, lower alkyl substituted with hydroxy, and lower alkyl substituted with lower alkoxy,
—C(O)NR₆R₇ wherein R₆ and R₇ are independently selected from hydrogen, lower alkyl, lower alkyl substituted with hydroxy, lower alkyl substituted with optionally substituted amino, cycloalkyl, aryl, heteroaryl, and heterocycloalkyl, or R₆ and R₇ together with the nitrogen to which they are bound form a 3- to 7-membered heterocycloalkyl ring optionally substituted with one or two groups chosen from hydroxy, lower alkyl, and lower alkyl substituted with hydroxy,
—S(O)₂NR₆R₇ wherein R₆ and R₇ are independently selected from hydrogen, lower alkyl, lower alkyl substituted with hydroxy, lower alkyl substituted with optionally substituted amino, cycloalkyl, aryl, heteroaryl, and heterocycloalkyl, or R₆ and R₇ together with the nitrogen to which they are bound form a 3- to 7-membered heterocycloalkyl ring optionally substituted with one or two groups chosen from hydroxy, lower alkyl, and lower alkyl substituted with hydroxy, provided that at least one of R₆ and R₇ is not hydrogen,
lower alkoxy optionally substituted with one or two groups chosen from hydroxy, lower alkoxy, optionally substituted amino, carboxy, aminocarbonyl, and heterocycloalkyl,
heteroaryloxy, and
lower alkyl optionally substituted with one or two groups chosen from hydroxy, lower alkoxy, halo, trifluoromethyl, optionally substituted amino, and heterocycloalkyl optionally substituted with lower alkyl; or R₁ is

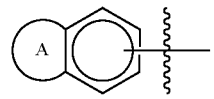

wherein A is chosen from aryl, cycloalkyl and heterocycloalkyl groups, each of which groups having from 5 to 7 ring atoms including the atoms shared with the 6 membered aromatic ring and each of which groups being optionally substituted;
R₂ is chosen from optionally substituted aryl and optionally substituted heteroaryl;
R₃ is hydrogen;
R₄ is hydrogen; and
R₅ is hydrogen,
provided that
if R₁ is 3-methoxy-4-methylphenyl, 4-methoxy-3-methylphenyl, 2-(dimethylamino)ethoxy-3-methoxyphenyl, 3-ethoxy-4-methoxyphenyl, or 4-ethoxy-3-methoxyphenyl, then R₂ is not phenyl substituted with —(CO)NHR₆ where R₆ is optionally substituted aryl;
if R₁ is 3,4-dimethoxyphenyl, then R₂ is not phenyl substituted with
—(CO)NR₈R₉ where R₈ and R₉ taken together form an optionally substituted heterocycloalkyl or optionally substituted heteroaryl or where R₈ is hydrogen and R₉ is optionally substituted aryl, optionally substituted cycloalkyl, optionally substituted heterocycloalkyl, optionally substituted alkyl, or optionally substituted heteroaryl, or
—(SO₂)NHR₁₀ where R₁₀ is optionally substituted phenyl;
if R₁ is 4-(morpholin-4-yl)phenyl, then R₂ is not pyridinyl, 2-fluorophenyl, benzo[d][1,3]dioxolyl, 2-methoxyphenyl, 2,6-dimethoxyphenyl, 3-acetamidophenyl, 3-carboxyphenyl, 2-(hydroxymethyl)phenyl, furanyl, or 3-(hyroxyethylcarbamoyl)phenyl;
if R₁ is chlorophenyl, then R₂ is not phenyl substituted with piperidin-1-yl-carbonyl or NH(CO)NR₁₂ where R₁₂ is phenyl substituted with trifluoromethyl or one or more halogens;
if R₁ is optionally substituted piperazinyl then R₂ is not 3-aminophenyl;
if R₁ is 4-chlorophenyl, then R₂ is not 4-carboxyphenyl, 3-(2-(dimethylamino)ethylcarbamoyl)phenyl, or 4-(2-(dimethylamino)ethylcarbamoyl)phenyl; and
if R₁ is 4-(2-hydroxy-ethyl)phenyl or 4-(hydroxyethyl)phenyl, then R₂ is not 2-methoxyphenyl or 2-fluorophenyl; and
further provided that R₂ is not phenyl substituted with —NHC(O)R₁₁ where R₁₁ is optionally substituted aryl.

In some embodiments, R₁ is phenyl substituted with one or two groups chosen from
halo,
hydroxy,
carboxy, cycloalkyl optionally substituted with one or two groups chosen from hydroxy, lower alkoxy, and lower alkyl,
heterocycloalkyl optionally substituted with one or two groups chosen from hydroxy, lower alkoxy, lower alkyl, lower alkyl substituted with hydroxy, optionally substituted amino, and oxo,
heteroaryl,
amino optionally substituted with one or two groups chosen from lower alkyl, lower alkyl substituted with halo, lower alkyl substituted with hydroxy, and lower alkyl substituted with lower alkoxy,
—C(O)NR$_6$R$_7$ wherein R$_6$ and R$_7$ are independently selected from hydrogen, lower alkyl, lower alkyl substituted with hydroxy, lower alkyl substituted with optionally substituted amino, cycloalkyl, aryl, heteroaryl, and heterocycloalkyl, or R$_6$ and R$_7$ together with the nitrogen to which they are bound form a 3- to 7-membered heterocycloalkyl ring optionally substituted with one or two groups chosen from hydroxy, lower alkyl, and lower alkyl substituted with hydroxy,
—S(O)$_2$NR$_6$R$_7$ wherein R$_6$ and R$_7$ are independently selected from hydrogen, lower alkyl, lower alkyl substituted with hydroxy, lower alkyl substituted with optionally substituted amino, cycloalkyl, aryl, heteroaryl, and heterocycloalkyl, or R$_6$ and R$_7$ together with the nitrogen to which they are bound form a 3- to 7-membered heterocycloalkyl ring optionally substituted with one or two groups chosen from hydroxy, lower alkyl, and lower alkyl substituted with hydroxy, provided that at least one of R$_6$ and R$_7$ is not hydrogen,
lower alkoxy optionally substituted with one or two groups chosen from hydroxy, lower alkoxy, optionally substituted amino, carboxy, aminocarbonyl, and heterocycloalkyl,
heteroaryloxy, and
lower alkyl optionally substituted with one or two groups chosen from hydroxy, lower alkoxy, halo, trifluoromethyl, optionally substituted amino, and heterocycloalkyl optionally substituted with lower alkyl.

In some embodiments, R$_1$ is phenyl substituted with one or two groups chosen from
halo,
hydroxy,
heterocycloalkyl optionally substituted with one or two groups chosen from hydroxy, lower alkoxy, lower alkyl, and lower alkyl substituted with hydroxy,
amino optionally substituted with one or two groups chosen from lower alkyl, lower alkyl substituted with hydroxy, and lower alkyl substituted with lower alkoxy,
lower alkoxy optionally substituted with one or two groups chosen from hydroxy, lower alkoxy, and optionally substituted amino,
lower alkyl optionally substituted with one or two groups chosen from hydroxy, lower alkoxy, trifluoromethyl, optionally substituted amino, and heterocycloalkyl, and
—C(O)NR$_6$R$_7$ wherein R$_6$ and R$_7$ are independently selected from hydrogen, lower alkyl, lower alkyl substituted with hydroxy, lower alkyl substituted with optionally substituted amino, cycloalkyl, aryl, heteroaryl, and heterocycloalkyl, or R$_6$ and R$_7$ together with the nitrogen to which they are bound form a 3- to 7-membered heterocycloalkyl ring optionally substituted with one or two groups chosen from hydroxy, lower alkyl, and lower alkyl substituted with hydroxy.

In some embodiments, R$_1$ is phenyl substituted with one or two groups chosen from
hydroxy,
heterocycloalkyl optionally substituted with one or two groups chosen from hydroxy, lower alkoxy, lower alkyl, and lower alkyl substituted with hydroxy,
lower alkoxy optionally substituted with one or two groups chosen from hydroxy and lower alkoxy, and
lower alkyl substituted with one or two groups chosen from hydroxy, lower alkoxy, trifluoromethyl, optionally substituted amino, and heterocycloalkyl.

Also provided is at least one chemical entity chosen from compounds of Formula I:

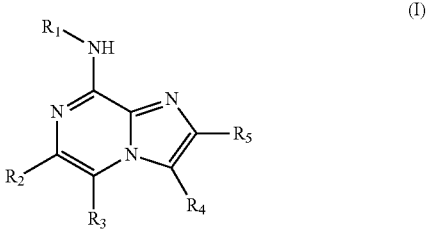

and pharmaceutically acceptable salts thereof, wherein
R$_1$ is phenyl substituted with one or two groups chosen from
halo,
hydroxy,
cycloalkyl optionally substituted with one or two groups chosen from hydroxy, lower alkoxy, and lower alkyl,
heterocycloalkyl optionally substituted with one or two groups chosen from hydroxy, lower alkoxy, and lower alkyl,
amino optionally substituted with one or two groups chosen from lower alkyl, lower alkyl substituted with halo, lower alkyl substituted with hydroxy, and lower alkyl substituted with lower alkoxy,
lower alkoxy optionally substituted with one or two groups chosen from hydroxy, lower alkoxy, and optionally substituted amino, and
lower alkyl optionally substituted with one or two groups chosen from hydroxy, lower alkoxy, halo, trifluoromethyl, and optionally substituted amino; or
R$_1$ is

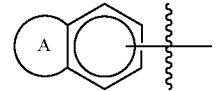

wherein A is chosen from aryl, cycloalkyl and heterocycloalkyl groups, each of which groups having from 5 to 7 ring atoms including the atoms shared with the 6 membered aromatic ring and each of which groups being optionally substituted;
R$_2$ is chosen from optionally substituted aryl and optionally substituted heteroaryl;
R$_3$ is hydrogen;
R$_4$ is hydrogen; and
R$_5$ is hydrogen,
provided that
if R$_1$ is 3-methoxy-4-methylphenyl, 4-methoxy-3-methylphenyl, 2-(dimethylamino)ethoxy-3-methoxyphenyl, 3-ethoxy-4-methoxyphenyl, or 4-ethoxy-3-methoxyphenyl, then $R_2$ is not phenyl substituted with —(CO)NHR$_6$ where $R_6$ is optionally substituted aryl;

if $R_1$ is 3,4-dimethoxyphenyl, then $R_2$ is not phenyl substituted with
—(CO)NR$_8$R$_9$ where $R_8$ and $R_9$ taken together form an optionally substituted heterocycloalkyl or optionally substituted heteroaryl or where $R_8$ is hydrogen and $R_9$ is optionally substituted aryl, optionally substituted cycloalkyl, optionally substituted heterocycloalkyl, optionally substituted alkyl, or optionally substituted heteroaryl, or
—(SO$_2$)NHR$_{10}$ where $R_{10}$ is optionally substituted phenyl;

if $R_1$ is 4-(morpholin-4-yl)phenyl, then $R_2$ is not pyridinyl, 2-fluorophenyl, benzo[d][1,3]dioxolyl, 2-methoxyphenyl, 2,6-dimethoxyphenyl, 3-acetamidophenyl, 3-carboxyphenyl, 2-(hydroxymethyl)phenyl, furanyl, or 3-(hyroxyethylcarbamoyl)phenyl;

if $R_1$ is chlorophenyl, then $R_2$ is not phenyl substituted with piperidin-1-yl-carbonyl or NH(CO)NR$_{12}$ where $R_{12}$ is phenyl substituted with trifluoromethyl or one or more halogens;

if $R_1$ is optionally substituted piperazinyl then $R_2$ is not 3-aminophenyl;

if $R_1$ is 4-chlorophenyl, then $R_2$ is not 4-carboxyphenyl, 3-(2-(dimethylamino)ethylcarbamoyl)phenyl, or 4-(2-(dimethylamino)ethylcarbamoyl)phenyl; and if $R_1$ is 4-(2-hydroxy-ethyl)phenyl or 4-(hydroxyethyl)phenyl, then $R_2$ is not 2-methoxyphenyl or 2-fluorophenyl; and further provided that $R_2$ is not phenyl substituted with —NHC(O)R$_{11}$ where $R_{11}$ is optionally substituted aryl.

In some embodiments, $R_1$ is phenyl substituted with one or two groups chosen from
halo,
hydroxy,
heterocycloalkyl optionally substituted with one or two groups chosen from hydroxy, lower alkoxy, and lower alkyl,
lower alkoxy optionally substituted with optionally substituted amino, and
lower alkyl optionally substituted with one or two groups chosen from hydroxy, lower alkoxy, and optionally substituted amino; or
$R_1$ is

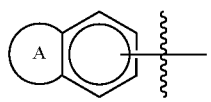

wherein A is chosen from aryl, cycloalkyl and heterocycloalkyl groups, each of which groups having from 5 to 7 ring atoms including the atoms shared with the 6 membered aromatic ring and each of which groups being optionally substituted.

In some embodiments, $R_1$ is phenyl substituted with one or two groups chosen from
hydroxy,
heterocycloalkyl optionally substituted with one or two groups chosen from hydroxy, lower alkoxy, and lower alkyl,
amino optionally substituted with one or two groups chosen from lower alkyl, lower alkyl substituted with hydroxy, and lower alkyl substituted with lower alkoxy,
lower alkoxy optionally substituted with one or two groups chosen from hydroxy and optionally substituted amino, and
lower alkyl optionally substituted with one or two groups chosen from hydroxy, lower alkoxy, trifluoromethyl, and optionally substituted amino.

In some embodiments, $R_1$ is phenyl substituted with one or two groups chosen from
hydroxy,
heterocycloalkyl optionally substituted with one or two groups chosen from hydroxy, lower alkoxy, and lower alkyl,
lower alkoxy, and
lower alkyl substituted with one or two groups chosen from hydroxy, lower alkoxy, trifluoromethyl, and optionally substituted amino.

In some embodiments, $R_1$ is chosen from (1-hydroxycyclobutyl)phenyl, (1,1,1-trifluoro-2-hydroxypropan-2-yl)phenyl, (2,2,2-trifluoro-1-hydroxyethyl)phenyl, (1,1,1,3,3,3-hexafluoro-2-hydroxypropan-2-yl)phenyl, (2-hydroxy-2-methylpropoxy)-3-methoxyphenyl, (2-hydroxyethyl)(methyl)amino)-3-methoxyphenyl, (2-methoxyethyl)(methyl)amino)-3-methoxyphenyl, (1-hydroxyethyl)phenyl, 3,4-dimethoxyphenyl, 3-methoxyphenyl, 4-ethoxy-3-methoxyphenyl, 4-hydroxymethyl-3-methoxyphenyl, 3-hydroxymethyl-4-methoxyphenyl, 2-fluoro-4-methoxyphenyl, 4-(dimethylamino)propoxy-3-methoxyphenyl, 4-hydroxypropoxy-3-methoxyphenyl, 4-(2-hydroxy-1,1-dimethylethyl)phenyl, 4-(1-hydroxy-1-methylethyl)phenyl, 4-methoxy-3-(pyrrolidin-1-yl)phenyl, 3-methoxy-4-(pyrrolidin-1-yl)phenyl, 3-methoxy-4-(propan-2-yloxy)phenyl, 3-methoxy-4-(morpholin-4-yl)phenyl, 4-(pyrrolidin-1-yl)phenyl, 4-(3-hydroxypyrrolidinyl)phenyl, 4-(4-hydroxypiperidinyl)-3-methoxyphenyl, 4-(3-hydroxyazetidinyl)-3-methoxyphenyl, 4-(3-hydroxypyrrolidinyl)-3-methoxyphenyl, 4-(2-methoxypropan-2-yl)phenyl, 4-(4-ethylpiperazin-1-yl)-3-methoxyphenyl, 4-(4-ethylpiperazin-1-yl)phenyl, 4-(3-hydroxy-3-methylpiperidinyl)phenyl, and 3-hydroxymethylphenyl.

In some embodiments, $R_1$ is phenyl substituted with one or two groups chosen from
hydroxy,
heterocycloalkyl optionally substituted with one or two groups chosen from hydroxy, lower alkoxy, and lower alkyl,
lower alkoxy optionally substituted with optionally substituted amino, and
lower alkyl optionally substituted with one or two groups chosen from hydroxy, lower alkoxy, and optionally substituted amino.

In some embodiments, $R_1$ is phenyl substituted with one or two groups chosen from
hydroxy,
heterocycloalkyl optionally substituted with one or two groups chosen from hydroxy, lower alkoxy, and lower alkyl,
lower alkoxy, and
lower alkyl substituted with one or two groups chosen from hydroxy, lower alkoxy, and optionally substituted amino.

In some embodiments, $R_1$ is phenyl substituted with one or two groups chosen from
hydroxy,
heterocycloalkyl optionally substituted with one or two groups chosen from hydroxy and lower alkyl,
lower alkoxy, and
lower alkyl substituted with one or two groups chosen from hydroxy and lower alkoxy.

In some embodiments, $R_1$ is chosen from (1-hydroxyethyl)phenyl, 3,4-dimethoxyphenyl, 3-methoxyphenyl, 4-ethoxy- 3-methoxyphenyl, 4-hydroxymethyl-3-methoxyphenyl, 3-hydroxymethyl-4-methoxyphenyl, 2-fluoro-4-methoxyphenyl, 4-(dimethylamino)propoxy-3-methoxyphenyl, 4-hydroxypropoxy-3-methoxyphenyl, 4-(2-hydroxy-1,1-dimethylethyl)phenyl, 4-(1-hydroxy-1-methylethyl)phenyl, 4-methoxy-3-(pyrrolidin-1-yl)phenyl, 3-methoxy-4-(pyrrolidin-1-yl)phenyl, 3-methoxy-4-(propan-2-yloxy)phenyl, 3-methoxy-4-(morpholin-4-yl)phenyl, 4-(pyrrolidin-1-yl)phenyl, 4-(3-hydroxypyrrolidinyl)phenyl, 4-(4-hydroxypiperidinyl)-3-methoxyphenyl, 4-(3-hydroxyazetidinyl)-3-methoxyphenyl, 4-(3-hydroxypyrrolidinyl)-3-methoxyphenyl, 4-(2-methoxypropan-2-yl)phenyl, 4-(4-ethylpiperazin-1-yl)-3-methoxyphenyl, 4-(4-ethylpiperazin-1-yl)phenyl, 4-(3-hydroxy-3-methylpiperidinyl)phenyl, and 3-hydroxymethylphenyl.

In some embodiments, $R_1$ is

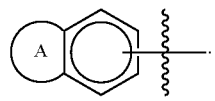

In some embodiments, A is an optionally substituted heterocycloalkyl group comprising one or more heteroatoms chosen from O and N. In some embodiments, the heterocylcloalkyl group is substituted with one or more groups chosen from lower alkyl and oxo. In some embodiments, the heteroatom N is substituted by lower alkyl.

In some embodiments, $R_1$ is chosen from 3,4-dihydro-2H-benzo[b][1,4]oxazin-6-yl, 4-methyl-3,4-dihydro-2H-benzo[b][1,4]oxazin-6-yl, 2,3,4,5-tetrahydrobenzo[b][1,4]oxazepin-7-yl, 5-methyl-2,3,4,5-tetrahydrobenzo[b][1,4]oxazepin-7-yl, 2,3-dihydro-1H-indol-2-one-6-yl, and 2,3-dihydro-1H-indol-2-one-5-yl.

In some embodiments, $R_2$ is chosen from
optionally substituted heteroaryl;
dihydrobenzoxazinyl optionally substituted with one or more groups chosen from lower alkyl, halo, and oxo,
dihydroquinoxalinyl optionally substituted with one or more groups chosen from lower alkyl and oxo;
dihydrobenzodiazolyl optionally substituted with oxo;
dihydroindolyl optionally substituted with one or more groups chosen from lower alkyl and oxo, and
phenyl substituted with one or more groups chosen from optionally substituted alkyl, cyano, nitro, lower alkoxy, halo, sulfonyl, optionally substituted amino, and optionally substituted heteroaryl.

In some embodiments, $R_2$ is chosen from
optionally substituted pyridinyl,
pyrimidinyl,
thiophenyl,
quinolinyl optionally substituted with amino,
indazolyl optionally substituted with one or two groups chosen from carbamoyl, halo, lower alkyl, and amino,
indolyl optionally substituted with one or two groups chosen from lower alkyl, carbamoyl,
benzoimidazolyl optionally substituted with methyl or amino, benzothiozolyl optionally substituted with lower alkyl,
benzoxazolyl,
benzotriazolyl,
quinoxalinyl optionally substituted with amino,
quinazolinyl optionally substituted with amino, dihydrobenzoxazinyl optionally substituted with one or more groups chosen from methyl, halo, and oxo,
1H-pyrrolo[3,2-b]pyridinyl,
dihydrobenzoxazinyl optionally substituted with one or more groups chosen from lower alkyl, halo, and oxo,
dihydroindolyl optionally substituted with one or more groups chosen from lower alkyl and oxo, and
phenyl substituted with one or more groups chosen from optionally substituted alkyl, cyano, chloro, fluoro, nitro, methoxy, sulfonyl, heteroaryl, amino, and NHC(O)$R_{12}$ where $R_{12}$ is lower alkyl.

In some embodiments, $R_2$ is chosen from 2,3-dihydro-1,4-benzodioxin-6-yl, 4-methyl-3,4-dihydro-2H-1,4-benzoxazin-6-yl, 1,3-benzoxazol-5-yl, 2H-1,3-benzodioxol-5-yl, 2,3-dihydro-1H-indol-6-yl, 2-methyl-1,2,3,4-tetrahydroisoquinolin-6-yl, 1-methyl-2,3-dihydro-1H-indol-2-one-6-yl, 1,2,3,4-tetrahydroisoquinolin-2-yl-ethan-1-one-6-yl, 2-ethyl-1,2,3,4-tetrahydroisoquinolin-7-yl, 2-aminoquinazolin-6-yl, 2-hydroxyethyl-2H-indazol-6-yl, 1-hydroxyethyl-2H-indazol-6-yl 1H-indazol-7-yl, 1,2,3,4-tetrahydroisoquinolin-6-yl, 3-(diethylamino)methyl-1H-indazol-6-yl, 1,2-dihydroquinoxalin-2-one-6-yl, 1,2-dihydroquinolin-2-one-6-yl, 1H-pyrazol-4-yl, 1,3-thiazol-5-yl, 2-methyl-1,3-benzothiazol-5-yl, 1 '2'-dihydrospiro[cyclopropane-1,3'-indole]-2'-one-6-yl, 3,3-dimethyl-2-oxo-2,3-dihydro-1H-indol-6-yl, 3-(1,3-thizaol-4-ylmethylidene)-2,3-dihydro-1H-indole-2-one-6-yl, 1-methyl-1H-indazol-6-yl, (N,N-dimethylaminocarbonyl)indol-6-yl, 1,3-benzothiazol-5-yl, 1,3-benzothiazol-6-yl, 1H,2H,3H-pyrido[2,3-b][1,4]oxazin-2-one-6-yl, 2,2-difluoro-3,4-dihydro-2H-1,4-benzoxazin-3-one-6-yl, 3-ethyl-1H-indazol-6-yl, 1H-indol-2-yl, 1H-indol-3-yl, 4-fluoro-1H-indazol-6-yl, 1H-1,2,3-benzotriazol-6-yl, 2,3-dihydro-1H-1,3-benzodiazol-2-one-6-yl, 1H-1,3-benzodiazol-6-yl, 1H-indol-6-yl, 1H-pyrrolo[3,2-b]pyridin-6-yl, 1-methyl-1H-1,3-benzodiazol-5-yl, 1-methyl-1H-1,3-benzodiazol-6-yl, 1-methyl-1H-benzo[d]imidazol-5-yl, 2-methyl-1H-benzo[d]imidazol-5-yl, 2-oxoindolin-6-yl, 3,3-dimethyl-2-oxoindolin-6-yl, 3,4-dihydro-2H-1,4-benzoxazin-6-yl, 3,4-dihydro-2H-1,4-benzoxazin-7-yl, 3-amino-1H-indazol-5-yl, 3-amino-1H-indazol-6-yl, 3-carbamoyl-1H-indazol-6-yl, 3-methyl-1H-indazol-6-yl, 3-oxo-3,4-dihydro-2H-benzo[b][1,4]oxazin-6-yl, 4-(1-hydroxy-2-methylpropan-2-yl)phenyl, 5-fluoro-1H-indazol-6-yl, and indolin-6-yl.

In some embodiments, $R_2$ is chosen from optionally substituted heteroaryl, dihydrobenzoxazinyl optionally substituted with lower alkyl and oxo, and phenyl substituted with one or more groups chosen from optionally substituted alkyl, cyano, nitro, lower alkoxy, halo, sulfonyl, optionally substituted amino, and optionally substituted heteroaryl.

In some embodiments, $R_2$ is chosen from optionally substituted pyridinyl, pyrimidinyl, thiophenyl, quinolinyl optionally substituted with amino, indazolyl optionally substituted with halo, carbamoyl, methyl or amino, indolyl, indolinyl optionally substituted with one or two groups chosen from lower alkyl and oxo, benzoimidazolyl optionally substituted with methyl or amino, benzothiozolyl, benzoxazolyl, benzotriazolyl, quinoxalinyl optionally substituted with amino, quinazolinyl optionally substituted with amino, dihydrobenzoxazinyl optionally substituted with methyl and oxo, 1H-pyrrolo[3,2-b]pyridinyl, and phenyl substituted with one or more groups chosen from optionally substituted alkyl, cyano, chloro, fluoro, nitro, methoxy, sulfonyl, heteroaryl, amino, and NHC(O)$R_{12}$ where $R_{12}$ is lower alkyl.

In some embodiments, $R_2$ is chosen from 1H-1,3-benzodiazol-6-yl, 1H-indol-6-yl, 1H-pyrrolo[3,2-b]pyridin-6-yl, 1-methyl-1H-1,3-benzodiazol-5-yl, 1-methyl-1H-1,3-benzodiazol-6-yl, 1-methyl-1H-benzo[d]imidazol-5-yl, 2-methyl-1H-benzo[d]imidazol-5-yl, 2-oxoindolin-6-yl, 3,3-dimethyl-2-oxoindolin-6-yl, 3,4-dihydro-2H-1,4-benzoxazin-6- yl, 3,4-dihydro-2H-1,4-benzoxazin-7-yl, 3-amino-1H-indazol-5-yl, 3-amino-1H-indazol-6-yl, 3-carbamoyl-1H-indazol-6-yl, 3-methyl-1H-indazol-6-yl, 3-oxo-3,4-dihydro-2H-benzo[b][1,4]oxazin-6-yl, 4-(1-hydroxy-2-methylpropan-2-yl)phenyl, 5-fluoro-1H-indazol-6-yl, and indolin-6-yl.

In some embodiments, $R_2$ is chosen from optionally substituted pyridinyl, pyrimidinyl, thiophenyl, quinolinyl optionally substituted with amino, indazolyl optionally substituted with methyl or amino, indolyl, benzoimidazolyl optionally substituted with methyl or amino, benzothiozolyl, benzoxazolyl, benzotriazolyl, quinoxalinyl optionally substituted with amino, quinazolinyl optionally substituted with amino, dihydrobenzoxazinyl optionally substituted with methyl and oxo, and phenyl substituted with one or more groups chosen from optionally substituted alkyl, cyano, chloro, fluoro, nitro, methoxy, sulfonyl, heteroaryl, amino, and $NHC(O)R_{12}$ where $R_{12}$ is lower alkyl.

In some embodiments, $R_2$ is chosen from 3-methylphenyl, 4-methylphenyl, 3-nitrophenyl, 3-[(ethylamino)methyl]phenyl, 4-[(ethylamino)methyl]phenyl, 3-(trifluoromethyl)phenyl, 3-methoxyphenyl, 4-pyridinyl, 3-pyridinyl, 4-cyanophenyl, 3-cyanophenyl, 4-chlorophenyl, 3-chlorophenyl, 4-chloro-3-methylphenyl, 3-chloro-4-methylphenyl, 4-fluorophenyl, 3-fluorophenyl, 4-fluoro-3-methylphenyl, 3-fluoro-4-methylphenyl, 3,4-difluorophenyl, 4-sulfonamidophenyl, 3-sulfonamidophenyl, 4-methanesulfonylphenyl, 3-methanesulfonylphenyl, 2-fluoropyridin-4-yl, 5-methylpyridin-3-yl, 5-chloropyridin-3-yl, pyrimidin-5-yl, (4-acetylpiperazin-1-yl)methylphenyl, (3-acetylpiperazin-1-yl)methylphenyl, (3-piperazin-1-ylmethyl)phenyl, (4-piperazin-1-ylmethyl)phenyl, 3-acetamidophenyl, 4-acetamidophenyl, 4-aminophenyl, 3-aminophenyl, thiophen-3-yl, thiophen-2-yl, 1H-indazol-5-yl, 1H-indazol-6-yl, 3-amino-1H-indazol-5-yl, 1-methyl-1H-indazol-5-yl, 1-methyl-1H-indazol-6-yl, 3-methyl-1H-indazol-5-yl, 2,3-dimethyl-2H-indazol-5-yl, 3-amino-1H-indazol-6-yl, 3-amino-1H-indazol-5-yl, 4-(1H-imidazol-2-yl)phenyl, 4-(1H-imidazol-5-yl)phenyl, 3-(1H-imidazol-5-yl)phenyl, quinolin-6-yl, 2-aminoquinoline-6-yl, 3-aminoquinoline-6-yl, 1,3-benzothiazol-5-yl, 1,3-benzothiazol-6-yl, 2-aminoquinazoline-6-yl, 3-(1,3-thiazol-2-yl)phenyl, 4-(1,3-thiazol-2-yl)phenyl, 3-(1,3-thiazol-2-yl)phenyl, 1,2-dihydropyridin-2-one-5-yl, 4-(1,3-oxazol-2-yl)phenyl, 3-(1,3-oxazol-2-yl)phenyl, 2-aminopyridine-5-yl, 1H-1,2,3-benzotriazol-6-yl, 1H-imidazo[4,5-b]pyridin-6-yl, 1,3-benzoxazol-5-yl, 1,3-benzoxazol-6-yl, 1H-indol-6-yl, 1H-indol-5-yl, 1-methyl-1H-1,3-benzodiazol-5-yl, 2-amino-1H-1,3-benzodiazol-6-yl, 1-methyl-1H-1,3-benzodiazol-6-yl, 2H,3H,4H-pyrido[3,2-b][1,4]oxazin-3-one-6-yl, 1H,2H,3H-pyrido[3,2-b][1,4]oxazin-3-one-6-yl, 3,4-dihydro-2H-1,4-benzoxazin-3-one-6-yl, 3,4-dihydro-2H-1,4-benzoxazin-3-one-7-yl, 4-methyl-3,4-dihydro-2H-1,4-benzoxazin-3-one-6-yl, 2-methyl-3,4-dihydro-2H-1,4-benzoxazin-3-one-6-yl, 2,2-dimethyl-3,4-dihydro-2H-1,4-benzoxazin-3-one-6-yl, 2-hydroxyquinolin-6-yl, 1-methyl-1,2-dihydropyridin-2-one-5-yl, and quinoxalin-2-ol-7-yl.

Also provided is at least one chemical entity chosen from:
N-(3,4-dimethoxyphenyl)-6-(3-methylphenyl)imidazo[1,2-a]pyrazin-8-amine;
N-(3,4-dimethoxyphenyl)-6-(3-nitrophenyl)imidazo[1,2-a]pyrazin-8-amine;
N-(3,4-dimethoxyphenyl)-6-{3-[(ethylamino)methyl]phenyl}imidazo[1,2-a]pyrazin-8-amine;
N-(3,4-dimethoxyphenyl)-6-{3-(trifluoromethyl)phenyl}imidazo[1,2-a]pyrazin-8-amine;
N-(3,4-dimethoxyphenyl)-6-(3-methoxyphenyl)imidazo[1,2-a]pyrazin-8-amine;
N-(3,4-dimethoxyphenyl)-6-(pyridin-4-yl)imidazo[1,2-a]pyrazin-8-amine;
N-(3,4-dimethoxyphenyl)-6-(pyridin-3-yl)imidazo[1,2-a]pyrazin-8-amine;
N-(3,4-dimethoxyphenyl)-6-phenylimidazo[1,2-a]pyrazin-8-amine;
3-{8-[(3,4-dimethoxyphenyl)amino]imidazo[1,2-a]pyrazin-6-yl}benzonitrile;
N-(3,4-dimethoxyphenyl)-6-(4-fluorophenyl)imidazo[1,2-a]pyrazin-8-amine;
4-{8-[(3,4-dimethoxyphenyl)amino]imidazo[1,2-a]pyrazin-6-yl}benzene-1-sulfonamide;
N-(3,4-dimethoxyphenyl)-6-{4-[(ethylamino)methyl]phenyl}imidazo[1,2-a]pyrazin-8-amine;
6-(4-chlorophenyl)-N-(3,4-dimethoxyphenyl)imidazo[1,2-a]pyrazin-8-amine;
6-(3-chlorophenyl)-N-(4-ethoxy-3-methoxyphenyl)imidazo[1,2-a]pyrazin-8-amine;
N-(3,4-dimethoxyphenyl)-6-(4-methanesulfonylphenyl)imidazo[1,2-a]pyrazin-8-amine;
4-{8-[(3,4-dimethoxyphenyl)amino]imidazo[1,2-a]pyrazin-6-yl}benzonitrile;
N-(3,4-dimethoxyphenyl)-6-(4-methylphenyl)imidazo[1,2-a]pyrazin-8-amine;
N-(4-ethoxy-3-methoxyphenyl)-6-(3-methylphenyl)imidazo[1,2-a]pyrazin-8-amine;
N-(4-ethoxy-3-methoxyphenyl)-6-(3-fluorophenyl)imidazo[1,2-a]pyrazin-8-amine;
6-(3,4-difluorophenyl)-N-(4-ethoxy-3-methoxyphenyl)imidazo[1,2-a]pyrazin-8-amine;
6-(4-chloro-3-methylphenyl)-N-(4-ethoxy-3-methoxyphenyl)imidazo[1,2-a]pyrazin-8-amine;
3-{8-[(4-ethoxy-3-methoxyphenyl)amino]imidazo[1,2-a]pyrazin-6-yl}benzene-1-sulfonamide;
N-(4-ethoxy-3-methoxyphenyl)-6-(3-methanesulfonylphenyl)imidazo[1,2-a]pyrazin-8-amine;
N-(4-ethoxy-3-methoxyphenyl)-6-(4-fluoro-3-methylphenyl)imidazo[1,2-a]pyrazin-8-amine;
N-(4-ethoxy-3-methoxyphenyl)-6-(3-fluoro-4-methylphenyl)imidazo[1,2-a]pyrazin-8-amine;
6-(3-chloro-4-methylphenyl)-N-(4-ethoxy-3-methoxyphenyl)imidazo[1,2-a]pyrazin-8-amine;
N-(4-ethoxy-3-methoxyphenyl)-6-(2-fluoropyridin-4-yl)imidazo[1,2-a]pyrazin-8-amine;
N-(4-ethoxy-3-methoxyphenyl)-6-(5-methylpyridin-3-yl)imidazo[1,2-a]pyrazin-8-amine;
6-(5-chloropyridin-3-yl)-N-(4-ethoxy-3-methoxyphenyl)imidazo[1,2-a]pyrazin-8-amine;
N-(4-ethoxy-3-methoxyphenyl)-6-(pyrimidin-5-yl)imidazo[1,2-a]pyrazin-8-amine;
1-{4-[(4-{8-[(4-ethoxy-3-methoxyphenyl)amino]imidazo[1,2-a]pyrazin-6-yl}phenyl)methyl]piperazin-1-yl}ethan-1-one;
1-{4-[(3-{8-[(3,4-dimethoxyphenyl)amino]imidazo[1,2-a]pyrazin-6-yl}phenyl)methyl]piperazin-1-yl}ethan-1-one;
N-(3,4-dimethoxyphenyl)-6-[3-(piperazin-1-ylmethyl)phenyl]imidazo[1,2-a]pyrazin-8-amine;
N-(3,4-dimethoxyphenyl)-6-[4-(piperazin-1-ylmethyl)phenyl]imidazo[1,2-a]pyrazin-8-amine;
6-(2,3-dihydro-1,4-benzodioxin-6-yl)-N-(3,4-dimethoxyphenyl)imidazo[1,2-a]pyrazin-8-amine;
N-(3-{8-[(3,4-dimethoxyphenyl)amino]imidazo[1,2-a]pyrazin-6-yl}phenyl)acetamide;
6-(3-aminophenyl)-N-(3,4-dimethoxyphenyl)imidazo[1,2-a]pyrazin-8-amine;

N-(4-{8-[(3,4-dimethoxyphenyl)amino]imidazo[1,2-a]pyrazin-6-yl}phenyl)acetamide;
N-(3,4-dimethoxyphenyl)-6-(thiophen-3-yl)imidazo[1,2-a]pyrazin-8-amine;
N-(3,4-dimethoxyphenyl)-6-(1H-indazol-5-yl)imidazo[1,2-a]pyrazin-8-amine;
N-(3,4-dimethoxyphenyl)-6-[4-(1H-imidazol-2-yl)phenyl]imidazo[1,2-a]pyrazin-8-amine;
N-(3,4-dimethoxyphenyl)-6-(quinolin-6-yl)imidazo[1,2-a]pyrazin-8-amine;
N-(3,4-dimethoxyphenyl)-6-(1H-indazol-6-yl)imidazo[1,2-a]pyrazin-8-amine;
6-{8-[(3,4-dimethoxyphenyl)amino]imidazo[1,2-a]pyrazin-6-yl}-3,4-dihydro-2H-1,4-benzoxazin-3-one;
6-(1,3-benzothiazol-5-yl)-N-(3,4-dimethoxyphenyl)imidazo[1,2-a]pyrazin-8-amine;
6-(1,3-benzothiazol-6-yl)-N-(3,4-dimethoxyphenyl)imidazo[1,2-a]pyrazin-8-amine;
6-{8-[(3,4-dimethoxyphenyl)amino]imidazo[1,2-a]pyrazin-6-yl}quinazolin-2-amine;
N-(3,4-dimethoxyphenyl)-6-(thiophen-2-yl)imidazo[1,2-a]pyrazin-8-amine;
3-amino-5-{8-[(3,4-dimethoxyphenyl)amino]imidazo[1,2-a]pyrazin-6-yl}-1-methyl-1,2-dihydropyridin-2-one;
6-{8-[(3,4-dimethoxyphenyl)amino]imidazo[1,2-a]pyrazin-6-yl}quinolin-2-amine;
6-(4-aminophenyl)-N-(3,4-dimethoxyphenyl)imidazo[1,2-a]pyrazin-8-amine;
6-(1H-1,3-benzodiazol-5-yl)-N-(3,4-dimethoxyphenyl)imidazo[1,2-a]pyrazin-8-amine;
N-(3,4-dimethoxyphenyl)-6-[3-(1H-imidazol-5-yl)phenyl]imidazo[1,2-a]pyrazin-8-amine;
7-{8-[(3,4-dimethoxyphenyl)amino]imidazo[1,2-a]pyrazin-6-yl}-3,4-dihydro-2H-1,4-benzoxazin-3-one;
N-(4-ethoxy-3-methoxyphenyl)-6-(1H-indazol-5-yl)imidazo[1,2-a]pyrazin-8-amine;
N-(3,4-dimethoxyphenyl)-6-[4-(1H-imidazol-5-yl)phenyl]imidazo[1,2-a]pyrazin-8-amine;
N-(4-ethoxy-3-methoxyphenyl)-6-(1H-indazol-6-yl)imidazo[1,2-a]pyrazin-8-amine;
6-(1,3-benzothiazol-6-yl)-N-(4-ethoxy-3-methoxyphenyl)imidazo[1,2-a]pyrazin-8-amine;
N-(3,4-dimethoxyphenyl)-6-[3-(1,3-thiazol-2-yl)phenyl]imidazo[1,2-a]pyrazin-8-amine;
N-(3,4-dimethoxyphenyl)-6-(1-methyl-1H-1,3-benzodiazol-5-yl)imidazo[1,2-a]pyrazin-8-amine;
5-{8-[(3,4-dimethoxyphenyl)amino]imidazo[1,2-a]pyrazin-6-yl}-1,2-dihydropyridin-2-one;
6-(1,3-benzothiazol-5-yl)-N-(4-ethoxy-3-methoxyphenyl)imidazo[1,2-a]pyrazin-8-amine;
N-(3,4-dimethoxyphenyl)-6-[4-(1,3-oxazol-2-yl)phenyl]imidazo[1,2-a]pyrazin-8-amine;
(3-{[6-(1H-indazol-6-yl)imidazo[1,2-a]pyrazin-8-yl]amino}phenyl)methanol;
5-{8-[(3,4-dimethoxyphenyl)amino]imidazo[1,2-a]pyrazin-6-yl}pyridin-2-amine;
N-(3,4-dimethoxyphenyl)-6-[3-(1,3-oxazol-2-yl)phenyl]imidazo[1,2-a]pyrazin-8-amine;
N-[6-(1H-indazol-6-yl)imidazo[1,2-a]pyrazin-8-yl]-3,4-dihydro-2H-1,4-benzoxazin-6-amine;
1-(4-{[6-(1H-imidazol-6-yl)imidazo[1,2-a]pyrazin-8-yl]amino}phenyl)ethan-1-ol;
N-(3,4-dimethoxyphenyl)-6-[4-(1,3-thiazol-2-yl)phenyl]imidazo[1,2-a]pyrazin-8-amine;
(5-{[6-(1H-indazol-6-yl)imidazo[1,2-a]pyrazin-8-yl]amino}-2-methoxyphenyl)methanol;
N-(3,4-dimethoxyphenyl)-6-(1H-indol-6-yl)imidazo[1,2-a]pyrazin-8-amine;
N-(3,4-dimethoxyphenyl)-6-(1-methyl-1H-1,3-benzodiazol-6-yl)imidazo[1,2-a]pyrazin-8-amine;
N-(4-ethoxy-3-methoxyphenyl)-6-(1-methyl-1H-indazol-5-yl)imidazo[1,2-a]pyrazin-8-amine;
N-(4-ethoxy-3-methoxyphenyl)-6-(1-methyl-1H-indazol-6-yl)imidazo[1,2-a]pyrazin-8-amine;
N-(3,4-dimethoxyphenyl)-6-(1-methyl-1H-indazol-5-yl)imidazo[1,2-a]pyrazin-8-amine;
6-(1H-1,2,3-benzotriazol-6-yl)-N-(3,4-dimethoxyphenyl)imidazo[1,2-a]pyrazin-8-amine;
N-(3,4-dimethoxyphenyl)-6-{1H-imidazo[4,5-b]pyridin-6-yl}imidazo[1,2-a]pyrazin-8-amine;
6-(1,3-benzoxazol-5-yl)-N-(3,4-dimethoxyphenyl)imidazo[1,2-a]pyrazin-8-amine;
6-(1,3-benzoxazol-6-yl)-N-(3,4-dimethoxyphenyl)imidazo[1,2-a]pyrazin-8-amine;
6-{8-[(3,4-dimethoxyphenyl)amino]imidazo[1,2-a]pyrazin-6-yl}-4-methyl-3,4-dihydro-2H-1,4-benzoxazin-3-one;
N-(3,4-dimethoxyphenyl)-6-(1-methyl-1H-indazol-6-yl)imidazo[1,2-a]pyrazin-8-amine;
N-(3,4-dimethoxyphenyl)-6-(1H-indol-5-yl)imidazo[1,2-a]pyrazin-8-amine;
6-{8-[(3,4-dimethoxyphenyl)amino]imidazo[1,2-a]pyrazin-6-yl}quinolin-3-amine;
2-(4-{[6-(1H-indazol-6-yl)imidazo[1,2-a]pyrazin-8-yl]amino}phenyl)propan-2-ol;
5-{8-[(3,4-dimethoxyphenyl)amino]imidazo[1,2-a]pyrazin-6-yl}-1H-indazol-3-amine;
6-{8-[(3,4-dimethoxyphenyl)amino]imidazo[1,2-a]pyrazin-6-yl}-1H-1,3-benzodiazol-2-amine;
6-{8-[(3,4-dimethoxyphenyl)amino]imidazo[1,2-a]pyrazin-6-yl}-2H,3H,4H-pyrido[3,2-b][1,4]oxazin-3-one;
6-{8-[(3,4-dimethoxyphenyl)amino]imidazo[1,2-a]pyrazin-6-yl}-2-methyl-3,4-dihydro-2H-1,4-benzoxazin-3-one;
6-{8-[(3,4-dimethoxyphenyl)amino]imidazo[1,2-a]pyrazin-6-yl}-2,2-dimethyl-3,4-dihydro-2H-1,4-benzoxazin-3-one;
7-{8-[(3,4-dimethoxyphenyl)amino]imidazo[1,2-a]pyrazin-6-yl}quinolin-2-ol;
2-(4-{[6-(1H-indazol-6-yl)imidazo[1,2-a]pyrazin-8-yl]amino}phenyl)-2-methylpropan-1-ol;
6-{8-[(3,4-dimethoxyphenyl)amino]imidazo[1,2-a]pyrazin-6-yl}-1H-indazol-3-amine;
(4-{[6-(1H-indazol-6-yl)imidazo[1,2-a]pyrazin-8-yl]amino}-2-methoxyphenyl)methanol;
6-(2,3-dihydro-1H-indol-6-yl)-N-(3,4-dimethoxyphenyl)imidazo[1,2-a]pyrazin-8-amine;
N-[6-(3-amino-1H-indazol-5-yl)imidazo[1,2-a]pyrazin-8-yl]-3,4-dihydro-2H-1,4-benzoxazin-6-amine;
N-{4-[3-(dimethylamino)propoxy]-3-methoxyphenyl}-6-(1H-indazol-6-yl)imidazo[1,2-a]pyrazin-8-amine;
3-(4-{[6-(1H-indazol-6-yl)imidazo[1,2-a]pyrazin-8-yl]amino}-2-methoxyphenoxy)propan-1-ol;
6-(1H-indazol-6-yl)-N-[4-methoxy-3-(pyrrolidin-1-yl)phenyl]imidazo[1,2-a]pyrazin-8-amine;
5-{[6-(1H-indazol-6-yl)imidazo[1,2-a]pyrazin-8-yl]amino}-2,3-dihydro-1H-indol-2-one;
7-{8-[(3,4-dimethoxyphenyl)amino]imidazo[1,2-a]pyrazin-6-yl}quinoxalin-2-ol;
7-{8-[(3,4-dimethoxyphenyl)amino]imidazo[1,2-a]pyrazin-6-yl}-1H,2H,3H-pyrido[2,3-b][1,4]oxazin-2-one;
N-[6-(1H-indazol-6-yl)imidazo[1,2-a]pyrazin-8-yl]-4-methyl-3,4-dihydro-2H-1,4-benzoxazin-7-amine;
N-(2-fluoro-4-methoxyphenyl)-6-(1H-indazol-6-yl)imidazo[1,2-a]pyrazin-8-amine;

6-(1H-indazol-6-yl)-N-[3-methoxy-4-(pyrrolidin-1-yl)phenyl]imidazo[1,2-a]pyrazin-8-amine;
N-[6-(1H-indazol-6-yl)imidazo[1,2-a]pyrazin-8-yl]-2,3,4,5-tetrahydro-1,5-benzoxazepin-7-amine;
1-(4-{[6-(3-amino-1H-indazol-6-yl)imidazo[1,2-a]pyrazin-8-yl]amino}phenyl)ethan-1-ol;
6-(3,4-dihydro-2H-1,4-benzoxazin-6-yl)-N-(3,4-dimethoxyphenyl)imidazo[1,2-a]pyrazin-8-amine;
N-[6-(1H-indazol-6-yl)imidazo[1,2-a]pyrazin-8-yl]-4-methyl-3,4-dihydro-2H-1,4-benzoxazin-6-amine;
6-{[6-(1H-indazol-6-yl)imidazo[1,2-a]pyrazin-8-yl]amino}-2,3-dihydro-1H-indol-2-one;
N-(3,4-dimethoxyphenyl)-6-{1H-pyrrolo[3,2-b]pyridin-6-yl}imidazo[1,2-a]pyrazin-8-amine;
N-[6-(1H-indazol-6-yl)imidazo[1,2-a]pyrazin-8-yl]-3,4-dihydro-2H-1,4-benzoxazin-7-amine;
6-{8-[(4-ethoxy-3-methoxyphenyl)amino]imidazo[1,2-a]pyrazin-6-yl}-1H-indazol-3-amine;
N-[6-(2-aminoquinazolin-6-yl)imidazo[1,2-a]pyrazin-8-yl]-4-methyl-3,4-dihydro-2H-1,4-benzoxazin-6-amine;
2-methyl-2-(4-{[6-(1-methyl-1H-1,3-benzodiazol-5-yl)imidazo[1,2-a]pyrazin-8-yl]amino}phenyl)propan-1-ol;
6-(3,4-dihydro-2H-1,4-benzoxazin-6-yl)-N-(4-ethoxy-3methoxyphenyl)imidazo[1,2-a]pyrazin-8-amine;
N-[6-(2,3-dihydro-1H-indol-6-yl)imidazo[1,2-a]pyrazin-8-yl]-3,4-dihydro-2H-1,4-benzoxazin-6-amine;
(2-methoxy-5-{[6-(1-methyl-1H-1,3-benzodiazol-6-yl)imidazo[1,2-a]pyrazin-8-yl]amino}phenyl)methanol;
6-(1H-indazol-6-yl)-N-{4-[2-methyl-1-(morpholin-4-yl)propan-2-yl]phenyl}imidazo[1,2-a]pyrazin-8-amine;
N-[6-(1H-indol-6-yl)imidazo[1,2-a]pyrazin-8-yl]-3,4-dihydro-2H-1,4-benzoxazin-6-amine;
7-{8-[(4-methyl-3,4-dihydro-2H-1,4-benzoxazin-7-yl)amino]imidazo[1,2-a]pyrazin-6-yl}quinoxalin-2-ol;
1-(4-{[6-(1,3-benzothiazol-5-yl)imidazo[1,2-a]pyrazin-8-yl]amino}phenyl)ethan-1-ol;
6-(1H-1,2,3-benzotnazol-6-yl)-N-[3-methoxy-4-(propan-2-yloxy)phenyl]imidazo[1,2-a]pyrazin-8-amine;
5-(8-{[3-methoxy-4-(pyrrolidin-1-yl)phenyl]amino}imidazo[1,2-a]pyrazin-6-yl)-1H-indazol-3-amine;
2-(4-{[6-(2-aminoquinazolin-6-yl)imidazo[1,2-a]pyrazin-8-yl]amino}phenyl)propan-2-ol,
6-(1H-indazol-6-yl)-N-[3-methoxy-4-(morpholin-4-yl)phenyl]imidazo[1,2-a]pyrazin-8-amine;
2-(4-{[6-(1,3-benzothiazol-5-yl)imidazo[1,2-a]pyrazin-8-yl]amino}phenyl)propan-2-ol;
6-(8-{[4-(2-hydroxypropan-2-yl)phenyl]amino}imidazo[1,2-a]pyrazin-6-yl)-3,4-dihydro-2H-1,4-benzoxazin-3-one;
6-(1H-indazol-6-yl)-N-(3-methoxyphenyl)imidazo[1,2-a]pyrazin-8-amine;
6-(1H-indazol-6-yl)-N-(4-methoxyphenyl)imidazo[1,2-a]pyrazin-8-amine;
2-(4-{[6-(1-methyl-1H-1,3-benzodiazol-5-yl)imidazo[1,2-a]pyrazin-8-yl]amino}phenyl)propan-2-ol;
2-(4-{[6-(1-methyl-1H-1,3-benzodiazol-6-yl)imidazo[1,2-a]pyrazin-8-yl]amino}phenyl)propan-2-ol;
1-(4-{[6-(1H-indazol-6-yl)imidazo[1,2-a]pyrazin-8-yl]amino}-2-methoxyphenyl)pipendin-4-ol;
6-(1H-indazol-6-yl)-N-[4-(pyrrolidin-1-yl)phenyl]imidazo[1,2-a]pyrazin-8-amine;
1-(4-{[6-(1H-indazol-6-yl)imidazo[1,2-a]pyrazin-8-yl]amino}phenyl)pyrrolidin-3-ol;
2-(4-{[6-(4-methyl-3,4-dihydro-2H-1,4-benzoxazin-7-yl)imidazo[1,2-a]pyrazin-8-yl]amino}phenyl)propan-2-ol;
2-(4-{[6-(3,4-dihydro-2H-1,4-benzoxazin-6-yl)imidazo[1,2-a]pyrazin-8-yl]amino}phenyl)propan-2-ol;
2-(4-{[6-(1,4-dimethyl-1,2,3,4-tetrahydroquinoxalin-6-yl)imidazo[1,2-a]pyrazin-8-yl]amino}phenyl)propan-2-ol;
1-(4-{[6-(1H-indazol-6-yl)imidazo[1,2-a]pyrazin-8-yl]amino}-2-methoxyphenyl)azetidin-3-ol;
2-(4-{[6-(1H-indol-6-yl)imidazo[1,2-a]pyrazin-8-yl]amino}phenyl)propan-2-ol
2-(4-{[6-(3,4-dihydro-2H-1,4-benzoxazin-7-yl)imidazo[1,2-a]pyrazin-8-yl]amino}phenyl)propan-2-ol;
2-(4-{[6-(4-methyl-3,4-dihydro-2H-1,4-benzoxazin-6-yl)imidazo[1,2-a]pyrazin-8-yl]amino}phenyl)propan-2-ol;
2-(4-{[6-(2,3-dimethyl-2H-indazol-5-yl)imidazo[1,2-a]pyrazin-8-yl]amino}phenyl)propan-2-ol;
2-(4-{[6-(3-methyl-1H-indazol-5-yl)imidazo[1,2-a]pyrazin-8-yl]amino}phenyl)propan-2-ol;
N-[3-methoxy-4-(morpholin-4-yl)phenyl]-6-(1-methyl-1H-1,3-benzodiazol-6-yl)imidazo[1,2-a]pyrazin-8-amine;
6-(8-{[3-methoxy-4-(morpholin-4-yl)phenyl]amino}imidazo[1,2-a]pyrazin-6-yl)quinazolin-2-amine;
1-(4-{[6-(1H-indazol-6-yl)imidazo[1,2-a]pyrazin-8-yl]amino}phenyl)azetidin-3-ol;
1-(4-{[6-(1H-indazol-6-yl)imidazo[1,2-a]pyrazin-8-yl]amino}-2-methoxyphenyl)pyrrolidin-3-ol;
6-(3,4-dihydro-2H-1,4-benzoxazin-6-yl)-N-[3-methoxy-4-(morpholin-4-yl)phenyl]imidazo[1,2-a]pyrazin-8-amine;
6-(1H-indazol-6-yl)-N-[4-(2-methoxypropan-2-yl)phenyl]imidazo[1,2-a]pyrazin-8-amine;
N-(4-ethoxy-3-methoxyphenyl)-6-(1H-indol-6-yl)imidazo[1,2-a]pyrazin-8-amine;
N-[3-methoxy-4-(morpholin-4-yl)phenyl]-6-(1-methyl-1H-1,3-benzodiazol-5-yl)imidazo[1,2-a]pyrazin-8-amine;
N-[4-(4-ethylpiperazin-1-yl)-3-methoxyphenyl]-6-(1H-indazol-6-yl)imidazo[1,2-a]pyrazin-8-amine;
1-(4-{[6-(1H-indazol-6-yl)imidazo[1,2-a]pyrazin-8-yl]amino}phenyl)-3-methylpiperidin-3-ol; and
N-[4-(4-ethylpiperazin-1-yl)phenyl]-6-(1H-indazol-6-yl)imidazo[1,2-a]pyrazin-8-amine,
and pharmaceutically acceptable salts thereof.

Also provided is at least one chemical entity chosen from:
6-(8-{[3-methoxy-4-(morpholin-4-yl)phenyl]amino}imidazo[1,2-a]pyrazin-6-yl)-1H-indazol-3-amine;
5-(8-{[3-methoxy-4-(morpholin-4-yl)phenyl]amino}imidazo[1,2-a]pyrazin-6-yl)-1H-indazol-3-amine;
6-(8-{[4-(2-hydroxypropan-2-yl)phenyl]amino}imidazo[1,2-a]pyrazin-6-yl)-2,3-dihydro-1H-indol-2-one;
1-(4-{[6-(1H-indazol-6-yl)imidazo[1,2-a]pyrazin-8-yl]amino}phenyl)piperidin-4-ol;
1-(4-{[6-(1H-indazol-6-yl)imidazo[1,2-a]pyrazin-8-yl]amino}-2-methoxyphenoxy)-2-methylpropan-2-ol;
1-(4-{[6-(1H-indazol-6-yl)imidazo[1,2-a]pyrazin-8-yl]amino}-2-methoxyphenyl)-4-methylpiperidin-4-ol;
2-[(4-{[6-(1H-indazol-6-yl)imidazo[1,2-a]pyrazin-8-yl]amino}-2-methoxyphenyl)(methyl)amino]ethan-1-ol;
1-(4-{[6-(1H-indazol-6-yl)imidazo[1,2-a]pyrazin-8-yl]amino}phenyl)-4-methylpiperidin-4-ol;
4-{[6-(1H-indazol-6-yl)imidazo[1,2-a]pyrazin-8-yl]amino}phenol;
2-(4-{[6-(2,3-dihydro-1H-indol-6-yl)imidazo[1,2-a]pyrazin-8-yl]amino}phenyl)propan-2-ol;
1-(4-{[6-(1H-indazol-6-yl)imidazo[1,2-a]pyrazin-8-yl]amino}phenyl)-3-methylpyrrolidin-3-ol;
N-[3-methoxy-4-(morpholin-4-yl)phenyl]-6-(2-methyl-1H-1,3-benzodiazol-5-yl)imidazo[1,2-a]pyrazin-8-amine;
N-(4-ethoxy-3-methoxyphenyl)-6-(1-methyl-1H-1,3-benzodiazol-5-yl)imidazo[1,2-a]pyrazin-8-amine;
(3R)-1-(4-{[6-(1H-indazol-6-yl)imidazo[1,2-a]pyrazin-8-yl]amino}phenyl)pyrrolidin-3-ol;

(3R)-1-(4-{[6-(1H-indazol-6-yl)imidazo[1,2-a]pyrazin-8-yl]amino}-2-methoxyphenyl)pyrrolidin-3-ol;
(3S)-1-(4-{[6-(1H-indazol-6-yl)imidazo[1,2-a]pyrazin-8-yl]amino}-2-methoxyphenyl)pyrrolidin-3-ol;
[4-(4-{[6-(1H-indazol-6-yl)imidazo[1,2-a]pyrazin-8-yl]amino}phenyl)morpholin-2-yl]methanol;
N-(4-ethoxy-3-methoxyphenyl)-6-(1-methyl-1H-1,3-benzodiazol-6-yl)imidazo[1,2-a]pyrazin-8-amine;
6-(5-fluoro-1H-indazol-6-yl)-N-[3-methoxy-4-(morpholin-4-yl)phenyl]imidazo[1,2-a]pyrazin-8-amine;
2-[1-(4-{[6-(1H-indazol-6-yl)imidazo[1,2-a]pyrazin-8-yl]amino}phenyl)piperidin-4-yl]propan-2-ol;
(3S)-1-(4-{[6-(1H-indazol-6-yl)imidazo[1,2-a]pyrazin-8-yl]amino}phenyl)pyrrolidin-3-ol,
N-[3-methoxy-4-(morpholin-4-yl)phenyl]-6-(3-methyl-1H-indazol-6-yl)imidazo[1,2-a]pyrazin-8-amine;
1-(4-{[6-(1H-indazol-6-yl)imidazo[1,2-a]pyrazin-8-yl]amino}-2-methoxyphenyl)-3-methylpyrrolidin-3-ol;
6-(1H-1,3-benzodiazol-6-yl)-N-(4-ethoxy-3-methoxyphenyl)imidazo[1,2-a]pyrazin-8-amine;
6-(8-{[3-methoxy-4-(morpholin-4-yl)phenyl]amino}imidazo[1,2-a]pyrazin-6-yl)-2,3-dihydro-1H-indol-2-one;
6-(8-{[3-methoxy-4-(morpholin-4-yl)phenyl]amino}imidazo[1,2-a]pyrazin-6-yl)-3,3-dimethyl-2,3-dihydro-1H-indol-2-one;
N-(4-ethoxy-3-methoxyphenyl)-6-{1H-pyrrolo[3,2-b]pyridin-6-yl}imidazo[1,2-a]pyrazin-8-amine;
4-N-[6-(1H-indazol-6-yl)imidazo[1,2-a]pyrazin-8-yl]-2-methoxy-1-N-(2-methoxyethyl)-1-N-methylbenzene-1,4-diamine;
4-methyl-1-(4-{[6-(1-methyl-1H-1,3-benzodiazol-6-yl)imidazo[1,2-a]pyrazin-8-yl]amino}phenyl)piperidin-4-ol;
6-(3,4-dihydro-2H-1,4-benzoxazin-7-yl)-N-[3-methoxy-4-(morpholin-4-yl)phenyl]imidazo[1,2-a]pyrazin-8-amine;
6-(8-{[4-(1-hydroxy-2-methylpropan-2-yl)phenyl]amino}imidazo[1,2-a]pyrazin-6-yl)-3,4-dihydro-2H-1,4-benzoxazin-3-one;
1-(4-{[6-(1H-1,3-benzodiazol-6-yl)imidazo[1,2-a]pyrazin-8-yl]amino}phenyl)-2-methylpropan-2-ol;
N-[3-methoxy-4-(morpholin-4-yl)phenyl]-6-{1H-pyrrolo[3,2-b]pyridin-6-yl}imidazo[1,2-a]pyrazin-8-amine;
2-(4-{[6-(1H-1,3-benzodiazol-6-yl)imidazo[1,2-a]pyrazin-8-yl]amino}phenyl)-1,1,1,3,3,3-hexafluoropropan-2-ol;
2-methyl-2-(4-{[6-(1-methyl-1H-1,3-benzodiazol-6-yl)imidazo[1,2-a]pyrazin-8-yl]amino}phenyl)propan-1-ol;
2-methyl-2-{4-[(6-{1H-pyrrolo[3,2-b]pyridin-6-yl}imidazo[1,2-a]pyrazin-8-yl)amino]phenyl}propan-1-ol;
2,2,2-trifluoro-1-(4-{[6-(1H-indazol-6-yl)imidazo[1,2-a]pyrazin-8-yl]amino}phenyl)ethan-1-ol;
2-(4-{[6-(3,4-dihydro-2H-1,4-benzoxazin-6-yl)imidazo[1,2-a]pyrazin-8-yl]amino}phenyl)-2-methylpropan-1-ol;
6-(8-{[4-(4-hydroxy-4-methylpiperidin-1-yl)phenyl]amino}imidazo[1,2-a]pyrazin-6-yl)-3,4-dihydro-2H-1,4-benzoxazin-3-one;
4-methyl-1-{4-[(6-{1H-pyrrolo[3,2-b]pyridin-6-yl}imidazo[1,2-a]pyrazin-8-yl)amino]phenyl}piperidin-4-ol;
1-(4-{[6-(1H-1,3-benzodiazol-6-yl)imidazo[1,2-a]pyrazin-8-yl]amino}phenyl)-4-methylpiperidin-4-ol;
6-(1H-indazol-6-yl)-N-[4-(1-methoxy-2-methylpropan-2-yl)phenyl]imidazo[1,2-a]pyrazin-8-amine;
4-methyl-1-(4-{[6-(1-methyl-1H-1,3-benzodiazol-5-yl)imidazo[1,2-a]pyrazin-8-yl]amino}phenyl)piperidin-4-ol;
6-(1H-1,3-benzodiazol-6-yl)-N-[3-methoxy-4-(morpholin-4-yl)phenyl]imidazo[1,2-a]pyrazin-8-amine;
1,1,1-trifluoro-2-(4-{[6-(1H-indazol-6-yl)imidazo[1,2-a]pyrazin-8-yl]amino}phenyl)propan-2-ol;
1-(4-{[6-(1H-indazol-6-yl)imidazo[1,2-a]pyrazin-8-yl]amino}phenyl)-2-methylpropan-2-ol;
1-(4-{[6-(1H-indazol-6-yl)imidazo[1,2-a]pyrazin-8-yl]amino}phenyl)cyclobutan-1-ol;
1-(4-{[6-(1H-indazol-6-yl)imidazo[1,2-a]pyrazin-8-yl]amino}-2-methoxyphenyl)-3-methylpiperidin-3-ol;
4-N-[6-(1H-indazol-6-yl)imidazo[1,2-a]pyrazin-8-yl]-1-N-(2-methoxyethyl)-1-N-methylbenzene-1,4-diamine;
6-{8-[(4-ethoxy-3-methoxyphenyl)amino]imidazo[1,2-a]pyrazin-6-yl}-1H-indazole-3-carboxamide;
2-[(4-{[6-(1H-indazol-6-yl)imidazo[1,2-a]pyrazin-8-yl]amino}phenyl)(methyl)amino]ethan-1-ol;
1-(4-{[6-(3,4-dihydro-2H-1,4-benzoxazin-6-yl)imidazo[1,2-a]pyrazin-8-yl]amino}phenyl)-4-methylpiperidin-4-ol;
6-(1H-indazol-6-yl)-N-[4-(morpholin-4-yl)phenyl]imidazo[1,2-a]pyrazin-8-amine;
N-[4-(morpholin-4-yl)phenyl]-6-{1H-pyrrolo[3,2-b]pyridin-6-yl}imidazo[1,2-a]pyrazin-8-amine;
1-(4-{[6-(1H-indazol-6-yl)imidazo[1,2-a]pyrazin-8-yl]amino}phenyl)piperidin-3-ol;
6-(1H-indol-6-yl)-N-[4-(morpholin-4-yl)phenyl]imidazo[1,2-a]pyrazin-8-amine;
2-(4-{[6-(1H-1,3-benzodiazol-6-yl)imidazo[1,2-a]pyrazin-8-yl]amino}phenyl)-2-methylpropan-1-ol;
6-(8-{[4-(1-hydroxy-2-methylpropan-2-yl)phenyl]amino}imidazo[1,2-a]pyrazin-6-yl)-2,3-dihydro-1H-indol-2-one;
2-(4-{[6-(1H-indol-6-yl)imidazo[1,2-a]pyrazin-8-yl]amino}phenyl)-2-methylpropan-1-ol
6-{8-[(4-ethoxy-3-methoxyphenyl)amino]imidazo[1,2-a]pyrazin-6-yl}-2,3-dihydro-1H-indol-2-one;
2-(4-{[6-(3-amino-1H-indazol-6-yl)imidazo[1,2-a]pyrazin-8-yl]amino}phenyl)-2-methylpropan-1-ol;
5-{8-[(4-ethoxy-3-methoxyphenyl)amino]imidazo[1,2-a]pyrazin-6-yl}-1H-indazol-3-amine; and
2-(4-{[6-(3-amino-1H-indazol-5-yl)imidazo[1,2-a]pyrazin-8-yl]amino}phenyl)-2-methylpropan-1-ol;
and pharmaceutically acceptable salts thereof.

Also provided is at least one chemical entity chosen from:
(3S)-1-(4-{[6-(1H-indazol-6-yl)imidazo[1,2-a]pyrazin-8-yl]amino}-2-methoxyphenyl)-3-methylpyrrolidin-3-ol;
(3R)-1-(4-{[6-(1H-indazol-6-yl)imidazo[1,2-a]pyrazin-8-yl]amino}-2-methoxyphenyl)-3-methylpyrrolidin-3-ol;
7-(8-{[4-(morpholin-4-yl)phenyl]amino}imidazo[1,2-a]pyrazin-6-yl)-1,2-dihydroquinoxalin-2-one;
N,N-dimethyl-6-(8-{[4-(morpholin-4-yl)phenyl]amino}imidazo[1,2-a]pyrazin-6-yl)-1H-indazole-3-carboxamide;
5-(8-{[4-(morpholin-4-yl)phenyl]amino}imidazo[1,2-a]pyrazin-6-yl)-2,3-dihydro-1H-1,3-benzodiazol-2-one;
1-(4-{[6-(3,4-dihydro-2H-1,4-benzoxazin-6-yl)imidazo[1,2-a]pyrazin-8-yl]amino}phenyl)-2-methylpropan-2-ol;
N-methyl-2-(4-{[6-(2-oxo-2,3-dihydro-1H-indol-6-yl)imidazo[1,2-a]pyrazin-8-yl]amino}phenoxy)acetamide;
N-[3-(8-{[4-(morpholin-4-yl)phenyl]amino}imidazo[1,2-a]pyrazin-6-yl)phenyl]methanesulfonamide;
N-[4-(8-{[4-(morpholin-4-yl)phenyl]amino}imidazo[1,2-a]pyrazin-6-yl)phenyl]methanesulfonamide;
[(2S)-4-(4-{[6-(1H-indazol-6-yl)imidazo[1,2-a]pyrazin-8-yl]amino}phenyl)morpholin-2-yl]methanol;
[(2R)-4-(4-{[6-(1H-indazol-6-yl)imidazo[1,2-a]pyrazin-8-yl]amino}phenyl)morpholin-2-yl]methanol;
6-(8-{[4-(2-hydroxy-2-methylpropyl)phenyl]amino}imidazo[1,2-a]pyrazin-6-yl)-3,4-dihydro-2H-1,4-benzoxazin-3-one;

1-(4-{[6-(3,4-dihydro-2H-1,4-benzoxazin-7-yl)imidazo[1,2-a]pyrazin-8-yl]amino}-2-methoxyphenyl)-4-methylpiperidin-4-ol;

N-(2-hydroxyethyl)-N-methyl-6-(8-{[4-(morpholin-4-yl)phenyl]amino}imidazo[1,2-a]pyrazin-6-yl)-1H-indole-3-carboxamide;

6'-(8-{[4-(morpholin-4-yl)phenyl]amino}imidazo[1,2-a]pyrazin-6-yl)-1',2'-dihydrospiro[cyclopropane-1,3'-indole]-2'-one;

3-methyl-1-(4-{[6-(1-methyl-1H-indazol-6-yl)imidazo[1,2-a]pyrazin-8-yl]amino}phenyl)azetidin-3-ol;

4-{[6-(1H-indazol-6-yl)imidazo[1,2-a]pyrazin-8-yl]amino}-2-methoxyphenol;

N-[3-methoxy-4-(morpholin-4-yl)phenyl]-6-(6-methoxypyridin-3-yl)imidazo[1,2-a]pyrazin-8-amine;

6-(1H-1,2,3-benzotriazol-6-yl)-N-[4-(morpholin-4-yl)phenyl]imidazo[1,2-a]pyrazin-8-amine;

N,N-dimethyl-6-(8-{[4-(morpholin-4-yl)phenyl]amino}imidazo[1,2-a]pyrazin-6-yl)-1H-indole-3-carboxamide;

N-[3-methoxy-4-(morpholin-4-yl)phenyl]-6-(5-methoxypyridin-3-yl)imidazo[1,2-a]pyrazin-8-amine;

6-(8-{[4-(morpholin-4-yl)phenyl]amino}imidazo[1,2-a]pyrazin-6-yl)-1H-indazol-3-amine;

7-{8-([4-[(3S)-3-hydroxypyrrolidin-1-yl]phenyl}amino)imidazo[1,2-a]pyrazin-6-yl]-1H,2H,3H-pyrido[2,3-b][1,4]oxazin-2-one;

4-{[6-(1H-indazol-6-yl)imidazo[1,2-a]pyrazin-8-yl]amino}-N-methyl-N-(oxan-4-yl)benzamide;

6-(3-ethyl-1H-indazol-6-yl)-N-[4-{2-methyl-1-(morpholin-4-yl)propan-2-yl]phenyl}imidazo[1,2-a]pyrazin-8-amine;

2,2-difluoro-6-(8-{[4-(morpholin-4-yl)phenyl]amino}imidazo[1,2-a]pyrazin-6-yl)-3,4-dihydro-2H-1,4-benzoxazin-3-one;

1-(4-{[6-(3,4-dihydro-2H-1,4-benzoxazin-7-yl)imidazo[1,2-a]pyrazin-8-yl]amino}-2-methoxyphenyl)-3-methylazetidin-3-ol;

6-(1H-indol-2-yl)-N-[4-(morpholin-4-yl)phenyl]imidazo[1,2-a]pyrazin-8-amine;

(3S)-1-(4-{[6-(3,4-dihydro-2H-1,4-benzoxazin-7-yl)imidazo[1,2-a]pyrazin-8-yl]amino}-2-methoxyphenyl)pyrrolidin-3-ol;

1-(4-{[6-(4-fluoro-1H-indazol-6-yl)imidazo[1,2-a]pyrazin-8-yl]amino}phenyl)-3-methylazetidin-3-ol;

6-(1H-indazol-6-yl)-N-[4-(2H-1,2,3,4-tetrazol-5-yl)phenyl]imidazo[1,2-a]pyrazin-8-amine;

7-(8-{[4-(3-hydroxy-3-methylazetidin-1-yl)phenyl]amino}imidazo[1,2-a]pyrazin-6-yl)-1H,2H,3H-pyrido[2,3-b][1,4]oxazin-2-one;

6-(1H-indazol-6-yl)-N-[3-methoxy-4-(2-methoxyethoxy)phenyl]imidazo[1,2-a]pyrazin-8-amine;

6-(2-ethyl-1,2,3,4-tetrahydroisoquinolin-6-yl)-N-[4-(morpholin-4-yl)phenyl]imidazo[1,2-a]pyrazin-8-amine;

4-{[6-(3,3-dimethyl-2-oxo-2,3-dihydro-1H-indol-6-yl)imidazo[1,2-a]pyrazin-8-yl]amino}-N-propylbenzamide;

6-(8-{[3-ethoxy-4-(morpholin-4-yl)phenyl]amino}imidazo[1,2-a]pyrazin-6-yl)-3,3-dimethyl-2,3-dihydro-1H-indol-2-one;

6-(1H-indol-3-yl)-N-[4-(morpholin-4-yl)phenyl]imidazo[1,2-a]pyrazin-8-amine;

6-(1,3-benzothiazol-5-yl)-N-[4-{2-methyl-1-(morpholin-4-yl)propan-2-yl]phenyl}imidazo[1,2-a]pyrazin-8-amine;

(3E)-6-(8-{[4-(morpholin-4-yl)phenyl]amino}imidazo[1,2-a]pyrazin-6-yl)-3-(1,3-thiazol-4-ylmethylidene)-2,3-dihydro-1H-indol-2-one;

4-{[6-(1H-indazol-6-yl)imidazo[1,2-a]pyrazin-8-yl]amino}-N-(oxan-4-yl)benzamide;

6-(2-methyl-1,3-benzothiazol-5-yl)-N-{4-[2-methyl-1-(morpholin-4-yl)propan-2-yl]phenyl}imidazo[1,2-a]pyrazin-8-amine;

6-(2,3-dihydro-1,4-benzodioxin-6-yl)-N-[3-methoxy-4-(morpholin-4-yl)phenyl]imidazo[1,2-a]pyrazin-8-amine;

6-(1H-indazol-6-yl)-N-[4-(2-methoxyethoxy)phenyl]imidazo[1,2-a]pyrazin-8-amine;

6-(8-{[4-(morpholin-4-yl)phenyl]amino}imidazo[1,2-a]pyrazin-6-yl)quinazolin-2-amine;

6-(8-{[4-(4-hydroxy-4-methylpiperidin-1-yl)phenyl]amino}imidazo[1,2-a]pyrazin-6-yl)-3,3-dimethyl-2,3-dihydro-1H-indol-2-one;

6-(1H-indazol-6-yl)-N-{4-[(2S)-oxolan-2-ylmethoxy]phenyl}imidazo[1,2-a]pyrazin-8-amine;

6-(3-ethyl-1H-indazol-6-yl)-N-[4-(morpholin-4-yl)phenyl]imidazo[1,2-a]pyrazin-8-amine;

N-(2,3-dihydro-1,4-benzodioxin-6-yl)-6-(1H-indazol-6-yl)imidazo[1,2-a]pyrazin-8-amine;

N-(2H-1,3-benzodioxol-5-yl)-6-(1H-indazol-6-yl)imidazo[1,2-a]pyrazin-8-amine;

1-(2-ethoxy-4-{[6-(1H-indazol-6-yl)imidazo[1,2-a]pyrazin-8-yl]amino}phenyl)-4-methylpiperidin-4-ol;

6-{8-([4-[(3S)-3-hydroxypyrrolidin-1-yl]phenyl}amino)imidazo[1,2-a]pyrazin-6-yl]-3,3-dimethyl-2,3-dihydro-1H-indol-2-one;

6-(8-{[4-(3-hydroxy-3-methylazetidin-1-yl)phenyl]amino}imidazo[1,2-a]pyrazin-6-yl)-3,3-dimethyl-2,3-dihydro-1H-indol-2-one;

6-(2H-1,3-benzodioxol-5-yl)-N-[3-methoxy-4-(morpholin-4-yl)phenyl]imidazo[1,2-a]pyrazin-8-amine;

6-(1H-indol-6-yl)-N-{4-[2-methyl-1-(morpholin-4-yl)propan-2-yl]phenyl}imidazo[1,2-a]pyrazin-8-amine;

6-(1H-indazol-6-yl)-N-[4-(pyridin-4-yloxy)phenyl]imidazo[1,2-a]pyrazin-8-amine;

(3E)-6-(8-{[4-(morpholin-4-yl)phenyl]amino}imidazo[1,2-a]pyrazin-6-yl)-3-(pyridin-4-ylmethylidene)-2,3-dihydro-1H-indol-2-one;

4-{[6-(1H-indazol-6-yl)imidazo[1,2-a]pyrazin-8-yl]amino}-N-(oxetan-3-yl)benzamide;

6-{3-[(diethylamino)methyl]-1H-indazol-6-yl}-N-[4-(morpholin-4-yl)phenyl]imidazo[1,2-a]pyrazin-8-amine;

1-[(4-{[6-(1H-indazol-6-yl)imidazo[1,2-a]pyrazin-8-yl]amino}phenyl)carbonyl]-3-methylazetidin-3-ol;

[6-(8-{[4-(morpholin-4-yl)phenyl]amino}imidazo[1,2-a]pyrazin-6-yl)-1H-indazol-3-yl]methanol;

N-[4-(morpholin-4-yl)phenyl]-6-(1H-pyrazol-4-yl)imidazo[1,2-a]pyrazin-8-amine;

6-(4-fluoro-1H-indazol-6-yl)-N-[4-(morpholin-4-yl)phenyl]imidazo[1,2-a]pyrazin-8-amine;

N-[4-(morpholin-4-yl)phenyl]-6-{1H,2H,3H-pyrido[2,3-b][1,4]oxazin-6-yl}imidazo[1,2-a]pyrazin-8-amine;

N-[4-(morpholin-4-yl)phenyl]-6-(1,3-thiazol-5-yl)imidazo[1,2-a]pyrazin-8-amine;

{4-[(4-{[6-(1H-indazol-6-yl)imidazo[1,2-a]pyrazin-8-yl]amino}phenyl)carbonyl]morpholin-2-yl}methanol;

1-[(4-{[6-(1H-indazol-6-yl)imidazo[1,2-a]pyrazin-8-yl]amino}phenyl)carbonyl]piperidin-4-ol;

N-ethyl-N-(2-hydroxyethyl)-4-{[6-(1H-indazol-6-yl)imidazo[1,2-a]pyrazin-8-yl]amino}benzamide;

2-(4-{[6-(3,4-dihydro-2H-1,4-benzoxazin-6-yl)imidazo[1,2-a]pyrazin-8-yl]amino}-2-methoxyphenoxy)-N-methylacetamide;

7-(8-{[4-(morpholin-4-yl)phenyl]amino}imidazo[1,2-a]pyrazin-6-yl)-1,2-dihydroquinolin-2-one;

6-(2-ethyl-1,2,3,4-tetrahydroisoquinolin-7-yl)-N-[4-(morpholin-4-yl)phenyl]imidazo[1,2-a]pyrazin-8-amine;

1-[(4-{[6-(1H-indazol-6-yl)imidazo[1,2-a]pyrazin-8-yl]amino}phenyl)carbonyl]-4-methylpiperidin-4-ol;
4-{[6-(1H-indazol-6-yl)imidazo[1,2-a]pyrazin-8-yl]amino}-2-methoxybenzoic acid;
6-(1H-indazol-6-yl)-N-{4-[(4-methylpiperazin-1-yl)carbonyl]phenyl}imidazo[1,2-a]pyrazin-8-amine;
1-[(4-{[6-(1H-indazol-6-yl)imidazo[1,2-a]pyrazin-8-yl]amino}phenyl)carbonyl]azetidin-3-ol;
3,3-dimethyl-6-(8-{[4-(morpholin-4-yl)phenyl]amino}imidazo[1,2-a]pyrazin-6-yl)-2,3-dihydro-1H-indol-2-one;
6-(1H-indazol-6-yl)-N-[4-(1-methylpiperidin-4-yl)phenyl]imidazo[1,2-a]pyrazin-8-amine;
2-(4-{[6-(4-fluoro-1H-indazol-6-yl)imidazo[1,2-a]pyrazin-8-yl]amino}phenyl)-2-methylpropan-1-ol;
2-[ethyl(4-{[6-(4-fluoro-1H-indazol-6-yl)imidazo[1,2-a]pyrazin-8-yl]amino}phenyl)amino]ethan-1-ol;
6-(1H-indazol-7-yl)-N-[4-(morpholin-4-yl)phenyl]imidazo[1,2-a]pyrazin-8-amine;
6-{8-([4-[ethyl(2-hydroxyethyl)amino]phenyl}amino)imidazo[1,2-a]pyrazin-6-yl]-3,3-dimethyl-2,3-dihydro-1H-indol-2-one;
N-{4-[2-(dimethylamino)ethoxy]phenyl}-6-(1H-indazol-6-yl)imidazo[1,2-a]pyrazin-8-amine;
6-(3,4-dihydro-2H-1,4-benzoxazin-6-yl)-N-{4-[2-(dimethylamino)ethoxy]phenyl}imidazo[1,2-a]pyrazin-8-amine;
1-(4-{[6-(3,4-dihydro-2H-1,4-benzoxazin-6-yl)imidazo[1,2-a]pyrazin-8-yl]amino}phenyl)-3-methylazetidin-3-ol;
2-[6-(8-{[4-(morpholin-4-yl)phenyl]amino}imidazo[1,2-a]pyrazin-6-yl)-2H-indazol-2-yl]ethan-1-ol;
3-(2-ethoxy-4-{[6-(1H-indazol-6-yl)imidazo[1,2-a]pyrazin-8-yl]amino}phenoxy)-2,2-dimethylpropan-1-ol;
3-(4-{[6-(1H-indazol-6-yl)imidazo[1,2-a]pyrazin-8-yl]amino}phenoxy)-2,2-dimethylpropan-1-ol;
2-(4-{[6-(1H-indazol-6-yl)imidazo[1,2-a]pyrazin-8-yl]amino}-2-methoxyphenoxy)-N-methylacetamide;
2-(4-{[6-(3,4-dihydro-2H-1,4-benzoxazin-6-yl)imidazo[1,2-a]pyrazin-8-yl]amino}phenoxy)-N-methylacetamide;
2-(4-{[6-(1H-indazol-6-yl)imidazo[1,2-a]pyrazin-8-yl]amino}phenoxy)-N-methylacetamide;
2-(4-{[6-(1H-indazol-6-yl)imidazo[1,2-a]pyrazin-8-yl]amino}phenoxy)acetic acid;
N-(2-hydroxyethyl)-4-{[6-(1H-indazol-6-yl)imidazo[1,2-a]pyrazin-8-yl]amino}-2-methoxybenzamide;
6-(1,3-benzothiazol-5-yl)-N-[3-ethoxy-4-(morpholin-4-yl)phenyl]imidazo[1,2-a]pyrazin-8-amine;
6-(1H-indazol-6-yl)-N-{3-methoxy-4-[(2R)-oxolan-2-ylmethoxy]phenyl}imidazo[1,2-a]pyrazin-8-amine;
6-(1H-indazol-6-yl)-N-{4-[(2R)-oxolan-2-ylmethoxy]phenyl}imidazo[1,2-a]pyrazin-8-amine;
6-(8-{[4-(3-hydroxy-3-methylazetidin-1-yl)phenyl]amino}imidazo[1,2-a]pyrazin-6-yl)-3,4-dihydro-2H-1,4-benzoxazin-3-one;
6-(1H-indazol-6-yl)-N-[4-(morpholin-4-ylcarbonyl)phenyl]imidazo[1,2-a]pyrazin-8-amine;
N-(2-hydroxyethyl)-4-{[6-(1H-indazol-6-yl)imidazo[1,2-a]pyrazin-8-yl]amino}-N-methylbenzamide;
2-[(2-ethoxy-4-{[6-(1H-indazol-6-yl)imidazo[1,2-a]pyrazin-8-yl]amino}phenyl)(methyl)amino]ethan-1-ol;
N-[2-(dimethylamino)ethyl]-4-{[6-(1H-indazol-6-yl)imidazo[1,2-a]pyrazin-8-yl]amino}-N-methylbenzamide;
1-(2-fluoro-4-{[6-(1H-indazol-6-yl)imidazo[1,2-a]pyrazin-8-yl]amino}phenyl)-3-methylazetidin-3-ol;
(3S)-1-(4-{[6-(4-fluoro-1H-indazol-6-yl)imidazo[1,2-a]pyrazin-8-yl]amino}phenyl)pyrrolidin-3-ol;
2-[6-(8-{[4-(morpholin-4-yl)phenyl]amino}imidazo[1,2-a]pyrazin-6-yl)-1H-indazol-1-yl]ethan-1-ol;
6-(8-{[4-(3-hydroxy-3-methylazetidin-1-yl)phenyl]amino}imidazo[1,2-a]pyrazin-6-yl)-2,3-dihydro-1H-indol-2-one;
N-[6-(1H-indazol-6-yl)imidazo[1,2-a]pyrazin-8-yl]-2-methyl-1,2,3,4-tetrahydroisoquinolin-6-amine;
N-[3-ethoxy-4-(morpholin-4-yl)phenyl]-6-(4-fluoro-1H-indazol-6-yl)imidazo[1,2-a]pyrazin-8-amine;
1-(2-ethoxy-4-{[6-(1H-indazol-6-yl)imidazo[1,2-a]pyrazin-8-yl]amino}phenoxy)-2-methylpropan-2-ol;
(3R)-3-(4-{[6-(1H-indazol-6-yl)imidazo[1,2-a]pyrazin-8-yl]amino}phenyl)-1,4-dimethylpiperazin-2-one;
N-(2-hydroxyethyl)-4-{[6-(1H-indazol-6-yl)imidazo[1,2-a]pyrazin-8-yl]amino}benzamide;
6-(8-{[3-ethoxy-4-(morpholin-4-yl)phenyl]amino}imidazo[1,2-a]pyrazin-6-yl)-2,3-dihydro-1H-indol-2-one;
6-(3,4-dihydro-2H-1,4-benzoxazin-6-yl)-N-[3-ethoxy-4-(morpholin-4-yl)phenyl]imidazo[1,2-a]pyrazin-8-amine;
1-(4-{[6-(1H-indazol-6-yl)imidazo[1,2-a]pyrazin-8-yl]amino}phenyl)-N,N-dimethylpiperidin-4-amine;
1-(4-{[6-(1,3-benzothiazol-5-yl)imidazo[1,2-a]pyrazin-8-yl]amino}phenoxy)-2-methylpropan-2-ol;
(3R)-1-(2-ethoxy-4-{[6-(1H-indazol-6-yl)imidazo[1,2-a]pyrazin-8-yl]amino}phenyl)pyrrolidin-3-ol;
2-(4-{[6-(1H-indazol-6-yl)imidazo[1,2-a]pyrazin-8-yl]amino}phenoxy)ethan-1-ol;
1-(2-ethoxy-4-{[6-(1H-indazol-6-yl)imidazo[1,2-a]pyrazin-8-yl]amino}phenyl)-3-methylazetidin-3-ol;
1-(4-{[6-(1H-indazol-6-yl)imidazo[1,2-a]pyrazin-8-yl]amino}-2-methoxyphenyl)-3-methylazetidin-3-ol;
4-{[6-(1H-indazol-6-yl)imidazo[1,2-a]pyrazin-8-yl]amino}benzoic acid;
N-[3-ethoxy-4-(4-ethylpiperazin-1-yl)phenyl]-6-(1H-indazol-6-yl)imidazo[1,2-a]pyrazin-8-amine;
4-{[6-(1H-indazol-6-yl)imidazo[1,2-a]pyrazin-8-yl]amino}-N-propylbenzamide;
1-(4-{[6-(4-fluoro-1H-indazol-6-yl)imidazo[1,2-a]pyrazin-8-yl]amino}phenyl)-4-methylpiperidin-4-ol;
3-(4-{[6-(1H-indazol-6-yl)imidazo[1,2-a]pyrazin-8-yl]amino}-2-methoxyphenoxy)-2,2-dimethylpropan-1-ol;
6-(4-fluoro-1H-indazol-6-yl)-N-[4-(1,4-oxazepan-4-yl)phenyl]imidazo[1,2-a]pyrazin-8-amine;
6-(8-{[3-ethoxy-4-(morpholin-4-yl)phenyl]amino}imidazo[1,2-a]pyrazin-6-yl)-3,4-dihydro-2H-1,4-benzoxazin-3-one;
1-(4-{[6-(3,4-dihydro-2H-1,4-benzoxazin-6-yl)imidazo[1,2-a]pyrazin-8-yl]amino}phenoxy)-2-methylpropan-2-ol;
2-methyl-1-(4-{[6-(1-methyl-1H-1,3-benzodiazol-6-yl)imidazo[1,2-a]pyrazin-8-yl]amino}phenoxy)propan-2-ol;
6-(8-{[4-(2-hydroxy-2-methylpropoxy)phenyl]amino}imidazo[1,2-a]pyrazin-6-yl)-2,3-dihydro-1H-indol-2-one;
N-[3-fluoro-4-(morpholin-4-yl)phenyl]-6-(1H-indazol-6-yl)imidazo[1,2-a]pyrazin-8-amine;
1-(4-{[6-(1,3-benzothiazol-5-yl)imidazo[1,2-a]pyrazin-8-yl]amino}phenyl)-3-methylazetidin-3-ol;
N-[6-(1H-indazol-6-yl)imidazo[1,2-a]pyrazin-8-yl]-1,2,3,4-tetrahydroisoquinolin-6-amine;
N-[6-(1H-indazol-6-yl)imidazo[1,2-a]pyrazin-8-yl]-2,3-dihydro-1H-indol-6-amine;
1-[6-(8-{[4-(morpholin-4-yl)phenyl]amino}imidazo[1,2-a]pyrazin-6-yl)-1,2,3,4-tetrahydroisoquinolin-2-yl]ethan-1-one;
1-[7-(8-{[4-(morpholin-4-yl)phenyl]amino}imidazo[1,2-a]pyrazin-6-yl)-1,2,3,4-tetrahydroisoquinolin-2-yl]ethan-1-one;
N-[4-(morpholin-4-yl)phenyl]-6-{1H,2H,3H-pyrido[2,3-b][1,4]oxazin-7-yl}imidazo[1,2-a]pyrazin-8-amine;

6-(1-methyl-1H-indazol-6-yl)-N-[4-(morpholin-4-yl)phenyl]imidazo[1,2-a]pyrazin-8-amine;
N-[4-(morpholin-4-yl)phenyl]-6-{2H,3H,4H-pyrido[3,2-b][1,4]oxazin-7-yl}imidazo[1,2-a]pyrazin-8-amine;
6-(8-{[4-(morpholin-4-yl)phenyl]amino}imidazo[1,2-a]pyrazin-6-yl)-1H,2H,3H-pyrido[2,3-b][1,4]oxazin-2-one;
(3S)-1-(4-{[6-(3,4-dihydro-2H-1,4-benzoxazin-7-yl)imidazo[1,2-a]pyrazin-8-yl]amino}phenyl)-3-methylpiperidin-3-ol;
5-(8-{[4-(morpholin-4-yl)phenyl]amino}imidazo[1,2-a]pyrazin-6-yl)-2,3-dihydro-1H-indol-2-one;
1-methyl-6-(8-{[4-(morpholin-4-yl)phenyl]amino}imidazo[1,2-a]pyrazin-6-yl)-2,3-dihydro-1H-indol-2-one;
6-(8-{[4-(2-hydroxy-2-methylpropoxy)phenyl]amino}imidazo[1,2-a]pyrazin-6-yl)-3,4-dihydro-2H-1,4-benzoxazin-3-one;
2-[4-(4-{[6-(1H-indazol-6-yl)imidazo[1,2-a]pyrazin-8-yl]amino}phenyl)piperazin-1-yl]ethan-1-ol;
6-(1H-indazol-4-yl)-N-[4-(morpholin-4-yl)phenyl]imidazo[1,2-a]pyrazin-8-amine;
N-[3-ethoxy-4-(morpholin-4-yl)phenyl]-6-(1-methyl-1H-1,3-benzodiazol-6-yl)imidazo[1,2-a]pyrazin-8-amine;
6-(1H-indazol-6-yl)-N-[4-(piperazin-1-yl)phenyl]imidazo[1,2-a]pyrazin-8-amine;
N-[4-(morpholin-4-yl)phenyl]-6-(1,2,3,4-tetrahydroisoquinolin-7-yl)imidazo[1,2-a]pyrazin-8-amine;
N-[4-(morpholin-4-yl)phenyl]-6-(1,2,3,4-tetrahydroisoquinolin-6-yl)imidazo[1,2-a]pyrazin-8-amine;
7-(8-{[4-(morpholin-4-yl)phenyl]amino}imidazo[1,2-a]pyrazin-6-yl)-1H,2H,3H-pyrido[2,3-b][1,4]oxazin-2-one;
6-{1-methyl-1H-pyrrolo[3,2-b]pyridin-6-yl}-N-[4-(morpholin-4-yl)phenyl]imidazo[1,2-a]pyrazin-8-amine;
6-(1-methyl-1H-indol-6-yl)-N-[4-(morpholin-4-yl)phenyl]imidazo[1,2-a]pyrazin-8-amine;
6-(1,3-benzoxazol-5-yl)-N-[4-(morpholin-4-yl)phenyl]imidazo[1,2-a]pyrazin-8-amine;
6-(4-methyl-3,4-dihydro-2H-1,4-benzoxazin-7-yl)-N-[4-(morpholin-4-yl)phenyl]imidazo[1,2-a]pyrazin-8-amine;
6-(4-methyl-3,4-dihydro-2H-1,4-benzoxazin-6-yl)-N-[4-(morpholin-4-yl)phenyl]imidazo[1,2-a]pyrazin-8-amine;
6-{8-([4-[(3S)-3-hydroxypyrrolidin-1-yl]phenyl}amino)imidazo[1,2-a]pyrazin-6-yl]-3,4-dihydro-2H-1,4-benzoxazin-3-one;
(3R)-1-(4-{[6-(3,4-dihydro-2H-1,4-benzoxazin-7-yl)imidazo[1,2-a]pyrazin-8-yl]amino}phenyl)-3-methylpiperidin-3-ol;
6-{8-([4-[(3S)-3-hydroxy-3-methylpiperidin-1-yl]phenyl}amino)imidazo[1,2-a]pyrazin-6-yl]-3,4-dihydro-2H-1,4-benzoxazin-3-one;
6-{8-([4-[(3R)-3-hydroxy-3-methylpiperidin-1-yl]phenyl}amino)imidazo[1,2-a]pyrazin-6-yl]-3,4-dihydro-2H-1,4-benzoxazin-3-one;
6-{8-([4-[(3S)-3-hydroxy-3-methylpiperidin-1-yl]phenyl}amino)imidazo[1,2-a]pyrazin-6-yl]-2,3-dihydro-1H-indol-2-one;
6-{8-([4-[(3R)-3-hydroxy-3-methylpiperidin-1-yl]phenyl}amino)imidazo[1,2-a]pyrazin-6-yl]-2,3-dihydro-1H-indol-2-one;
(3R)-1-(4-{[6-(3,4-dihydro-2H-1,4-benzoxazin-6-yl)imidazo[1,2-a]pyrazin-8-yl]amino}phenyl)-3-methylpiperidin-3-ol;
(3S)-3-methyl-1-(4-{[6-(1-methyl-1H-1,3-benzodiazol-5-yl)imidazo[1,2-a]pyrazin-8-yl]amino}phenyl)piperidin-3-ol;
(3R)-3-methyl-1-(4-{[6-(1-methyl-1H-1,3-benzodiazol-5-yl)imidazo[1,2-a]pyrazin-8-yl]amino}phenyl)piperidin-3-ol;
(3R)-3-methyl-1-(4-{[6-(1-methyl-1H-1,3-benzodiazol-6-yl)imidazo[1,2-a]pyrazin-8-yl]amino}phenyl)piperidin-3-ol;
6-(8-{[4-(4-ethylpiperazin-1-yl)phenyl]amino}imidazo[1,2-a]pyrazin-6-yl)-3,4-dihydro-2H-1,4-benzoxazin-3-one;
6-(1,3-benzothiazol-6-yl)-N-[4-(morpholin-4-yl)phenyl]imidazo[1,2-a]pyrazin-8-amine;
6-(1,3-benzothiazol-5-yl)-N-[4-(morpholin-4-yl)phenyl]imidazo[1,2-a]pyrazin-8-amine;
6-(1,3-benzoxazol-6-yl)-N-[4-(morpholin-4-yl)phenyl]imidazo[1,2-a]pyrazin-8-amine;
6-(1H-indazol-5-yl)-N-[4-(morpholin-4-yl)phenyl]imidazo[1,2-a]pyrazin-8-amine;
(3S)-1-(4-{[6-(3,4-dihydro-2H-1,4-benzoxazin-6-yl)imidazo[1,2-a]pyrazin-8-yl]amino}phenyl)-3-methylpiperidin-3-ol;
(3S)-3-methyl-1-(4-{[6-(1-methyl-1H-1,3-benzodiazol-6-yl)imidazo[1,2-a]pyrazin-8-yl]amino}phenyl)piperidin-3-ol;
1-(4-{[6-(1H-indazol-6-yl)imidazo[1,2-a]pyrazin-8-yl]amino}phenyl)-3-methylazetidin-3-ol;
N-{4-[(4-ethylpiperazin-1-yl)methyl]phenyl}-6-(1-methyl-1H-1,3-benzodiazol-6-yl)imidazo[1,2-a]pyrazin-8-amine;
2-[ethyl(4-{[6-(1H-indazol-6-yl)imidazo[1,2-a]pyrazin-8-yl]amino}phenyl)amino]ethan-1-ol;
1-(4-{[6-(3,4-dihydro-2H-1,4-benzoxazin-7-yl)imidazo[1,2-a]pyrazin-8-yl]amino}phenyl)azetidin-3-ol;
7-(8-{[4-(morpholin-4-yl)phenyl]amino}imidazo[1,2-a]pyrazin-6-yl)-2H,3H,4H-pyrido[3,2-b][1,4]oxazin-3-one;
6-(1-methyl-1H-indazol-5-yl)-N-[4-(morpholin-4-yl)phenyl]imidazo[1,2-a]pyrazin-8-amine;
1-(4-{[6-(1H-indazol-6-yl)imidazo[1,2-a]pyrazin-8-yl]amino}phenoxy)-2-methylpropan-2-ol;
6-(3,4-dihydro-2H-1,4-benzoxazin-6-yl)-N-[4-(morpholin-4-yl)phenyl]imidazo[1,2-a]pyrazin-8-amine;
4-(4-{[6-(1H-indazol-6-yl)imidazo[1,2-a]pyrazin-8-yl]amino}phenyl)piperazin-2-one;
6-(1-methyl-1H-1,3-benzodiazol-6-yl)-N-[4-(morpholin-4-ylmethyl)phenyl]imidazo[1,2-a]pyrazin-8-amine;
6-(1H-1,3-benzodiazol-6-yl)-N-[4-(morpholin-4-yl)phenyl]imidazo[1,2-a]pyrazin-8-amine;
1-(4-{[6-(3,4-dihydro-2H-1,4-benzoxazin-6-yl)imidazo[1,2-a]pyrazin-8-yl]amino}phenyl)azetidin-3-ol;
6-(1H-indazol-6-yl)-N-[4-(1,4-oxazepan-4-yl)phenyl]imidazo[1,2-a]pyrazin-8-amine;
(3S)-1-(4-{[6-(1H-indazol-6-yl)imidazo[1,2-a]pyrazin-8-yl]amino}phenyl)-3-methylpiperdin-3-ol;
(3R)-1-(4-{[6-(1H-indazol-6-yl)imidazo[1,2-a]pyrazin-8-yl]amino}phenyl)-3-methylpiperdin-3-ol;
(3S)-1-(4-{[6-(1H-indazol-6-yl)imidazo[1,2-a]pyrazin-8-yl]amino}phenyl)-3-methylpyrrolidin-3-ol;
(3R)-1-(4-{[6-(1H-indazol-6-yl)imidazo[1,2-a]pyrazin-8-yl]amino}phenyl)-3-methylpyrrolidin-3-ol;
6-(8-{[4-(morpholin-4-yl)phenyl]amino}imidazo[1,2-a]pyrazin-6-yl)-3,4-dihydro-2H-1,4-benzoxazin-3-one;
6-(8-{[4-(3-hydroxyazetidin-1-yl)phenyl]amino}imidazo[1,2-a]pyrazin-6-yl)-2,3-dihydro-1H-indol-2-one;
6-(8-{[4-(3-hydroxy-3-methylpyrrolidin-1-yl)phenyl]amino}imidazo[1,2-a]pyrazin-6-yl)-3,4-dihydro-2H-1,4-benzoxazin-3-one;
6-(1-methyl-1H-1,3-benzodiazol-6-yl)-N-[4-(morpholin-4-yl)phenyl]imidazo[1,2-a]pyrazin-8-amine;
6-(3,4-dihydro-2H-1,4-benzoxazin-7-yl)-N-[4-(morpholin-4-yl)phenyl]imidazo[1,2-a]pyrazin-8-amine;
1-(4-{[6-(3,4-dihydro-2H-1,4-benzoxazin-7-yl)imidazo[1,2-a]pyrazin-8-yl]amino}phenyl)-4-methylpiperidin-4-ol;

1-(4-{[6-(1H-indol-6-yl)imidazo[1,2-a]pyrazin-8-yl]
  amino}phenyl)-4-methylpiperidin-4-ol;
1-(4-{[6-(1H-indol-6-yl)imidazo[1,2-a]pyrazin-8-yl]
  amino}phenyl)azetidin-3-ol;
1-(4-{[6-(1-methyl-1H-1,3-benzodiazol-6-yl)imidazo[1,2-
  a]pyrazin-8-yl]amino}phenyl)azetidin-3-ol;
1-(4-{[6-(1-methyl-1H-1,3-benzodiazol-5-yl)imidazo[1,2-
  a]pyrazin-8-yl]amino}phenyl)azetidin-3-ol;
6-(1-methyl-1H-1,3-benzodiazol-5-yl)-N-[4-(morpholin-4-
  yl)phenyl]imidazo[1,2-a]pyrazin-8-amine;
6-(8-{[4-(morpholin-4-yl)phenyl]amino}imidazo[1,2-a]
  pyrazin-6-yl)-2,3-dihydro-1H-indol-2-one;
6-(8-{[4-(3-hydroxyazetidin-1-yl)phenyl]amino}imidazo[1,
  2-a]pyrazin-6-yl)-3,4-dihydro-2H-1,4-benzoxazin-3-one;
5-(8-{[4-(morpholin-4-yl)phenyl]amino}imidazo[1,2-a]
  pyrazin-6-yl)-2,3-dihydro-1,3-benzoxazol-2-one;
4-{[6-(1H-indazol-6-yl)imidazo[1,2-a]pyrazin-8-yl]
  amino}-N,N-dimethylbenzene-1-sulfonamide;
6-(1H-indazol-6-yl)-N-{4-[4-(propan-2-yl)piperazin-1-yl]
  phenyl}imidazo[1,2-a]pyrazin-8-amine;
2-(4-{[6-(3,4-dihydro-2H-1,4-benzoxazin-7-yl)imidazo[1,
  2-a]pyrazin-8-yl]amino}phenyl)-2-methylpropan-1-ol;
4-(4-{[6-(1H-indazol-6-yl)imidazo[1,2-a]pyrazin-8-yl]
  amino}phenyl)thiomorpholine-1,1-dione;
6-(1H-indazol-6-yl)-N-[4-(2-methylmorpholin-4-yl)phenyl]
  imidazo[1,2-a]pyrazin-8-amine;
and pharmaceutically acceptable salts thereof.

Also provided is at least one chemical entity chosen from:
N-(4-ethoxy-3-methoxyphenyl)-6-(1H-indazol-6-yl)-5-me-
  thylimidazo[1,2-a]pyrazin-8-amine,
1-(4-{[6-(1H-indazol-6-yl)-5-methylimidazo[1,2-a]pyrazin-
  8-yl]amino}phenyl)-4-methylpiperidin-4-ol,
N,6-bis[4-(morpholin-4-yl)phenyl]imidazo[1,2-a]pyrazin-
  8-amine,
2-[1-(4-{[6-(1H-indazol-6-yl)imidazo[1,2-a]pyrazin-8-yl]
  amino}phenyl)piperidin-4-yl]ethan-1-ol,
6-[3-(morpholin-4-yl)phenyl]-N-[4-(morpholin-4-yl)phe-
  nyl]imidazo[1,2-a]pyrazin-8-amine,
2-[6-(8-{[4-(morpholin-4-yl)phenyl]amino}imidazo[1,2-a]
  pyrazin-6-yl)-1H-indol-3-yl]ethan-1-ol,
[1-(4-{[6-(1H-indazol-6-yl)imidazo[1,2-a]pyrazin-8-yl]
  amino}phenyl)piperidin-4-yl]methanol,
1-[4-(4-{[6-(1H-indazol-6-yl)imidazo[1,2-a]pyrazin-8-yl]
  amino}phenyl)piperazin-1-yl]ethan-1-one,
6-(5-chloro-8-{[3-methoxy-4-(morpholin-4-yl)phenyl]
  amino}imidazo[1,2-a]pyrazin-6-yl)-2,3-dihydro-1H-in-
  dol-2-one,
5-chloro-N-[3-methoxy-4-(morpholin-4-yl)phenyl]-6-{1H-
  pyrrolo[3,2-b]pyridin-6-yl}imidazo[1,2-a]pyrazin-8-
  amine,
N-methyl-5-(8-{[4-(morpholin-4-yl)phenyl]amino}imidazo
  [1,2-a]pyrazin-6-yl)pyridin-3-amine,
6-(1H-indazol-6-yl)-N-(4-{7-oxa-2-azaspiro[3.5]nonan-2-
  yl}phenyl)imidazo[1,2-a]pyrazin-8-amine,
6-(2-methyl-1H-1,3-benzodiazol-6-yl)-N-[4-(morpholin-4-
  yl)phenyl]imidazo[1,2-a]pyrazin-8-amine,
5-(8-{[4-(3-hydroxy-3-methylazetidin-1-yl)phenyl]
  amino}imidazo[1,2-a]pyrazin-6-yl)-1-methyl-2,3-dihy-
  dro-1H-1,3-benzodiazol-2-one,
N-{4-[(2R,6S)-2,6-dimethylmorpholin-4-yl]phenyl}-6-(1H-
  indazol-6-yl)imidazo[1,2-a]pyrazin-8-amine,
N-[6-(1H-indazol-6-yl)-5-methylimidazo[1,2-a]pyrazin-8-
  yl]-5-(morpholin-4-yl)pyridin-2-amine,
[(2R)-6-(8-{[4-(morpholin-4-yl)phenyl]amino}imidazo[1,
  2-a]pyrazin-6-yl)-3,4-dihydro-2H-1,4-benzoxazin-2-yl]
  methanol,
6-(1H-indazol-6-yl)-N-[3-(methoxymethyl)-4-(morpholin-
  4-yl)phenyl]imidazo[1,2-a]pyrazin-8-amine,
7-(8-{[4-(morpholin-4-yl)phenyl]amino}imidazo[1,2-a]
  pyrazin-6-yl)-1,2,3,4-tetrahydroquinoxalin-2-one,
5-chloro-6-(1H-indazol-6-yl)-N-[3-methoxy-4-(morpholin-
  4-yl)phenyl]imidazo[1,2-a]pyrazin-8-amine,
1-(4-{[6-(1H-indazol-6-yl)imidazo[1,2-a]pyrazin-8-yl]
  amino}phenyl)-3-methylazetidin-3-amine,
[(2S)-6-(8-{[4-(morpholin-4-yl)phenyl]amino}imidazo[1,2-
  a]pyrazin-6-yl)-3,4-dihydro-2H-1,4-benzoxazin-2-yl]
  methanol,
7-(8-{[4-(morpholin-4-yl)phenyl]amino}imidazo[1,2-a]
  pyrazin-6-yl)-1,2,3,4-tetrahydroquinolin-2-one,
5-{[6-(1H-indazol-6-yl)imidazo[1,2-a]pyrazin-8-yl]
  amino}-2-(morpholin-4-yl)benzonitrile,
6-(3,4-dihydro-2H-1,4-benzoxazin-6-yl)-3-methyl-N-[4-
  (morpholin-4-yl)phenyl]imidazo[1,2-a]pyrazin-8-amine,
N-[3-methoxy-4-(morpholin-4-yl)phenyl]-3-methyl-6-{1H-
  pyrrolo[3,2-b]pyridin-6-yl}imidazo[1,2-a]pyrazin-8-
  amine,
5-methyl-6-(2-methyl-1H-1,3-benzodiazol-6-yl)-N-[4-
  (morpholin-4-yl)phenyl]imidazo[1,2-a]pyrazin-8-amine,
5-ethyl-6-(1H-indazol-6-yl)-N-[4-(morpholin-4-yl)phenyl]
  imidazo[1,2-a]pyrazin-8-amine,
1-methyl-6-(8-{[4-(morpholin-4-yl)phenyl]amino}imidazo
  [1,2-a]pyrazin-6-yl)-2,3-dihydro-1H-1,3-benzodiazol-2-
  one,
6-(3-methyl-8-{[4-(morpholin-4-yl)phenyl]amino}imidazo
  [1,2-a]pyrazin-6-yl)-2,3-dihydro-1H-indol-2-one,
1,3-dimethyl-5-(8-{[4-(morpholin-4-yl)phenyl]
  amino}imidazo[1,2-a]pyrazin-6-yl)-2,3-dihydro-1H-1,3-
  benzodiazol-2-one,
2-[6-(8-{[4-(morpholin-4-yl)phenyl]amino}imidazo[1,2-a]
  pyrazin-6-yl)-1H-indazol-3-yl]propan-2-ol,
6-(4-fluoro-1H-indol-6-yl)-N-[4-(morpholin-4-yl)phenyl]
  imidazo[1,2-a]pyrazin-8-amine,
5-{[6-(1H-indazol-6-yl)imidazo[1,2-a]pyrazin-8-yl]
  amino}-2-(morpholin-4-yl)benzamide,
5-(8-{[3-methoxy-4-(morpholin-4-yl)phenyl]amino}-5-me-
  thylimidazo[1,2-a]pyrazin-6-yl)-2,3-dihydro-1H-1,3-ben-
  zodiazol-2-one,
5-(5-methyl-8-{[4-(morpholin-4-yl)phenyl]amino}imidazo
  [1,2-a]pyrazin-6-yl)-2,3-dihydro-1H-1,3-benzodiazol-2-
  one,
[2-(8-{[4-(morpholin-4-yl)phenyl]amino}imidazo[1,2-a]
  pyrazin-6-yl)phenyl]methanol,
1-methyl-5-(8-{[4-(morpholin-4-yl)phenyl]amino}imidazo
  [1,2-a]pyrazin-6-yl)-2,3-dihydro-1H-1,3-benzodiazol-2-
  one,
2-[6-(8-{[4-(morpholin-4-yl)phenyl]amino}imidazo[1,2-a]
  pyrazin-6-yl)-3,4-dihydro-2H-1,4-benzoxazin-4-yl]
  ethan-1-ol,
(3R)-2,2-dimethyl-6-(8-{[4-(morpholin-4-yl)phenyl]
  amino}imidazo[1,2-a]pyrazin-6-yl)-2,3-dihydro-1H-in-
  dol-3-ol,
6-(1H-indazol-6-yl)-N-[3-methoxy-4-{4-(2-methoxyethyl)
  piperazin-1-yl]phenyl}imidazo[1,2-a]pyrazin-8-amine,
2-(4-{2-methoxy-4-[(6-{1H-pyrrolo[3,2-b]pyridin-6-
  yl}imidazo[1,2-a]pyrazin-8-yl)amino]phenyl}piperazin-
  1-yl)ethan-1-ol,
1-[6-(8-{[4-(morpholin-4-yl)phenyl]amino}imidazo[1,2-a]
  pyrazin-6-yl)-1H-indazol-3-yl]ethan-1-ol,
2-[6-(8-{[4-(morpholin-4-yl)phenyl]amino}imidazo[1,2-a]
  pyrazin-6-yl)-1H-indazol-3-yl]ethan-1-ol,
2-{[5-(8-{[4-(morpholin-4-yl)phenyl]amino}imidazo[1,2-a]
  pyrazin-6-yl)pyridin-3-yl]amino}ethan-1-ol, N-[3-methoxy-4-(morpholin-4-yl)phenyl]-5-methyl-6-{1H-pyrrolo[3,2-b]pyridin-6-yl}imidazo[1,2-a]pyrazin-8-amine, (3S)-2,2-dimethyl-6-(8-{[4-(morpholin-4-yl)phenyl]amino}imidazo[1,2-a]pyrazin-6-yl)-2,3-dihydro-1H-indol-3-ol, N-{4-[4-(3-fluoropropyl)piperazin-1-yl]phenyl}-6-(1H-indazol-6-yl)imidazo[1,2-a]pyrazin-8-amine, 6-(1H-indazol-6-yl)-N-[4-(oxan-4-yl)phenyl]imidazo[1,2-a]pyrazin-8-amine, N-[4-(4-fluoropiperidin-1-yl)phenyl]-6-(1H-indazol-6-yl)imidazo[1,2-a]pyrazin-8-amine, 6-(1H-indazol-6-yl)-N-[3-(2-methoxyethoxy)-4-(morpholin-4-yl)phenyl]imidazo[1,2-a]pyrazin-8-amine, 6-(1H-indazol-6-yl)-N-[4-(4H-1,2,4-triazol-4-yl)phenyl]imidazo[1,2-a]pyrazin-8-amine, N-[4-(3,3-difluoropyrrolidin-1-yl)phenyl]-6-(1H-indazol-6-yl)imidazo[1,2-a]pyrazin-8-amine, 6-(1H-indazol-6-yl)-N-[3-methoxy-4-(morpholin-4-yl)phenyl]-5-methylimidazo[1,2-a]pyrazin-8-amine, 2,2-dimethyl-6-(8-{[4-(morpholin-4-yl)phenyl]amino}imidazo[1,2-a]pyrazin-6-yl)-2,3-dihydro-1H-indol-3-one 6-(1H-indazol-6-yl)-N-[3-methoxy-4-(methoxymethyl)phenyl]imidazo[1,2-a]pyrazin-8-amine, 1-(4-{[6-(1H-indazol-6-yl)imidazo[1,2-a]pyrazin-8-yl]amino}-2-methoxyphenyl)-2-methylpropan-2-ol,

[(2S)-4-(4-{[6-(3,4-dihydro-2H-1,4-benzoxazin-6-yl)imidazo[1,2-a]pyrazin-8-yl]amino}phenyl)morpholin-2-yl]methanol, N-[4-(4,4-difluoropiperidin-1-yl)phenyl]-6-(1H-indazol-6-yl)imidazo[1,2-a]pyrazin-8-amine, 6-(1H-indazol-6-yl)-N-{3-methoxy-4-[(2-methoxyethoxy)methyl]phenyl}imidazo[1,2-a]pyrazin-8-amine, 2-[2-(morpholin-4-yl)-5-[(6-{1H-pyrrolo[3,2-b]pyridin-6-yl}imidazo[1,2-a]pyrazin-8-yl)amino]phenoxy]ethan-1-ol, 6-(1H-indazol-6-yl)-N-[4-(3-methoxy-3-methylazetidin-1-yl)phenyl]imidazo[1,2-a]pyrazin-8-amine, 5-(8-{[4-(morpholin-4-yl)phenyl]amino}imidazo[1,2-a]pyrazin-6-yl)pyridin-3-amine, N-[4-(morpholin-4-yl)phenyl]-6-(1,5-naphthyridin-3-yl)imidazo[1,2-a]pyrazin-8-amine, 3-ethyl-1-(4-{[6-(1H-indazol-6-yl)imidazo[1,2-a]pyrazin-8-yl]amino}phenyl)azetidin-3-ol, N-[4-(3-fluoro-3-methylazetidin-1-yl)phenyl]-6-(1H-indazol-6-yl)imidazo[1,2-a]pyrazin-8-amine, N-[4-(3,3-difluoropiperidin-1-yl)phenyl]-6-(1H-indazol-6-yl)imidazo[1,2-a]pyrazin-8-amine,

[(2R)-4-(4-{[6-(3,4-dihydro-2H-1,4-benzoxazin-6-yl)imidazo[1,2-a]pyrazin-8-yl]amino}phenyl)morpholin-2-yl]methanol, N-[4-(3,3-difluoroazetidin-1-yl)phenyl]-6-(1H-indazol-6-yl)imidazo[1,2-a]pyrazin-8-amine, (3S)-1-(4-{[6-(3,4-dihydro-2H-1,4-benzoxazin-6-yl)imidazo[1,2-a]pyrazin-8-yl]amino}-2-methoxyphenyl)pyrrolidin-3-ol, (3R)-1-(4-{[6-(3,4-dihydro-2H-1,4-benzoxazin-6-yl)imidazo[1,2-a]pyrazin-8-yl]amino}-2-methoxyphenyl)pyrrolidin-3-ol, N-[4-(3-fluoroazetidin-1-yl)phenyl]-6-(1H-indazol-6-yl)imidazo[1,2-a]pyrazin-8-amine, 6-(3,4-dihydro-2H-1,4-benzoxazin-6-yl)-N-[3-methoxy-4-(morpholin-4-yl)phenyl]-5-methylimidazo[1,2-a]pyrazin-8-amine, N,N-diethyl-6-(8-{[4-(morpholin-4-yl)phenyl]amino}imidazo[1,2-a]pyrazin-6-yl)-1H-indazol-3-amine, (3S)-3-hydroxy-3-methyl-6-(8-{[4-(morpholin-4-yl)phenyl]amino}imidazo[1,2-a]pyrazin-6-yl)-2,3-dihydro-1H-indol-2-one, N-[4-(morpholin-4-yl)phenyl]-6-(quinoxalin-6-yl)imidazo[1,2-a]pyrazin-8-amine, (3R)-3-hydroxy-3-methyl-6-(8-{[4-(morpholin-4-yl)phenyl]amino}imidazo[1,2-a]pyrazin-6-yl)-2,3-dihydro-1H-indol-2-one, 6-(1H-indazol-6-yl)-N-{3-methoxy-4-[(2S)-oxolan-2-ylmethoxy]phenyl}imidazo[1,2-a]pyrazin-8-amine, 6-(8-{[3-methoxy-4-(morpholin-4-yl)phenyl]amino}-5-methylimidazo[1,2-a]pyrazin-6-yl)-2,3-dihydro-1H-indol-2-one, 6-(8-{[3-methoxy-4-(morpholin-4-yl)phenyl]amino}-5-methylimidazo[1,2-a]pyrazin-6-yl)-3,4-dihydro-2H-1,4-benzoxazin-3-one, (3S)-1-{4-[(6-{1H,2H,3H-pyrido[2,3-b][1,4]oxazin-7-yl}imidazo[1,2-a]pyrazin-8-yl)amino]phenyl}pyrrolidin-3-ol, (3R)-1-(4-{[6-(3,4-dihydro-2H-1,4-benzoxazin-6-yl)imidazo[1,2-a]pyrazin-8-yl]amino}phenyl)pyrrolidin-3-ol, 6-{8-([4-[(3R)-3-hydroxypyrrolidin-1-yl]-3-methoxyphenyl}amino)imidazo[1,2-a]pyrazin-6-yl]-2,3-dihydro-1H-indol-2-one, N-[4-(1H-imidazol-1-yl)phenyl]-6-(1H-indazol-6-yl)imidazo[1,2-a]pyrazin-8-amine, 6-(1H-indazol-6-yl)-N-[4-(1H-pyrazol-1-yl)phenyl]imidazo[1,2-a]pyrazin-8-amine, 6-{8-({4-[(3R)-3-hydroxypyrrolidin-1-yl]phenyl}amino)imidazo[1,2-a]pyrazin-6-yl]-2,3-dihydro-1H-indol-2-one, 6-{8-({4-[(3S)-3-hydroxypyrrolidin-1-yl]phenyl}amino)imidazo[1,2-a]pyrazin-6-yl]-2,3-dihydro-1H-indol-2-one, 1-(4-{[6-(1H-indazol-6-yl)-5-methylimidazo[1,2-a]pyrazin-8-yl]amino}phenyl)-3-methylazetidin-3-ol, (3S)-1-(4-{[6-(1H-indazol-6-yl)imidazo[1,2-a]pyrazin-8-yl]amino}phenyl)piperidin-3-ol, (3R)-1-(4-{[6-(1H-indazol-6-yl)imidazo[1,2-a]pyrazin-8-yl]amino}phenyl)piperidin-3-ol, 2-[3-(8-{[4-(morpholin-4-yl)phenyl]amino}imidazo[1,2-a]pyrazin-6-yl)phenyl]propan-2-ol, 6-(5-methyl-8-{[4-(morpholin-4-yl)phenyl]amino}imidazo[1,2-a]pyrazin-6-yl)-3,4-dihydro-2H-1,4-benzoxazin-3-one, N-ethyl-6-(8-{[4-(morpholin-4-yl)phenyl]amino}imidazo[1,2-a]pyrazin-6-yl)-1H-indazol-3-amine, 2-[4-(4-{[6-(1H-indazol-6-yl)imidazo[1,2-a]pyrazin-8-yl]amino}-2-methoxyphenyl)piperazin-1-yl]ethan-1-ol, 6-{8-({4-[(3S)-3-hydroxypyrrolidin-1-yl]-3-methoxyphenyl}amino)imidazo[1,2-a]pyrazin-6-yl]-2,3-dihydro-1H-indol-2-one, 2-(5-{[6-(1H-indazol-6-yl)imidazo[1,2-a]pyrazin-8-yl]amino}-2-(morpholin-4-yl)phenoxy)ethan-1-ol, (3S)-1-(4-{[6-(1-methyl-1H-indazol-6-yl)imidazo[1,2-a]pyrazin-8-yl]amino}phenyl)pyrrolidin-3-ol, 6-(5-methyl-8-{[4-(morpholin-4-yl)phenyl]amino}imidazo[1,2-a]pyrazin-6-yl)-2,3-dihydro-1H-indol-2-one, 2-methyl-1-[6-(8-{[4-(morpholin-4-yl)phenyl]amino}imidazo[1,2-a]pyrazin-6-yl)-2H-indazol-2-yl]propan-2-ol, 2-methyl-1-{4-[(6-{1H-pyrrolo[3,2-b]pyridin-6-yl}imidazo[1,2-a]pyrazin-8-yl)amino]phenyl}propan-2-ol, (3S)-1-(4-{[6-(3,4-dihydro-2H-1,4-benzoxazin-6-yl)imidazo[1,2-a]pyrazin-8-yl]amino}phenyl)pyrrolidin-3-ol, 2-[4-(8-{[4-(morpholin-4-yl)phenyl]amino}imidazo[1,2-a]pyrazin-6-yl)phenyl]propan-2-ol, 6-(1H-indazol-6-yl)-3-methyl-N-[4-(morpholin-4-yl)phenyl]imidazo[1,2-a]pyrazin-8-amine, N-(2-hydroxyethyl)-N-methyl-6-(8-{[4-(morpholin-4-yl)phenyl]amino}imidazo[1,2-a]pyrazin-6-yl)-1H-indazole-3-carboxamide, 5-chloro-6-(1H-indazol-6-yl)-N-[4-(morpholin-4-yl)phenyl]imidazo[1,2-a]pyrazin-8-amine, N-(2-hydroxyethyl)-2-(4-{[6-(1H-indazol-6-yl)imidazo[1,2-a]pyrazin-8-yl]amino}phenoxy)acetamide, 1-(4-{[6-(1H-indol-6-yl)imidazo[1,2-a]pyrazin-8-yl]amino}-2-methoxyphenyl)-3-methylazetidin-3-ol, 1-(4-{[6-(1H-indol-6-yl)imidazo[1,2-a]pyrazin-8-yl]amino}phenyl)-3-methylazetidin-3-ol, 2-methyl-1-[6-(8-{[4-(morpholin-4-yl)phenyl]amino}imidazo[1,2-a]pyrazin-6-yl)-1H-indazol-1-yl]propan-2-ol, 6-(1H-indazol-6-yl)-N-[3-methoxy-4-(oxan-4-yloxy)phenyl]imidazo[1,2-a]pyrazin-8-amine, N-[3-methoxy-4-(morpholin-4-yl)phenyl]-6-(1-methyl-1H-indazol-6-yl)imidazo[1,2-a]pyrazin-8-amine, 6-(3,4-dihydro-2H-1,4-benzoxazin-6-yl)-5-methyl-N-[4-(morpholin-4-yl)phenyl]imidazo[1,2-a]pyrazin-8-amine, 2-methyl-2-(4-{[6-(1-methyl-1H-indazol-6-yl)imidazo[1,2-a]pyrazin-8-yl]amino}phenyl)propan-1-ol, 1-(3-hydroxy-3-methylazetidin-1-yl)-2-(4-{[6-(1H-indazol-6-yl)imidazo[1,2-a]pyrazin-8-yl]amino}phenoxy)ethan-1-one, 1-[6-(1,3-benzothiazol-5-yl)imidazo[1,2-a]pyridin-8-yl]-3-methylurea, 1-[6-(1,3-benzothiazol-5-yl)imidazo[1,2-a]pyridin-8-yl]-3-ethylurea, 1-{2-ethoxy-4-[(6-{1H-pyrrolo[3,2-b]pyridin-6-yl}imidazo[1,2-a]pyrazin-8-yl)amino]phenyl}-3-methylazetidin-3-ol, 1-{2-methoxy-4-[(6-{1H-pyrrolo[3,2-b]pyridin-6-yl}imidazo[1,2-a]pyrazin-8-yl)amino]phenyl}-3-methylazetidin-3-ol, 6-(1H-indol-6-yl)-N-[3-methoxy-4-(morpholin-4-yl)phenyl]imidazo[1,2-a]pyrazin-8-amine, 6-(1H-indazol-6-yl)-N-[4-(oxan-4-yloxy)phenyl]imidazo[1,2-a]pyrazin-8-amine, 6-(8-{[3-methoxy-4-(morpholin-4-yl)phenyl]amino}imidazo[1,2-a]pyrazin-6-yl)-3,4-dihydro-2H-1,4-benzoxazin-3-one, 6-(1H-indazol-6-yl)-N-[3-(morpholin-4-yl)phenyl]imidazo[1,2-a]pyrazin-8-amine, 2-(4-{[6-(1H-indazol-6-yl)imidazo[1,2-a]pyrazin-8-yl]amino}phenoxy)-N,N-dimethylacetamide, 3-methyl-1-{4-[(6-{1H-pyrrolo[3,2-b]pyridin-6-yl}imidazo[1,2-a]pyrazin-8-yl)amino]phenyl}azetidin-3-ol, 1-methyl-5-(5-methyl-8-{[4-(morpholin-4-yl)phenyl]amino}imidazo[1,2-a]pyrazin-6-yl)-2,3-dihydro-1H-1,3-benzodiazol-2-one, 1-ethyl-5-(8-{[4-(morpholin-4-yl)phenyl]amino}imidazo[1,2-a]pyrazin-6-yl)-2,3-dihydro-1H-1,3-benzodiazol-2-one,6-(3,4-dihydro-2H-1,4-benzoxazin-6-yl)-5-ethyl-N-[4-(morpholin-4-yl)phenyl]imidazo[1,2-a]pyrazin-8-amine, 6-(5-ethyl-8-{[4-(morpholin-4-yl)phenyl]amino}imidazo[1,2-a]pyrazin-6-yl)-2,3-dihydro-1H-indol-2-one, (3S)-1-{4-[(6-{1H-pyrrolo[3,2-b]pyridin-6-yl}imidazo[1,2-a]pyrazin-8-yl)amino]phenyl}piperidin-3-ol, (3S)-1-{2-methoxy-4-[(6-{1H-pyrrolo[3,2-b]pyridin-6-yl}imidazo[1,2-a]pyrazin-8-yl)amino]phenyl}piperidin-3-ol, 2-(1-{4-[(6-{1H-pyrrolo[3,2-b]pyridin-6-yl}imidazo[1,2-a]pyrazin-8-yl)amino]phenyl}piperidin-4-yl)ethan-1-ol, 2-[6-(5-methyl-8-{[4-(morpholin-4-yl)phenyl]amino}imidazo[1,2-a]pyrazin-6-yl)-1H-indazol-3-yl]ethan-1-ol, 1-[4-({6-[3-(2-hydroxyethyl)-1H-indazol-6-yl]imidazo[1,2-a]pyrazin-8-yl}amino)phenyl]-3-methylazetidin-3-ol, 6-{8-([4-[(2R)-2-(hydroxymethyl)morpholin-4-yl]phenyl}amino)imidazo[1,2-a]pyrazin-6-yl]-2,3-dihydro-1H-indol-2-one, 6-{8-([4-[(2S)-2-(hydroxymethyl)morpholin-4-yl]phenyl}amino)imidazo[1,2-a]pyrazin-6-yl]-2,3-dihydro-1H-indol-2-one, 5-(5-ethyl-8-{[4-(morpholin-4-yl)phenyl]amino}imidazo[1,2-a]pyrazin-6-yl)-1-methyl-2,3-dihydro-1H-1,3-benzodiazol-2-one, 5-ethyl-N-[4-(morpholin-4-yl)phenyl]-6-{1H-pyrrolo[3,2-b]pyridin-6-yl}imidazo[1,2-a]pyrazin-8-amine, (3R)-1-(4-{[6-(3,4-dihydro-2H-1,4-benzoxazin-6-yl)imidazo[1,2-a]pyrazin-8-yl]amino}-2-methoxyphenyl)piperidin-3-ol, N-[4-(morpholin-4-yl)phenyl]-6-(1,2,3,5-tetrahydro-4,1-benzoxazepin-8-yl)imidazo[1,2-a]pyrazin-8-amine,

[(3R)-4-(4-{[6-(1H-indazol-6-yl)imidazo[1,2-a]pyrazin-8-yl]amino}phenyl)morpholin-3-yl]methanol,

[(3S)-4-(4-{[6-(1H-indazol-6-yl)imidazo[1,2-a]pyrazin-8-yl]amino}phenyl)morpholin-3-yl]methanol, (3S)-1-(4-{[6-(3,4-dihydro-2H-1,4-benzoxazin-6-yl)imidazo[1,2-a]pyrazin-8-yl]amino}-2-methoxyphenyl)piperidin-3-ol, (1-{4-[(6-{1H-pyrrolo[3,2-b]pyridin-6-yl}imidazo[1,2-a]pyrazin-8-yl)amino]phenyl}piperidin-4-yl) methanol,

[(2R)-4-(4-{[6-(3,4-dihydro-2H-1,4-benzoxazin-6-yl)imidazo[1,2-a]pyrazin-8-yl]amino}-2-methoxyphenyl)morpholin-2-yl]methanol,

[(2S)-4-(4-{[6-(3,4-dihydro-2H-1,4-benzoxazin-6-yl)imidazo[1,2-a]pyrazin-8-yl]amino}-2-methoxyphenyl)morpholin-2-yl]methanol, 4-(4-{[6-(1H-indazol-6-yl)imidazo[1,2-a]pyrazin-8-yl]amino}phenoxy)cyclohexan-1-ol, 6-(1H-indazol-6-yl)-N-(4-{2-oxa-6-azaspiro[3.3]heptan-6-yl}phenyl)imidazo[1,2-a]pyrazin-8-amine, 2-[6-(8-{[3-methoxy-4-(morpholin-4-yl)phenyl]amino}imidazo[1,2-a]pyrazin-6-yl)-1H-indazol-3-yl]ethan-1-ol,

[(2S)-4-(4-{[6-(1H-indazol-6-yl)imidazo[1,2-a]pyrazin-8-yl]amino}-2-methoxyphenyl)morpholin-2-yl]methanol,

[(2R)-4-(4-{[6-(1H-indazol-6-yl)imidazo[1,2-a]pyrazin-8-yl]amino}-2-methoxyphenyl)morpholin-2-yl]methanol, 2-[1-(4-{[6-(3,4-dihydro-2H-1,4-benzoxazin-6-yl)imidazo[1,2-a]pyrazin-8-yl]amino}phenyl)piperidin-4-yl]ethan-1-ol, 6-(1H-indazol-6-yl)-N-(4-{8-oxa-3-azabicyclo[3.2.1]octan-3-yl}phenyl)imidazo[1,2-a]pyrazin-8-amine,

[(3R)-1-(4-{[6-(1H-indazol-6-yl)imidazo[1,2-a]pyrazin-8-yl]amino}phenyl)pyrrolidin-3-yl]methanol,

[(3S)-1-(4-{[6-(1H-indazol-6-yl)imidazo[1,2-a]pyrazin-8-yl]amino}phenyl)pyrrolidin-3-yl]methanol, 5-chloro-6-(3,4-dihydro-2H-1,4-benzoxazin-6-yl)-N-[3-methoxy-4-(morpholin-4-yl)phenyl]imidazo[1,2-a]pyrazin-8-amine, 2-[6-(8-{[3-methoxy-4-(morpholin-4-yl)phenyl]amino}imidazo[1,2-a]pyrazin-6-yl)-1H-indol-3-yl]ethan-1-ol, (3R)-1-(4-{[6-(3,4-dihydro-2H-1,4-benzoxazin-6-yl)imidazo[1,2-a]pyrazin-8-yl]amino}phenyl)piperidin-3-ol,

[1-(4-{[6-(3,4-dihydro-2H-1,4-benzoxazin-6-yl)imidazo[1,2-a]pyrazin-8-yl]amino}phenyl)piperidin-4-yl]methanol, (3S)-1-(4-{[6-(3,4-dihydro-2H-1,4-benzoxazin-6-yl)imidazo[1,2-a]pyrazin-8-yl]amino}phenyl)piperidin-3-ol,
[(2S)-4-{4-[(6-{1H-pyrrolo[3,2-b]pyridin-6-yl}imidazo[1,2-a]pyrazin-8-yl)amino]phenyl}morpholin-2-yl]methanol,
[(2R)-4-{4-[(6-{1H-pyrrolo[3,2-b]pyridin-6-yl}imidazo[1,2-a]pyrazin-8-yl)amino]phenyl}morpholin-2-yl]methanol,
2-[1-(4-{[6-(1H-indazol-6-yl)imidazo[1,2-a]pyrazin-8-yl]amino}phenyl)pyrrolidin-3-yl]ethan-1-ol,
6-(1H-indazol-6-yl)-N-[4-(oxan-4-ylmethoxy)phenyl]imidazo[1,2-a]pyrazin-8-amine,
N-[5-(8-{[4-(morpholin-4-yl)phenyl]amino}imidazo[1,2-a]pyrazin-6-yl)pyridin-3-yl]acetamide,
6-(8-{[3-methoxy-4-(oxan-4-yloxy)phenyl]amino}imidazo[1,2-a]pyrazin-6-yl)-2,3-dihydro-1H-indol-2-one,
6-(1H-indol-6-yl)-N-[3-methoxy-4-(morpholin-4-yl)phenyl]-5-methylimidazo[1,2-a]pyrazin-8-amine,
6-(1H-indol-6-yl)-5-methyl-N-[4-(morpholin-4-yl)phenyl]imidazo[1,2-a]pyrazin-8-amine,
1-(4-{[6-(3,4-dihydro-2H-1,4-benzoxazin-6-yl)-5-methylimidazo[1,2-a]pyrazin-8-yl]amino}phenyl)-4-methylpiperidin-4-ol,
N-[3-methoxy-4-(oxan-4-yloxy)phenyl]-6-{1H-pyrrolo[3,2-b]pyridin-6-yl}imidazo[1,2-a]pyrazin-8-amine,
6-(1H-indazol-6-yl)-N-(4-{2-oxa-7-azaspiro[3.5]nonan-7-yl}phenyl)imidazo[1,2-a]pyrazin-8-amine, and 6-(1H-indazol-6-yl)-N-[3-methoxy-4-(oxan-4-ylmethoxy)phenyl]imidazo[1,2-a]pyrazin-8-amine,
1-(4-14-[(6-{1H-pyrrolo[3,2-b]pyridin-6-yl}imidazo[1,2-a]pyrazin-8-yl)amino]phenyl}piperazin-1-ypethan-1-one,
5-(8-{[3-(2-hydroxyethoxy)-4-(morpholin-4-yl)phenyl]amino}imidazo[1,2-a]pyrazin-6-yl)-1-methyl-2,3-dihydro-1H-1,3-benzodiazol-2-one,
[(3S)-1-{2-methoxy-4-[(6-{1H-pyrrolo[3,2-b]pyridin-6-yl}imidazo[1,2-a]pyrazin-8-yl)amino]phenyl}pyrrolidin-3-yl]methanol,
5-(8-{[3-methoxy-4-(morpholin-4-yl)phenyl]amino}imidazo[1,2-a]pyrazin-6-yl)-Nmethylpyridin-3-amine,
5-(8-{[3-methoxy-4-(morpholin-4-yl)phenyl]amino}imidazo[1,2-a]pyrazin-6-yl)-1-methyl-2,3-dihydro-1H-1,3-benzodiazol-2-one,
5-[8-({4-[(3R)-3-hydroxypiperidin-1-yl]phenyl}amino)imidazo[1,2-a]pyrazin-6-yl]-1-methyl-2,3-dihydro-1H-1,3-benzodiazol-2-one,
(3R)-1-{2-methoxy-4-[(6-{1H-pyrrolo[3,2-b]pyridin-6-yl}imidazo[1,2-a]pyrazin-8-yl)amino]phenyl}piperidin-3-ol,
4-methyl-7-(8-{[4-(morpholin-4-yl)phenyl]amino}imidazo[1,2-a]pyrazin-6-yl)-1,2,3,4-tetrahydroquinoxalin-2-one,
[(2R)-4-{2-methoxy-4-[(6-{1H-pyrrolo[3,2-b]pyridin-6-yl}imidazo[1,2-a]pyrazin-8-yl)amino]phenyl}morpholin-2-yl]methanol, and
(3R)-1-{4-[(6-{1H-pyrrolo[3,2-b]pyridin-6-yl}imidazo[1,2-a]pyrazin-8-yl)amino]phenyl}piperidin-3-ol,
and pharmaceutically acceptable salts thereof.

In all of the foregoing examples, one or more hydrogen atoms in the compound of the present application is optionally replaced with a deuterium atom or D. As known in the art, the deuterium atom is a non-radioactive isotope of the hydrogen atom. The compound having a deuterium atom may have a reduced rate of metabolism. In all of the foregoing examples, the chemical entities can be administered alone, as mixtures, or in combination with other active agents.

Methods for obtaining the novel compounds described herein will be apparent to those of ordinary skill in the art, suitable procedures being described, for example, in the reaction schemes and examples below, and in the references cited herein.

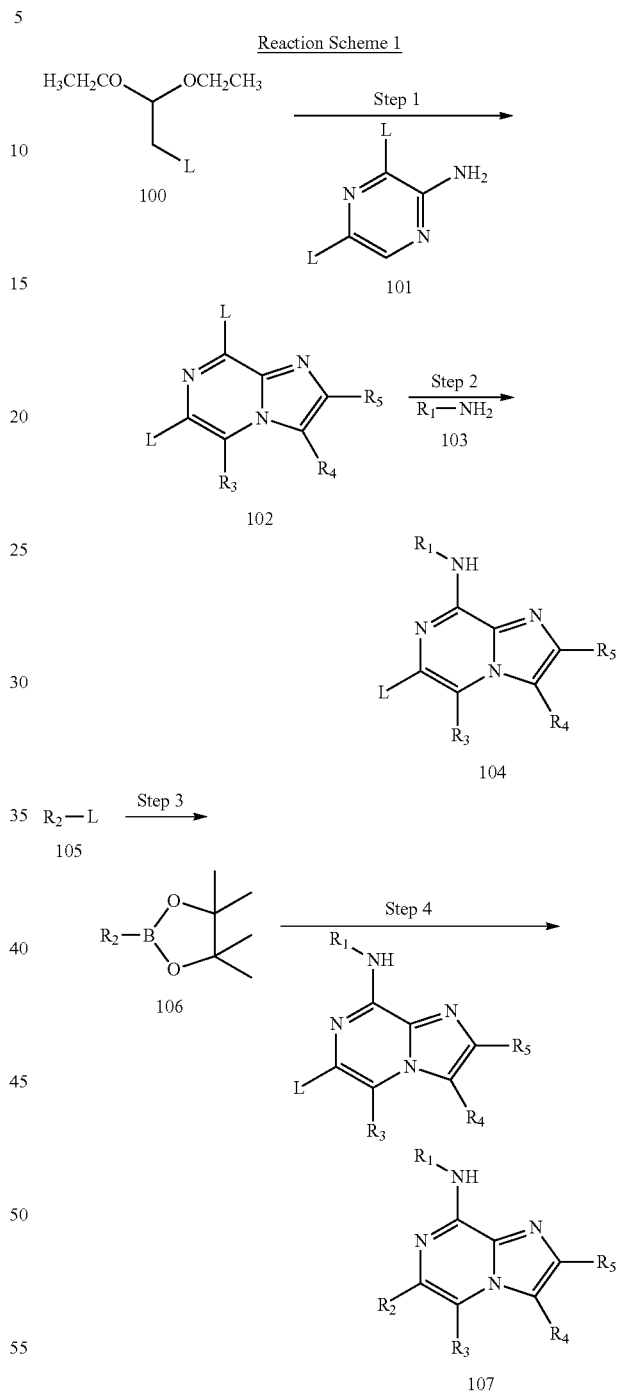

Referring to Reaction Scheme 1, Step 1, an excess (such as about 3.5 equivalents) of a compound of Formula 100, where L is a leaving group such as bromide is combined with an aqueous solution of acid (such as 48% aqueous hydrogen bromide), and the mixture is stirred at reflux for about 2 h. The mixture is cooled to about 40° C. and base (such as solid sodium bicarbonate) is added. The reaction mixture is filtered and a compound of Formula 101, where L is a leaving group such as bromide is added, and the reaction mixture is stirred at reflux for about 16 h. The product, a compound of Formula 102, is isolated and optionally purified.

Referring to Reaction Scheme 1, Step 2, a solution of a compound of Formula 103 in a polar solvent such as N,N-dimethylformamide is added an excess (such as about 1.3 equivalents) to a compound of Formula 102, where L is a leaving group such as bromide. An organic base such as N,N-diisopropylethylamine is added and the mixture is stirred at about 120° C. for about 13 h. The product, a compound of Formula 104, is isolated and optionally purified.

Referring to the Reaction Scheme 1, Step 3, a mixture of a compound of Formula 105, where L is a leaving group such as bromide is combined with an excess of bis(pinacolato)diboron (such as about 1.1 equivalents) and an excess of an inorganic base (such as about 3.0 equivalents), such as potassium acetate in a polar solvent such as dimethyl sulfoxide. The reaction mixture is sparged with nitrogen and stirred for about 5 min. The reaction mixture is treated with about 0.2 equivalent of dichloro 1,1-bis(diphenylphosphino)ferrocene palladium(II) dichloromethane and stirred at about 80° C. for about 3 h. The product, a compound of Formula 106, is isolated and optionally purified.

Referring to Reaction Scheme 1, Step 4, an excess of compound of Formula 106 (such as about 1.1 equivalents) and a compound of Formula 104 where L is a leaving group such as bromide are taken up in an aqueous solution of base (such as 1M sodium carbonate) and an inert solvent such as 1,4-dioxane. The reaction mixture is sparged with nitrogen and stirred for about 5 min. The resulting mixture is treated with about 0.1 equivalent of tetrakis(triphenylphosphine)palladium(0) and reacted under microwave irradiation at about 135° C. for about 30 min. The resulting product, a compound of Formula 107, is isolated and optionally purified.

Accordingly, provided is a method of treating a patient, for example, a mammal, such as a human, having a disease responsive to inhibition of Syk activity, comprising administrating to the patient having such a disease, an effective amount of at least one chemical entity described herein.

In some embodiments, the chemical entities described herein may also inhibit other kinases, such that disease, disease symptoms, and conditions associated with these kinases is also treated. In other embodiments, a compound having a deuterium atom may have a reduced rate of metabolism and be suitable for certain therapeutic treatments.

Methods of treatment also include inhibiting Syk activity and/or inhibiting B-cell activity, by inhibiting ATP binding or hydrolysis by Syk or by some other mechanism, in vivo, in a patient suffering from a disease responsive to inhibition of Syk activity, by administering an effective concentration of at least one chemical entity chosen described herein. An example of an effective concentration would be that concentration sufficient to inhibit Syk activity in vitro. An effective concentration may be ascertained experimentally, for example by assaying blood concentration of the chemical entity, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction.

Also provided is a method of treating a patient having cancer, an allergic disorder and/or an autoimmune and/or inflammatory disease, and/or an acute inflammatory reaction, by administering an effective amount of at least one chemical entity described herein.

In some embodiments, the conditions and diseases that can be affected using chemical entities described herein, include, but are not limited to: allergic disorders, including but not limited to eczema, allergic rhinitis or coryza, hay fever, bronchial asthma, urticaria (hives) and food allergies, and other atopic conditions; autoimmune and/or inflammatory diseases, including but not limited to psoriasis, ulcerative colitis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, myasthenia gravis, and the like; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis; polycystic kidney disease, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Syk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Syk comprising contacting the cell with at least one chemical entity described herein.

Also provided are methods of treatment in which at least one chemical entity described herein is the only active agent given to a patient and also includes methods of treatment in which at least one chemical entity described herein is given to a patient in combination with one or more additional active agents.

Thus in some embodiments, a method of treating cancer, an allergic disorder and/or an autoimmune and/or inflammatory disease, and/or an acute inflammatory reaction comprises administering to a patient in need thereof an effective amount of at least one chemical entity described herein, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with at least one chemical entity described herein. In some embodiments, at least one chemical entity described herein is combined with another active agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Chemical entities described herein can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with at least one chemical entity described herein in an amount sufficient to increase the sensitivity of cancer cells to the chemotherapeutic agent is also provided herein.

Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the chemical entities described herein are used in combination with Rituxan® (Rituximab) or other agents that work by selectively depleting CD20+ B-cells.

Included herein are methods of treatment in which at least one chemical entity described herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one active agent is an immunosuppressant compound such as methotrexate, leflunomide, cyclosporine, tacrolimus, azathioprine, or mycophenolate mofetil are used.

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a chemical entity described herein can be used as a diagnostic for identifying and/or obtaining compounds that have the function of modulating an activity of a kinase as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

EXAMPLES

The invention is further illustrated by the following non-limiting examples.

In the examples below, the following abbreviations have the following meanings. If an abbreviation is not defined, it has its generally accepted meaning.

| | |
|---|---|
| DME = | dimethyl ether |
| DMEM = | Dulbecco's modified Eagle's medium |
| DMF = | N,N-dimethylformamide |
| DMSO = | dimethylsulfoxide |
| $Et_2O$ = | diethylether |
| g = | gram |
| h = | hour |
| mg = | milligram |
| min = | minutes |
| mL = | milliliter |
| mmol = | millimoles |
| mM = | millimolar |
| ng = | nanogram |
| nm = | nanometer |
| nM = | nanomolar |
| PBS = | phosphate buffered saline |
| μL = | microliter |
| μM = | micromolar |

Example I

Preparation of 6-(benzo[d]thiazol-5-yl)-N-(3,4-dimethoxy-phenyl)imidazo[1,2-a]pyrazin-8-amine (4)

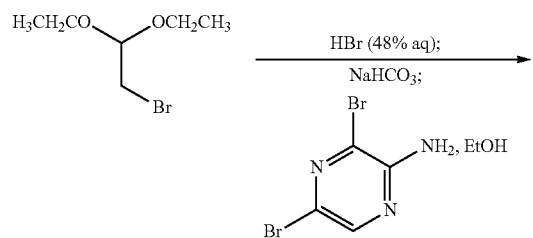

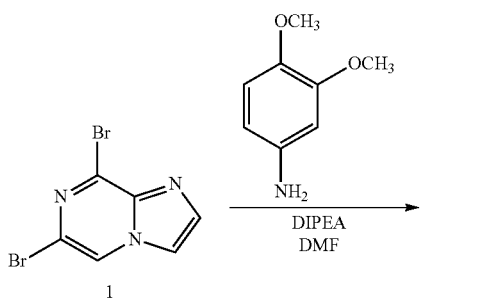

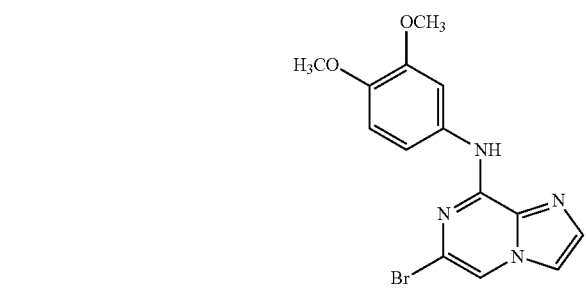

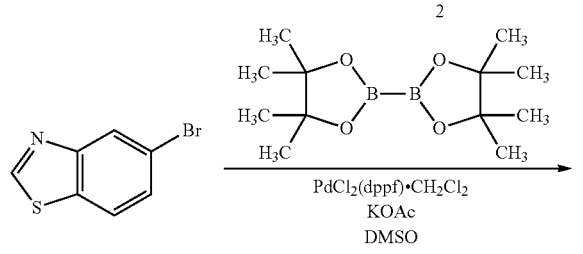

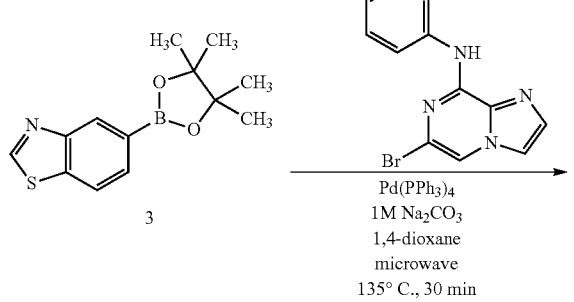

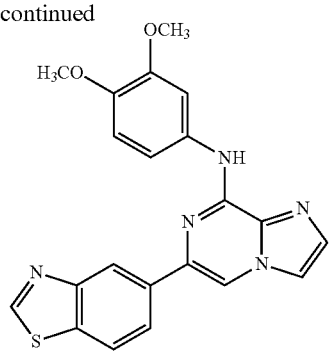

Preparation of 6,8-dibromoimidazo[1,2-a]pyrazine (1)

A 1-L four-neck round bottom flask equipped with a temperature probe, mechanical stirrer and reflux condenser was charged with 2-bromo-1,1-diethoxyethane (68.1 g, 346 mmol) and 48% aqueous hydrogen bromide (11.3 mL, 99.2 mmol), and the reaction mixture was stirred at reflux for 2 h. The resulting mixture was allowed to cool to 40° C. and solid sodium bicarbonate (8.50 g, 101 mmol) was added in small portions until gas evolution was observed to cease. Caution: initial addition of sodium bicarbonate to the warm solution resulted in vigorous gas evolution (foaming). The resulting suspension was filtered into a 1-L four-neck round bottomed flask and the filter cake was washed with ethanol (200 mL). The flask was equipped with a temperature probe, mechanical stirrer and reflux condenser. 3,5-Dibromopyrazin-2-amine (50.0 g, 198 mmol) was added and the reaction mixture was heated at reflux, with vigorous stirring, for 16 h. After this time, the suspension was cooled to 0° C. and filtered. The filter cake was washed with cold ethanol (50 mL), dried under vacuum and added to a 1-L three-neck round bottomed flask equipped with a mechanical stirrer. Water (200 mL) was added and the vigorously stirred suspension was treated portion-wise with solid potassium carbonate (27.4 g, 198 mmol). Caution: gas evolution upon the addition of potassium carbonate observed. After stirring for 30 min, the resulting precipitate was isolated by filtration and the filter cake washed with water (100 mL) followed by ethanol (50 mL). The filter cake was dried at 50° C. to a constant weight, under vacuum to provide 6,8-dibromoimidazo[1,2-a]pyrazine (1) (52.0 g, 94%) as a light yellow solid: $^{1}$H NMR (300 MHz, DMSO-$d_6$) δ 9.02 (s, 1H), 8.23 (s, 1H), 7.90 (s, 1H).

Preparation of 6-bromo-N-(3,4-dimethoxyphenyl) imidazo[1,2-a]pyrazin-8-amine (2)

A mixture of 3,4-dimethoxyaniline (18.0 g, 118 mmol), 6,8-dibromoimidazo[1,2-a]pyrazine (25.0 g, 90.4 mmol), and N,N-diisopropylethylamine (11.7 g, 90.4 mmol) in DMF (500 mL) was stirred at 120° C. overnight. After this time, the reaction was cooled to room temperature and concentrated to approximately 100 mL under reduced pressure. The dark brown reaction mixture was poured into ice-cold water (300 mL) and stirred for 10 min. The resulting brown precipitate was filtered and the filter cake washed with water (100 mL). The filter cake was dried under vacuum and recrystallization from methanol (~800 mL) to afford 6-bromo-N-(3,4,5-trimethoxyphenyl)imidazo[1,2-a]pyrazin-8-amine (2) (23.3 g, 74%) as a light brown needle-shaped solid: $^1$H NMR (300 MHz, DMSO-$d_6$) 9.81 (s, 1H), 8.22 (s, 1H), 7.93 (s, 1H), 7.75 (d, J=2.4 Hz, 1H), 7.62 (s, 1H), 7.53 (dd, J=8.7, 2.4, 1H), 6.94 (d, J=8.7 Hz, 1H), 3.77 (s, 3H), 3.75 (s, 3H); ESI MS m/z 349.2 [M+H]$^+$; HPLC, 6.92 min, >99% (AUC).

Preparation of 5-(4,4,5,5-tetramethyl-1,3,2-dioxaborolan-2-yl)benzo[d]thiazole (3)

A mixture of 5-bromobenzo[d]thiazole (428 mg, 2.00 mmol), bis(pinacolato)diboron (558 mg, 2.20 mmol) and potassium acetate (588 mg, 6.00 mmol) in dimethyl sulfoxide (7 mL) was sparged with nitrogen while stirring for 5 min. Dichloro 1,1-bis(diphenylphosphino)ferrocene palladium (II) dichloromethane (293 mg, 0.40 mmol) was then added and the reaction stirred at 85° C. for 3 h. After this time, the mixture was filtered through a pad of Celite and the filter cake was washed with ethyl acetate (75 mL) then water (20 mL). The filtrate was diluted with ethyl acetate (100 mL) and washed with water (2×75 mL), then brine (75 mL). The organic phase was dried over anhydrous sodium sulfate, filtered and concentrated under reduced pressure. The resulting residue was purified by chromatography (silica, gradient 0% to 50% ethyl acetate in methylene chloride) to afford 5-(4,4,5,5-tetramethyl-1,3,2-dioxaborolan-2-yl)benzo[d]thiazole (3) (200 mg, 38%) as a light brown solid: $^1$H NMR (300 MHz, DMSO-$d_6$) δ 9.41 (s, 1H), 8.32 (s, 1H), 8.18 (d, 1H, J=8.0 Hz), 7.72 (d, 1H, J=8.0 Hz), 1.33 (s, 12H); ESI MS m/z 262.1 [M+H]$^+$.

Preparation of 6-(benzo[d]thiazol-5-yl)-N-(3,4-dimethoxyphenyl)imidazo[1,2-a]pyrazin-8-amine (4)

A mixture of 6-bromo-N-(3,4-dimethoxyphenyl)imidazo[1,2-a]pyrazin-8-amine (2) (209 mg, 0.601 mmol), and 5-(4,4,5,5-tetramethyl-1,3,2-dioxaborolan-2-yl)benzo[d]thiazole (3) (180 mg, 0.689 mmol) in 1 M aqueous sodium carbonate (0.76 mL) and 1,4-dioxane (2.4 mL) was sparged with nitrogen while stirring for 5 min. Tetrakis(triphenyl-phosphine)palladium(0) (69 mg, 0.06 mmol) was then added and the resulting mixture reacted under microwave irradiation at 135° C. for 30 min. After this time, the reaction was cooled to ambient temperature, diluted with 1:9 methanol/ethyl acetate (75 mL), and washed with water (50 mL) then brine (50 mL). The organic phase was dried over anhydrous sodium sulfate, filtered and concentrated under reduced pressure. The resulting residue was purified by chromatography (silica, gradient 0% to 10% methanol in methylene chloride) to afford 6-(benzo[d]thiazol-5-yl)-N-(3,4-dimethoxyphenyl)imidazo[1,2-a]pyrazin-8-amine (4) (169 mg, 70%) as an off-white solid: mp 179-181° C.; $^1$H NMR (300 MHz, DMSO-$d_6$) δ 9.56 (s, 1H), 9.45 (s, 1H), 8.78 (s, 1H), 8.76 (d, 1H, J=1.2 Hz), 8.26 (d, 1H, J=8.7 Hz), 8.14 (m, 2H), 8.00 (s, 1H), 7.66 (s, 1H), 7.58 (dd, 1H, J=8.7, 2.4 Hz), 6.99 (d, 1H, J=8.7 Hz), 3.87 (s, 3H), 3.76 (s, 3H); MS m/z 404.6 [M+H]$^+$; HPLC, 6.475 min, 98.6% (AUC).

Example 2

The following compounds were prepared using procedures similar to those described above. Those of ordinary skill in the art of organic synthesis will recognize when starting materials or reaction conditions should be varied to obtain the desired compound.

MS data reported in this example was obtained as follows: MS conditions: Electrospray MS is performed on a MICROMASS LCT equipped with a LockSpray source for accurate mass measurements. Spectra are acquired in positive ion mode from 100-1000 Da at an acquisition rate of 1 spectrum/0.9 s with a 0.1 s interscan delay. The instrument is tuned for a resolution of 5000 (FWHM). Every 5$^{th}$ scan is taken from the reference position of the Lockspray source. Leucine enkephalin (556.2771 [M+H]$^+$) is used as the reference, or lock mass.

| Structure | Name | [M + H]$^+$ |
|---|---|---|
| 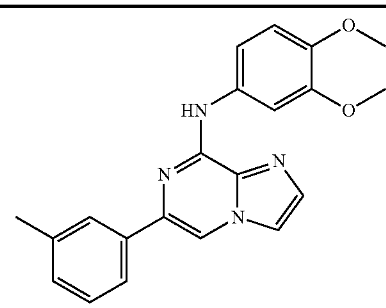 | N-(3,4-dimethoxyphenyl)-6-(3-methylphenyl)imidazo[1,2-a]pyrazin-8-amine | 361.2 |
| 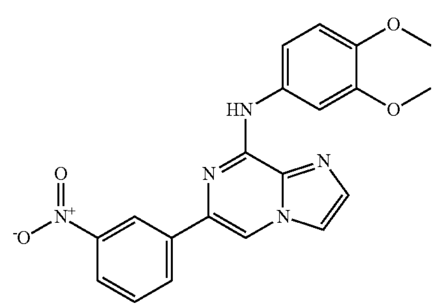 | N-(3,4-dimethoxyphenyl)-6-(3-nitrophenyl)imidazo[1,2-a]pyrazin-8-amine | 392.1 |

-continued

| Structure | Name | [M + H]+ |
|---|---|---|
| 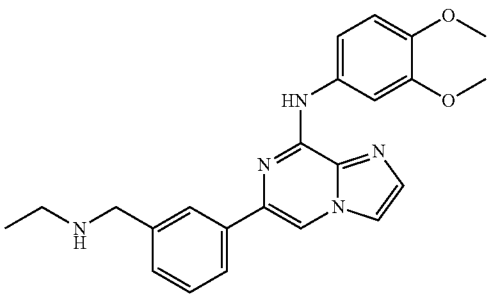 [SMILES: CCNCc1cccc(-c2cn3ccnc3c(Nc3ccc(OC)c(OC)c3)n2)c1] | N-(3,4-dimethoxyphenyl)-6-{3-[(ethylamino)methyl]phenyl}imidazo[1,2-a]pyrazin-8-amine | 404.7 |
| 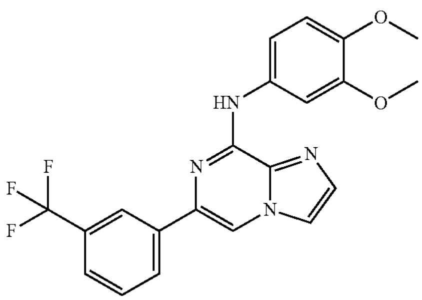 [SMILES: COc1ccc(Nc2nc(-c3cccc(C(F)(F)F)c3)cn3ccnc23)cc1OC] | N-(3,4-dimethoxyphenyl)-6-[3-(trifluoromethyl)phenyl]imidazo[1,2-a]pyrazin-8-amine | 415.5 |
| 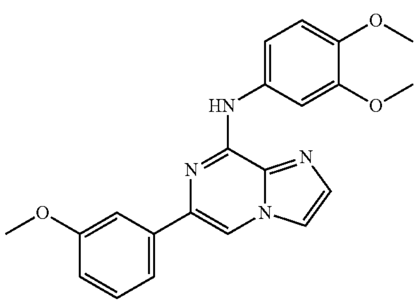 | N-(3,4-dimethoxyphenyl)-6-(3-methoxyphenyl)imidazo[1,2-a]pyrazin-8-amine | 377.5 |
| 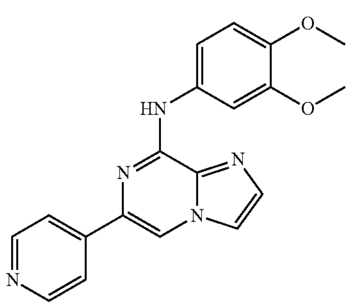 [SMILES: COc1ccc(Nc2nc(-c3ccncc3)cn3ccnc23)cc1OC] | N-(3,4-dimethoxyphenyl)-6-(pyridin-4-yl)imidazo[1,2-a]pyrazin-8-amine | 348.3 |
| 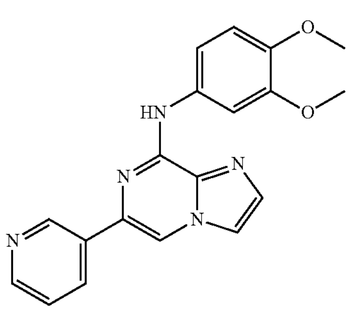 [SMILES: COc1ccc(Nc2nc(-c3cccnc3)cn3ccnc23)cc1OC] | N-(3,4-dimethoxyphenyl)-6-(pyridin-3-yl)imidazo[1,2-a]pyrazin-8-amine | 348.2 |

-continued

| Structure | Name | [M + H]⁺ |
|---|---|---|
| 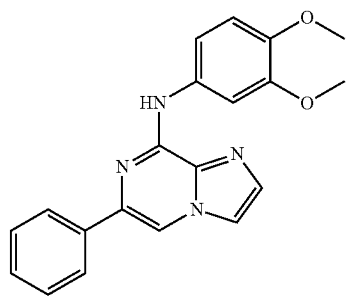 [SMILES: COc1ccc(Nc2nc(-c3ccccc3)cn3ccnc23)cc1OC] | N-(3,4-dimethoxyphenyl)-6-phenylimidazo[1,2-a]pyrazin-8-amine | 347 |
| 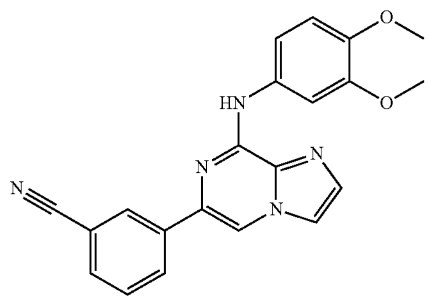 [SMILES: COc1ccc(Nc2nc(-c3cccc(C#N)c3)cn3ccnc23)cc1OC] | 3-{8-[(3,4-dimethoxyphenyl)amino]imidazo[1,2-a]pyrazin-6-yl}benzonitrile | 372 |
| 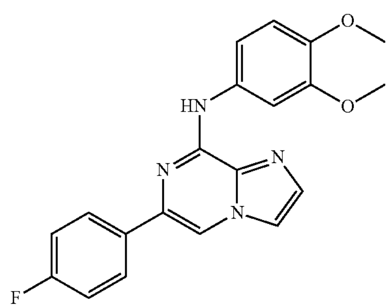 [SMILES: COc1ccc(Nc2nc(-c3ccc(F)cc3)cn3ccnc23)cc1OC] | N-(3,4-dimethoxyphenyl)-6-(4-fluorophenyl)imidazo[1,2-a]pyrazin-8-amine | 365.2 |
| 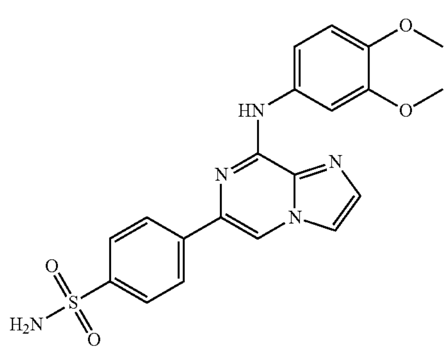 [SMILES: COc1ccc(Nc2nc(-c3ccc(S(N)(=O)=O)cc3)cn3ccnc23)cc1OC] | 4-{8-[(3,4-dimethoxyphenyl)amino]imidazo[1,2-a]pyrazin-6-yl}benzene-1-sulfonamide | 426.2 |
| 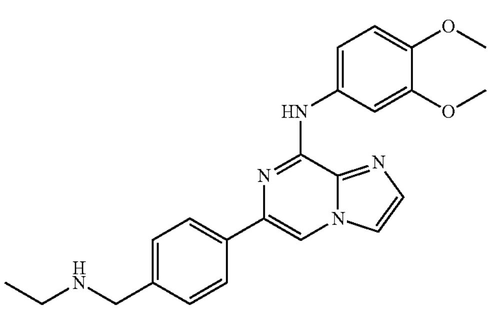 [SMILES: CCNCc1ccc(-c2cn3ccnc3c(Nc3ccc(OC)c(OC)c3)n2)cc1] | N-(3,4-dimethoxyphenyl)-6-{4-[(ethylamino)methyl]phenyl}imidazo[1,2-a]pyrazin-8-amine | 404.7 |

-continued

| Structure | Name | [M + H]⁺ |
|---|---|---|
| 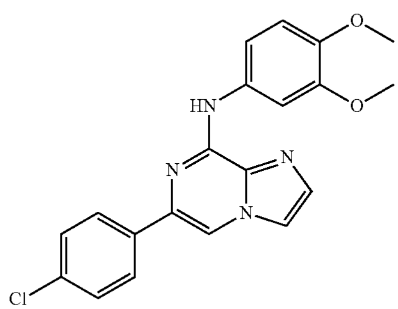 [SMILES: COc1ccc(Nc2nc(-c3ccc(Cl)cc3)cn3ccnc23)cc1OC] | 6-(4-chlorophenyl)-N-(3,4-dimethoxyphenyl)imidazo[1,2-a]pyrazin-8-amine | 381.2 |
| 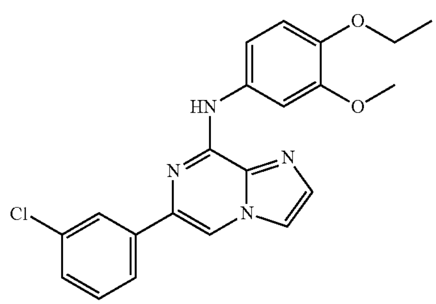 [SMILES: CCOc1ccc(Nc2nc(-c3cccc(Cl)c3)cn3ccnc23)cc1OC] | 6-(3-chlorophenyl)-N-(4-ethoxy-3-methoxyphenyl)imidazo[1,2-a]pyrazin-8-amine | 395.2 |
| 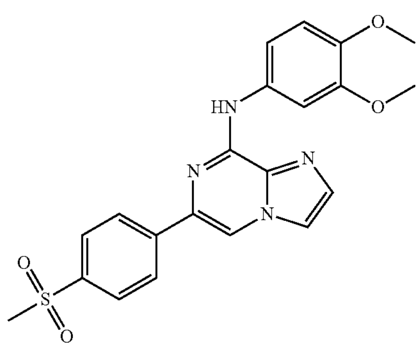 | N-(3,4-dimethoxyphenyl)-6-(4-methanesulfonylphenyl)imidazo[1,2-a]pyrazin-8-amine | 425.2 |
| 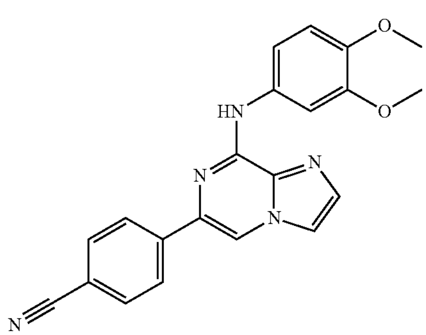 [SMILES: COc1ccc(Nc2nc(-c3ccc(C#N)cc3)cn3ccnc23)cc1OC] | 4-{8-[(3,4-dimethoxyphenyl)amino]imidazo[1,2-a]pyrazin-6-yl}benzonitrile | 372.1 |
| 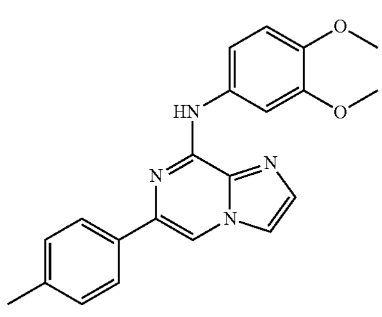 | N-(3,4-dimethoxyphenyl)-6-(4-methylphenyl)imidazo[1,2-a]pyrazin-8-amine | 361.2 |

-continued

| Structure | Name | [M + H]+ |
|---|---|---|
| 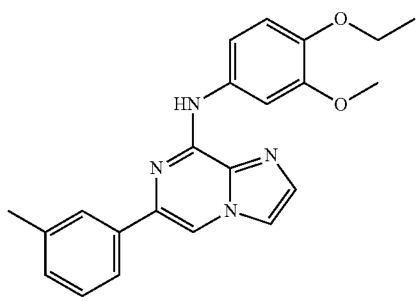 [SMILES: CCOc1ccc(Nc2nc(-c3cccc(C)c3)cn3ccnc23)cc1OC] | N-(4-ethoxy-3-methoxyphenyl)-6-(3-methylphenyl)imidazo[1,2-a]pyrazin-8-amine | 375.2 |
| 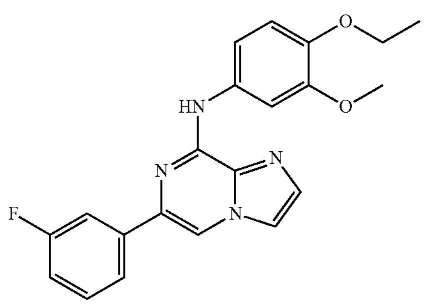 [SMILES: CCOc1ccc(Nc2nc(-c3cccc(F)c3)cn3ccnc23)cc1OC] | N-(4-ethoxy-3-methoxyphenyl)-6-(3-fluorophenyl)imidazo[1,2-a]pyrazin-8-amine | 379.1 |
| 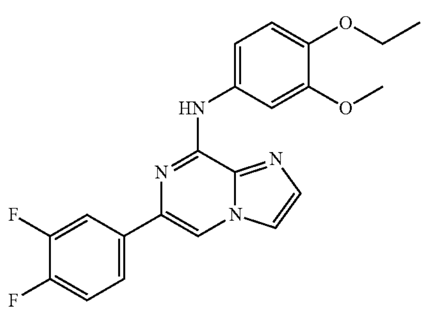 [SMILES: CCOc1ccc(Nc2nc(-c3ccc(F)c(F)c3)cn3ccnc23)cc1OC] | 6-(3,4-difluorophenyl)-N-(4-ethoxy-3-methoxyphenyl)imidazo[1,2-a]pyrazin-8-amine | 397.1 |
| 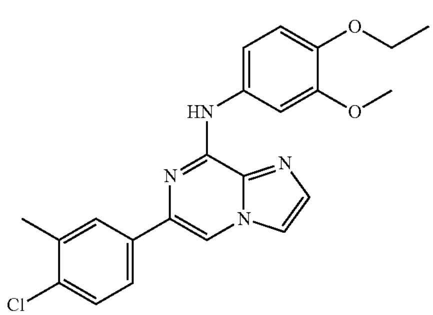 [SMILES: CCOc1ccc(Nc2nc(-c3ccc(Cl)c(C)c3)cn3ccnc23)cc1OC] | 6-(4-chloro-3-methylphenyl)-N-(4-ethoxy-3-methoxyphenyl)imidazo[1,2-a]pyrazin-8-amine | 409 |
| 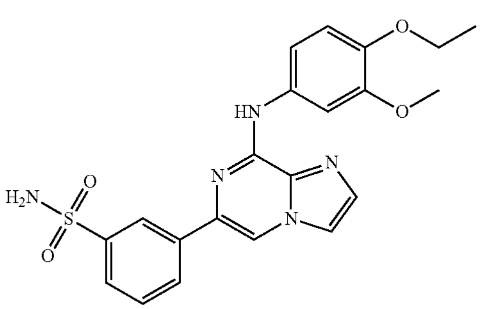 [SMILES: CCOc1ccc(Nc2nc(-c3cccc(S(N)(=O)=O)c3)cn3ccnc23)cc1OC] | 3-{8-[(4-ethoxy-3-methoxyphenyl)amino]imidazo[1,2-a]pyrazin-6-yl}benzene-1-sulfonamide | 440.1 |

| Structure | Name | [M + H]⁺ |
|---|---|---|
| 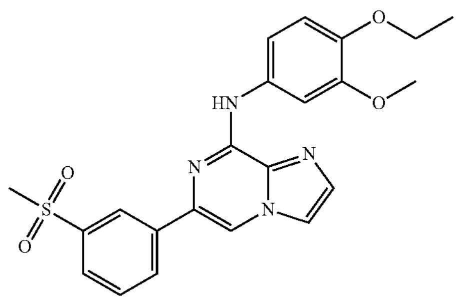 [SMILES: CCOc1ccc(Nc2nc(-c3cccc(S(C)(=O)=O)c3)cn3ccnc23)cc1OC] | N-(4-ethoxy-3-methoxyphenyl)-6-(3-methanesulfonylphenyl)imidazo[1,2-a]pyrazin-8-amine | 439.3 |
| 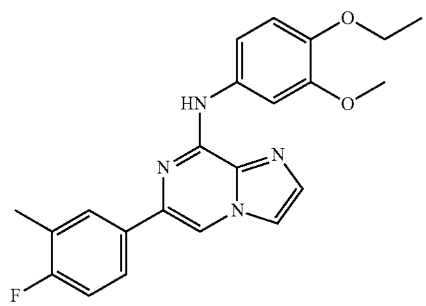 [SMILES: CCOc1ccc(Nc2nc(-c3ccc(F)c(C)c3)cn3ccnc23)cc1OC] | N-(4-ethoxy-3-methoxyphenyl)-6-(4-fluoro-3-methylphenyl)imidazo[1,2-a]pyrazin-8-amine | 393.2 |
| 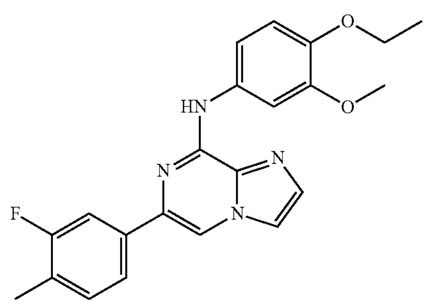 [SMILES: CCOc1ccc(Nc2nc(-c3ccc(C)c(F)c3)cn3ccnc23)cc1OC] | N-(4-ethoxy-3-methoxyphenyl)-6-(3-fluoro-4-methylphenyl)imidazo[1,2-a]pyrazin-8-amine | 393.2 |
| 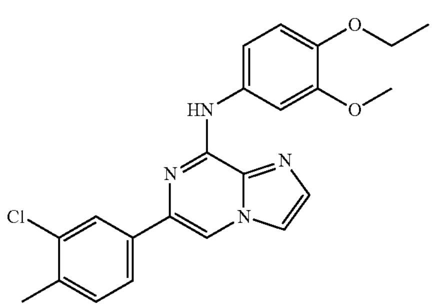 [SMILES: CCOc1ccc(Nc2nc(-c3ccc(C)c(Cl)c3)cn3ccnc23)cc1OC] | 6-(3-chloro-4-methylphenyl)-N-(4-ethoxy-3-methoxyphenyl)imidazo[1,2-a]pyrazin-8-amine | 409.2 |
| 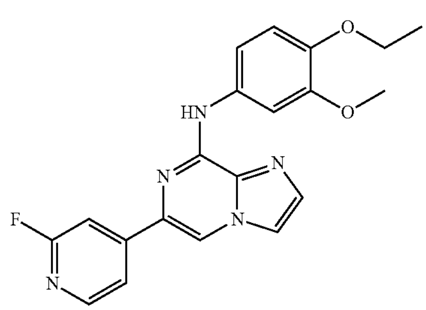 [SMILES: CCOc1ccc(Nc2nc(-c3ccnc(F)c3)cn3ccnc23)cc1OC] | N-(4-ethoxy-3-methoxyphenyl)-6-(2-fluoropyridin-4-yl)imidazo[1,2-a]pyrazin-8-amine | 380.3 |

-continued

| Structure | Name | [M + H]+ |
|---|---|---|
| 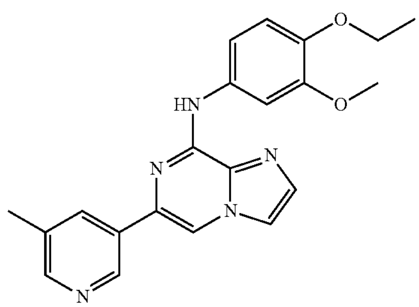 [SMILES: CCOc1ccc(Nc2nc(-c3cncc(C)c3)cn3ccnc23)cc1OC] | N-(4-ethoxy-3-methoxyphenyl)-6-(5-methylpyridin-3-yl)imidazo[1,2-a]pyrazin-8-amine | 376.5 |
| 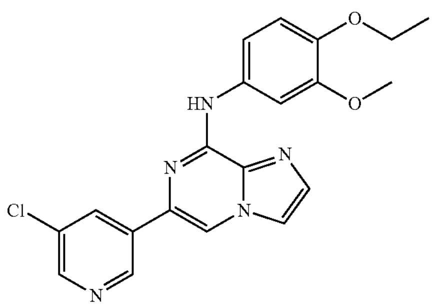 [SMILES: CCOc1ccc(Nc2nc(-c3cncc(Cl)c3)cn3ccnc23)cc1OC] | 6-(5-chloropyridin-3-yl)-N-(4-ethoxy-3-methoxyphenyl)imidazo[1,2-a]pyrazin-8-amine | 396.2 |
| 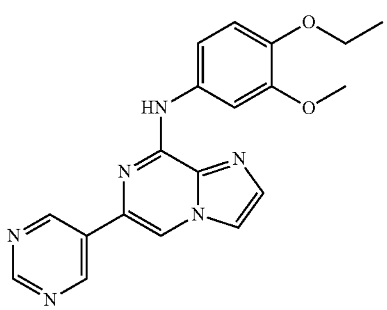 [SMILES: CCOc1ccc(Nc2nc(-c3cncnc3)cn3ccnc23)cc1OC] | N-(4-ethoxy-3-methoxyphenyl)-6-(pyrimidin-5-yl)imidazo[1,2-a]pyrazin-8-amine | 363.5 |
| 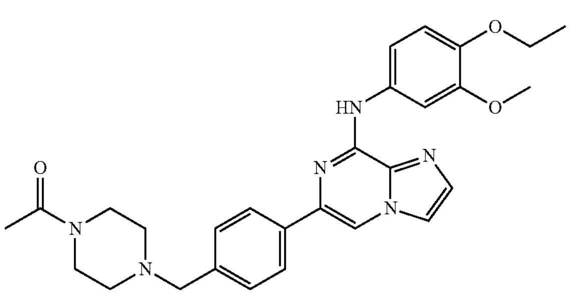 [SMILES: CCOc1ccc(Nc2nc(-c3ccc(CN4CCN(C(C)=O)CC4)cc3)cn3ccnc23)cc1OC] | 1-{4-[(4-{8-[(4-ethoxy-3-methoxyphenyl)amino]imidazo[1,2-a]pyrazin-6-yl}phenyl)methyl]piperazin-1-yl}ethan-1-one | 487.5 |
| 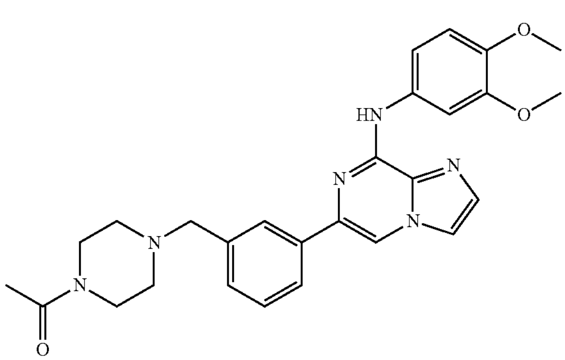 [SMILES: COc1ccc(Nc2nc(-c3cccc(CN4CCN(C(C)=O)CC4)c3)cn3ccnc23)cc1OC] | 1-{4-[(3-{8-[(3,4-dimethoxyphenyl)amino]imidazo[1,2-a]pyrazin-6-yl}phenyl)methyl]piperazin-1-yl}ethan-1-one | 487.1 |

-continued

| Structure | Name | [M + H]+ |
|---|---|---|
| 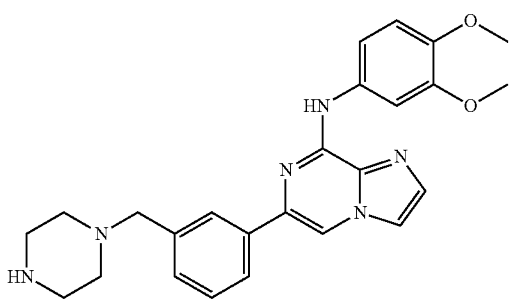 [SMILES: COc1ccc(Nc2nc(-c3cccc(CN4CCNCC4)c3)cn3ccnc23)cc1OC] | N-(3,4-dimethoxyphenyl)-6-[3-(piperazin-1-ylmethyl)phenyl]imidazo[1,2-a]pyrazin-8-amine | 445.3 |
| 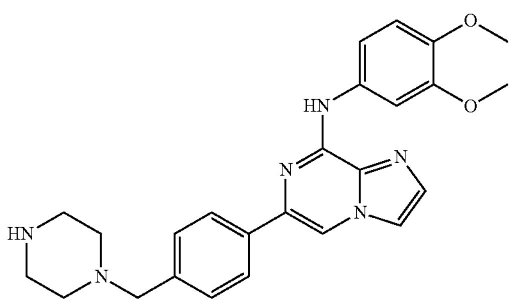 [SMILES: COc1ccc(Nc2nc(-c3ccc(CN4CCNCC4)cc3)cn3ccnc23)cc1OC] | N-(3,4-dimethoxyphenyl)-6-[4-(piperazin-1-ylmethyl)phenyl]imidazo[1,2-a]pyrazin-8-amine | 445.3 |
| 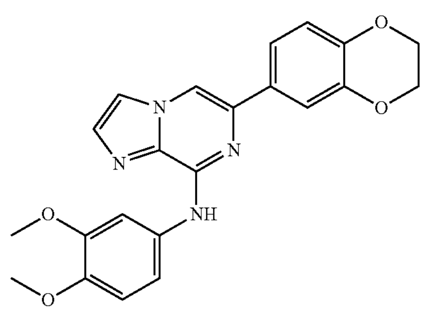 [SMILES: COc1ccc(Nc2nc(-c3ccc4c(c3)OCCO4)cn3ccnc23)cc1OC] | 6-(2,3-dihydro-1,4-benzodioxin-6-yl)-N-(3,4-dimethoxyphenyl)imidazo[1,2-a]pyrazin-8-amine | 404.42 |
| 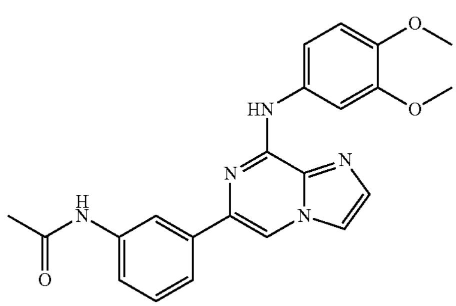 [SMILES: COc1ccc(Nc2nc(-c3cccc(NC(C)=O)c3)cn3ccnc23)cc1OC] | N-(3-{8-[(3,4-dimethoxyphenyl)amino]imidazo[1,2-a]pyrazin-6-yl}phenyl)acetamide | 404.9 |
| 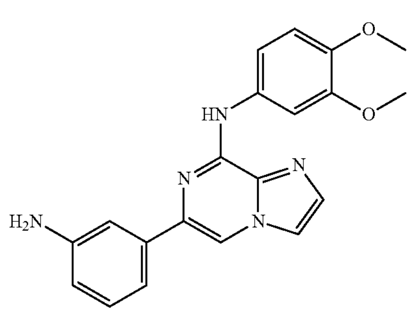 [SMILES: COc1ccc(Nc2nc(-c3cccc(N)c3)cn3ccnc23)cc1OC] | 6-(3-aminophenyl)-N-(3,4-dimethoxyphenyl)imidazo[1,2-a]pyrazin-8-amine | 362.8 |

-continued

| Structure | Name | [M + H]⁺ |
|---|---|---|
| 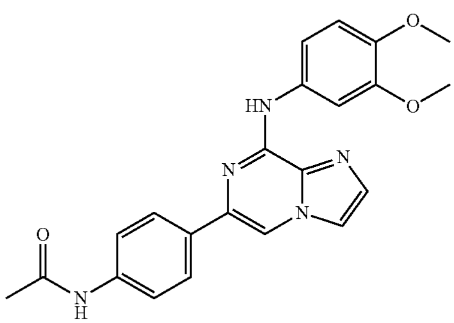 [SMILES: COc1ccc(Nc2nc(-c3ccc(NC(C)=O)cc3)cn3ccnc23)cc1OC] | N-(4-{8-[(3,4-dimethoxyphenyl)amino]imidazo[1,2-a]pyrazin-6-yl}phenyl)acetamide | 404.6 |
| 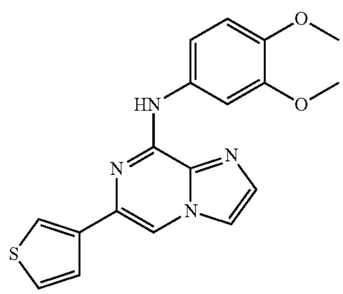 [SMILES: COc1ccc(Nc2nc(-c3ccsc3)cn3ccnc23)cc1OC] | N-(3,4-dimethoxyphenyl)-6-(thiophen-3-yl)imidazo[1,2-a]pyrazin-8-amine | 353.5 |
| 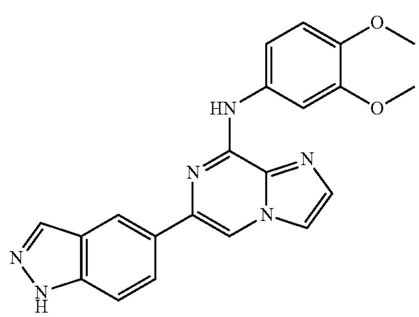 [SMILES: COc1ccc(Nc2nc(-c3ccc4[nH]ncc4c3)cn3ccnc23)cc1OC] | N-(3,4-dimethoxyphenyl)-6-(1H-indazol-5-yl)imidazo[1,2-a]pyrazin-8-amine | 387.2 |
| 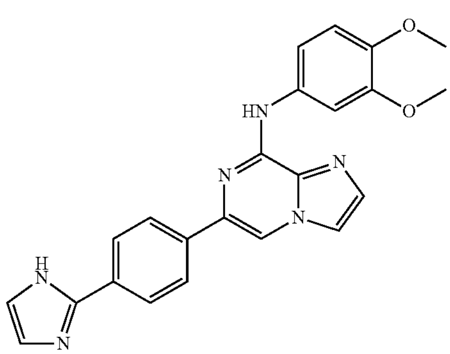 [SMILES: COc1ccc(Nc2nc(-c3ccc(-c4ncc[nH]4)cc3)cn3ccnc23)cc1OC] | N-(3,4-dimethoxyphenyl)-6-[4-(1H-imidazol-2-yl)phenyl]imidazo[1,2-a]pyrazin-8-amine | 413.3 |
| 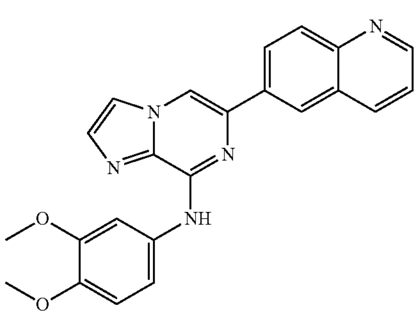 [SMILES: COc1ccc(Nc2nc(-c3ccc4ncccc4c3)cn3ccnc23)cc1OC] | N-(3,4-dimethoxyphenyl)-6-(quinolin-6-yl)imidazo[1,2-a]pyrazin-8-amine | 398 |

-continued

| Structure | Name | [M + H]+ |
|---|---|---|
| 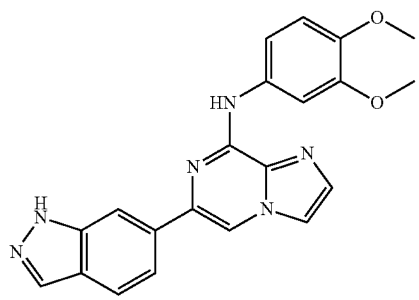 [SMILES: COc1ccc(Nc2nc(-c3ccc4cn[nH]c4c3)cn3ccnc23)cc1OC] | N-(3,4-dimethoxyphenyl)-6-(1H-indazol-6-yl)imidazo[1,2-a]pyrazin-8-amine | 387.4 |
| 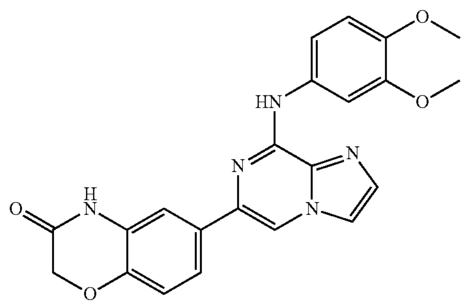 [SMILES: COc1ccc(Nc2nc(-c3ccc4c(c3)NC(=O)CO4)cn3ccnc23)cc1OC] | 6-{8-[(3,4-dimethoxyphenyl)amino]imidazo[1,2-a]pyrazin-6-yl}-3,4-dihydro-2H-1,4-benzoxazin-3-one | 418.6 |
| 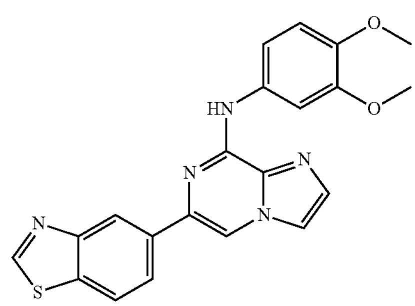 | 6-(1,3-benzothiazol-5-yl)-N-(3,4-dimethoxyphenyl)imidazo[1,2-a]pyrazin-8-amine | 404.6 |
| 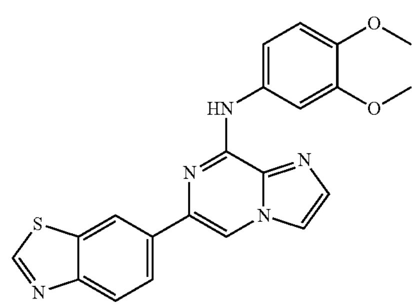 [SMILES: COc1ccc(Nc2nc(-c3ccc4ncsc4c3)cn3ccnc23)cc1OC] | 6-(1,3-benzothiazol-6-yl)-N-(3,4-dimethoxyphenyl)imidazo[1,2-a]pyrazin-8-amine | 404.9 |
| 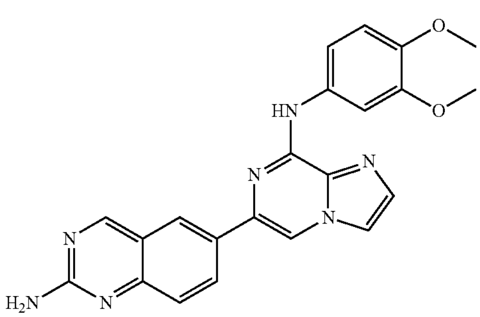 [SMILES: COc1ccc(Nc2nc(-c3ccc4nc(N)ncc4c3)cn3ccnc23)cc1OC] | 6-{8-[(3,4-dimethoxyphenyl)amino]imidazo[1,2-a]pyrazin-6-yl}quinazolin-2-amine | 414.4 |

-continued
| Structure | Name | [M + H]+ |
|---|---|---|
| 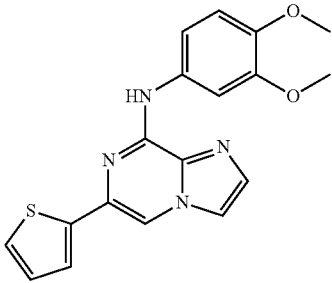 [SMILES: COc1ccc(Nc2nc(-c3cccs3)cn3ccnc23)cc1OC] | N-(3,4-dimethoxyphenyl)-6-(thiophen-2-yl)imidazo[1,2-a]pyrazin-8-amine | 353.4 |
| 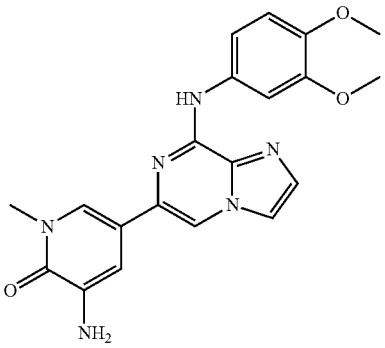 [SMILES: COc1ccc(Nc2nc(-c3cc(N)c(=O)n(C)c3)cn3ccnc23)cc1OC] | 3-amino-5-{8-[(3,4-dimethoxyphenyl)amino]imidazo[1,2-a]pyrazin-6-yl}-1-methyl-1,2-dihydropyridin-2-one | 393.3 |
| 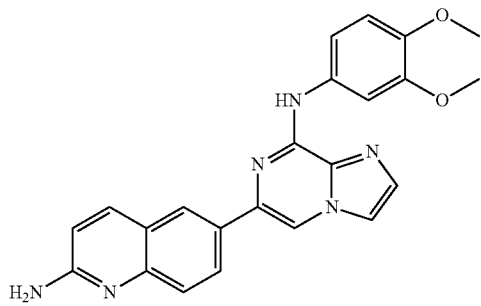 [SMILES: COc1ccc(Nc2nc(-c3ccc4nc(N)ccc4c3)cn3ccnc23)cc1OC] | 6-{8-[(3,4-dimethoxyphenyl)amino]imidazo[1,2-a]pyrazin-6-yl}quinolin-2-amine | 413.3 |
| 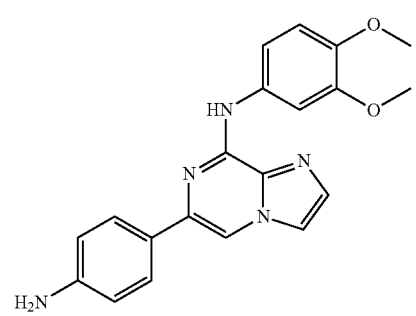 [SMILES: COc1ccc(Nc2nc(-c3ccc(N)cc3)cn3ccnc23)cc1OC] | 6-(4-aminophenyl)-N-(3,4-dimethoxyphenyl)imidazo[1,2-a]pyrazin-8-amine | 362.6 |
| 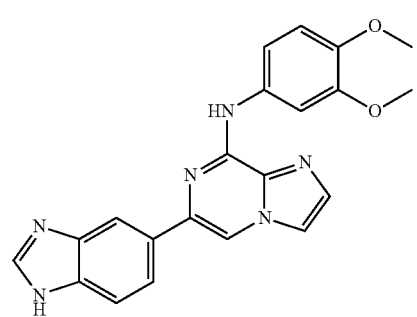 [SMILES: COc1ccc(Nc2nc(-c3ccc4[nH]cnc4c3)cn3ccnc23)cc1OC] | 6-(1H-1,3-benzodiazol-5-yl)-N-(3,4-dimethoxyphenyl)imidazo[1,2-a]pyrazin-8-amine | 387.1 |

| Structure | Name | [M + H]+ |
|---|---|---|
| 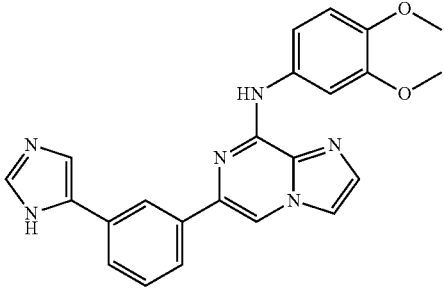 [SMILES: COc1ccc(Nc2nc(-c3cccc(-c4cnc[nH]4)c3)cn3ccnc23)cc1OC] | N-(3,4-dimethoxyphenyl)-6-[3-(1H-imidazol-5-yl)phenyl]imidazo[1,2-a]pyrazin-8-amine | 413.3 |
| 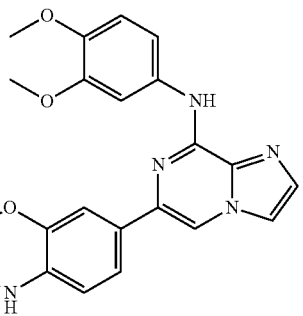 | 7-{8-[(3,4-dimethoxyphenyl)amino]imidazo[1,2-a]pyrazin-6-yl}-3,4-dihydro-2H-1,4-benzoxazin-3-one | 418.7 |
| 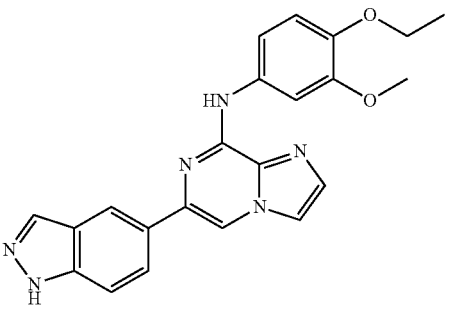 [SMILES: CCOc1ccc(Nc2nc(-c3ccc4[nH]ncc4c3)cn3ccnc23)cc1OC] | N-(4-ethoxy-3-methoxyphenyl)-6-(1H-indazol-5-yl)imidazo[1,2-a]pyrazin-8-amine | 401.2 |
| 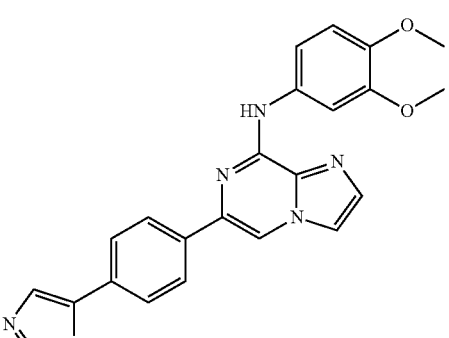 | N-(3,4-dimethoxyphenyl)-6-[4-(1H-imidazol-5-yl)phenyl]imidazo[1,2-a]pyrazin-8-amine | 413.4 |
| 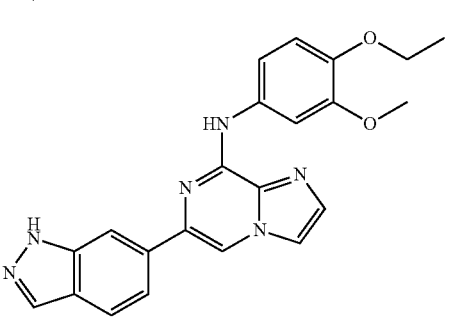 | N-(4-ethoxy-3-methoxyphenyl)-6-(1H-indazol-6-yl)imidazo[1,2-a]pyrazin-8-amine | 401.1 |

-continued

| Structure | Name | [M + H]⁺ |
|---|---|---|
| 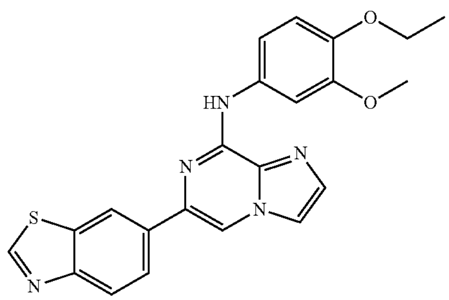 [SMILES: CCOc1ccc(Nc2nc(-c3ccc4ncsc4c3)cn3ccnc23)cc1OC] | 6-(1,3-benzothiazol-6-yl)-N-(4-ethoxy-3-methoxyphenyl)imidazo[1,2-a]pyrazin-8-amine | 418.7 |
| 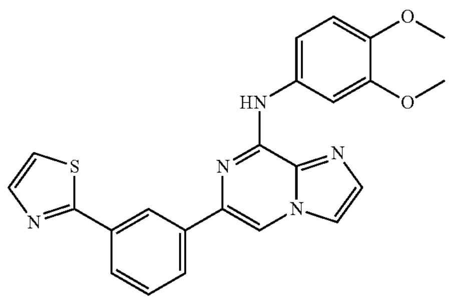 [SMILES: COc1ccc(Nc2nc(-c3cccc(-c4nccs4)c3)cn3ccnc23)cc1OC] | N-(3,4-dimethoxyphenyl)-6-[3-(1,3-thiazol-2-yl)phenyl]imidazo[1,2-a]pyrazin-8-amine | 430.5 |
| 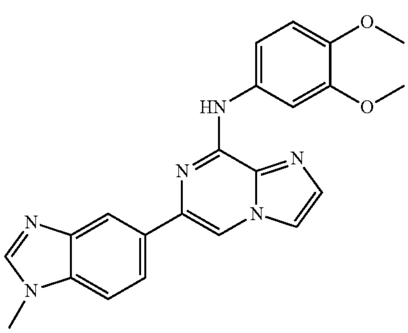 [SMILES: COc1ccc(Nc2nc(-c3ccc4c(c3)ncn4C)cn3ccnc23)cc1OC] | N-(3,4-dimethoxyphenyl)-6-(1-methyl-1H-1,3-benzodiazol-5-yl)imidazo[1,2-a]pyrazin-8-amine | 401.3 |
| 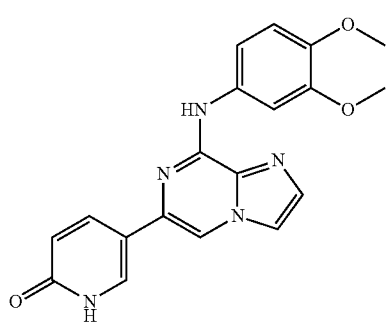 [SMILES: COc1ccc(Nc2nc(-c3ccc(=O)[nH]c3)cn3ccnc23)cc1OC] | 5-{8-[(3,4-dimethoxyphenyl)amino]imidazo[1,2-a]pyrazin-6-yl}-1,2-dihydropyridin-2-one | 364.5 |
| 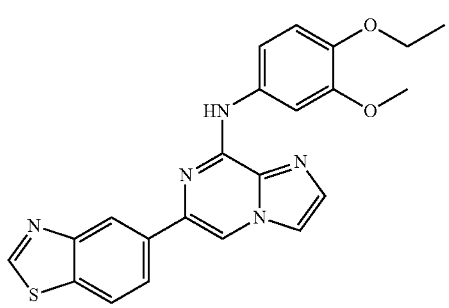 [SMILES: CCOc1ccc(Nc2nc(-c3ccc4scnc4c3)cn3ccnc23)cc1OC] | 6-(1,3-benzothiazol-5-yl)-N-(4-ethoxy-3-methoxyphenyl)imidazo[1,2-a]pyrazin-8-amine | 418.7 |

| Structure | Name | [M + H]+ |
|---|---|---|
| 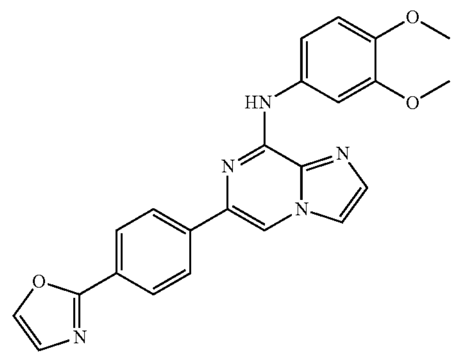 | N-(3,4-dimethoxyphenyl)-6-[4-(1,3-oxazol-2-yl)phenyl]imidazo[1,2-a]pyrazin-8-amine | 414.1 |
| 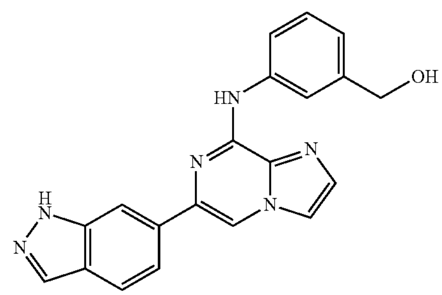 [SMILES: OCc1cccc(Nc2nc(-c3ccc4cn[nH]c4c3)cn3ccnc23)c1] | (3-{[6-(1H-indazol-6-yl)imidazo[1,2-a]pyrazin-8-yl]amino}phenyl)methanol | 357 |
| 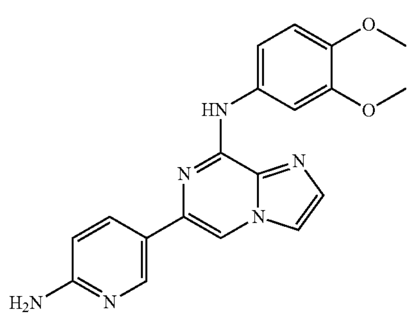 [SMILES: COc1ccc(Nc2nc(-c3ccc(N)nc3)cn3ccnc23)cc1OC] | 5-{8-[(3,4-dimethoxyphenyl)amino]imidazo[1,2-a]pyrazin-6-yl}pyridin-2-amine | 363.2 |
| 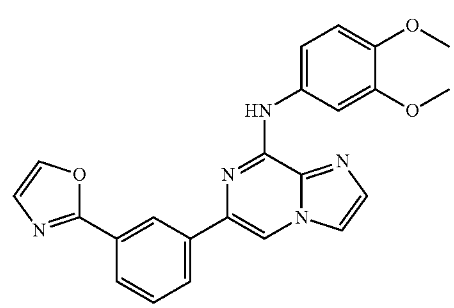 [SMILES: COc1ccc(Nc2nc(-c3cccc(-c4ncco4)c3)cn3ccnc23)cc1OC] | N-(3,4-dimethoxyphenyl)-6-[3-(1,3-oxazol-2-yl)phenyl]imidazo[1,2-a]pyrazin-8-amine | 414.3 |
| 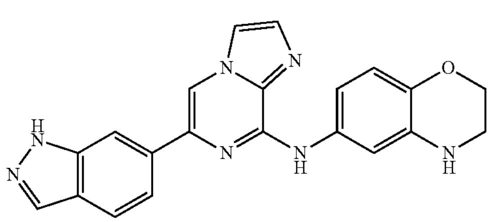 [SMILES: c1cn2cc(-c3ccc4cn[nH]c4c3)nc(Nc3ccc4c(c3)NCCO4)c2n1] | N-[6-(1H-indazol-6-yl)imidazo[1,2-a]pyrazin-8-yl]-3,4-dihydro-2H-1,4-benzoxazin-6-amine | 384 |

-continued

| Structure | Name | [M + H]+ |
|---|---|---|
| 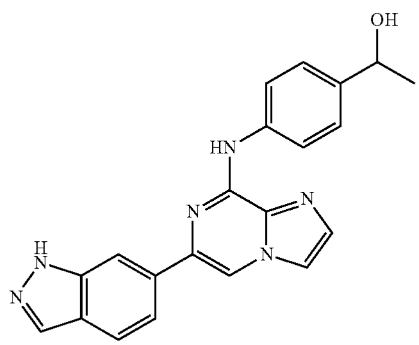 [SMILES: CC(O)c1ccc(Nc2nc(-c3ccc4cn[nH]c4c3)cn3ccnc23)cc1] | 1-(4-{[6-(1H-indazol-6-yl)imidazo[1,2-a]pyrazin-8-yl]amino}phenyl)ethan-1-ol | 371.1 |
| 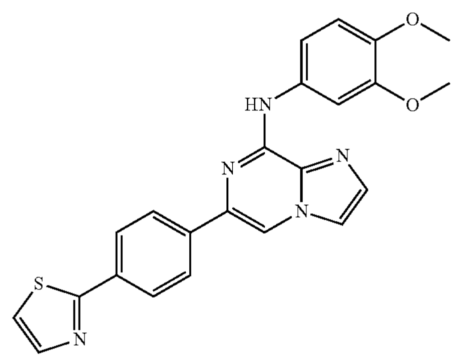 [SMILES: COc1ccc(Nc2nc(-c3ccc(-c4nccs4)cc3)cn3ccnc23)cc1OC] | N-(3,4-dimethoxyphenyl)-6-[4-(1,3-thiazol-2-yl)phenyl]imidazo[1,2-a]pyrazin-8-amine | 430.5 |
| 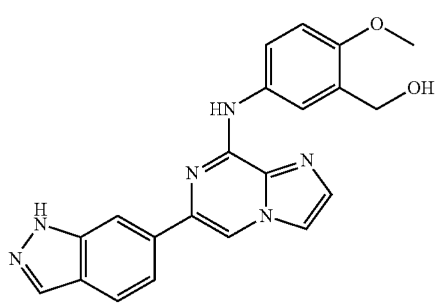 [SMILES: COc1ccc(Nc2nc(-c3ccc4cn[nH]c4c3)cn3ccnc23)cc1CO] | (5-{[6-(1H-indazol-6-yl)imidazo[1,2-a]pyrazin-8-yl]amino}-2-methoxyphenyl)methanol | 387.2 |
| 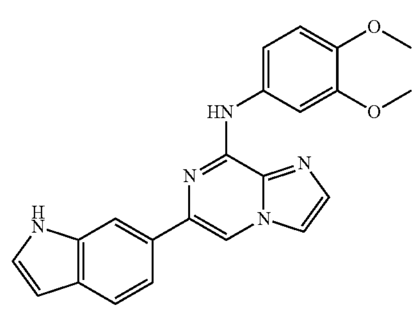 [SMILES: COc1ccc(Nc2nc(-c3ccc4cc[nH]c4c3)cn3ccnc23)cc1OC] | N-(3,4-dimethoxyphenyl)-6-(1H-indol-6-yl)imidazo[1,2-a]pyrazin-8-amine | 386.3 |
| 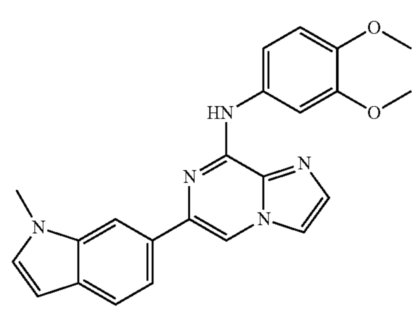 [SMILES: COc1ccc(Nc2nc(-c3ccc4ccn(C)c4c3)cn3ccnc23)cc1OC] | N-(3,4-dimethoxyphenyl)-6-(1-methyl-1H-1,3-benzodiazol-6-yl)imidazo[1,2-a]pyrazin-8-amine | 401.2 |

| Structure | Name | [M + H]+ |
|---|---|---|
| 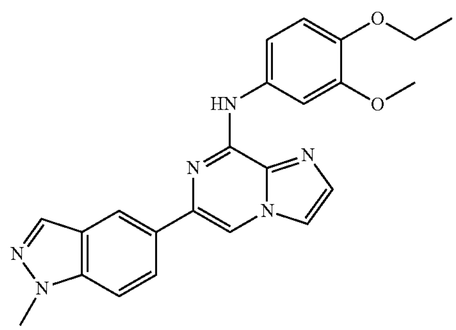 [SMILES: CCOc1ccc(Nc2nc(-c3ccc4c(cnn4C)c3)cn3ccnc23)cc1OC] | N-(4-ethoxy-3-methoxyphenyl)-6-(1-methyl-1H-indazol-5-yl)imidazo[1,2-a]pyrazin-8-amine | 415.6 |
| 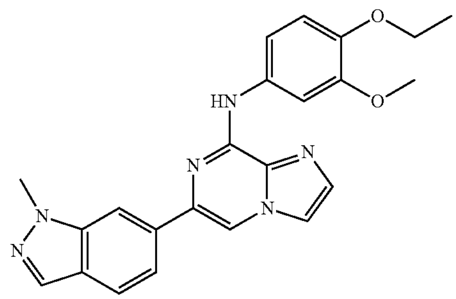 [SMILES: CCOc1ccc(Nc2nc(-c3ccc4cnn(C)c4c3)cn3ccnc23)cc1OC] | N-(4-ethoxy-3-methoxyphenyl)-6-(1-methyl-1H-indazol-6-yl)imidazo[1,2-a]pyrazin-8-amine | 415.5 |
| 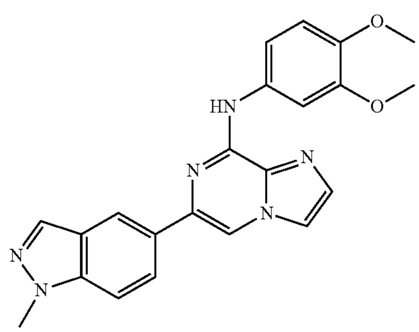 [SMILES: COc1ccc(Nc2nc(-c3ccc4c(cnn4C)c3)cn3ccnc23)cc1OC] | N-(3,4-dimethoxyphenyl)-6-(1-methyl-1H-indazol-5-yl)imidazo[1,2-a]pyrazin-8-amine | 401.3 |
| 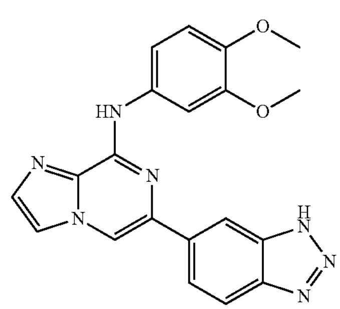 [SMILES: COc1ccc(Nc2nc(-c3ccc4nn[nH]c4c3)cn3ccnc23)cc1OC] | 6-(1H-1,2,3-benzotriazol-6-yl)-N-(3,4-dimethoxyphenyl)imidazo[1,2-a]pyrazin-8-amine | 388.2 |
| 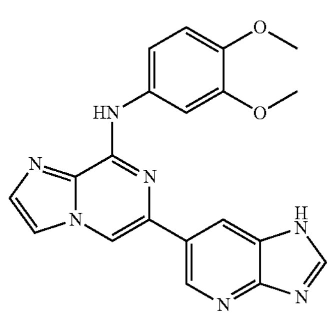 [SMILES: COc1ccc(Nc2nc(-c3cnc4nc[nH]c4c3)cn3ccnc23)cc1OC] | N-(3,4-dimethoxyphenyl)-6-{1H-imidazo[4,5-b]pyridin-6-yl}imidazo[1,2-a]pyrazin-8-amine | 388.3 |

| Structure | Name | [M + H]⁺ |
|---|---|---|
| 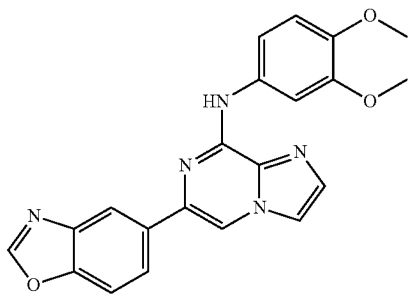 [SMILES: COc1ccc(Nc2nc(-c3ccc4ocnc4c3)cn3ccnc23)cc1OC] | 6-(1,3-benzoxazol-5-yl)-N-(3,4-dimethoxyphenyl)imidazo[1,2-a]pyrazin-8-amine | 388.7 |
| 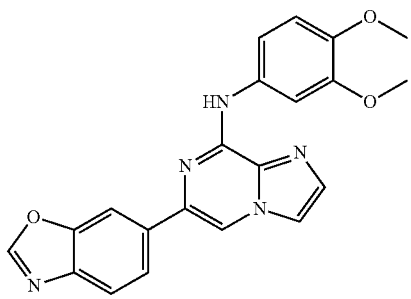 | 6-(1,3-benzoxazol-6-yl)-N-(3,4-dimethoxyphenyl)imidazo[1,2-a]pyrazin-8-amine | 388.3 |
| 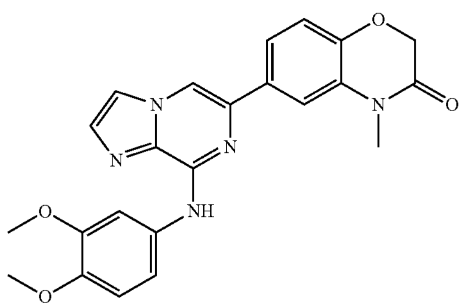 [SMILES: COc1ccc(Nc2nc(-c3ccc4c(c3)N(C)C(=O)CO4)cn3ccnc23)cc1OC] | 6-{8-[(3,4-dimethoxyphenyl)amino]imidazo[1,2-a]pyrazin-6-yl}-4-methyl-3,4-dihydro-2H-1,4-benzoxazin-3-one | 432.4 |
| 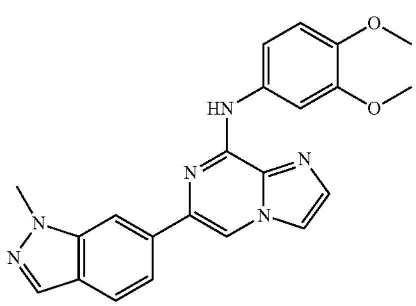 [SMILES: COc1ccc(Nc2nc(-c3ccc4cnn(C)c4c3)cn3ccnc23)cc1OC] | N-(3,4-dimethoxyphenyl)-6-(1-methyl-1H-indazol-6-yl)imidazo[1,2-a]pyrazin-8-amine | 400.3 |
| 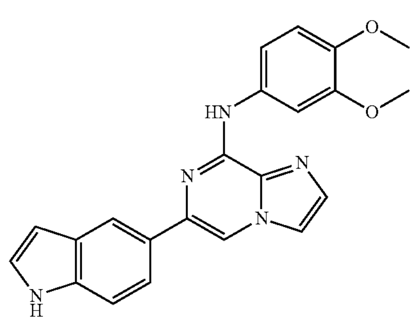 [SMILES: COc1ccc(Nc2nc(-c3ccc4[nH]ccc4c3)cn3ccnc23)cc1OC] | N-(3,4-dimethoxyphenyl)-6-(1H-indol-5-yl)imidazo[1,2-a]pyrazin-8-amine | 386.4 |

-continued

| Structure | Name | [M + H]⁺ |
|---|---|---|
| 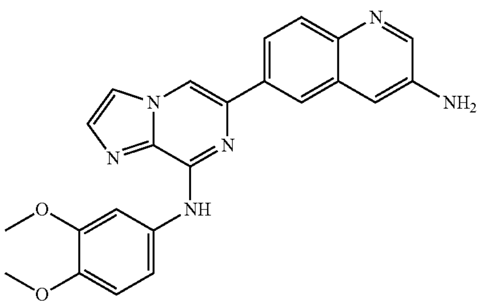 [SMILES: COc1ccc(Nc2nc(-c3ccc4ncc(N)cc4c3)cn3ccnc23)cc1OC] | 6-{8-[(3,4-dimethoxyphenyl)amino]imidazo[1,2-a]pyrazin-6-yl}quinolin-3-amine | 413.7 |
| 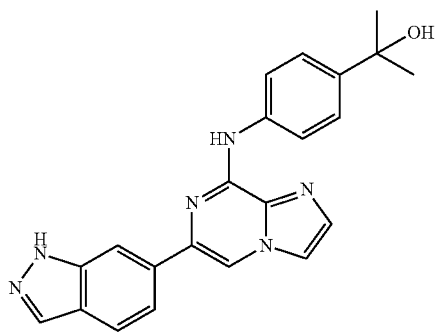 [SMILES: CC(C)(O)c1ccc(Nc2nc(-c3ccc4cn[nH]c4c3)cn3ccnc23)cc1] | 2-(4-{[6-(1H-indazol-6-yl)imidazo[1,2-a]pyrazin-8-yl]amino}phenyl)propan-2-ol | 385.1 |
| 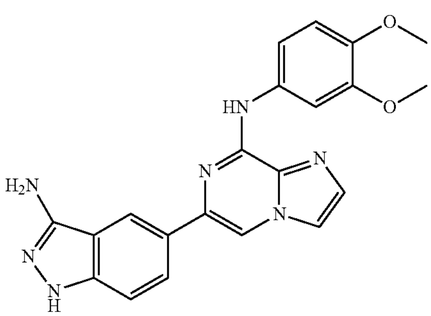 [SMILES: COc1ccc(Nc2nc(-c3ccc4[nH]nc(N)c4c3)cn3ccnc23)cc1OC] | 5-{8-[(3,4-dimethoxyphenyl)amino]imidazo[1,2-a]pyrazin-6-yl}-1H-indazol-3-amine | 402.1 |
| 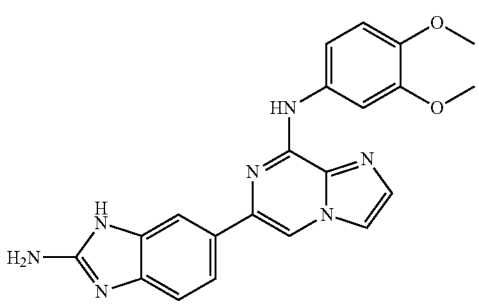 [SMILES: COc1ccc(Nc2nc(-c3ccc4nc(N)[nH]c4c3)cn3ccnc23)cc1OC] | 6-{8-[(3,4-dimethoxyphenyl)amino]imidazo[1,2-a]pyrazin-6-yl}-1H-1,3-benzodiazol-2-amine | 402.3 |
| 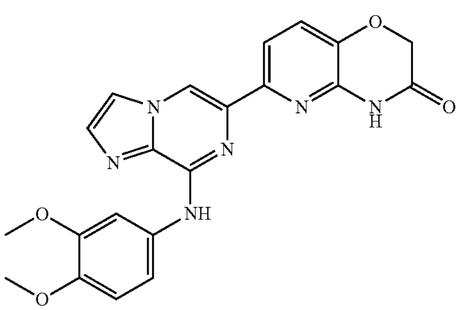 [SMILES: COc1ccc(Nc2nc(-c3ccc4c(n3)NC(=O)CO4)cn3ccnc23)cc1OC] | 6-{8-[(3,4-dimethoxyphenyl)amino]imidazo[1,2-a]pyrazin-6-yl}-2H,3H,4H-pyrido[3,2-b][1,4]oxazin-3-one | 419.5 |

| Structure | Name | [M + H]+ |
|---|---|---|
| 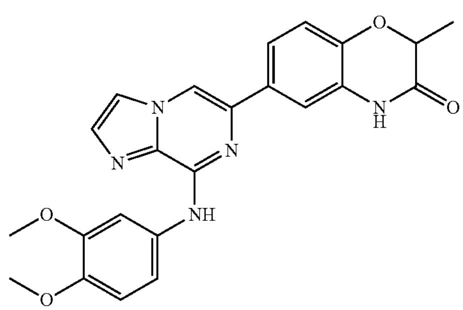 | 6-{8-[(3,4-dimethoxyphenyl)amino]imidazo[1,2-a]pyrazin-6-yl}-2-methyl-3,4-dihydro-2H-1,4-benzoxazin-3-one | 432.5 |
| 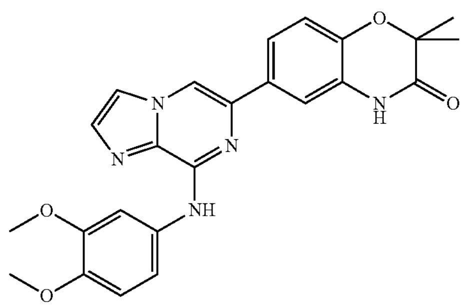 | 6-{8-[(3,4-dimethoxyphenyl)amino]imidazo[1,2-a]pyrazin-6-yl}-2,2-dimethyl-3,4-dihydro-2H-1,4-benzoxazin-3-one | 446.4 |
| 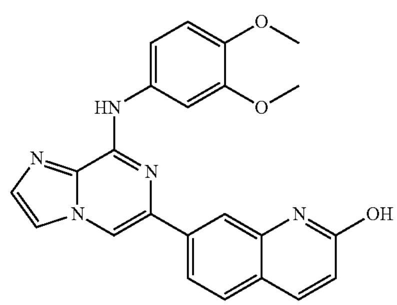 [SMILES: COc1ccc(Nc2nc(-c3ccc4ccc(O)nc4c3)cn3ccnc23)cc1OC] | 7-{8-[(3,4-dimethoxyphenyl)amino]imidazo[1,2-a]pyrazin-6-yl}quinolin-2-ol | 414.3 |
| 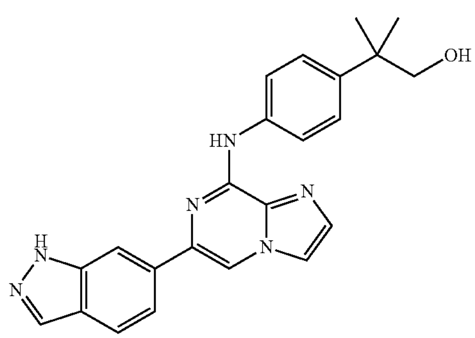 [SMILES: CC(C)(CO)c1ccc(Nc2nc(-c3ccc4cn[nH]c4c3)cn3ccnc23)cc1] | 2-(4-{[6-(1H-indazol-6-yl)imidazo[1,2-a]pyrazin-8-yl]amino}phenyl)-2-methylpropan-1-ol | 399.3 |
| 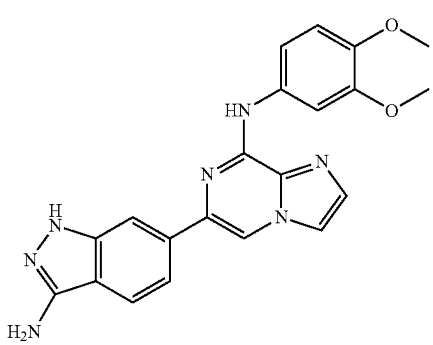 [SMILES: COc1ccc(Nc2nc(-c3ccc4c(N)n[nH]c4c3)cn3ccnc23)cc1OC] | 6-{8-[(3,4-dimethoxyphenyl)amino]imidazo[1,2-a]pyrazin-6-yl}-1H-indazol-3-amine | 400.2 |

-continued

| Structure | Name | [M + H]⁺ |
|---|---|---|
| 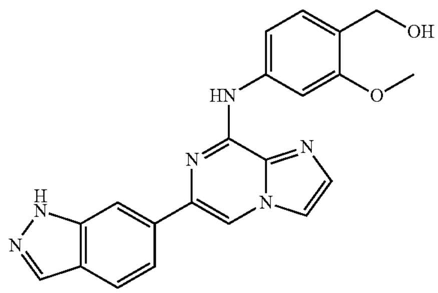 [SMILES: COc1cc(Nc2nc(-c3ccc4cn[nH]c4c3)cn3ccnc23)ccc1CO] | (4-{[6-(1H-indazol-6-yl)imidazo[1,2-a]pyrazin-8-yl]amino}-2-methoxyphenyl)methanol | 385.3 |
| 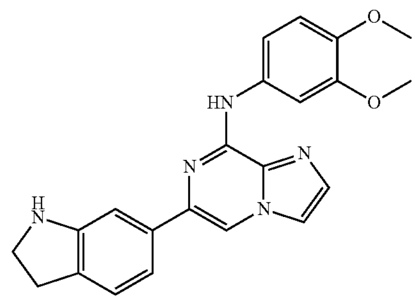 [SMILES: COc1ccc(Nc2nc(-c3ccc4c(c3)NCC4)cn3ccnc23)cc1OC] | 6-(2,3-dihydro-1H-indol-6-yl)-N-(3,4-dimethoxyphenyl)imidazo[1,2-a]pyrazin-8-amine | 388.8 |
| 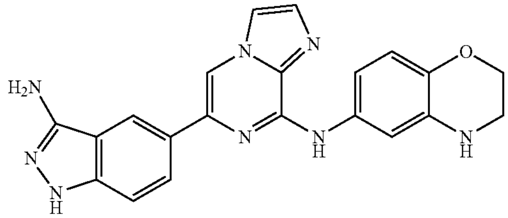 [SMILES: Nc1n[nH]c2ccc(-c3cn4ccnc4c(Nc4ccc5c(c4)NCCO5)n3)cc12] | N-[6-(3-amino-1H-indazol-5-yl)imidazo[1,2-a]pyrazin-8-yl]-3,4-dihydro-2H-1,4-benzoxazin-6-amine | 399.2 |
| 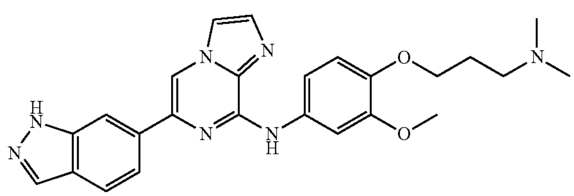 [SMILES: COc1cc(Nc2nc(-c3ccc4cn[nH]c4c3)cn3ccnc23)ccc1OCCCN(C)C] | N-{4-[3-(dimethylamino)propoxy]-3-methoxyphenyl}-6-(1H-indazol-6-yl)imidazo[1,2-a]pyrazin-8-amine | 458.7 |
| 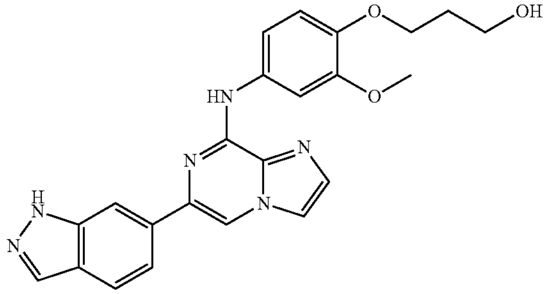 [SMILES: COc1cc(Nc2nc(-c3ccc4cn[nH]c4c3)cn3ccnc23)ccc1OCCCO] | 3-(4-{[6-(1H-indazol-6-yl)imidazo[1,2-a]pyrazin-8-yl]amino}-2-methoxyphenoxy)propan-1-ol | 431.6 |

-continued

| Structure | Name | [M + H]⁺ |
|---|---|---|
| 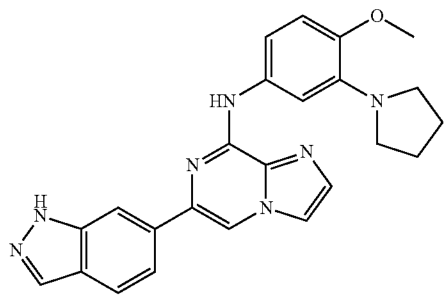 [SMILES: COc1ccc(Nc2nc(-c3ccc4cn[nH]c4c3)cn3ccnc23)cc1N1CCCC1] | 6-(1H-indazol-6-yl)-N-[4-methoxy-3-(pyrrolidin-1-yl)phenyl]imidazo[1,2-a]pyrazin-8-amine | 426.3 |
| 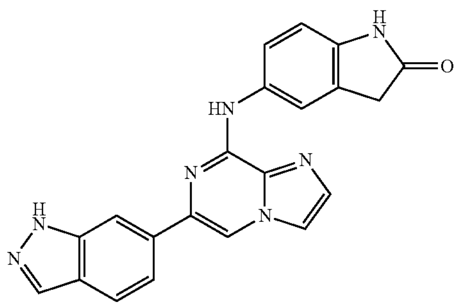 [SMILES: O=C1Cc2cc(Nc3nc(-c4ccc5cn[nH]c5c4)cn4ccnc34)ccc2N1] | 5-{[6-(1H-indazol-6-yl)imidazo[1,2-a]pyrazin-8-yl]amino}-2,3-dihydro-1H-indol-2-one | 382.3 |
| 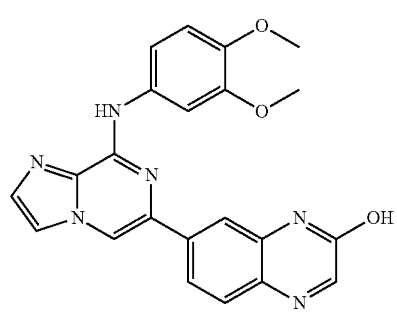 [SMILES: COc1ccc(Nc2nc(-c3ccc4ncc(O)nc4c3)cn3ccnc23)cc1OC] | 7-{8-[(3,4-dimethoxyphenyl)amino]imidazo[1,2-a]pyrazin-6-yl}quinoxalin-2-ol | 413.5 |
| 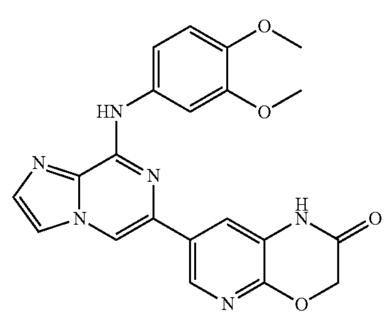 [SMILES: COc1ccc(Nc2nc(-c3cnc4c(c3)NC(=O)CO4)cn3ccnc23)cc1OC] | 7-{8-[(3,4-dimethoxyphenyl)amino]imidazo[1,2-a]pyrazin-6-yl}-1H,2H,3H-pyrido[2,3-b][1,4]oxazin-2-one | 419.5 |
| 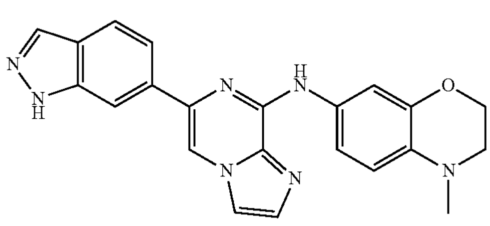 [SMILES: CN1CCOc2cc(Nc3nc(-c4ccc5cn[nH]c5c4)cn4ccnc34)ccc21] | N-[6-(1H-indazol-6-yl)imidazo[1,2-a]pyrazin-8-yl]-4-methyl-3,4-dihydro-2H-1,4-benzoxazin-7-amine | 398.3 |

| Structure | Name | [M + H]+ |
|---|---|---|
| 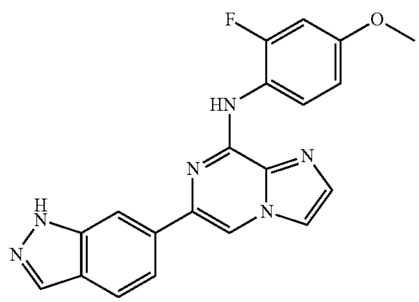 [SMILES: COc1ccc(Nc2nc(-c3ccc4cn[nH]c4c3)cn3ccnc23)c(F)c1] | N-(2-fluoro-4-methoxyphenyl)-6-(1H-indazol-6-yl)imidazo[1,2-a]pyrazin-8-amine | 375.3 |
| 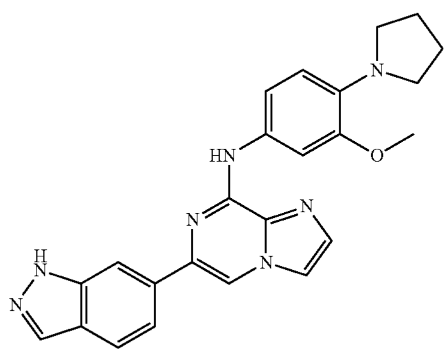 [SMILES: COc1cc(Nc2nc(-c3ccc4cn[nH]c4c3)cn3ccnc23)ccc1N1CCCC1] | 6-(1H-indazol-6-yl)-N-[3-methoxy-4-(pyrrolidin-1-yl)phenyl]imidazo[1,2-a]pyrazin-8-amine | 425.5 |
| 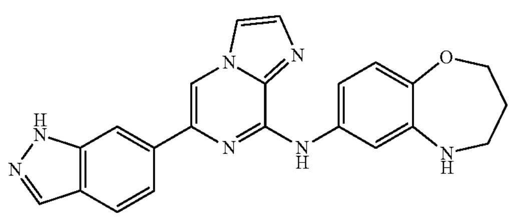 [SMILES: c1cn2cc(-c3ccc4cn[nH]c4c3)nc(Nc3ccc4c(c3)NCCCO4)c2n1] | N-[6-(1H-indazol-6-yl)imidazo[1,2-a]pyrazin-8-yl]-2,3,4,5-tetrahydro-1,5-benzoxazepin-7-amine | 398.5 |
| 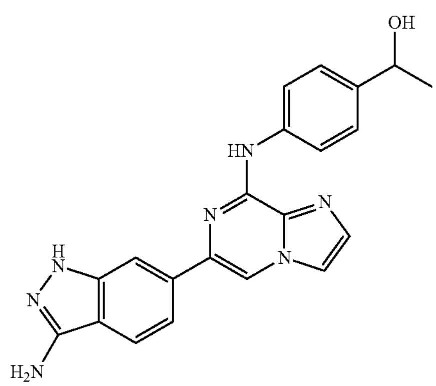 [SMILES: CC(O)c1ccc(Nc2nc(-c3ccc4c(N)n[nH]c4c3)cn3ccnc23)cc1] | 1-(4-{[6-(3-amino-1H-indazol-6-yl)imidazo[1,2-a]pyrazin-8-yl]amino}phenyl)ethan-1-ol | 386.4 |
| 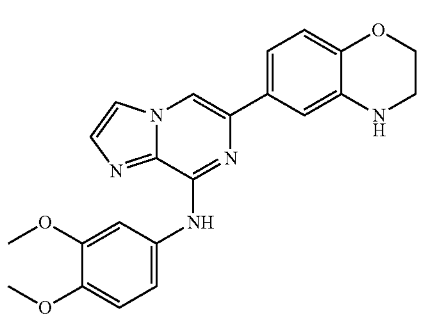 [SMILES: COc1ccc(Nc2nc(-c3ccc4c(c3)NCCO4)cn3ccnc23)cc1OC] | 6-(3,4-dihydro-2H-1,4-benzoxazin-6-yl)-N-(3,4-dimethoxyphenyl)imidazo[1,2-a]pyrazin-8-amine | 404.5 |

-continued

| Structure | Name | [M + H]+ |
|---|---|---|
| 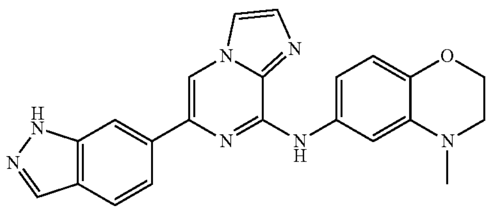 [SMILES: CN1CCOc2ccc(Nc3nc(-c4ccc5cn[nH]c5c4)cn4ccnc34)cc21] | N-[6-(1H-indazol-6-yl)imidazo[1,2-a]pyrazin-8-yl]-4-methyl-3,4-dihydro-2H-1,4-benzoxazin-6-amine | 396.3 |
| 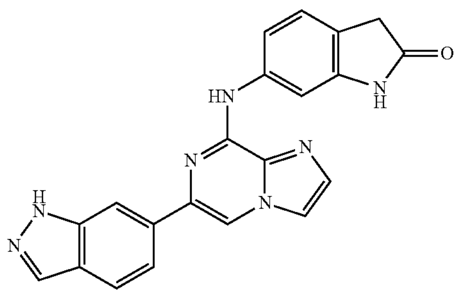 [SMILES: O=C1Cc2ccc(Nc3nc(-c4ccc5cn[nH]c5c4)cn4ccnc34)cc2N1] | 6-{[6-(1H-indazol-6-yl)imidazo[1,2-a]pyrazin-8-yl]amino}-2,3-dihydro-1H-indol-2-one | 382.3 |
| 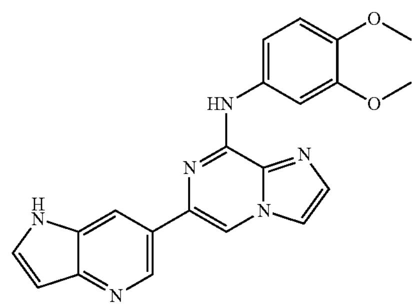 [SMILES: COc1ccc(Nc2nc(-c3cnc4cc[nH]c4c3)cn3ccnc23)cc1OC] | N-(3,4-dimethoxyphenyl)-6-{1H-pyrrolo[3,2-b]pyridin-6-yl}imidazo[1,2-a]pyrazin-8-amine | 387.6 |
| 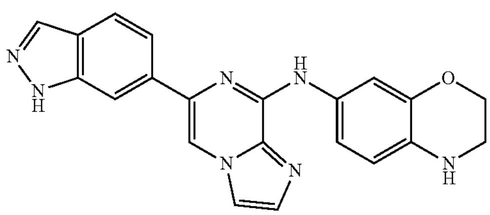 [SMILES: c1cn2cc(-c3ccc4cn[nH]c4c3)nc(Nc3ccc4c(c3)OCCN4)c2n1] | N-[6-(1H-indazol-6-yl)imidazo[1,2-a]pyrazin-8-yl]-3,4-dihydro-2H-1,4-benzoxazin-7-amine | 384.3 |
| 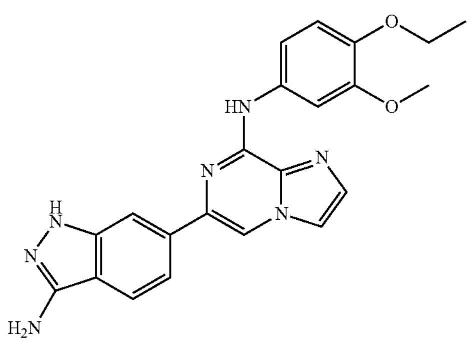 [SMILES: CCOc1ccc(Nc2nc(-c3ccc4c(N)n[nH]c4c3)cn3ccnc23)cc1OC] | 6-{8-[(4-ethoxy-3-methoxyphenyl)amino]imidazo[1,2-a]pyrazin-6-yl}-1H-indazol-3-amine | 416.8 |

-continued

| Structure | Name | [M + H]+ |
|---|---|---|
| 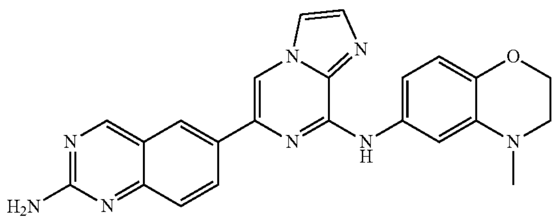 [SMILES: CN1CCOc2ccc(Nc3nc(-c4ccc5nc(N)ncc5c4)cn4ccnc34)cc21] | N-[6-(2-aminoquinazolin-6-yl)imidazo[1,2-a]pyrazin-8-yl]-4-methyl-3,4-dihydro-2H-1,4-benzoxazin-6-amine | 425.2 |
| 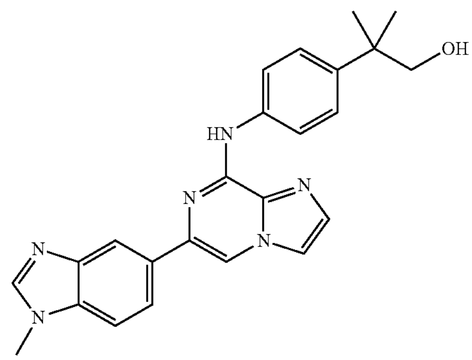 [SMILES: Cn1cnc2cc(-c3cn4ccnc4c(Nc4ccc(C(C)(C)CO)cc4)n3)ccc21] | 2-methyl-2-(4-{[6-(1-methyl-1H-1,3-benzodiazol-5-yl)imidazo[1,2-a]pyrazin-8-yl]amino}phenyl)propan-1-ol | 413.7 |
| 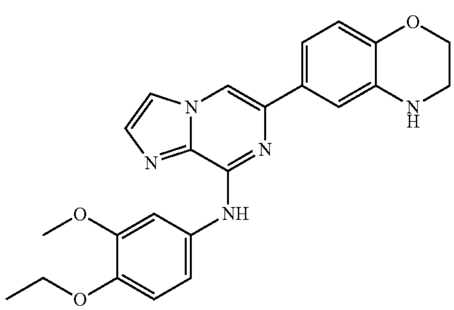 [SMILES: CCOc1ccc(Nc2nc(-c3ccc4c(c3)NCCO4)cn3ccnc23)cc1OC] | 6-(3,4-dihydro-2H-1,4-benzoxazin-6-yl)-N-(4-ethoxy-3-methoxyphenyl)imidazo[1,2-a]pyrazin-8-amine | 418.4 |
| 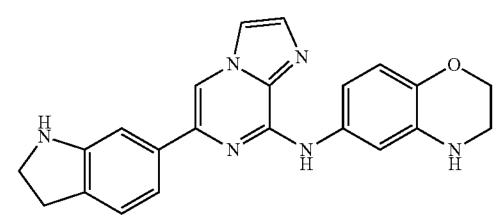 [SMILES: c1cn2cc(-c3ccc4c(c3)NCC4)nc(Nc3ccc4c(c3)NCCO4)c2n1] | N-[6-(2,3-dihydro-1H-indol-6-yl)imidazo[1,2-a]pyrazin-8-yl]-3,4-dihydro-2H-1,4-benzoxazin-6-amine | 385.3 |
| 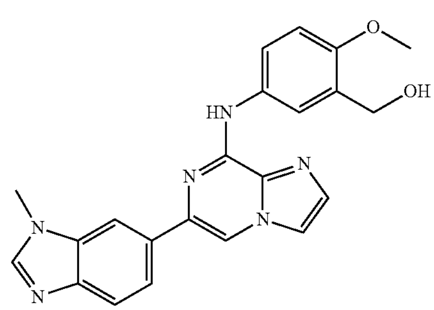 [SMILES: COc1ccc(Nc2nc(-c3ccc4ncn(C)c4c3)cn3ccnc23)cc1CO] | (2-methoxy-5-{[6-(1-methyl-1H-1,3-benzodiazol-6-yl)imidazo[1,2-a]pyrazin-8-yl]amino}phenyl)methanol | 401.2 |

| Structure | Name | [M + H]+ |
|---|---|---|
| 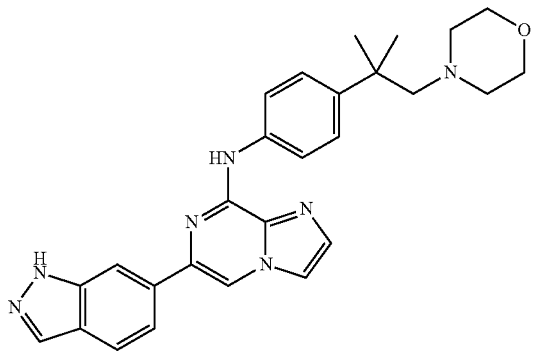 [SMILES: CC(C)(CN1CCOCC1)c1ccc(Nc2nc(-c3ccc4cn[nH]c4c3)cn3ccnc23)cc1] | 6-(1H-indazol-6-yl)-N-{4-[2-methyl-1-(morpholin-4-yl)propan-2-yl]phenyl}imidazo[1,2-a]pyrazin-8-amine | 468.6 |
| 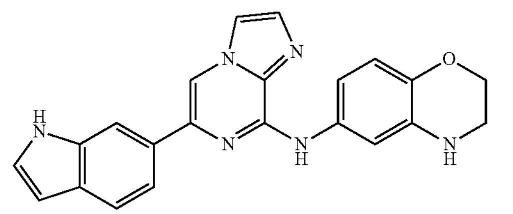 [SMILES: c1cn2cc(-c3ccc4cc[nH]c4c3)nc(Nc3ccc4c(c3)NCCO4)c2n1] | N-[6-(1H-indol-6-yl)imidazo[1,2-a]pyrazin-8-yl]-3,4-dihydro-2H-1,4-benzoxazin-6-amine | 383.4 |
| 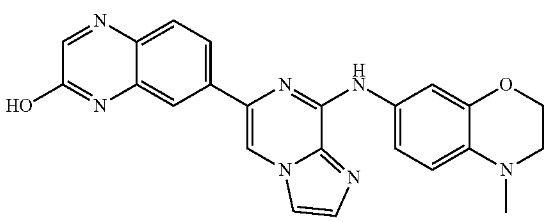 [SMILES: CN1CCOc2cc(Nc3nc(-c4ccc5ncc(O)nc5c4)cn4ccnc34)ccc21] | 7-{8-[(4-methyl-3,4-dihydro-2H-1,4-benzoxazin-7-yl)amino]imidazo[1,2-a]pyrazin-6-yl}quinoxalin-2-ol | 426.2 |
| 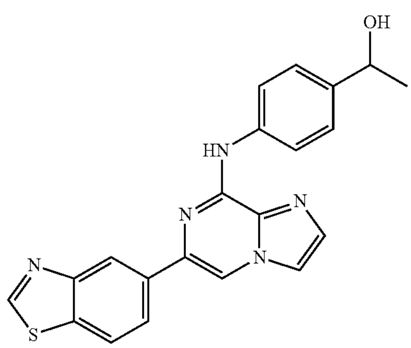 [SMILES: CC(O)c1ccc(Nc2nc(-c3ccc4scnc4c3)cn3ccnc23)cc1] | 1-(4-{[6-(1,3-benzothiazol-5-yl)imidazo[1,2-a]pyrazin-8-yl]amino}phenyl)ethan-1-ol | 388.7 |
| 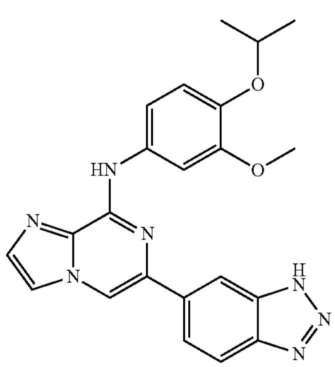 [SMILES: COc1cc(Nc2nc(-c3ccc4nn[nH]c4c3)cn3ccnc23)ccc1OC(C)C] | 6-(1H-1,2,3-benzotriazol-6-yl)-N-[3-methoxy-4-(propan-2-yloxy)phenyl]imidazo[1,2-a]pyrazin-8-amine | 416.6 |

-continued

| Structure | Name | [M + H]⁺ |
|---|---|---|
| 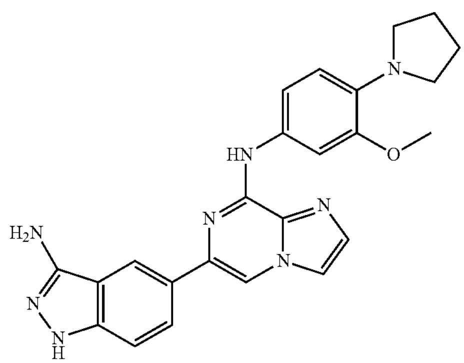 [SMILES: COc1cc(Nc2nc(-c3ccc4[nH]nc(N)c4c3)cn3ccnc23)ccc1N1CCCC1] | 5-(8-{[3-methoxy-4-(pyrrolidin-1-yl)phenyl]amino}imidazo[1,2-a]pyrazin-6-yl)-1H-indazol-3-amine | 441.4 |
| 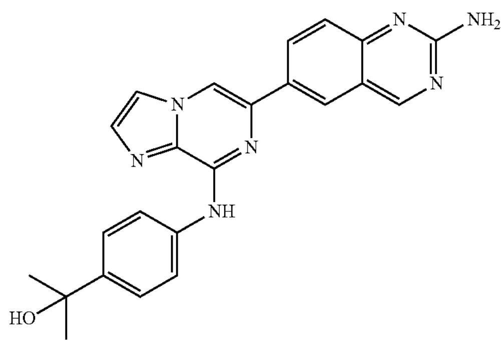 [SMILES: CC(C)(O)c1ccc(Nc2nc(-c3ccc4nc(N)ncc4c3)cn3ccnc23)cc1] | 2-(4-{[6-(2-aminoquinazolin-6-yl)imidazo[1,2-a]pyrazin-8-yl]amino}phenyl)propan-2-ol | 412.4 |
| 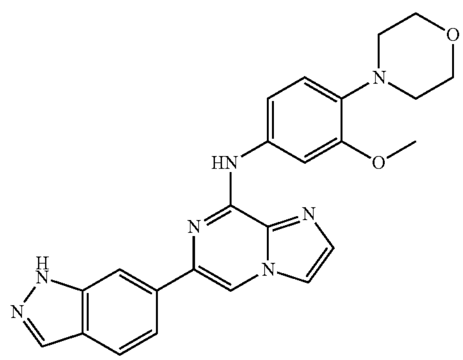 [SMILES: COc1cc(Nc2nc(-c3ccc4cn[nH]c4c3)cn3ccnc23)ccc1N1CCOCC1] | 6-(1H-indazol-6-yl)-N-[3-methoxy-4-(morpholin-4-yl)phenyl]imidazo[1,2-a]pyrazin-8-amine | 442.5 |
| 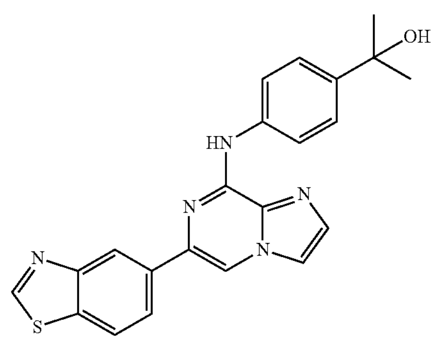 [SMILES: CC(C)(O)c1ccc(Nc2nc(-c3ccc4scnc4c3)cn3ccnc23)cc1] | 2-(4-{[6-(1,3-benzothiazol-5-yl)imidazo[1,2-a]pyrazin-8-yl]amino}phenyl)propan-2-ol | 402.3 |

-continued

| Structure | Name | [M + H]+ |
|---|---|---|
| 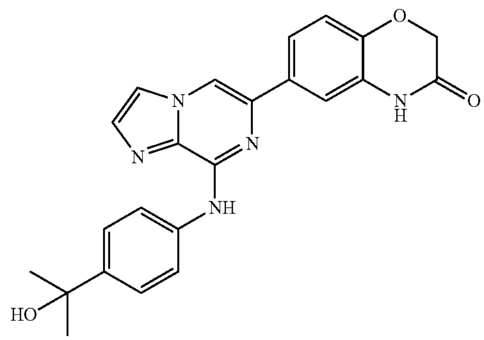 [SMILES: CC(C)(O)c1ccc(Nc2nc(-c3ccc4c(c3)NC(=O)CO4)cn3ccnc23)cc1] | 6-(8-{[4-(2-hydroxypropan-2-yl)phenyl]amino}imidazo[1,2-a]pyrazin-6-yl)-3,4-dihydro-2H-1,4-benzoxazin-3-one | 416.7 |
| 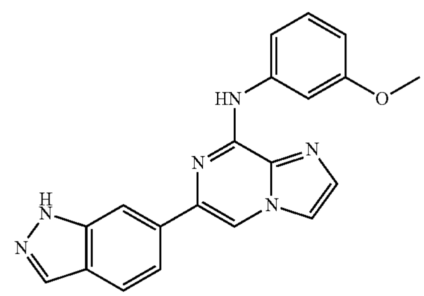 [SMILES: COc1cccc(Nc2nc(-c3ccc4cn[nH]c4c3)cn3ccnc23)c1] | 6-(1H-indazol-6-yl)-N-(3-methoxyphenyl)imidazo[1,2-a]pyrazin-8-amine | 357.3 |
| 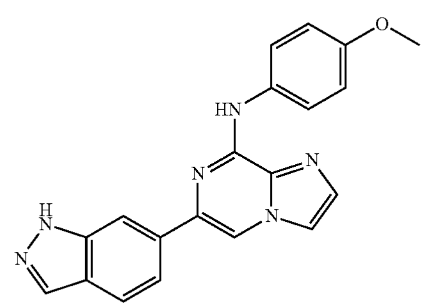 [SMILES: COc1ccc(Nc2nc(-c3ccc4cn[nH]c4c3)cn3ccnc23)cc1] | 6-(1H-indazol-6-yl)-N-(4-methoxyphenyl)imidazo[1,2-a]pyrazin-8-amine | 357.3 |
| 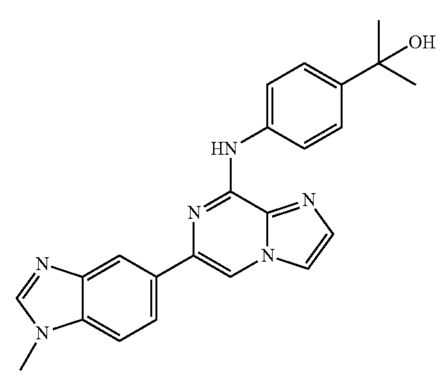 [SMILES: Cn1cnc2cc(-c3cn4ccnc4c(Nc4ccc(C(C)(C)O)cc4)n3)ccc21] | 2-(4-{[6-(1-methyl-1H-1,3-benzodiazol-5-yl)imidazo[1,2-a]pyrazin-8-yl]amino}phenyl)propan-2-ol | 399.1 |

| Structure | Name | [M + H]+ |
|---|---|---|
| 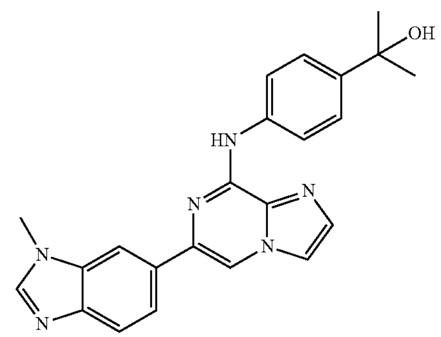 [SMILES: Cn1cnc2ccc(-c3cn4ccnc4c(Nc4ccc(C(C)(C)O)cc4)n3)cc21] | 2-(4-{[6-(1-methyl-1H-1,3-benzodiazol-6-yl)imidazo[1,2-a]pyrazin-8-yl]amino}phenyl)propan-2-ol | 399.2 |
| 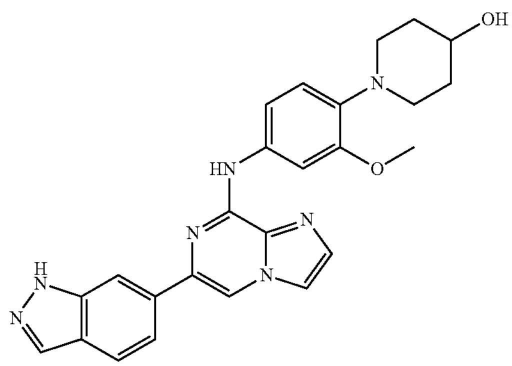 [SMILES: COc1cc(Nc2nc(-c3ccc4cn[nH]c4c3)cn3ccnc23)ccc1N1CCC(O)CC1] | 1-(4-{[6-(1H-indazol-6-yl)imidazo[1,2-a]pyrazin-8-yl]amino}-2-methoxyphenyl)piperidin-4-ol | 456.5 |
| 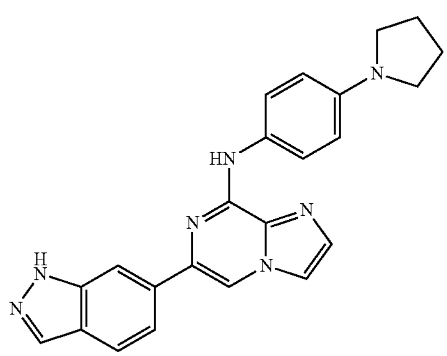 [SMILES: c1cn2cc(-c3ccc4cn[nH]c4c3)nc(Nc3ccc(N4CCCC4)cc3)c2n1] | 6-(1H-indazol-6-yl)-N-[4-(pyrrolidin-1-yl)phenyl]imidazo[1,2-a]pyrazin-8-amine | 396.1 |
| 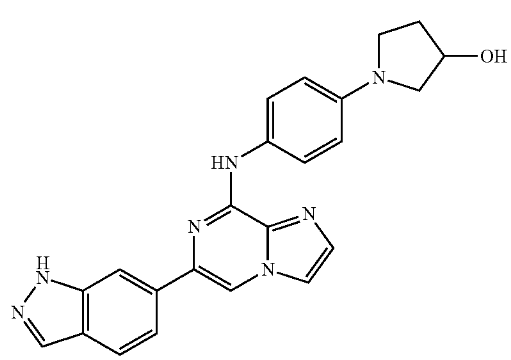 [SMILES: OC1CCN(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)pyrrolidin-3-ol | 412.3 |

-continued

| Structure | Name | [M + H]+ |
|---|---|---|
| 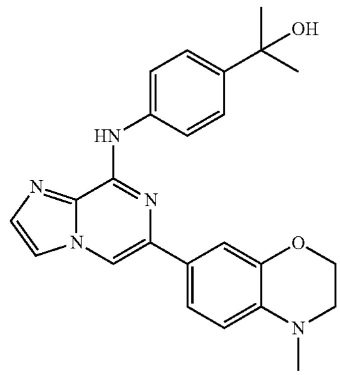 [SMILES: CN1CCOc2cc(-c3cn4ccnc4c(Nc4ccc(C(C)(C)O)cc4)n3)ccc21] | 2-(4-{[6-(4-methyl-3,4-dihydro-2H-1,4-benzoxazin-7-yl)imidazo[1,2-a]pyrazin-8-yl]amino}phenyl)propan-2-ol | 416.5 |
| 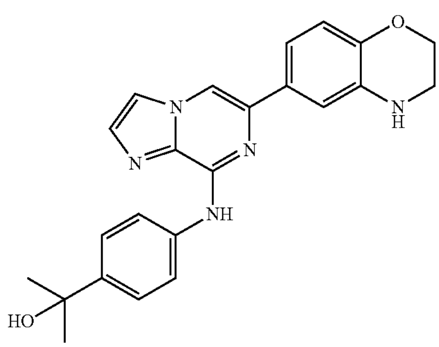 | 2-(4-{[6-(3,4-dihydro-2H-1,4-benzoxazin-6-yl)imidazo[1,2-a]pyrazin-8-yl]amino}phenyl)propan-2-ol | 402.5 |
| 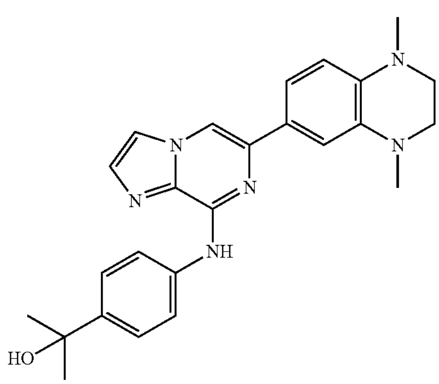 [SMILES: CN1CCN(C)c2cc(-c3cn4ccnc4c(Nc4ccc(C(C)(C)O)cc4)n3)ccc21] | 2-(4-{[6-(1,4-dimethyl-1,2,3,4-tetrahydroquinoxalin-6-yl)imidazo[1,2-a]pyrazin-8-yl]amino}phenyl)propan-2-ol | 429.4 |
| 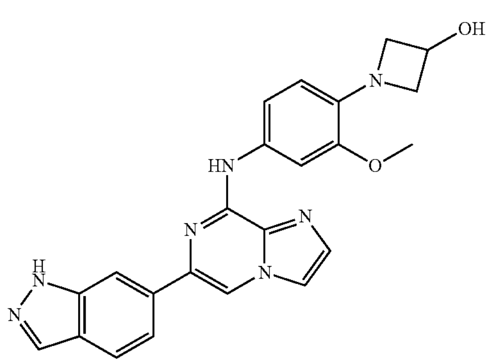 [SMILES: COc1cc(Nc2nc(-c3ccc4cn[nH]c4c3)cn3ccnc23)ccc1N1CC(O)C1] | 1-(4-{[6-(1H-indazol-6-yl)imidazo[1,2-a]pyrazin-8-yl]amino}-2-methoxyphenyl)azetidin-3-ol | 428.3 |

-continued
| Structure | Name | [M + H]+ |
|---|---|---|
| 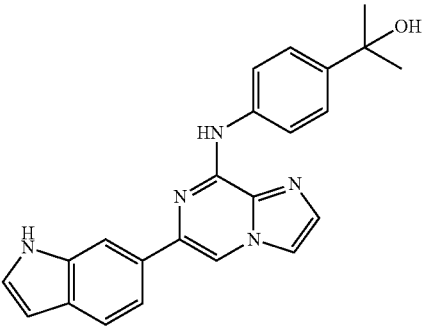 [SMILES: CC(C)(O)c1ccc(Nc2nc(-c3ccc4cc[nH]c4c3)cn3ccnc23)cc1] | 2-(4-{[6-(1H-indol-6-yl)imidazo[1,2-a]pyrazin-8-yl]amino}phenyl)propan-2-ol | 384.2 |
| 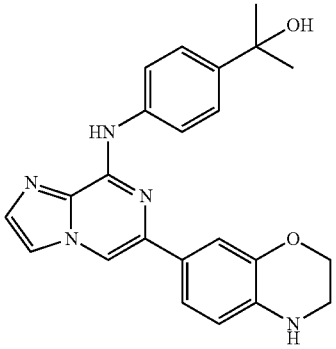 [SMILES: CC(C)(O)c1ccc(Nc2nc(-c3ccc4c(c3)OCCN4)cn3ccnc23)cc1] | 2-(4-{[6-(3,4-dihydro-2H-1,4-benzoxazin-7-yl)imidazo[1,2-a]pyrazin-8-yl]amino}phenyl)propan-2-ol | 402.5 |
| 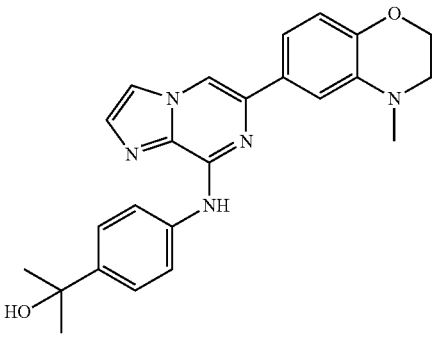 [SMILES: CN1CCOc2ccc(-c3cn4ccnc4c(Nc4ccc(C(C)(C)O)cc4)n3)cc21] | 2-(4-{[6-(4-methyl-3,4-dihydro-2H-1,4-benzoxazin-6-yl)imidazo[1,2-a]pyrazin-8-yl]amino}phenyl)propan-2-ol | 416.7 |
| 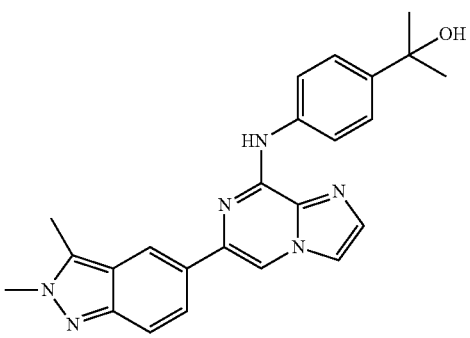 [SMILES: Cc1c2cc(-c3cn4ccnc4c(Nc4ccc(C(C)(C)O)cc4)n3)ccc2nn1C] | 2-(4-{[6-(2,3-dimethyl-2H-indazol-5-yl)imidazo[1,2-a]pyrazin-8-yl]amino}phenyl)propan-2-ol | 413.4 |

-continued

| Structure | Name | [M + H]+ |
|---|---|---|
| 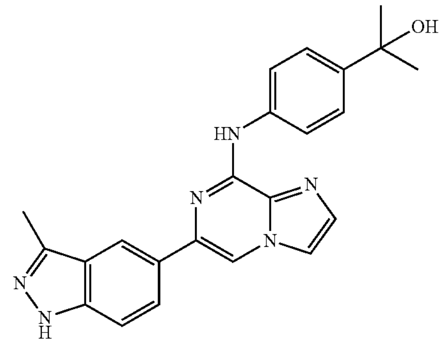 [SMILES: Cc1n[nH]c2ccc(-c3cn4ccnc4c(Nc4ccc(C(C)(C)O)cc4)n3)cc12] | 2-(4-{[6-(3-methyl-1H-indazol-5-yl)imidazo[1,2-a]pyrazin-8-yl]amino}phenyl)propan-2-ol | 399.2 |
| 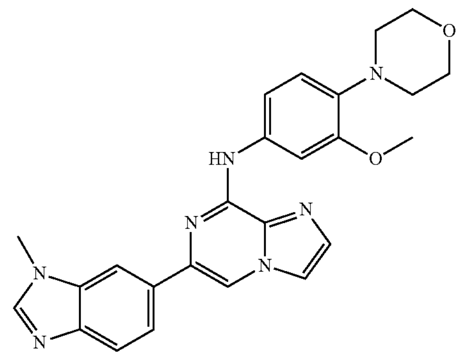 [SMILES: COc1cc(Nc2nc(-c3ccc4ncn(C)c4c3)cn3ccnc23)ccc1N1CCOCC1] | N-[3-methoxy-4-(morpholin-4-yl)phenyl]-6-(1-methyl-1H-1,3-benzodiazol-6-yl)imidazo[1,2-a]pyrazin-8-amine | 456.3 |
| 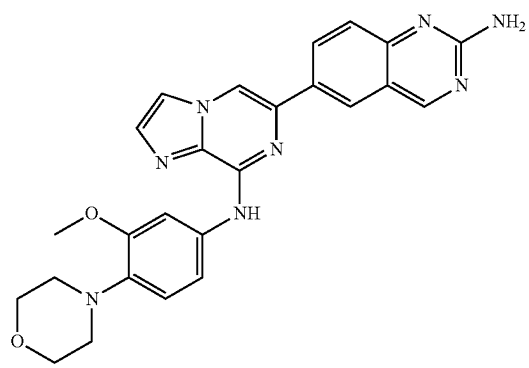 [SMILES: COc1cc(Nc2nc(-c3ccc4nc(N)ncc4c3)cn3ccnc23)ccc1N1CCOCC1] | 6-(8-{[3-methoxy-4-(morpholin-4-yl)phenyl]amino}imidazo[1,2-a]pyrazin-6-yl)quinazolin-2-amine | 469.4 |
| 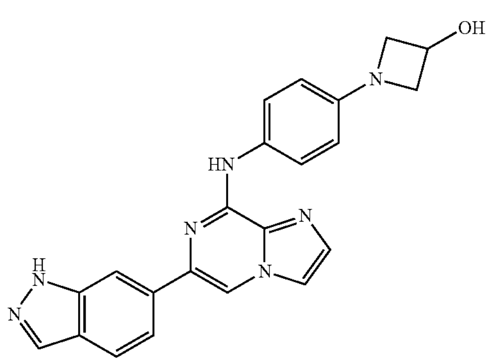 [SMILES: OC1CN(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)azetidin-3-ol | 398.3 |

-continued

| Structure | Name | [M + H]⁺ |
|---|---|---|
| 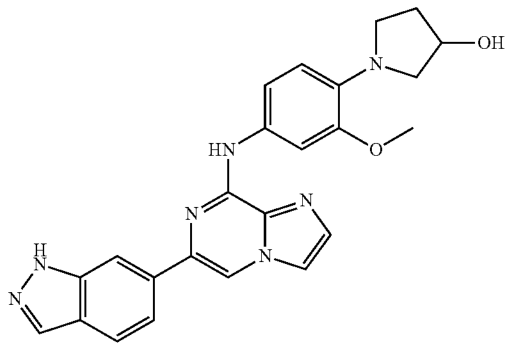 | 1-(4-{[6-(1H-indazol-6-yl)imidazo[1,2-a]pyrazin-8-yl]amino}-2-methoxyphenyl)pyrrolidin-3-ol | 442.5 |
| 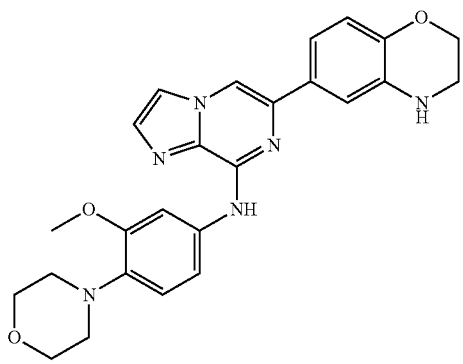 [SMILES: COc1cc(Nc2nc(-c3ccc4c(c3)NCCO4)cn3ccnc23)ccc1N1CCOCC1] | 6-(3,4-dihydro-2H-1,4-benzoxazin-6-yl)-N-[3-methoxy-4-(morpholin-4-yl)phenyl]imidazo[1,2-a]pyrazin-8-amine | 459.7 |
| 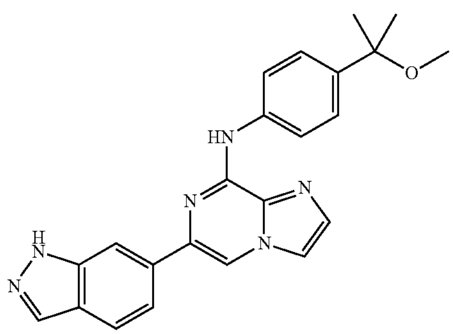 [SMILES: COC(C)(C)c1ccc(Nc2nc(-c3ccc4cn[nH]c4c3)cn3ccnc23)cc1] | 6-(1H-indazol-6-yl)-N-[4-(2-methoxypropan-2-yl)phenyl]imidazo[1,2-a]pyrazin-8-amine | 399.4 |
| 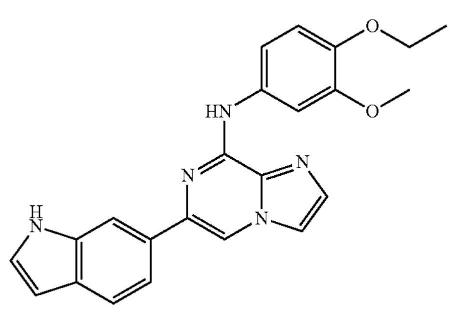 [SMILES: CCOc1ccc(Nc2nc(-c3ccc4cc[nH]c4c3)cn3ccnc23)cc1OC] | N-(4-ethoxy-3-methoxyphenyl)-6-(1H-indol-6-yl)imidazo[1,2-a]pyrazin-8-amine | 400.1 |

-continued

| Structure | Name | [M + H]⁺ |
|---|---|---|
| 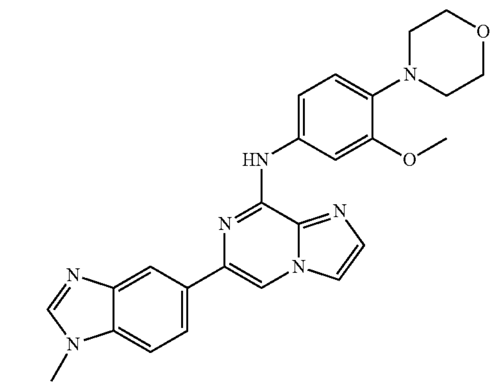 [SMILES: COc1cc(Nc2nc(-c3ccc4c(c3)ncn4C)cn3ccnc23)ccc1N1CCOCC1] | N-[3-methoxy-4-(morpholin-4-yl)phenyl]-6-(1-methyl-1H-1,3-benzodiazol-5-yl)imidazo[1,2-a]pyrazin-8-amine | 456.4 |
| 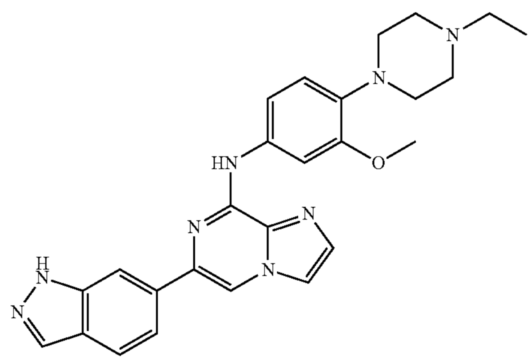 [SMILES: CCN1CCN(c2ccc(Nc3nc(-c4ccc5cn[nH]c5c4)cn4ccnc34)cc2OC)CC1] | N-[4-(4-ethylpiperazin-1-yl)-3-methoxyphenyl]-6-(1H-indazol-6-yl)imidazo[1,2-a]pyrazin-8-amine | 469.7 |
| 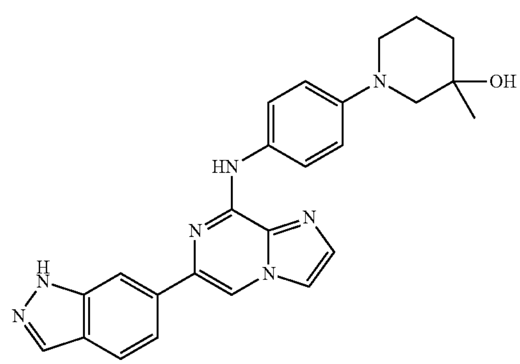 [SMILES: CC1(O)CCCN(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)-3-methylpiperidin-3-ol | 440.5 |
| 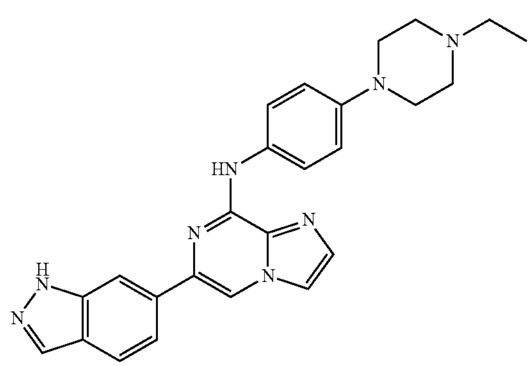 [SMILES: CCN1CCN(c2ccc(Nc3nc(-c4ccc5cn[nH]c5c4)cn4ccnc34)cc2)CC1] | N-[4-(4-ethylpiperazin-1-yl)phenyl]-6-(1H-indazol-6-yl)imidazo[1,2-a]pyrazin-8-amine | 439.4 |

| Structure | Name | [M + H]+ |
|---|---|---|
| 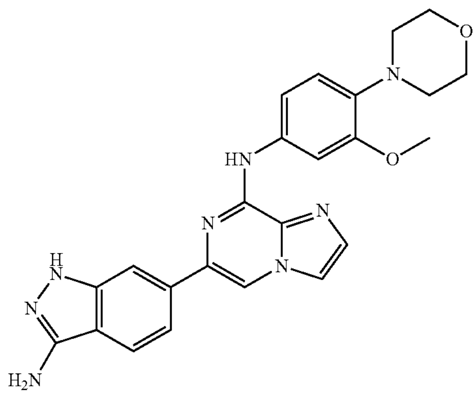 [SMILES: COc1cc(Nc2nc(-c3ccc4c(N)n[nH]c4c3)cn3ccnc23)ccc1N1CCOCC1] | 6-(8-{[3-methoxy-4-(morpholin-4-yl)phenyl]amino}imidazo[1,2-a]pyrazin-6-yl)-1H-indazol-3-amine | 457.6 |
| 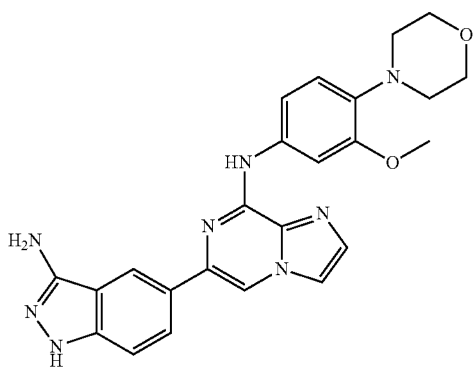 [SMILES: COc1cc(Nc2nc(-c3ccc4[nH]nc(N)c4c3)cn3ccnc23)ccc1N1CCOCC1] | 5-(8-{[3-methoxy-4-(morpholin-4-yl)phenyl]amino}imidazo[1,2-a]pyrazin-6-yl)-1H-indazol-3-amine | 457.5 |
| 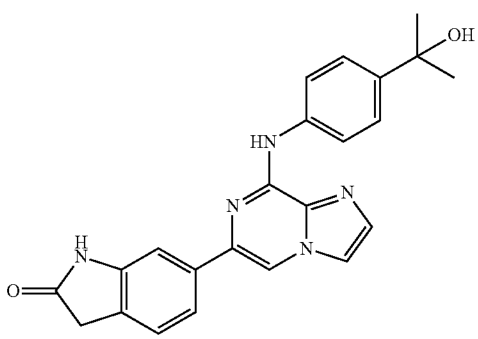 [SMILES: CC(C)(O)c1ccc(Nc2nc(-c3ccc4c(c3)NC(=O)C4)cn3ccnc23)cc1] | 6-(8-{[4-(2-hydroxypropan-2-yl)phenyl]amino}imidazo[1,2-a]pyrazin-6-yl)-2,3-dihydro-1H-indol-2-one | 399.45 |
| 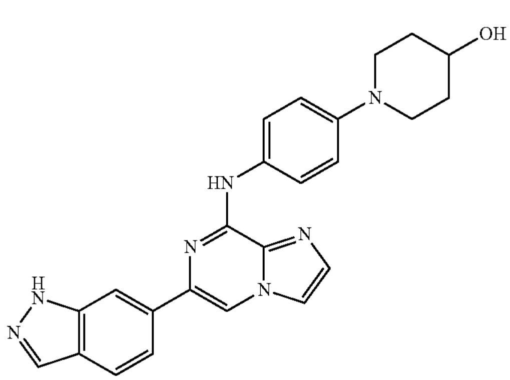 [SMILES: OC1CCN(c2ccc(Nc3nc(-c4ccc5cn[nH]c5c4)cn4ccnc34)cc2)CC1] | 1-(4-{[6-(1H-indazol-6-yl)imidazo[1,2-a]pyrazin-8-yl]amino}phenyl)piperidin-4-ol | 426.2 |

-continued
| Structure | Name | [M + H]+ |
|---|---|---|
| 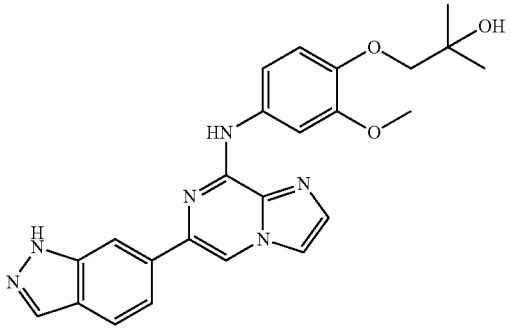 [SMILES: COc1cc(Nc2nc(-c3ccc4cn[nH]c4c3)cn3ccnc23)ccc1OCC(C)(C)O] | 1-(4-{[6-(1H-indazol-6-yl)imidazo[1,2-a]pyrazin-8-yl]amino}-2-methoxyphenoxy)-2-methylpropan-2-ol | 443.6 |
| 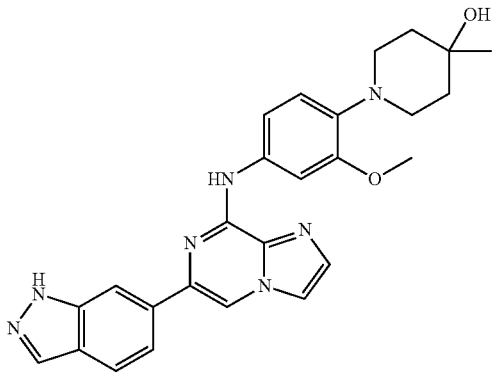 [SMILES: COc1cc(Nc2nc(-c3ccc4cn[nH]c4c3)cn3ccnc23)ccc1N1CCC(C)(O)CC1] | 1-(4-{[6-(1H-indazol-6-yl)imidazo[1,2-a]pyrazin-8-yl]amino}-2-methoxyphenyl)-4-methylpiperidin-4-ol | 470.9 |
| 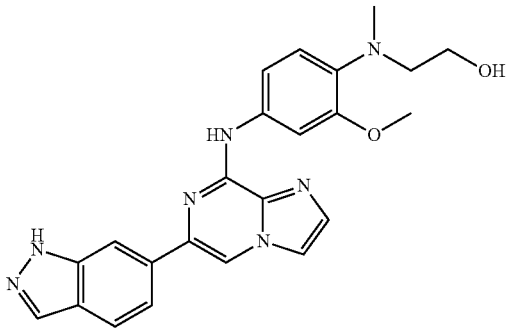 [SMILES: COc1cc(Nc2nc(-c3ccc4cn[nH]c4c3)cn3ccnc23)ccc1N(C)CCO] | 2-[(4-{[6-(1H-indazol-6-yl)imidazo[1,2-a]pyrazin-8-yl]amino}-2-methoxyphenyl)(methyl)amino]ethan-1-ol | 430.5 |
| 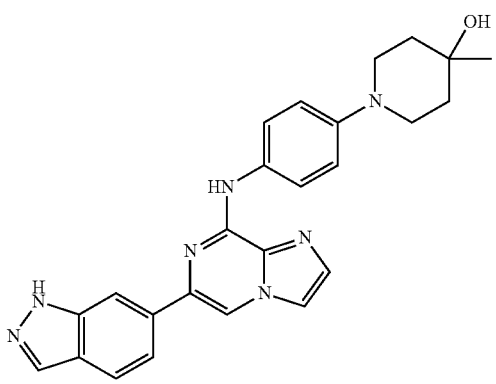 [SMILES: CC1(O)CCN(c2ccc(Nc3nc(-c4ccc5cn[nH]c5c4)cn4ccnc34)cc2)CC1] | 1-(4-{[6-(1H-indazol-6-yl)imidazo[1,2-a]pyrazin-8-yl]amino}phenyl)-4-methylpiperidin-4-ol | 440.4 |

-continued

| Structure | Name | [M + H]+ |
|---|---|---|
| 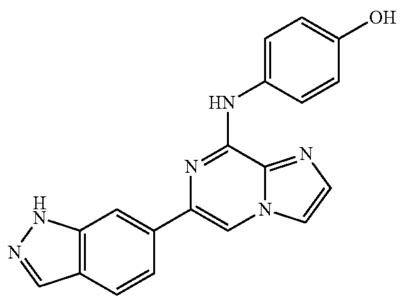 [SMILES: Oc1ccc(Nc2nc(-c3ccc4cn[nH]c4c3)cn3ccnc23)cc1] | 4-{[6-(1H-indazol-6-yl)imidazo[1,2-a]pyrazin-8-yl]amino}phenol | 343.2 |
| 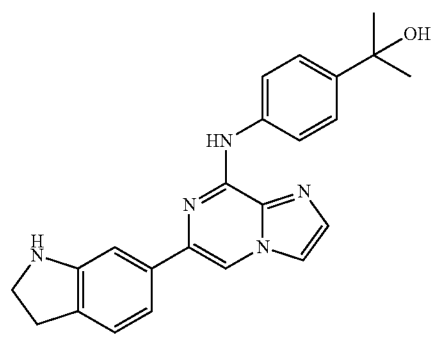 [SMILES: CC(C)(O)c1ccc(Nc2nc(-c3ccc4c(c3)NCC4)cn3ccnc23)cc1] | 2-(4-{[6-(2,3-dihydro-1H-indol-6-yl)imidazo[1,2-a]pyrazin-8-yl]amino}phenyl)propan-2-ol | 386.2 |
| 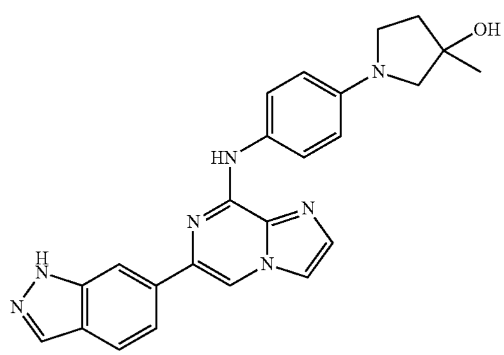 [SMILES: CC1(O)CCN(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)-3-methylpyrrolidin-3-ol | 426.2 |
| 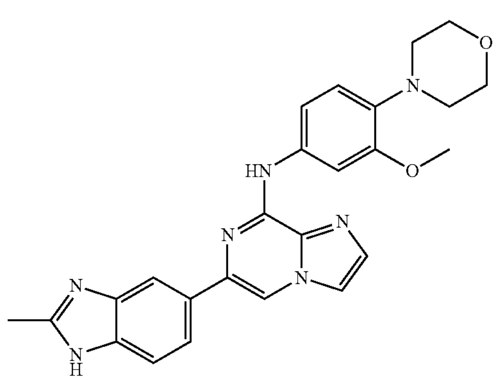 [SMILES: COc1cc(Nc2nc(-c3ccc4[nH]c(C)nc4c3)cn3ccnc23)ccc1N1CCOCC1] | N-[3-methoxy-4-(morpholin-4-yl)phenyl]-6-(2-methyl-1H-1,3-benzodiazol-5-yl)imidazo[1,2-a]pyrazin-8-amine | 456.3 |

-continued

| Structure | Name | [M + H]+ |
|---|---|---|
| 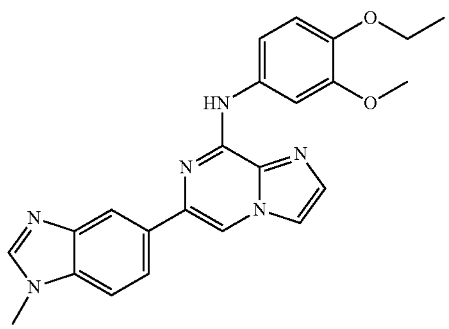 [SMILES: CCOc1ccc(Nc2nc(-c3ccc4c(c3)ncn4C)cn3ccnc23)cc1OC] | N-(4-ethoxy-3-methoxyphenyl)-6-(1-methyl-1H-1,3-benzodiazol-5-yl)imidazo[1,2-a]pyrazin-8-amine | 415.6 |
| 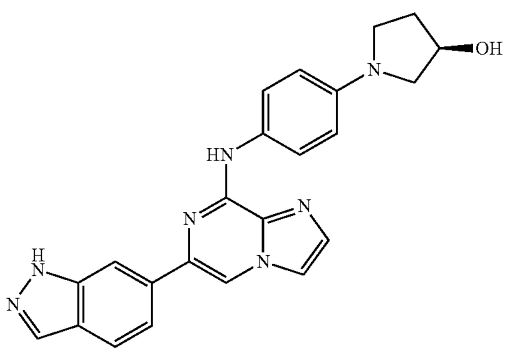 [SMILES: O[C@@H]1CCN(c2ccc(Nc3nc(-c4ccc5cn[nH]c5c4)cn4ccnc34)cc2)C1] | (3R)-1-(4-{[6-(1H-indazol-6-yl)imidazo[1,2-a]pyrazin-8-yl]amino}phenyl)pyrrolidin-3-ol | 412.2 |
| 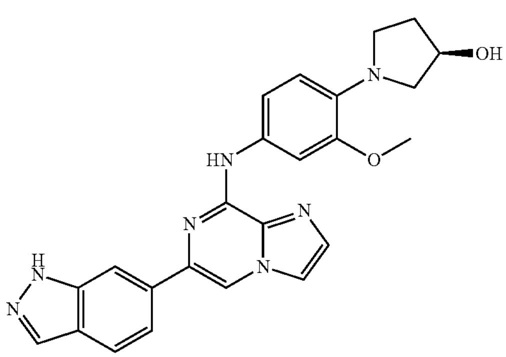 [SMILES: COc1cc(Nc2nc(-c3ccc4cn[nH]c4c3)cn3ccnc23)ccc1N1CC[C@@H](O)C1] | (3R)-1-(4-{[6-(1H-indazol-6-yl)imidazo[1,2-a]pyrazin-8-yl]amino}-2-methoxyphenyl)pyrrolidin-3-ol | 442.7 |
| 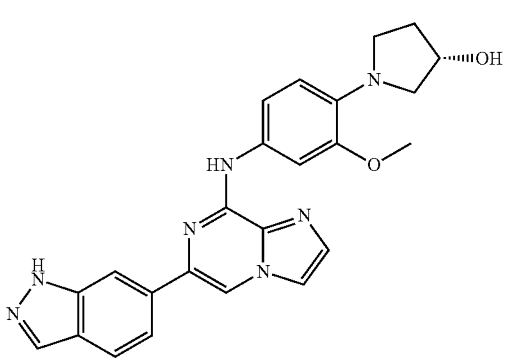 [SMILES: COc1cc(Nc2nc(-c3ccc4cn[nH]c4c3)cn3ccnc23)ccc1N1CC[C@H](O)C1] | (3S)-1-(4-{[6-(1H-indazol-6-yl)imidazo[1,2-a]pyrazin-8-yl]amino}-2-methoxyphenyl)pyrrolidin-3-ol | 442.7 |

-continued

| Structure | Name | [M + H]⁺ |
|---|---|---|
| 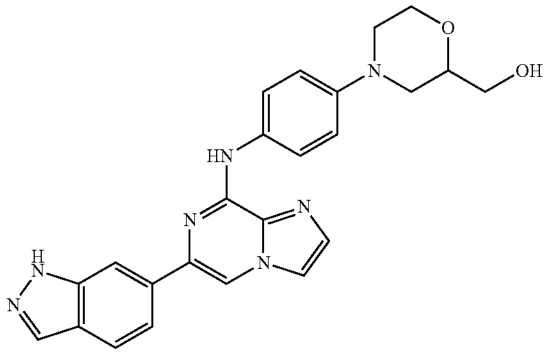 | [4-(4-{[6-(1H-indazol-6-yl)imidazo[1,2-a]pyrazin-8-yl]amino}phenyl)morpholin-2-yl]methanol | 442.7 |
| 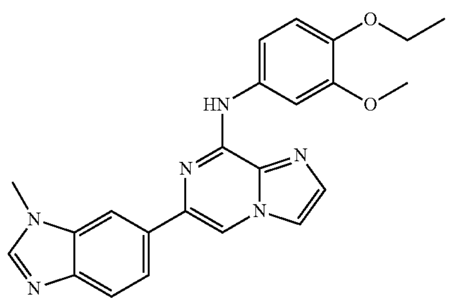 [SMILES: CCOc1ccc(Nc2nc(-c3ccc4ncn(C)c4c3)cn3ccnc23)cc1OC] | N-(4-ethoxy-3-methoxyphenyl)-6-(1-methyl-1H-1,3-benzodiazol-6-yl)imidazo[1,2-a]pyrazin-8-amine | 415.4 |
| 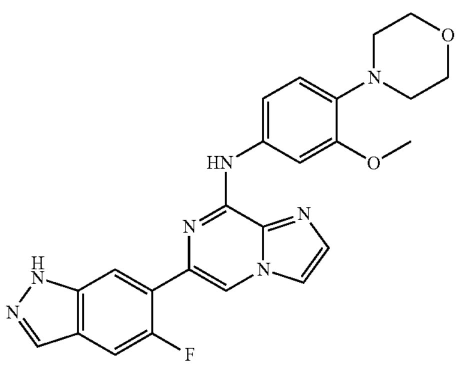 [SMILES: COc1cc(Nc2nc(-c3cc4[nH]ncc4cc3F)cn3ccnc23)ccc1N1CCOCC1] | 6-(5-fluoro-1H-indazol-6-yl)-N-[3-methoxy-4-(morpholin-4-yl)phenyl]imidazo[1,2-a]pyrazin-8-amine | 460.6 |
| 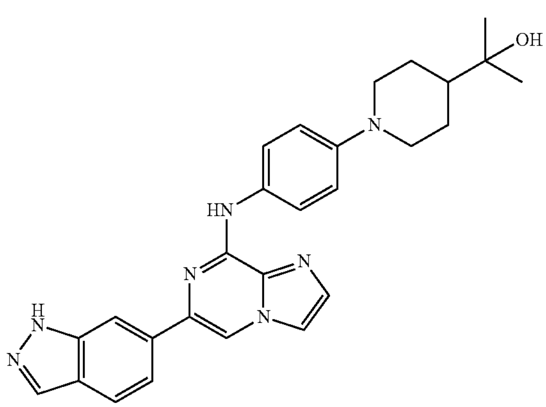 [SMILES: CC(C)(O)C1CCN(c2ccc(Nc3nc(-c4ccc5cn[nH]c5c4)cn4ccnc34)cc2)CC1] | 2-[1-(4-{[6-(1H-indazol-6-yl)imidazo[1,2-a]pyrazin-8-yl]amino}phenyl)piperidin-4-yl]propan-2-ol | 468.5 |

-continued

| Structure | Name | [M + H]+ |
|---|---|---|
| 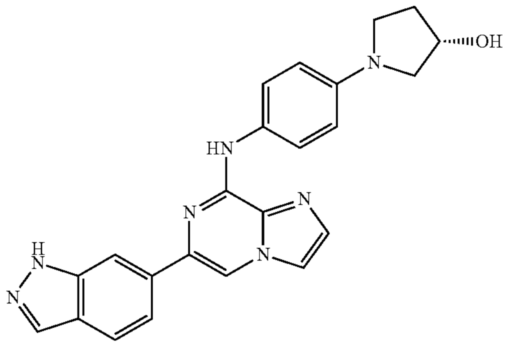 [SMILES: O[C@H]1CCN(c2ccc(Nc3nc(-c4ccc5cn[nH]c5c4)cn4ccnc34)cc2)C1] | (3S)-1-(4-{[6-(1H-indazol-6-yl)imidazo[1,2-a]pyrazin-8-yl]amino}phenyl)pyrrolidin-3-ol | 412.1 |
| 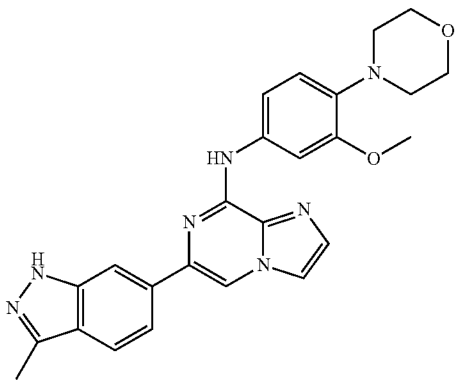 [SMILES: COc1cc(Nc2nc(-c3ccc4c(C)n[nH]c4c3)cn3ccnc23)ccc1N1CCOCC1] | N-[3-methoxy-4-(morpholin-4-yl)phenyl]-6-(3-methyl-1H-indazol-6-yl)imidazo[1,2-a]pyrazin-8-amine | 456.2 |
| 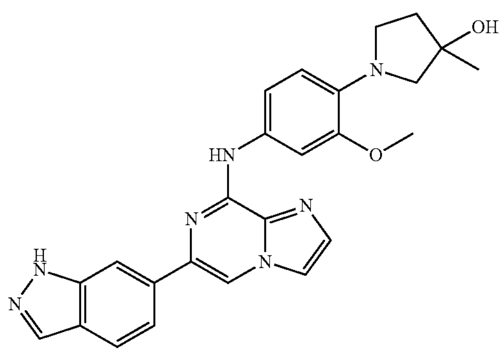 [SMILES: COc1cc(Nc2nc(-c3ccc4cn[nH]c4c3)cn3ccnc23)ccc1N1CCC(C)(O)C1] | 1-(4-{[6-(1H-indazol-6-yl)imidazo[1,2-a]pyrazin-8-yl]amino}-2-methoxyphenyl)-3-methylpyrrolidin-3-ol | 456.2 |
| 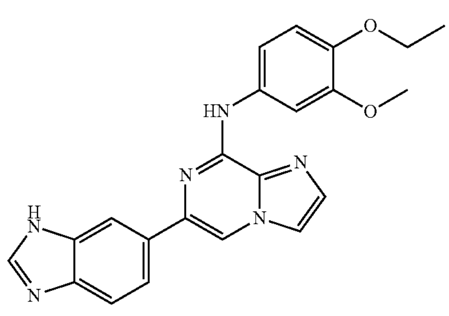 [SMILES: CCOc1ccc(Nc2nc(-c3ccc4nc[nH]c4c3)cn3ccnc23)cc1OC] | 6-(1H-1,3-benzodiazol-6-yl)-N-(4-ethoxy-3-methoxyphenyl)imidazo[1,2-a]pyrazin-8-amine | 401.2 |

-continued
| Structure | Name | [M + H]+ |
|---|---|---|
| 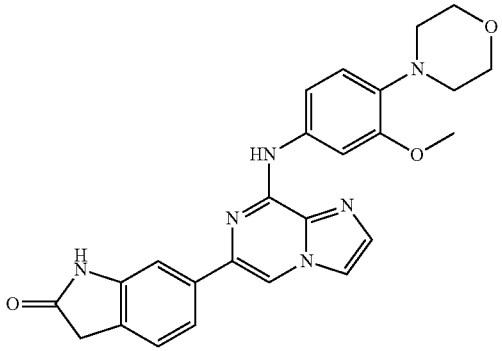 [SMILES: COc1cc(Nc2nc(-c3ccc4c(c3)NC(=O)C4)cn3ccnc23)ccc1N1CCOCC1] | 6-(8-{[3-methoxy-4-(morpholin-4-yl)phenyl]amino}imidazo[1,2-a]pyrazin-6-yl)-2,3-dihydro-1H-indol-2-one | 457.7 |
| 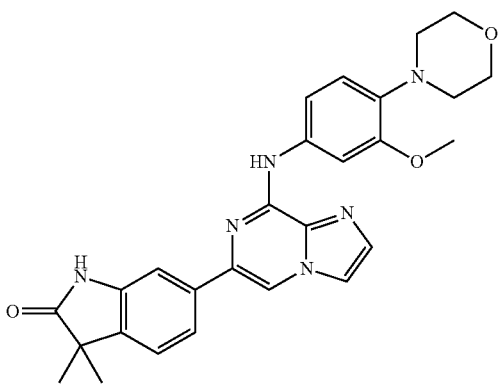 [SMILES: COc1cc(Nc2nc(-c3ccc4c(c3)NC(=O)C4(C)C)cn3ccnc23)ccc1N1CCOCC1] | 6-(8-{[3-methoxy-4-(morpholin-4-yl)phenyl]amino}imidazo[1,2-a]pyrazin-6-yl)-3,3-dimethyl-2,3-dihydro-1H-indol-2-one | 485.7 |
| 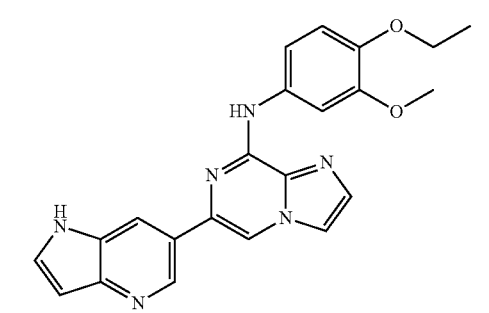 [SMILES: CCOc1ccc(Nc2nc(-c3cnc4cc[nH]c4c3)cn3ccnc23)cc1OC] | N-(4-ethoxy-3-methoxyphenyl)-6-{1H-pyrrolo[3,2-b]pyridin-6-yl}imidazo[1,2-a]pyrazin-8-amine | 401.2 |
| 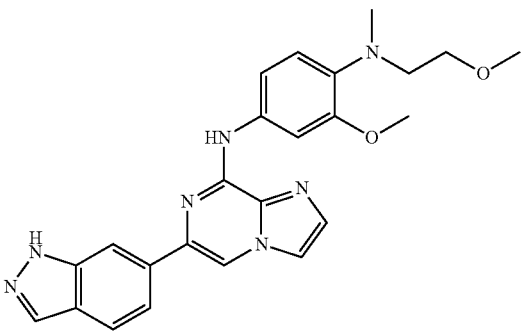 [SMILES: COCCN(C)c1ccc(Nc2nc(-c3ccc4cn[nH]c4c3)cn3ccnc23)cc1OC] | 4-N-[6-(1H-indazol-6-yl)imidazo[1,2-a]pyrazin-8-yl]-2-methoxy-1-N-(2-methoxyethyl)-1-N-methylbenzene-1,4-diamine | 444.3 |

-continued

| Structure | Name | [M + H]⁺ |
|---|---|---|
| 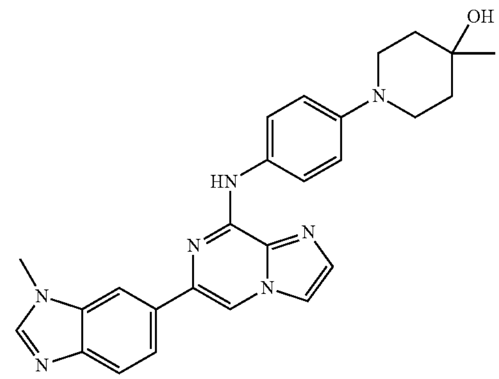 [SMILES: Cn1cnc2ccc(-c3cn4ccnc4c(Nc4ccc(N5CCC(C)(O)CC5)cc4)n3)cc21] | 4-methyl-1-(4-{[6-(1-methyl-1H-1,3-benzodiazol-6-yl)imidazo[1,2-a]pyrazin-8-yl]amino}phenyl)piperidin-4-ol | 454.1 |
| 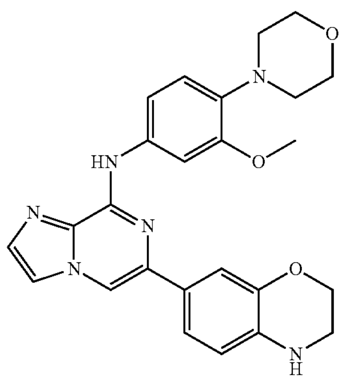 [SMILES: COc1cc(Nc2nc(-c3ccc4c(c3)OCCN4)cn3ccnc23)ccc1N1CCOCC1] | 6-(3,4-dihydro-2H-1,4-benzoxazin-7-yl)-N-[3-methoxy-4-(morpholin-4-yl)phenyl]imidazo[1,2-a]pyrazin-8-amine | 459.4 |
| 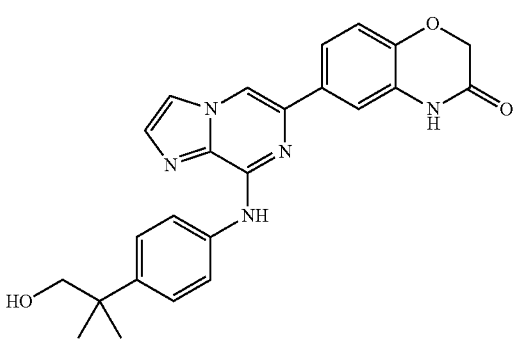 [SMILES: CC(C)(CO)c1ccc(Nc2nc(-c3ccc4c(c3)NC(=O)CO4)cn3ccnc23)cc1] | 6-(8-{[4-(1-hydroxy-2-methylpropan-2-yl)phenyl]amino}imidazo[1,2-a]pyrazin-6-yl)-3,4-dihydro-2H-1,4-benzoxazin-3-one | 430.2 |
| 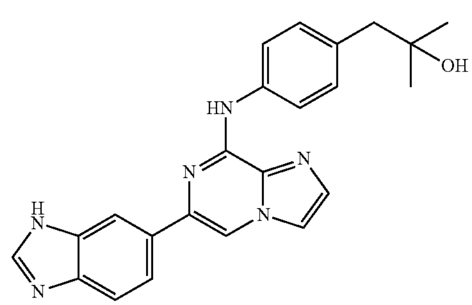 [SMILES: CC(C)(O)Cc1ccc(Nc2nc(-c3ccc4nc[nH]c4c3)cn3ccnc23)cc1] | 1-(4-{[6-(1H-1,3-benzodiazol-6-yl)imidazo[1,2-a]pyrazin-8-yl]amino}phenyl)-2-methylpropan-2-ol | 397.2 |

-continued

| Structure | Name | [M + H]+ |
|---|---|---|
| 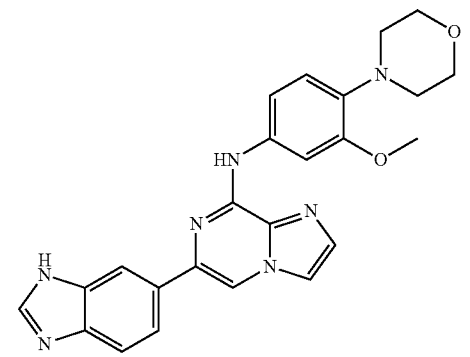 [SMILES: COc1cc(Nc2nc(-c3ccc4nc[nH]c4c3)cn3ccnc23)ccc1N1CCOCC1] | N-[3-methoxy-4-(morpholin-4-yl)phenyl]-6-{1H-pyrrolo[3,2-b]pyridin-6-yl}imidazo[1,2-a]pyrazin-8-amine | 442.7 |
| 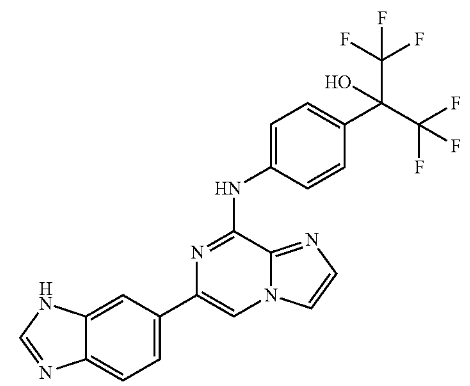 [SMILES: OC(c1ccc(Nc2nc(-c3ccc4nc[nH]c4c3)cn3ccnc23)cc1)(C(F)(F)F)C(F)(F)F] | 2-(4-{[6-(1H-1,3-benzodiazol-6-yl)imidazo[1,2-a]pyrazin-8-yl]amino}phenyl)-1,1,1,3,3,3-hexafluoropropan-2-ol | 493.5 |
| 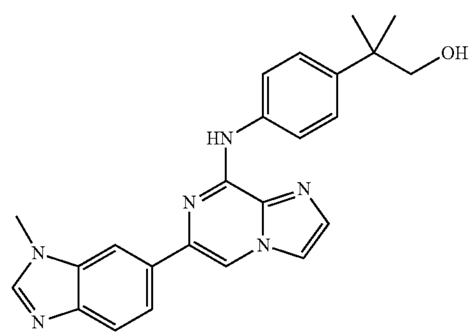 [SMILES: Cn1cnc2ccc(-c3cn4ccnc4c(Nc4ccc(C(C)(C)CO)cc4)n3)cc21] | 2-methyl-2-(4-{[6-(1-methyl-1H-1,3-benzodiazol-6-yl)imidazo[1,2-a]pyrazin-8-yl]amino}phenyl)propan-1-ol | 413.4 |
| 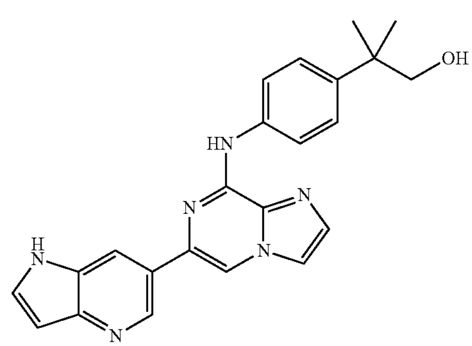 [SMILES: CC(C)(CO)c1ccc(Nc2nc(-c3cnc4cc[nH]c4c3)cn3ccnc23)cc1] | 2-methyl-2-{4-[(6-{1H-pyrrolo[3,2-b]pyridin-6-yl}imidazo[1,2-a]pyrazin-8-yl)amino]phenyl}propan-1-ol | 399.2 |

-continued

| Structure | Name | [M + H]⁺ |
|---|---|---|
| 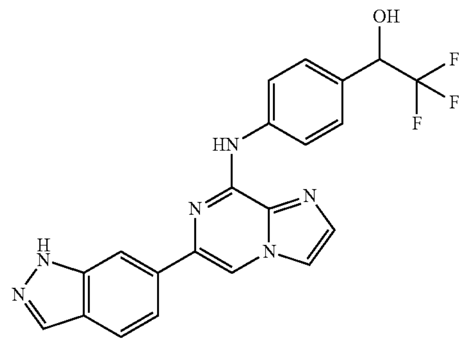 [SMILES: OC(c1ccc(Nc2nc(-c3ccc4cn[nH]c4c3)cn3ccnc23)cc1)C(F)(F)F] | 2,2,2-trifluoro-1-(4-{[6-(1H-indazol-6-yl)imidazo[1,2-a]pyrazin-8-yl]amino}phenyl)ethan-1-ol | 425.3 |
| 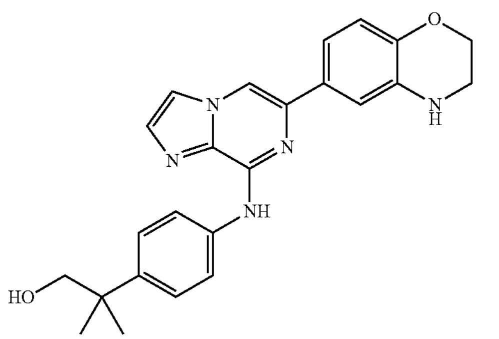 [SMILES: CC(C)(CO)c1ccc(Nc2nc(-c3ccc4c(c3)NCCO4)cn3ccnc23)cc1] | 2-(4-{[6-(3,4-dihydro-2H-1,4-benzoxazin-6-yl)imidazo[1,2-a]pyrazin-8-yl]amino}phenyl)-2-methylpropan-1-ol | 416.8 |
| 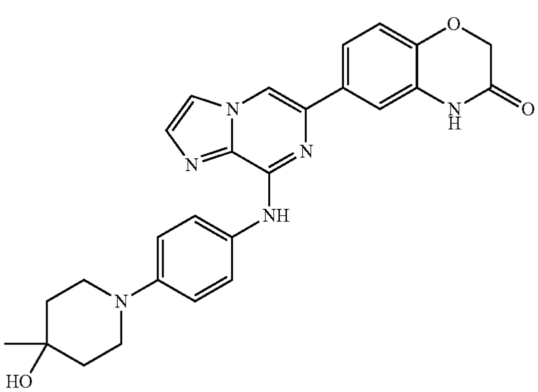 [SMILES: CC1(O)CCN(c2ccc(Nc3nc(-c4ccc5c(c4)NC(=O)CO5)cn4ccnc34)cc2)CC1] | 6-(8-{[4-(4-hydroxy-4-methylpiperidin-1-yl)phenyl]amino}imidazo[1,2-a]pyrazin-6-yl)-3,4-dihydro-2H-1,4-benzoxazin-3-one | 471.7 |
| 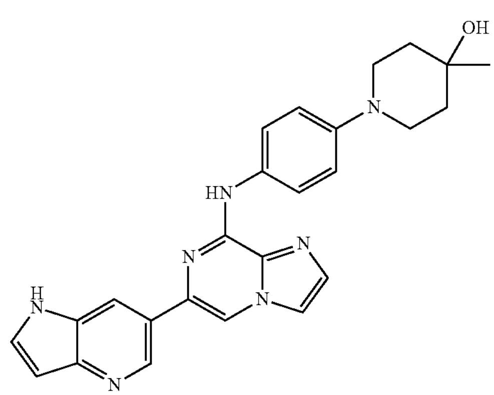 [SMILES: CC1(O)CCN(c2ccc(Nc3nc(-c4cnc5cc[nH]c5c4)cn4ccnc34)cc2)CC1] | 4-methyl-1-{4-[(6-{1H-pyrrolo[3,2-b]pyridin-6-yl}imidazo[1,2-a]pyrazin-8-yl)amino]phenyl}piperidin-4-ol | 440.5 |

-continued

| Structure | Name | [M + H]⁺ |
|---|---|---|
| 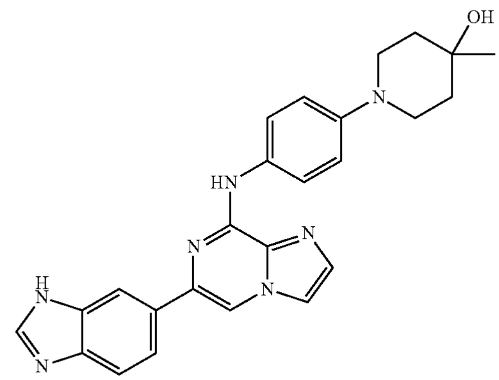 [SMILES: CC1(O)CCN(c2ccc(Nc3nc(-c4ccc5nc[nH]c5c4)cn4ccnc34)cc2)CC1] | 1-(4-{[6-(1H-1,3-benzodiazol-6-yl)imidazo[1,2-a]pyrazin-8-yl]amino}phenyl)-4-methylpiperidin-4-ol | 438.2 |
| 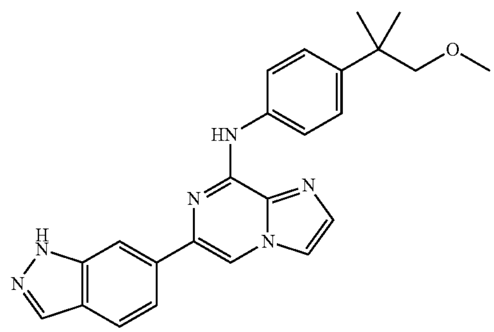 [SMILES: COCC(C)(C)c1ccc(Nc2nc(-c3ccc4cn[nH]c4c3)cn3ccnc23)cc1] | 6-(1H-indazol-6-yl)-N-[4-(1-methoxy-2-methylpropan-2-yl)phenyl]imidazo[1,2-a]pyrazin-8-amine | 413.3 |
| 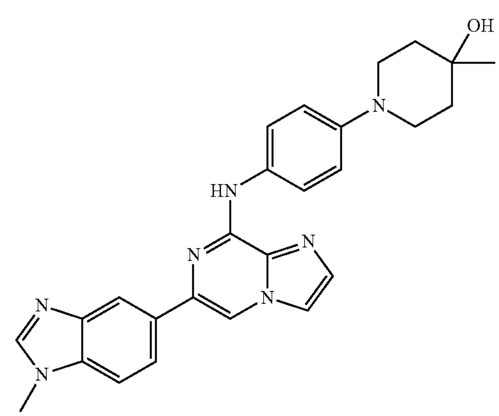 [SMILES: Cn1cnc2cc(-c3cn4ccnc4c(Nc4ccc(N5CCC(C)(O)CC5)cc4)n3)ccc21] | 4-methyl-1-(4-{[6-(1-methyl-1H-1,3-benzodiazol-5-yl)imidazo[1,2-a]pyrazin-8-yl]amino}phenyl)piperidin-4-ol | 454.1 |
| 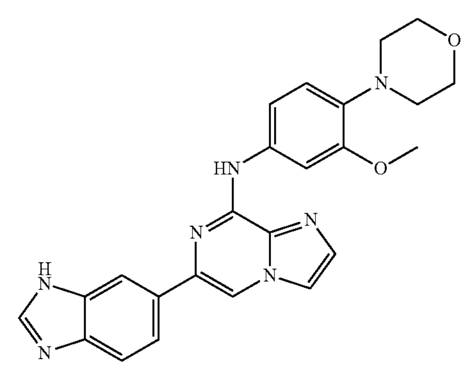 [SMILES: COc1cc(Nc2nc(-c3ccc4nc[nH]c4c3)cn3ccnc23)ccc1N1CCOCC1] | 6-(1H-1,3-benzodiazol-6-yl)-N-[3-methoxy-4-(morpholin-4-yl)phenyl]imidazo[1,2-a]pyrazin-8-amine | 442.8 |

-continued

| Structure | Name | [M + H]+ |
|---|---|---|
| 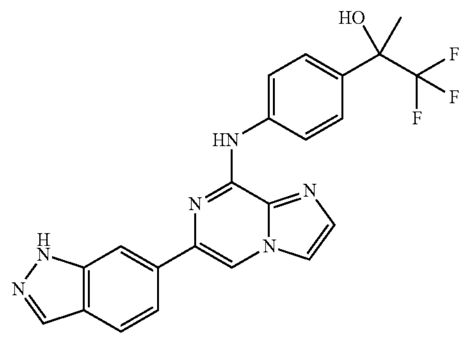 [SMILES: CC(O)(c1ccc(Nc2nc(-c3ccc4cn[nH]c4c3)cn3ccnc23)cc1)C(F)(F)F] | 1,1,1-trifluoro-2-(4-{[6-(1H-indazol-6-yl)imidazo[1,2-a]pyrazin-8-yl]amino}phenyl)propan-2-ol | 437.4 |
| 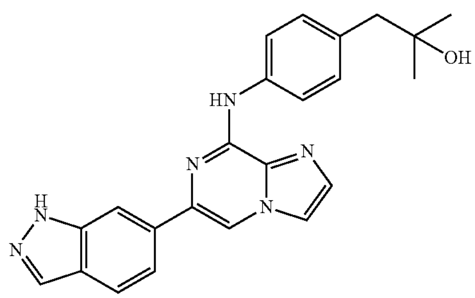 [SMILES: CC(C)(O)Cc1ccc(Nc2nc(-c3ccc4cn[nH]c4c3)cn3ccnc23)cc1] | 1-{4-{[6-(1H-indazol-6-yl)imidazo[1,2-a]pyrazin-8-yl]amino}phenyl)-2-methylpropan-2-ol | 399.3 |
| 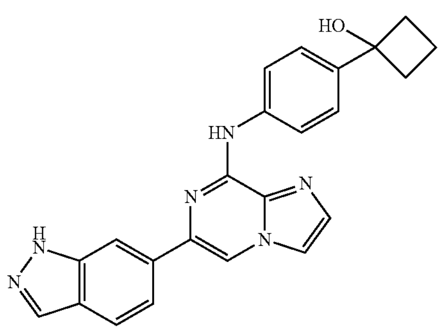 [SMILES: OC1(c2ccc(Nc3nc(-c4ccc5cn[nH]c5c4)cn4ccnc34)cc2)CCC1] | 1-(4-{[6-(1H-indazol-6-yl)imidazo[1,2-a]pyrazin-8-yl]amino}phenyl)cyclobutan-1-ol | 397.2 |
| 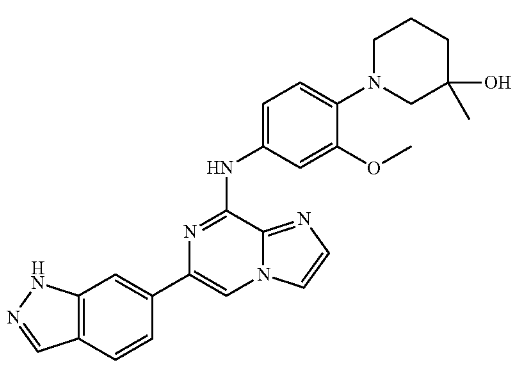 [SMILES: COc1cc(Nc2nc(-c3ccc4cn[nH]c4c3)cn3ccnc23)ccc1N1CCCC(C)(O)C1] | 1-(4-{[6-(1H-indazol-6-yl)imidazo[1,2-a]pyrazin-8-yl]amino}-2-methoxyphenyl)-3-methylpiperidin-3-ol | 470.9 |

-continued

| Structure | Name | [M + H]⁺ |
|---|---|---|
| 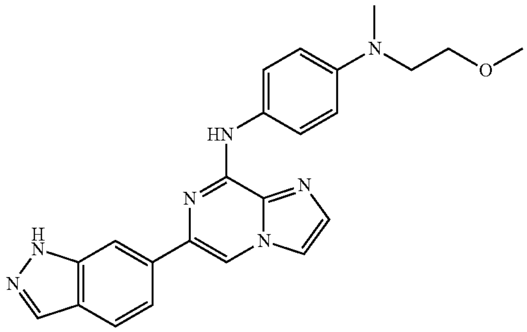 [SMILES: COCCN(C)c1ccc(Nc2nc(-c3ccc4cn[nH]c4c3)cn3ccnc23)cc1] | 4-N-[6-(1H-indazol-6-yl)imidazo[1,2-a]pyrazin-8-yl]-1-N-(2-methoxyethyl)-1-N-methylbenzene-1,4-diamine | 414.5 |
| 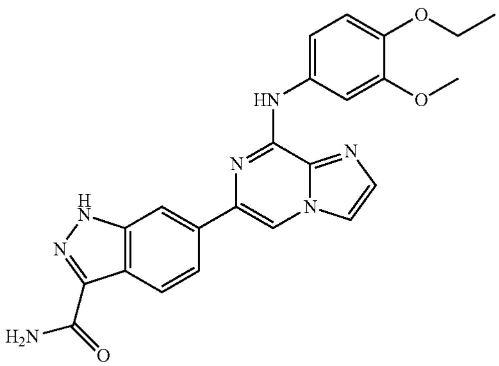 [SMILES: CCOc1ccc(Nc2nc(-c3ccc4c(C(N)=O)n[nH]c4c3)cn3ccnc23)cc1OC] | 6-{8-[(4-ethoxy-3-methoxyphenyl)amino]imidazo[1,2-a]pyrazin-6-yl}-1H-indazole-3-carboxamide | 444.8 |
| 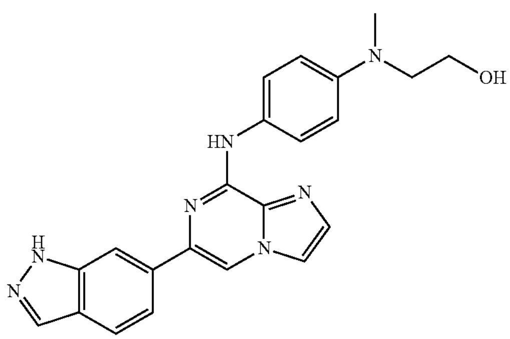 [SMILES: CN(CCO)c1ccc(Nc2nc(-c3ccc4cn[nH]c4c3)cn3ccnc23)cc1] | 2-[(4-{[6-(1H-indazol-6-yl)imidazo[1,2-a]pyrazin-8-yl]amino}phenyl)(methyl)amino]ethan-1-ol | 400.2 |
| 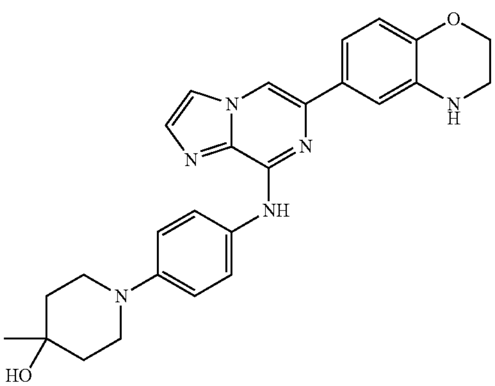 [SMILES: CC1(O)CCN(c2ccc(Nc3nc(-c4ccc5c(c4)NCCO5)cn4ccnc34)cc2)CC1] | 1-(4-{[6-(3,4-dihydro-2H-1,4-benzoxazin-6-yl)imidazo[1,2-a]pyrazin-8-yl]amino}phenyl)-4-methylpiperidin-4-ol | 457.6 |

-continued

| Structure | Name | [M + H]⁺ |
|---|---|---|
| 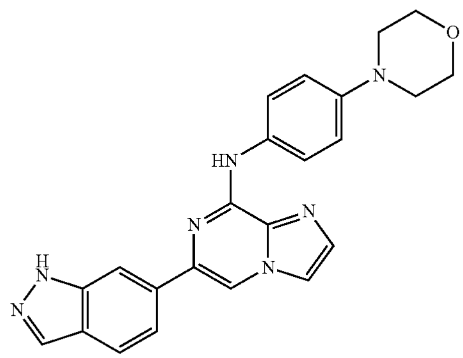 | 6-(1H-indazol-6-yl)-N-[4-(morpholin-4-yl)phenyl]imidazo[1,2-a]pyrazin-8-amine | 412.4 |
| 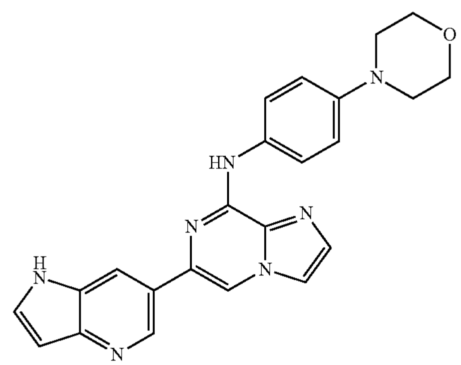 [SMILES: c1cn2cc(-c3cnc4cc[nH]c4c3)nc(Nc3ccc(N4CCOCC4)cc3)c2n1] | N-[4-(morpholin-4-yl)phenyl]-6-{1H-pyrrolo[3,2-b]pyridin-6-yl}imidazo[1,2-a]pyrazin-8-amine | 412.5 |
| 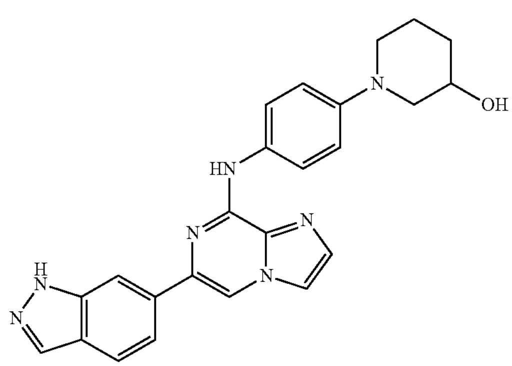 [SMILES: OC1CCCN(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)piperidin-3-ol | 426.2 |
| 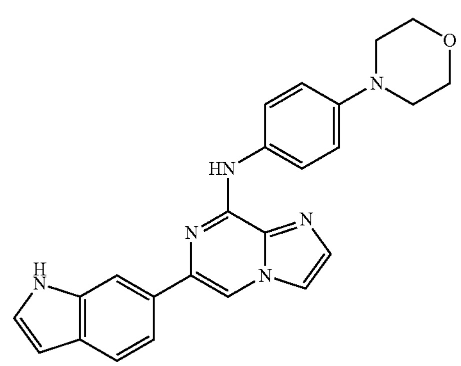 [SMILES: c1cn2cc(-c3ccc4cc[nH]c4c3)nc(Nc3ccc(N4CCOCC4)cc3)c2n1] | 6-(1H-indol-6-yl)-N-[4-(morpholin-4-yl)phenyl]imidazo[1,2-a]pyrazin-8-amine | 411.2 |

-continued

| Structure | Name | [M + H]+ |
|---|---|---|
| 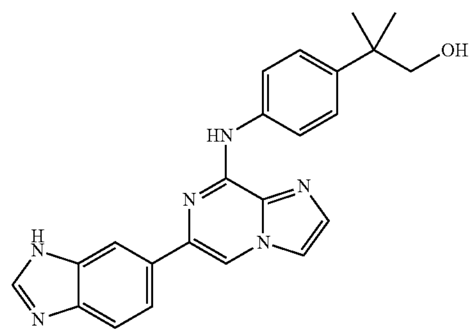 [SMILES: CC(C)(CO)c1ccc(Nc2nc(-c3ccc4nc[nH]c4c3)cn3ccnc23)cc1] | 2-(4-{[6-(1H-1,3-benzodiazol-6-yl)imidazo[1,2-a]pyrazin-8-yl]amino}phenyl)-2-methylpropan-1-ol | 399.1 |
| 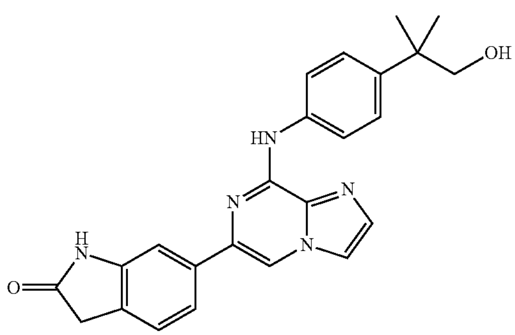 [SMILES: CC(C)(CO)c1ccc(Nc2nc(-c3ccc4c(c3)NC(=O)C4)cn3ccnc23)cc1] | 6-(8-{[4-(1-hydroxy-2-methylpropan-2-yl)phenyl]amino}imidazo[1,2-a]pyrazin-6-yl)-2,3-dihydro-1H-indol-2-one | 414.5 |
| 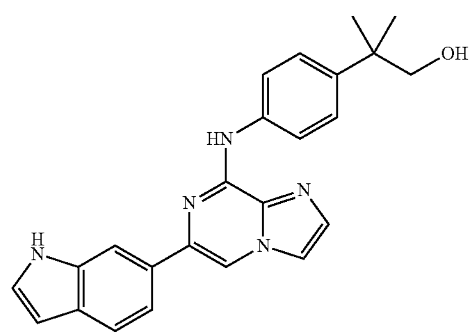 [SMILES: CC(C)(CO)c1ccc(Nc2nc(-c3ccc4cc[nH]c4c3)cn3ccnc23)cc1] | 2-(4-{[6-(1H-indol-6-yl)imidazo[1,2-a]pyrazin-8-yl]amino}phenyl)-2-methylpropan-1-ol | 398.2 |
| 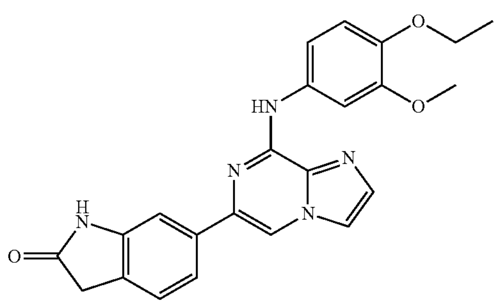 [SMILES: CCOc1ccc(Nc2nc(-c3ccc4c(c3)NC(=O)C4)cn3ccnc23)cc1OC] | 6-{8-[(4-ethoxy-3-methoxyphenyl)amino]imidazo[1,2-a]pyrazin-6-yl}-2,3-dihydro-1H-indol-2-one | 416.7 |

-continued

| Structure | Name | [M + H]+ |
|---|---|---|
| 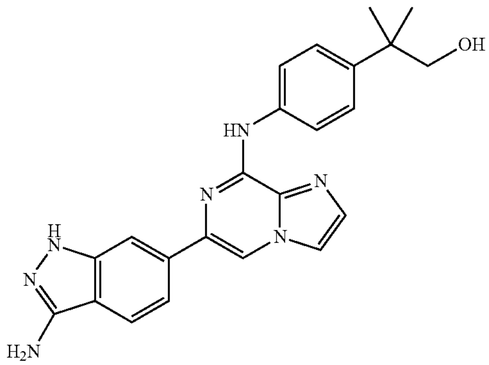 [SMILES: CC(C)(CO)c1ccc(Nc2nc(-c3ccc4c(N)n[nH]c4c3)cn3ccnc23)cc1] | 2-(4-{[6-(3-amino-1H-indazol-6-yl)imidazo[1,2-a]pyrazin-8-yl]amino}phenyl)-2-methylpropan-1-ol | 414.4 |
| 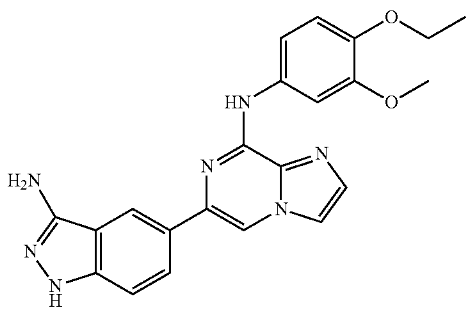 [SMILES: CCOc1ccc(Nc2nc(-c3ccc4[nH]nc(N)c4c3)cn3ccnc23)cc1OC] | 5-{8-[(4-ethoxy-3-methoxyphenyl)amino]imidazo[1,2-a]pyrazin-6-yl}-1H-indazol-3-amine | 416.7 |
| 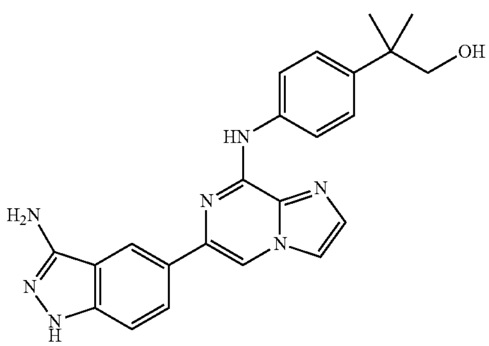 [SMILES: CC(C)(CO)c1ccc(Nc2nc(-c3ccc4[nH]nc(N)c4c3)cn3ccnc23)cc1] | 2-(4-{[6-(3-amino-1H-indazol-5-yl)imidazo[1,2-a]pyrazin-8-yl]amino}phenyl)-2-methylpropan-1-ol | 414.6 |
| 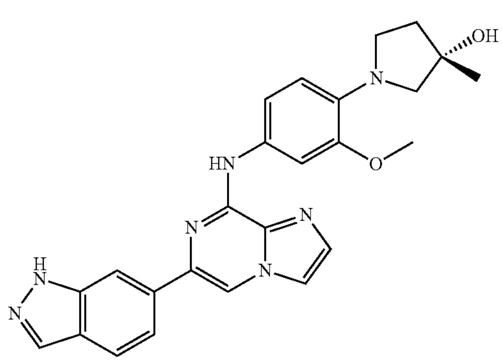 [SMILES: COc1cc(Nc2nc(-c3ccc4cn[nH]c4c3)cn3ccnc23)ccc1N1CC[C@](C)(O)C1] | (3S)-1-(4-{[6-(1H-indazol-6-yl)imidazo[1,2-a]pyrazin-8-yl]amino}-2-methoxyphenyl)-3-methylpyrrolidin-3-ol | 456.1 |

-continued

| Structure | Name | [M + H]+ |
|---|---|---|
| 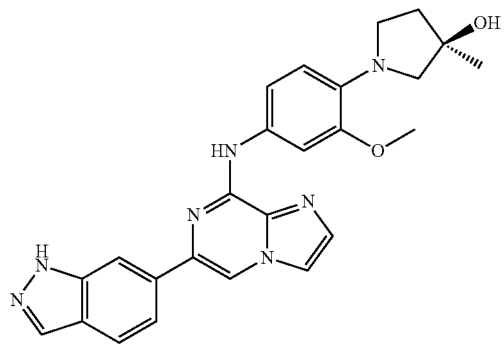 [SMILES: COc1cc(Nc2nc(-c3ccc4cn[nH]c4c3)cn3ccnc23)ccc1N1CC[C@@](C)(O)C1] | (3R)-1-(4-{[6-(1H-indazol-6-yl)imidazo[1,2-a]pyrazin-8-yl]amino}-2-methoxyphenyl)-3-methylpyrrolidin-3-ol | 456.2 |
| 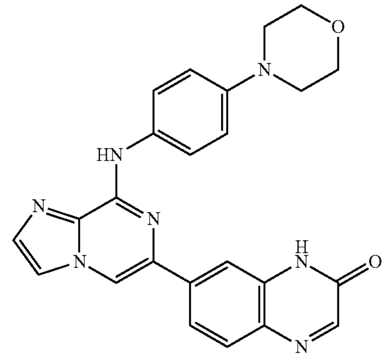 [SMILES: O=c1cnc2ccc(-c3cn4ccnc4c(Nc4ccc(N5CCOCC5)cc4)n3)cc2[nH]1] | 7-(8-{[4-(morpholin-4-yl)phenyl]amino}imidazo[1,2-a]pyrazin-6-yl)-1,2-dihydroquinoxalin-2-one | 440.5 |
| 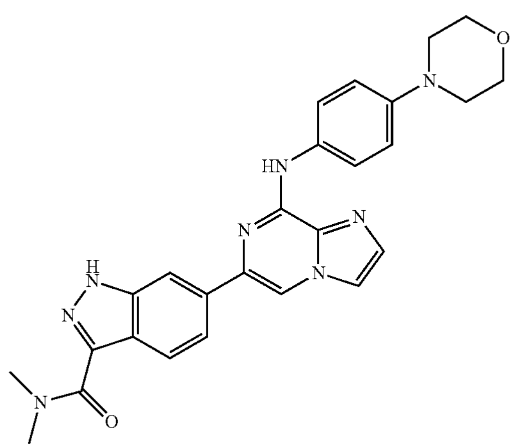 [SMILES: CN(C)C(=O)c1n[nH]c2cc(-c3cn4ccnc4c(Nc4ccc(N5CCOCC5)cc4)n3)ccc12] | N,N-dimethyl-6-(8-{[4-(morpholin-4-yl)phenyl]amino}imidazo[1,2-a]pyrazin-6-yl)-1H-indazole-3-carboxamide | 483.4 |
| 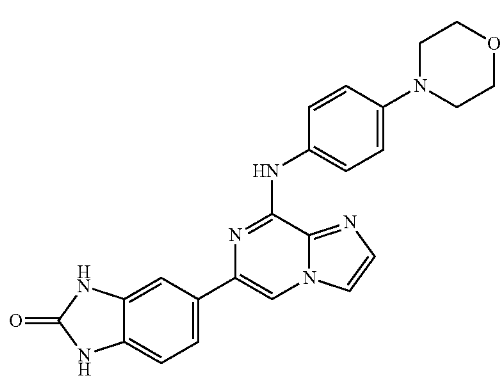 [SMILES: O=c1[nH]c2ccc(-c3cn4ccnc4c(Nc4ccc(N5CCOCC5)cc4)n3)cc2[nH]1] | 5-(8-{[4-(morpholin-4-yl)phenyl]amino}imidazo[1,2-a]pyrazin-6-yl)-2,3-dihydro-1H-1,3-benzodiazol-2-one | 428.3 |

| Structure | Name | [M + H]+ |
|---|---|---|
| 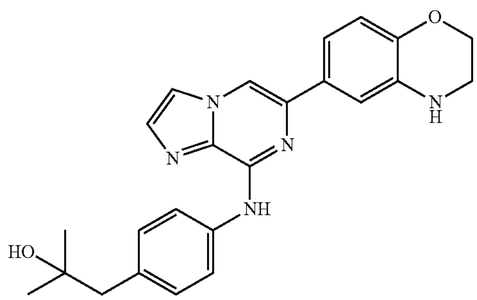 [SMILES: CC(C)(O)Cc1ccc(Nc2nc(-c3ccc4c(c3)NCCO4)cn3ccnc23)cc1] | 1-(4-{[6-(3,4-dihydro-2H-1,4-benzoxazin-6-yl)imidazo[1,2-a]pyrazin-8-yl]amino}phenyl)-2-methylpropan-2-ol | 416.8 |
| 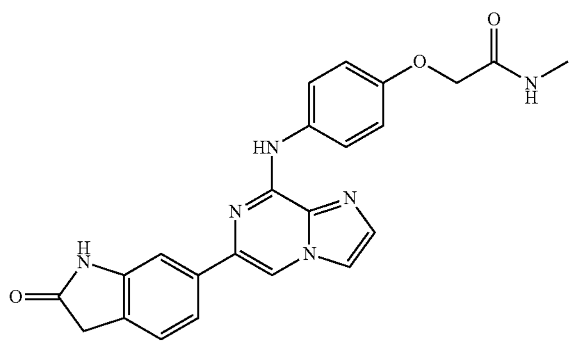 [SMILES: CNC(=O)COc1ccc(Nc2nc(-c3ccc4c(c3)NC(=O)C4)cn3ccnc23)cc1] | N-methyl-2-(4-{[6-(2-oxo-2,3-dihydro-1H-indol-6-yl)imidazo[1,2-a]pyrazin-8-yl]amino}phenoxy)acetamide | 429.4 |
| 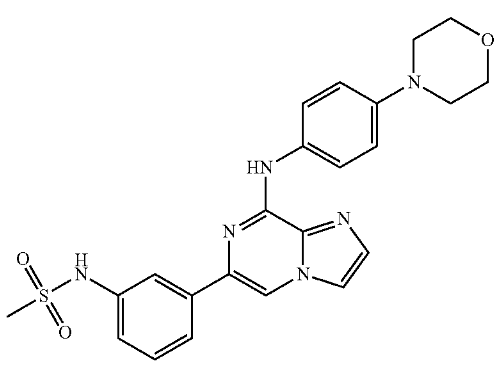 [SMILES: CS(=O)(=O)Nc1cccc(-c2cn3ccnc3c(Nc3ccc(N4CCOCC4)cc3)n2)c1] | N-[3-(8-{[4-(morpholin-4-yl)phenyl]amino}imidazo[1,2-a]pyrazin-6-yl)phenyl]methanesulfonamide | 465.4 |
| 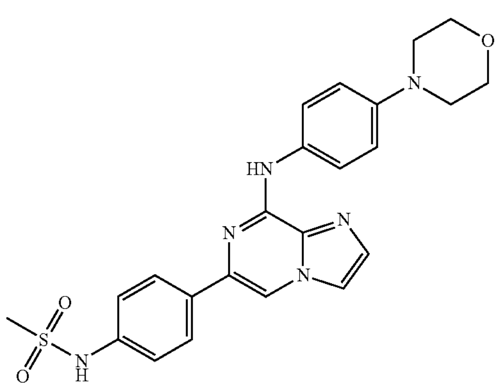 [SMILES: CS(=O)(=O)Nc1ccc(-c2cn3ccnc3c(Nc3ccc(N4CCOCC4)cc3)n2)cc1] | N-[4-(8-{[4-(morpholin-4-yl)phenyl]amino}imidazo[1,2-a]pyrazin-6-yl)phenyl]methanesulfonamide | 465.4 |

| Structure | Name | [M + H]⁺ |
|---|---|---|
| 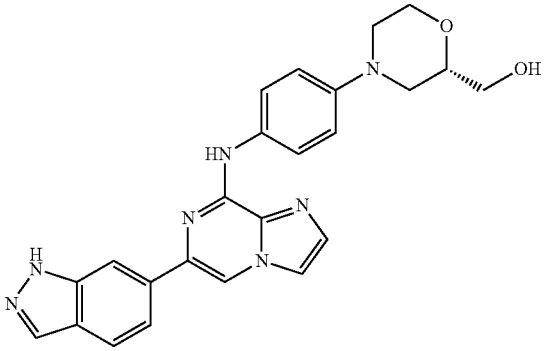 [SMILES: OC[C@@H]1CN(c2ccc(Nc3nc(-c4ccc5cn[nH]c5c4)cn4ccnc34)cc2)CCO1] | [(2S)-4-(4-{[6-(1H-indazol-6-yl)imidazo[1,2-a]pyrazin-8-yl]amino}phenyl)morpholin-2-yl]methanol | 442.3 |
| 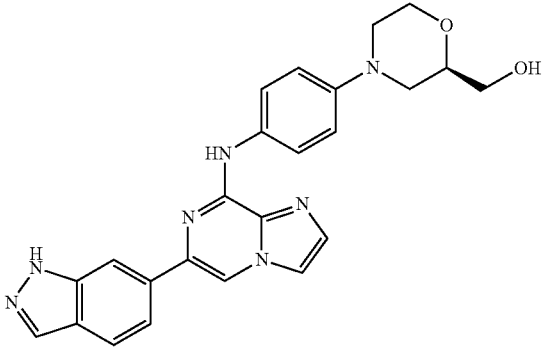 [SMILES: OC[C@H]1CN(c2ccc(Nc3nc(-c4ccc5cn[nH]c5c4)cn4ccnc34)cc2)CCO1] | [(2R)-4-(4-{[6-(1H-indazol-6-yl)imidazo[1,2-a]pyrazin-8-yl]amino}phenyl)morpholin-2-yl]methanol | 442.3 |
| 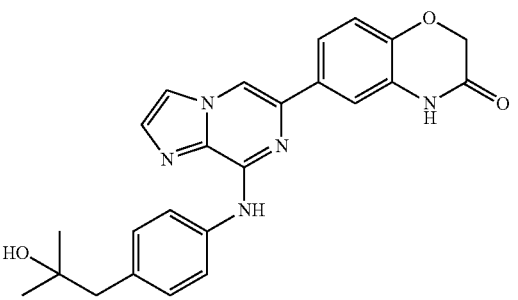 [SMILES: CC(C)(O)Cc1ccc(Nc2nc(-c3ccc4c(c3)NC(=O)CO4)cn3ccnc23)cc1] | 6-(8-{[4-(2-hydroxy-2-methylpropyl)phenyl]amino}imidazo[1,2-a]pyrazin-6-yl)-3,4-dihydro-2H-1,4-benzoxazin-3-one | 430.4 |
| 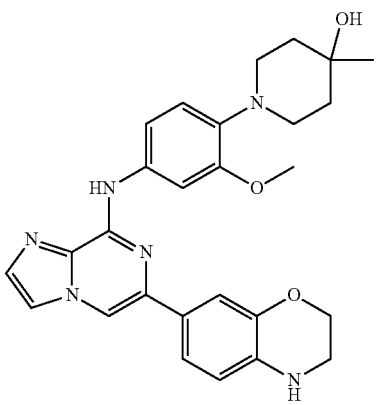 [SMILES: COc1cc(Nc2nc(-c3ccc4c(c3)OCCN4)cn3ccnc23)ccc1N1CCC(C)(O)CC1] | 1-(4-{[6-(3,4-dihydro-2H-1,4-benzoxazin-7-yl)imidazo[1,2-a]pyrazin-8-yl]amino}-2-methoxyphenyl)-4-methylpiperidin-4-ol | 487.5 |

-continued
| Structure | Name | [M + H]+ |
|---|---|---|
| 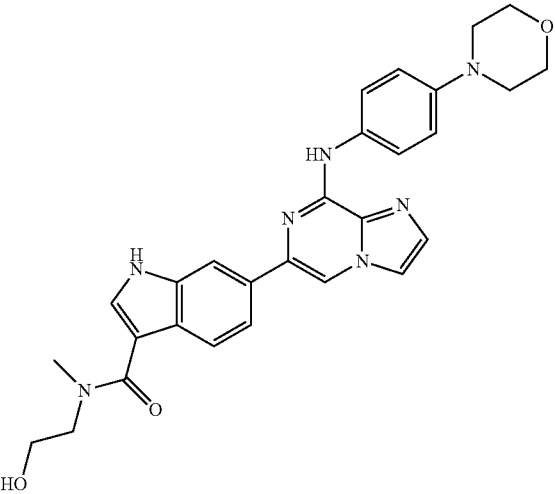 [SMILES: CN(CCO)C(=O)c1c[nH]c2cc(-c3cn4ccnc4c(Nc4ccc(N5CCOCC5)cc4)n3)ccc12] | N-(2-hydroxyethyl)-N-methyl-6-(8-{[4-(morpholin-4-yl)phenyl]amino}imidazo[1,2-a]pyrazin-6-yl)-1H-indole-3-carboxamide | 512.7 |
| 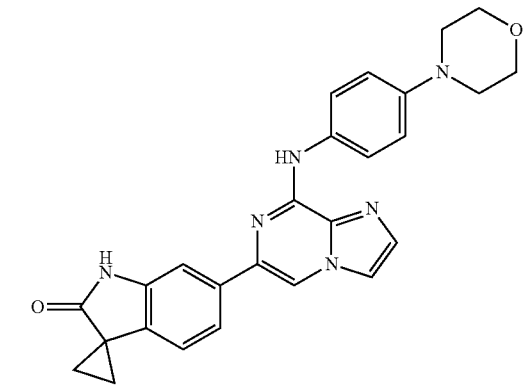 [SMILES: O=C1Nc2cc(-c3cn4ccnc4c(Nc4ccc(N5CCOCC5)cc4)n3)ccc2C12CC2] | 6'-(8-{[4-(morpholin-4-yl)phenyl]amino}imidazo[1,2-a]pyrazin-6-yl)-1',2'-dihydrospiro[cyclopropane-1,3'-indole]-2'-one | 453.1 |
| 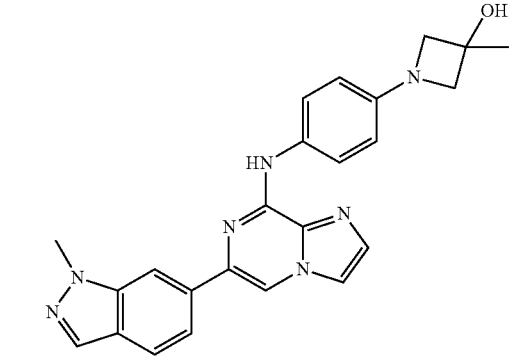 [SMILES: Cn1ncc2ccc(-c3cn4ccnc4c(Nc4ccc(N5CC(C)(O)C5)cc4)n3)cc21] | 3-methyl-1-(4-{[6-(1-methyl-1H-indazol-6-yl)imidazo[1,2-a]pyrazin-8-yl]amino}phenyl)azetidin-3-ol | 426.3 |
| 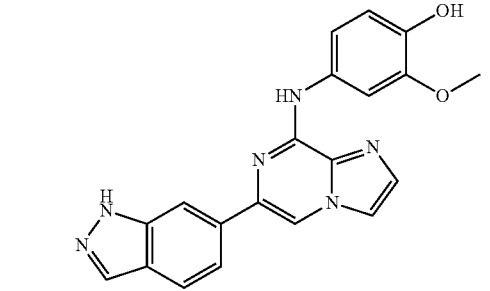 [SMILES: COc1cc(Nc2nc(-c3ccc4cn[nH]c4c3)cn3ccnc23)ccc1O] | 4-{[6-(1H-indazol-6-yl)imidazo[1,2-a]pyrazin-8-yl]amino}-2-methoxyphenol | 373.2 |

-continued

| Structure | Name | [M + H]+ |
|---|---|---|
| 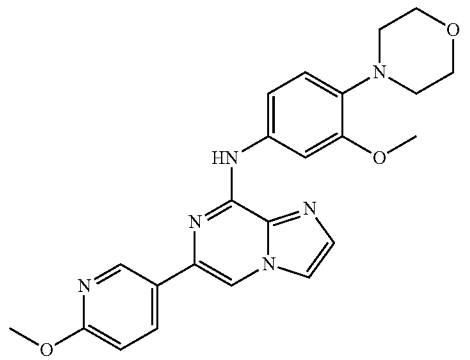 [SMILES: COc1ccc(-c2cn3ccnc3c(Nc3ccc(N4CCOCC4)c(OC)c3)n2)cn1] | N-[3-methoxy-4-(morpholin-4-yl)phenyl]-6-(6-methoxypyridin-3-yl)imidazo[1,2-a]pyrazin-8-amine | 433.5 |
| 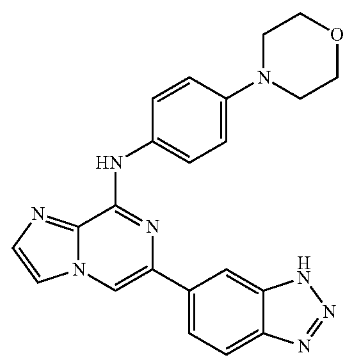 [SMILES: c1cn2cc(-c3ccc4nn[nH]c4c3)nc(Nc3ccc(N4CCOCC4)cc3)c2n1] | 6-(1H-1,2,3-benzotriazol-6-yl)-N-[4-(morpholin-4-yl)phenyl]imidazo[1,2-a]pyrazin-8-amine | 413.5 |
| 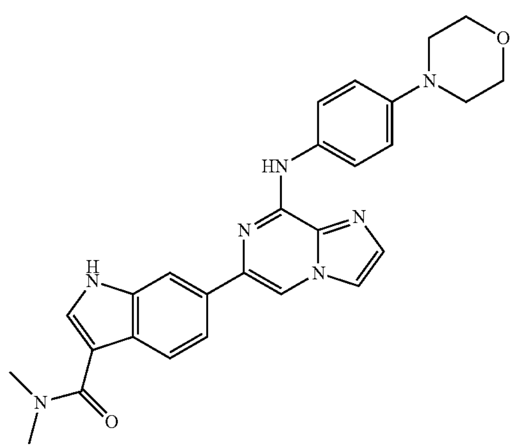 [SMILES: CN(C)C(=O)c1c[nH]c2cc(-c3cn4ccnc4c(Nc4ccc(N5CCOCC5)cc4)n3)ccc12] | N,N-dimethyl-6-(8-{[4-(morpholin-4-yl)phenyl]amino}imidazo[1,2-a]pyrazin-6-yl)-1H-indole-3-carboxamide | 482.4 |
| 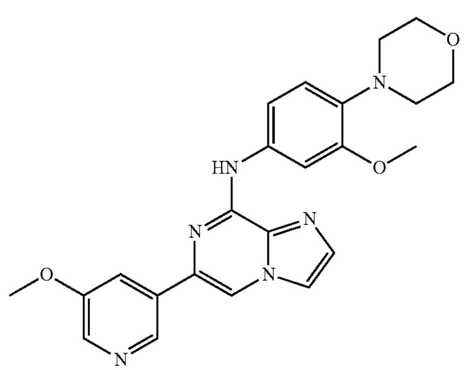 [SMILES: COc1cncc(-c2cn3ccnc3c(Nc3ccc(N4CCOCC4)c(OC)c3)n2)c1] | N-[3-methoxy-4-(morpholin-4-yl)phenyl]-6-(5-methoxypyridin-3-yl)imidazo[1,2-a]pyrazin-8-amine | 433.4 |

-continued

| Structure | Name | [M + H]⁺ |
|---|---|---|
| 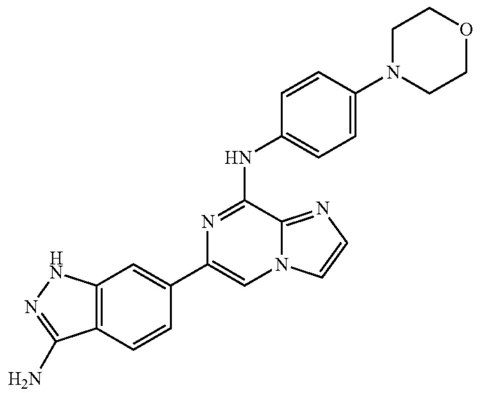 [SMILES: Nc1n[nH]c2cc(-c3cn4ccnc4c(Nc4ccc(N5CCOCC5)cc4)n3)ccc12] | 6-(8-{[4-(morpholin-4-yl)phenyl]amino}imidazo[1,2-a]pyrazin-6-yl)-1H-indazol-3-amine | 427.4 |
| 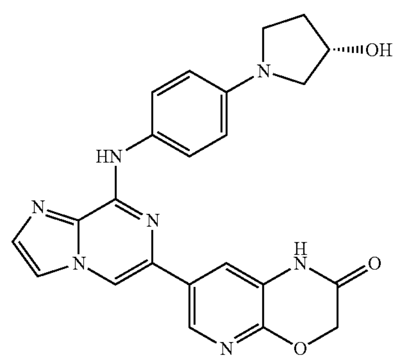 [SMILES: O=C1COc2ncc(-c3cn4ccnc4c(Nc4ccc(N5CC[C@H](O)C5)cc4)n3)cc2N1] | 7-[8-({4-[(3S)-3-hydroxypyrrolidin-1-yl]phenyl}amino)imidazo[1,2-a]pyrazin-6-yl]-1H,2H,3H-pyrido[2,3-b][1,4]oxazin-2-one | 444.8 |
| 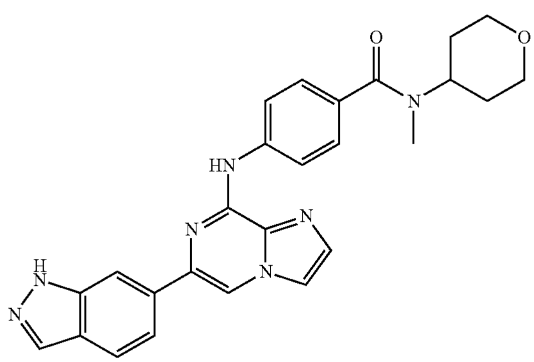 [SMILES: CN(C(=O)c1ccc(Nc2nc(-c3ccc4cn[nH]c4c3)cn3ccnc23)cc1)C1CCOCC1] | 4-{[6-(1H-indazol-6-yl)imidazo[1,2-a]pyrazin-8-yl]amino}-N-methyl-N-(oxan-4-yl)benzamide | 468.2 |
| 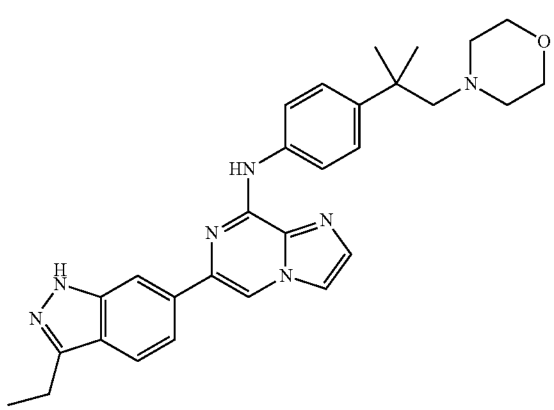 [SMILES: CCc1n[nH]c2cc(-c3cn4ccnc4c(Nc4ccc(C(C)(C)CN5CCOCC5)cc4)n3)ccc12] | 6-(3-ethyl-1H-indazol-6-yl)-N-{4-[2-methyl-1-(morpholin-4-yl)propan-2-yl]phenyl}imidazo[1,2-a]pyrazin-8-amine | 496.9 |

| Structure | Name | [M + H]+ |
|---|---|---|
| 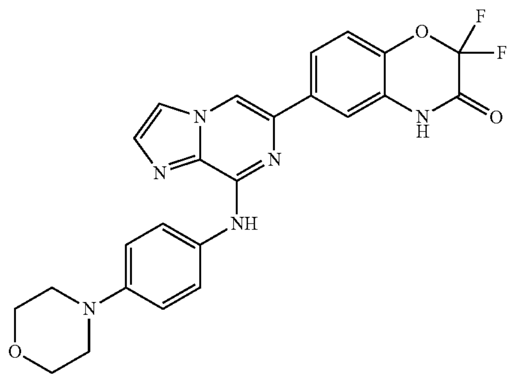 [SMILES: O=C1Nc2cc(-c3cn4ccnc4c(Nc4ccc(N5CCOCC5)cc4)n3)ccc2OC1(F)F] | 2,2-difluoro-6-(8-{[4-(morpholin-4-yl)phenyl]amino}imidazo[1,2-a]pyrazin-6-yl)-3,4-dihydro-2H-1,4-benzoxazin-3-one | 479.1 |
| 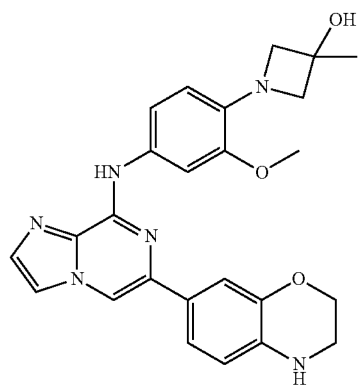 [SMILES: COc1cc(Nc2nc(-c3ccc4c(c3)OCCN4)cn3ccnc23)ccc1N1CC(C)(O)C1] | 1-(4-{[6-(3,4-dihydro-2H-1,4-benzoxazin-7-yl)imidazo[1,2-a]pyrazin-8-yl]amino}-2-methoxyphenyl)-3-methylazetidin-3-ol | 459.3 |
| 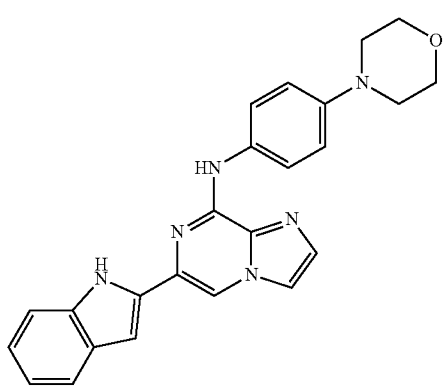 [SMILES: c1ccc2[nH]c(-c3cn4ccnc4c(Nc4ccc(N5CCOCC5)cc4)n3)cc2c1] | 6-(1H-indol-2-yl)-N-[4-(morpholin-4-yl)phenyl]imidazo[1,2-a]pyrazin-8-amine | 411.3 |
| 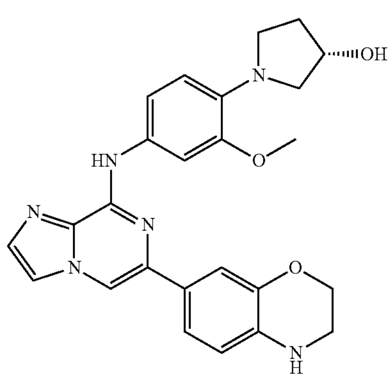 [SMILES: COc1cc(Nc2nc(-c3ccc4c(c3)OCCN4)cn3ccnc23)ccc1N1CC[C@H](O)C1] | (3S)-1-(4-{[6-(3,4-dihydro-2H-1,4-benzoxazin-7-yl)imidazo[1,2-a]pyrazin-8-yl]amino}-2-methoxyphenyl)pyrrolidin-3-ol | 459.6 |

-continued

| Structure | Name | [M + H]⁺ |
|---|---|---|
| 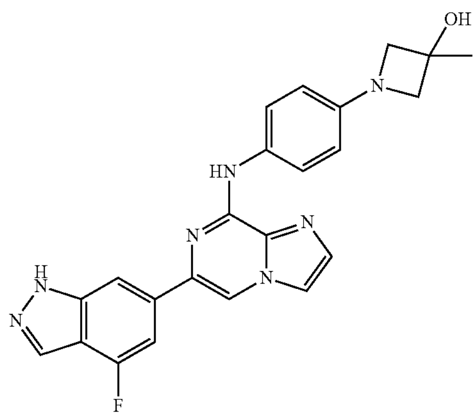 [SMILES: CC1(O)CN(c2ccc(Nc3nc(-c4cc(F)c5cn[nH]c5c4)cn4ccnc34)cc2)C1] | 1-(4-{[6-(4-fluoro-1H-indazol-6-yl)imidazo[1,2-a]pyrazin-8-yl]amino}phenyl)-3-methylazetidin-3-ol | 430.2 |
| 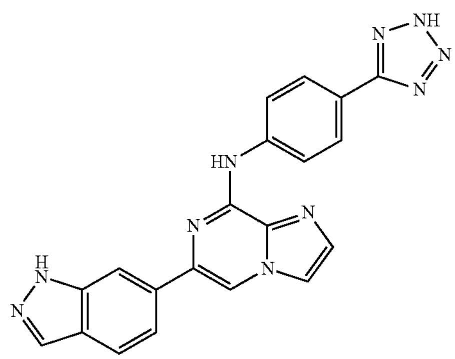 [SMILES: c1cn2cc(-c3ccc4cn[nH]c4c3)nc(Nc3ccc(-c4nn[nH]n4)cc3)c2n1] | 6-(1H-indazol-6-yl)-N-[4-(2H-1,2,3,4-tetrazol-5-yl)phenyl]imidazo[1,2-a]pyrazin-8-amine | 395.1 |
| 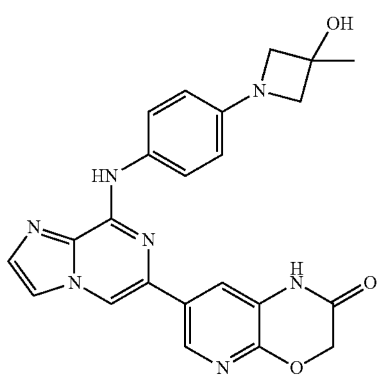 [SMILES: CC1(O)CN(c2ccc(Nc3nc(-c4cnc5c(c4)NC(=O)CO5)cn4ccnc34)cc2)C1] | 7-(8-{[4-(3-hydroxy-3-methylazetidin-1-yl)phenyl]amino}imidazo[1,2-a]pyrazin-6-yl)-1H,2H,3H-pyrido[2,3-b][1,4]oxazin-2-one | 444.2 |
| 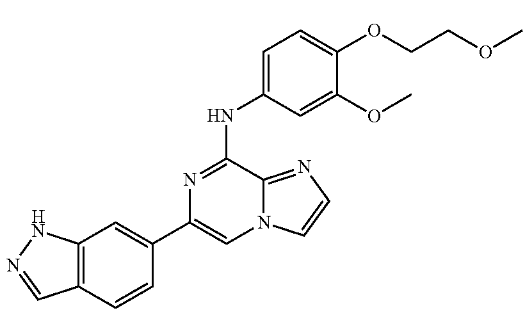 [SMILES: COCCOc1ccc(Nc2nc(-c3ccc4cn[nH]c4c3)cn3ccnc23)cc1OC] | 6-(1H-indazol-6-yl)-N-[3-methoxy-4-(2-methoxyethoxy)phenyl]imidazo[1,2-a]pyrazin-8-amine | 431.5 |

-continued

| Structure | Name | [M + H]+ |
|---|---|---|
| 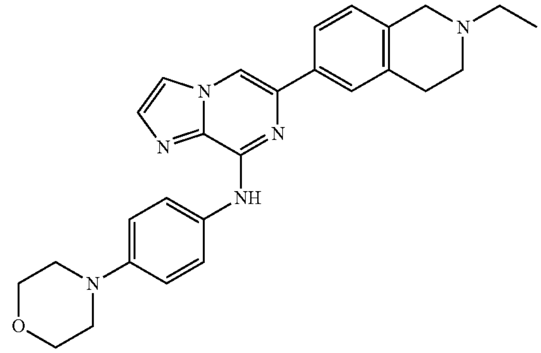 [SMILES: CCN1CCc2cc(-c3cn4ccnc4c(Nc4ccc(N5CCOCC5)cc4)n3)ccc2C1] | 6-(2-ethyl-1,2,3,4-tetrahydroisoquinolin-6-yl)-N-[4-(morpholin-4-yl)phenyl]imidazo[1,2-a]pyrazin-8-amine | 455.4 |
| 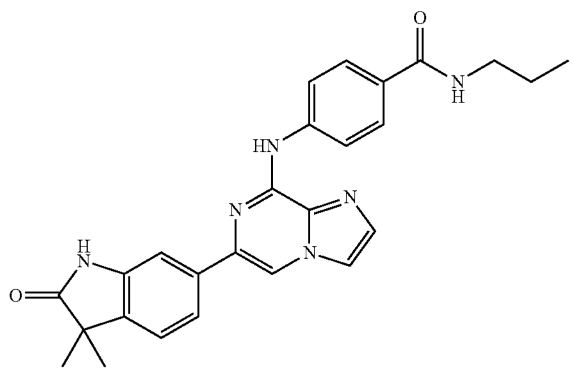 [SMILES: CCCNC(=O)c1ccc(Nc2nc(-c3ccc4c(c3)NC(=O)C4(C)C)cn3ccnc23)cc1] | 4-{[6-(3,3-dimethyl-2-oxo-2,3-dihydro-1H-indol-6-yl)imidazo[1,2-a]pyrazin-8-yl]amino}-N-propylbenzamide | 455.3 |
| 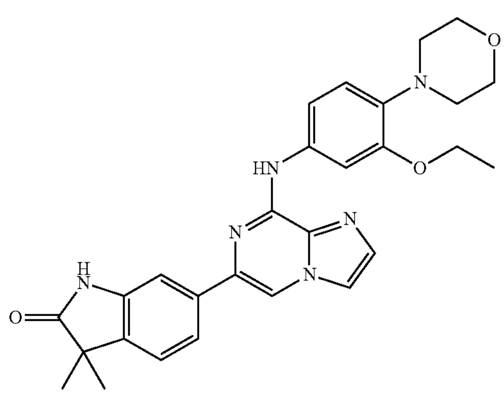 [SMILES: CCOc1cc(Nc2nc(-c3ccc4c(c3)NC(=O)C4(C)C)cn3ccnc23)ccc1N1CCOCC1] | 6-(8-{[3-ethoxy-4-(morpholin-4-yl)phenyl]amino}imidazo[1,2-a]pyrazin-6-yl)-3,3-dimethyl-2,3-dihydro-1H-indol-2-one | 499.7 |
| 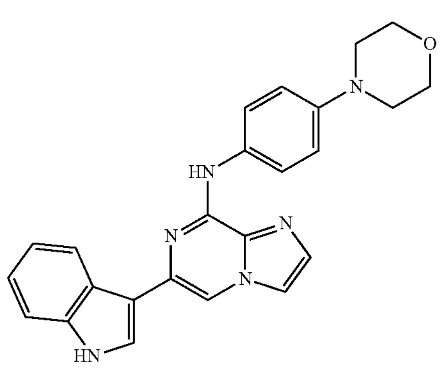 [SMILES: c1ccc2c(-c3cn4ccnc4c(Nc4ccc(N5CCOCC5)cc4)n3)c[nH]c2c1] | 6-(1H-indol-3-yl)-N-[4-(morpholin-4-yl)phenyl]imidazo[1,2-a]pyrazin-8-amine | 411.2 |

-continued

| Structure | Name | [M + H]+ |
|---|---|---|
| 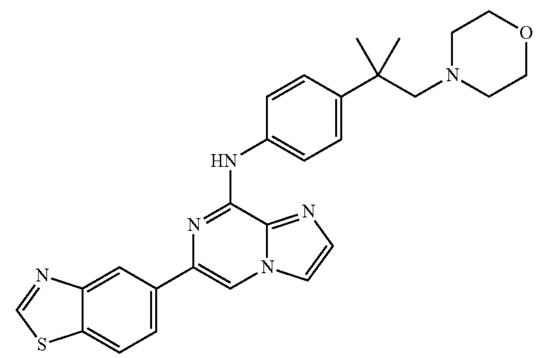 [SMILES: CC(C)(CN1CCOCC1)c1ccc(Nc2nc(-c3ccc4scnc4c3)cn3ccnc23)cc1] | 6-(1,3-benzothiazol-5-yl)-N-{4-[2-methyl-1-(morpholin-4-yl)propan-2-yl]phenyl}imidazo[1,2-a]pyrazin-8-amine | 485.7 |
| 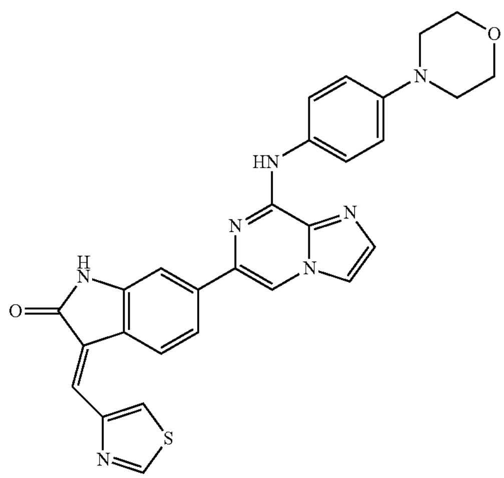 [SMILES: O=C1Nc2cc(-c3cn4ccnc4c(Nc4ccc(N5CCOCC5)cc4)n3)ccc2/C1=C\c1cscn1] | (3E)-6-(8-{[4-(morpholin-4-yl)phenyl]amino}imidazo[1,2-a]pyrazin-6-yl)-3-(1,3-thiazol-4-ylmethylidene)-2,3-dihydro-1H-indol-2-one | 522.6 |
| 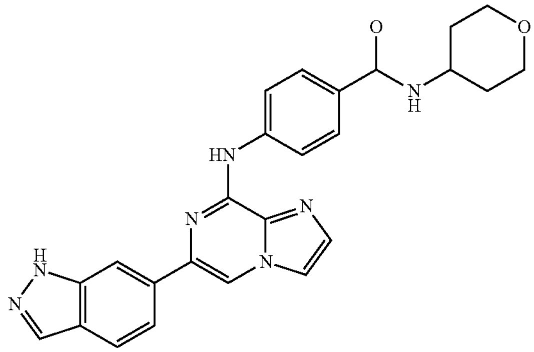 [SMILES: OC(NC1CCOCC1)c1ccc(Nc2nc(-c3ccc4cn[nH]c4c3)cn3ccnc23)cc1] | 4-{[6-(1H-indazol-6-yl)imidazo[1,2-a]pyrazin-8-yl]amino}-N-(oxan-4-yl)benzamide | 454 |
| 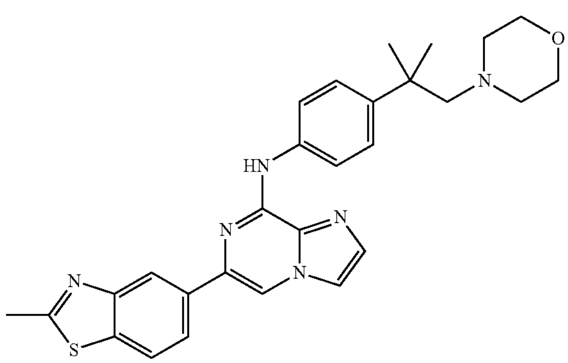 [SMILES: Cc1nc2cc(-c3cn4ccnc4c(Nc4ccc(C(C)(C)CN5CCOCC5)cc4)n3)ccc2s1] | 6-(2-methyl-1,3-benzothiazol-5-yl)-N-{4-[2-methyl-1-(morpholin-4-yl)propan-2-yl]phenyl}imidazo[1,2-a]pyrazin-8-amine | 499.5 |

-continued

| Structure | Name | [M + H]+ |
|---|---|---|
| 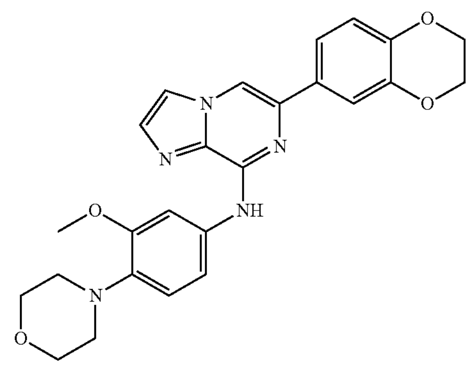 [SMILES: COc1cc(Nc2nc(-c3ccc4c(c3)OCCO4)cn3ccnc23)ccc1N1CCOCC1] | 6-(2,3-dihydro-1,4-benzodioxin-6-yl)-N-[3-methoxy-4-(morpholin-4-yl)phenyl]imidazo[1,2-a]pyrazin-8-amine | 460.6 |
| 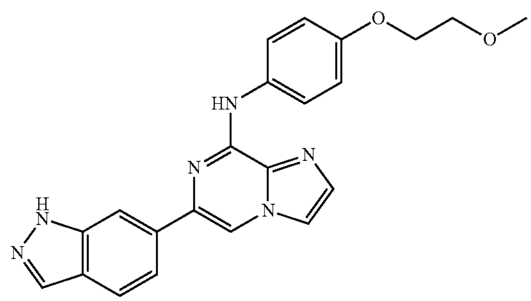 [SMILES: COCCOc1ccc(Nc2nc(-c3ccc4cn[nH]c4c3)cn3ccnc23)cc1] | 6-(1H-indazol-6-yl)-N-[4-(2-methoxyethoxy)phenyl]imidazo[1,2-a]pyrazin-8-amine | 401.1 |
| 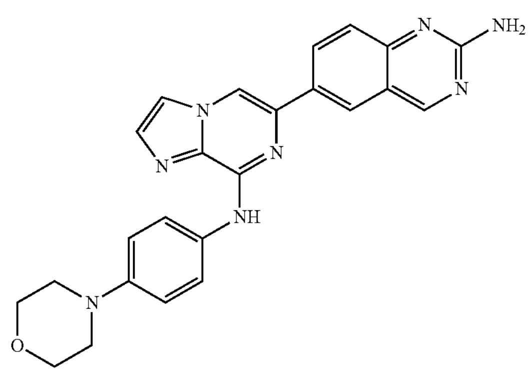 [SMILES: Nc1ncc2cc(-c3cn4ccnc4c(Nc4ccc(N5CCOCC5)cc4)n3)ccc2n1] | 6-(8-{[4-(morpholin-4-yl)phenyl]amino}imidazo[1,2-a]pyrazin-6-yl)quinazolin-2-amine | 439.7 |
| 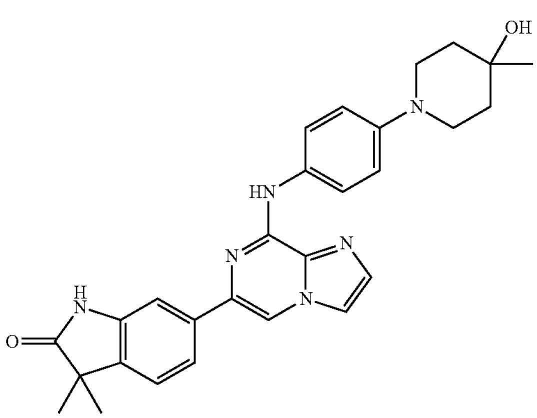 [SMILES: CC1(O)CCN(c2ccc(Nc3nc(-c4ccc5c(c4)NC(=O)C5(C)C)cn4ccnc34)cc2)CC1] | 6-(8-{[4-(4-hydroxy-4-methylpiperidin-1-yl)phenyl]amino}imidazo[1,2-a]pyrazin-6-yl)-3,3-dimethyl-2,3-dihydro-1H-indol-2-one | 483.5 |

| Structure | Name | [M + H]⁺ |
|---|---|---|
| 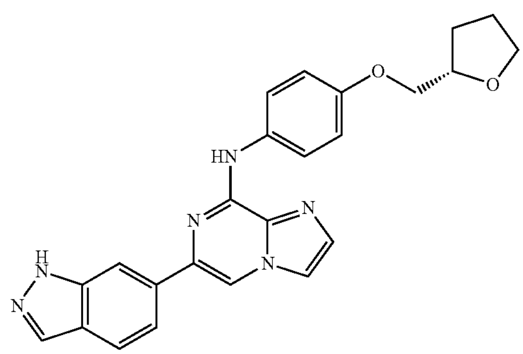 [SMILES: c1cn2cc(-c3ccc4cn[nH]c4c3)nc(Nc3ccc(OC[C@@H]4CCCO4)cc3)c2n1] | 6-(1H-indazol-6-yl)-N-{4-[(2S)-oxolan-2-ylmethoxy]phenyl}imidazo[1,2-a]pyrazin-8-amine | 427.1 |
| 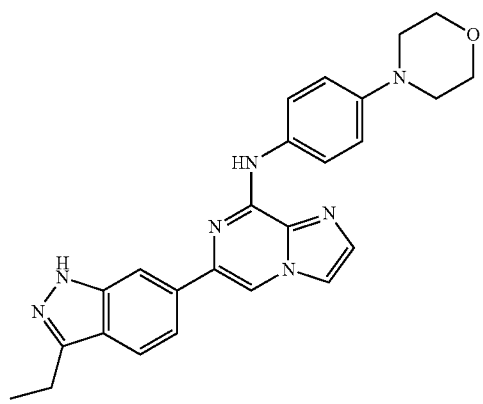 [SMILES: CCc1n[nH]c2cc(-c3cn4ccnc4c(Nc4ccc(N5CCOCC5)cc4)n3)ccc12] | 6-(3-ethyl-1H-indazol-6-yl)-N-[4-(morpholin-4-yl)phenyl]imidazo[1,2-a]pyrazin-8-amine | 440.5 |
| 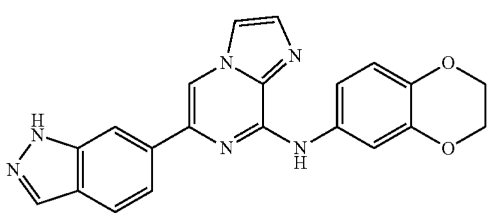 [SMILES: c1cn2cc(-c3ccc4cn[nH]c4c3)nc(Nc3ccc4c(c3)OCCO4)c2n1] | N-(2,3-dihydro-1,4-benzodioxin-6-yl)-6-(1H-indazol-6-yl)imidazo[1,2-a]pyrazin-8-amine | 385.3 |
| 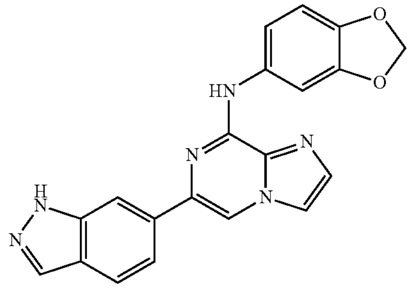 [SMILES: c1cn2cc(-c3ccc4cn[nH]c4c3)nc(Nc3ccc4c(c3)OCO4)c2n1] | N-(2H-1,3-benzodioxol-5-yl)-6-(1H-indazol-6-yl)imidazo[1,2-a]pyrazin-8-amine | 371.2 |

| Structure | Name | [M + H]+ |
|---|---|---|
| 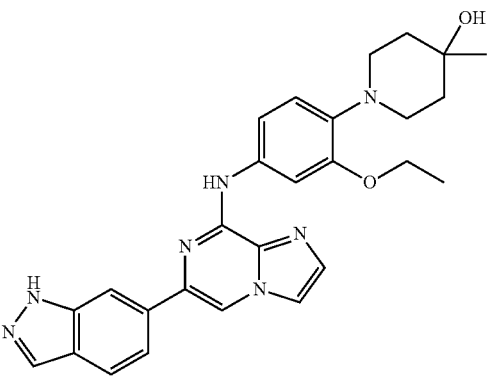 [SMILES: CCOc1cc(Nc2nc(-c3ccc4cn[nH]c4c3)cn3ccnc23)ccc1N1CCC(C)(O)CC1] | 1-(2-ethoxy-4-{[6-(1H-indazol-6-yl)imidazo[1,2-a]pyrazin-8-yl]amino}phenyl)-4-methylpiperidin-4-ol | 484.7 |
| 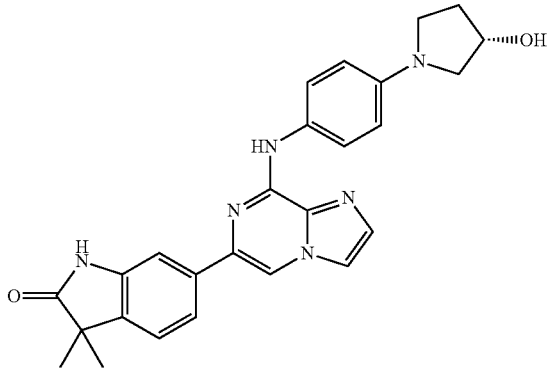 [SMILES: CC1(C)C(=O)Nc2cc(-c3cn4ccnc4c(Nc4ccc(N5CC[C@H](O)C5)cc4)n3)ccc21] | 6-[8-({4-[(3S)-3-hydroxypyrrolidin-1-yl]phenyl}amino)imidazo[1,2-a]pyrazin-6-yl]-3,3-dimethyl-2,3-dihydro-1H-indol-2-one | 455.2 |
| 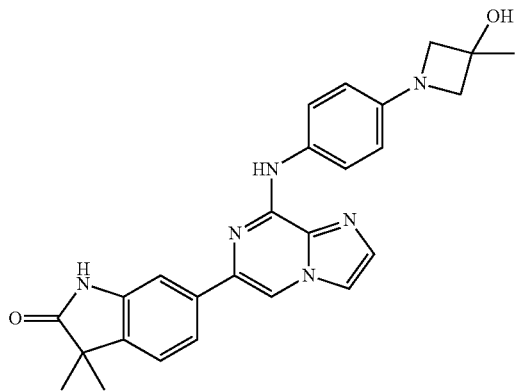 [SMILES: CC1(O)CN(c2ccc(Nc3nc(-c4ccc5c(c4)NC(=O)C5(C)C)cn4ccnc34)cc2)C1] | 6-(8-{[4-(3-hydroxy-3-methylazetidin-1-yl)phenyl]amino}imidazo[1,2-a]pyrazin-6-yl)-3,3-dimethyl-2,3-dihydro-1H-indol-2-one | 455.3 |
| 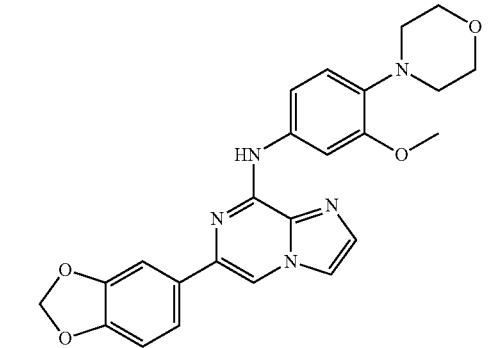 [SMILES: COc1cc(Nc2nc(-c3ccc4c(c3)OCO4)cn3ccnc23)ccc1N1CCOCC1] | 6-(2H-1,3-benzodioxol-5-yl)-N-[3-methoxy-4-(morpholin-4-yl)phenyl]imidazo[1,2-a]pyrazin-8-amine | 446.3 |

-continued

| Structure | Name | [M + H]+ |
|---|---|---|
| 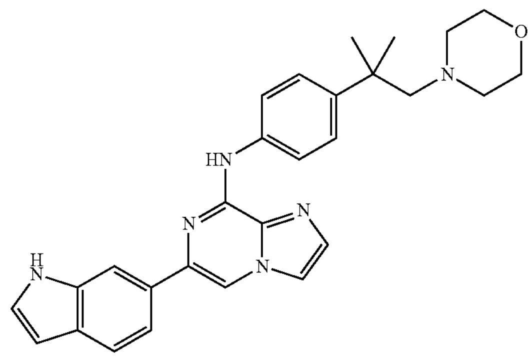 [SMILES: CC(C)(CN1CCOCC1)c1ccc(Nc2nc(-c3ccc4cc[nH]c4c3)cn3ccnc23)cc1] | 6-(1H-indol-6-yl)-N-{4-[2-methyl-1-(morpholin-4-yl)propan-2-yl]phenyl}imidazo[1,2-a]pyrazin-8-amine | 467.4 |
| 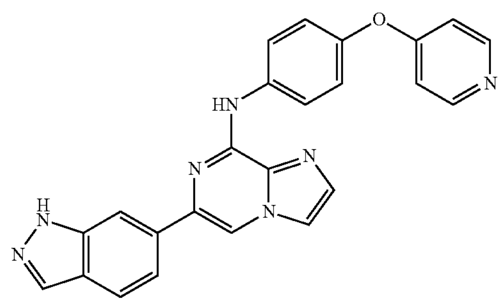 [SMILES: c1cc(Oc2ccc(Nc3nc(-c4ccc5cn[nH]c5c4)cn4ccnc34)cc2)ccn1] | 6-(1H-indazol-6-yl)-N-[4-(pyridin-4-yloxy)phenyl]imidazo[1,2-a]pyrazin-8-amine | 420.3 |
| 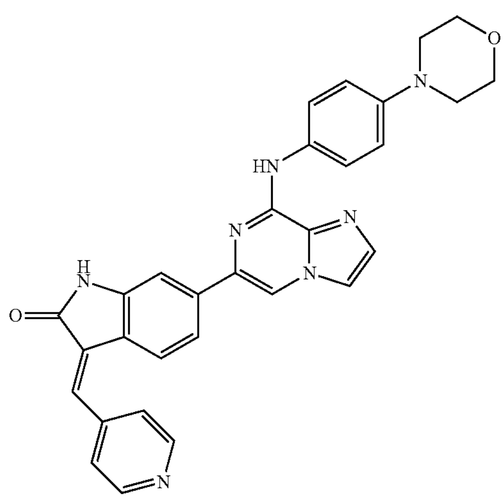 [SMILES: O=C1Nc2cc(-c3cn4ccnc4c(Nc4ccc(N5CCOCC5)cc4)n3)ccc2/C1=C\c1ccncc1] | (3E)-6-(8-{[4-(morpholin-4-yl)phenyl]amino}imidazo[1,2-a]pyrazin-6-yl)-3-(pyridin-4-ylmethylidene)-2,3-dihydro-1H-indol-2-one | 516.4 |
| 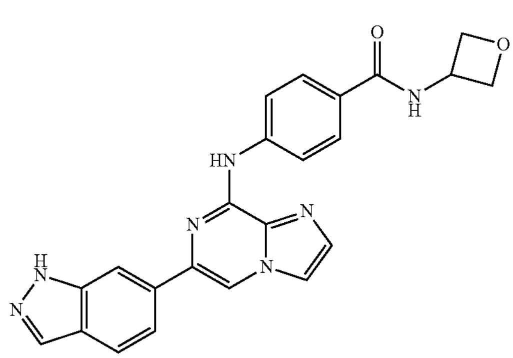 [SMILES: O=C(NC1COC1)c1ccc(Nc2nc(-c3ccc4cn[nH]c4c3)cn3ccnc23)cc1] | 4-{[6-(1H-indazol-6-yl)imidazo[1,2-a]pyrazin-8-yl]amino}-N-(oxetan-3-yl)benzamide | 426.1 |

-continued

| Structure | Name | [M + H]+ |
|---|---|---|
| 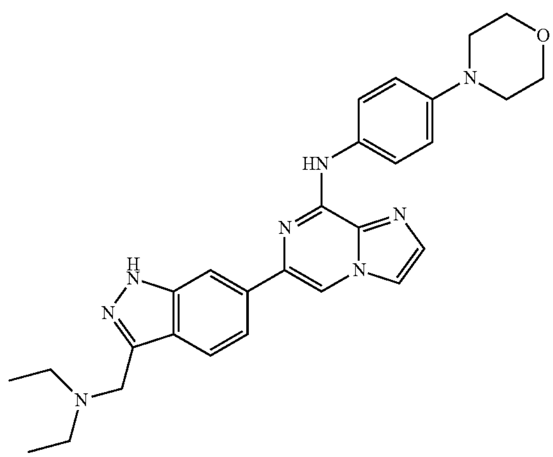 [SMILES: CCN(CC)Cc1n[nH]c2cc(-c3cn4ccnc4c(Nc4ccc(N5CCOCC5)cc4)n3)ccc12] | 6-{3-[(diethylamino)methyl]-1H-indazol-6-yl}-N-[4-(morpholin-4-yl)phenyl]imidazo[1,2-a]pyrazin-8-amine | 497.3 |
| 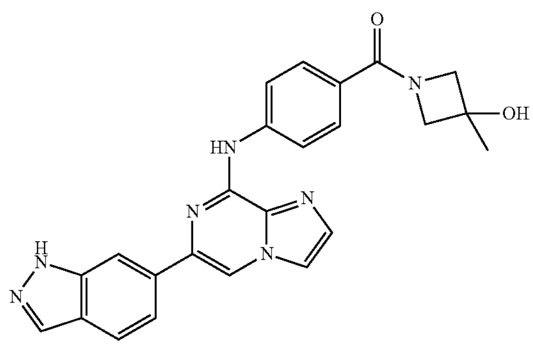 [SMILES: CC1(O)CN(C(=O)c2ccc(Nc3nc(-c4ccc5cn[nH]c5c4)cn4ccnc34)cc2)C1] | 1-[(4-{[6-(1H-indazol-6-yl)imidazo[1,2-a]pyrazin-8-yl]amino}phenyl)carbonyl]-3-methylazetidin-3-ol | 440.2 |
| 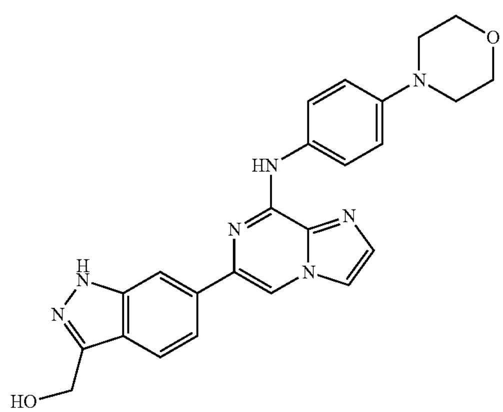 [SMILES: OCc1n[nH]c2cc(-c3cn4ccnc4c(Nc4ccc(N5CCOCC5)cc4)n3)ccc12] | [6-(8-{[4-(morpholin-4-yl)phenyl]amino}imidazo[1,2-a]pyrazin-6-yl)-1H-indazol-3-yl]methanol | 442.3 |
| 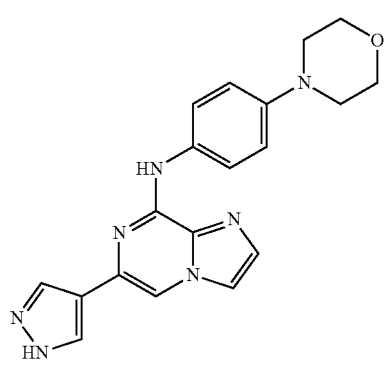 [SMILES: c1cn2cc(-c3cn[nH]c3)nc(Nc3ccc(N4CCOCC4)cc3)c2n1] | N-[4-(morpholin-4-yl)phenyl]-6-(1H-pyrazol-4-yl)imidazo[1,2-a]pyrazin-8-amine | 362.6 |

| Structure | Name | [M + H]+ |
|---|---|---|
| 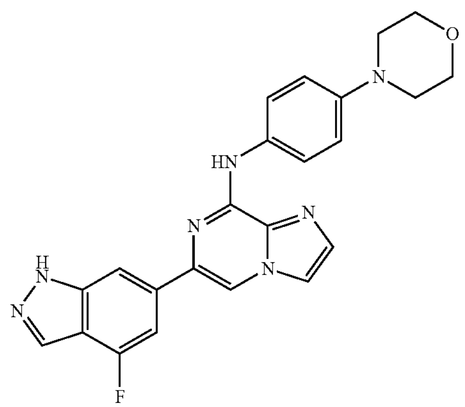 [SMILES: Fc1cc(-c2cn3ccnc3c(Nc3ccc(N4CCOCC4)cc3)n2)cc2[nH]ncc12] | 6-(4-fluoro-1H-indazol-6-yl)-N-[4-(morpholin-4-yl)phenyl]imidazo[1,2-a]pyrazin-8-amine | 430.3 |
| 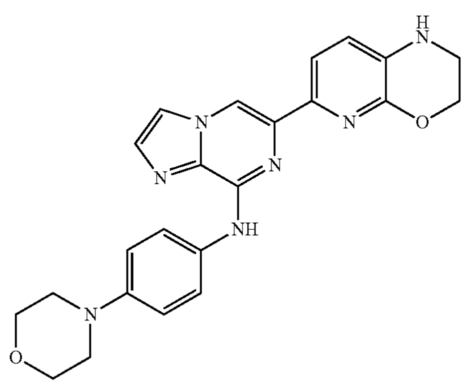 [SMILES: c1cn2cc(-c3ccc4c(n3)OCCN4)nc(Nc3ccc(N4CCOCC4)cc3)c2n1] | N-[4-(morpholin-4-yl)phenyl]-6-{1H,2H,3H-pyrido[2,3-b][1,4]oxazin-6-yl}imidazo[1,2-a]pyrazin-8-amine | 430.3 |
| 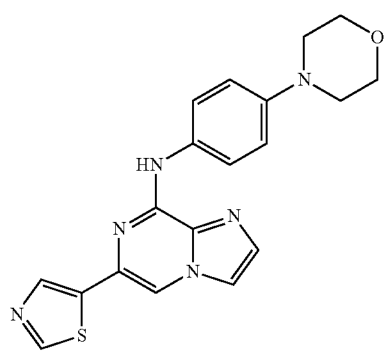 [SMILES: c1cn2cc(-c3cncs3)nc(Nc3ccc(N4CCOCC4)cc3)c2n1] | N-[4-(morpholin-4-yl)phenyl]-6-(1,3-thiazol-5-yl)imidazo[1,2-a]pyrazin-8-amine | 379.2 |
| 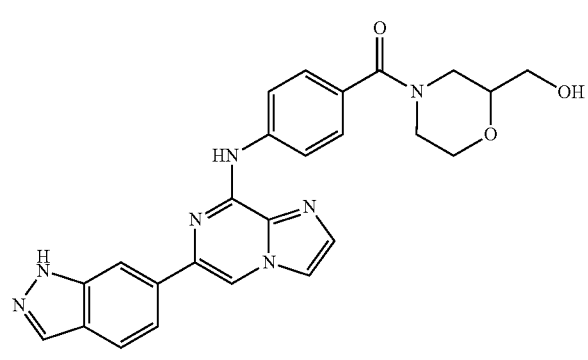 [SMILES: O=C(c1ccc(Nc2nc(-c3ccc4cn[nH]c4c3)cn3ccnc23)cc1)N1CCOC(CO)C1] | {4-[(4-{[6-(1H-indazol-6-yl)imidazo[1,2-a]pyrazin-8-yl]amino}phenyl)carbonyl]morpholin-2-yl}methanol | 470.8 |

-continued

| Structure | Name | [M + H]+ |
|---|---|---|
| 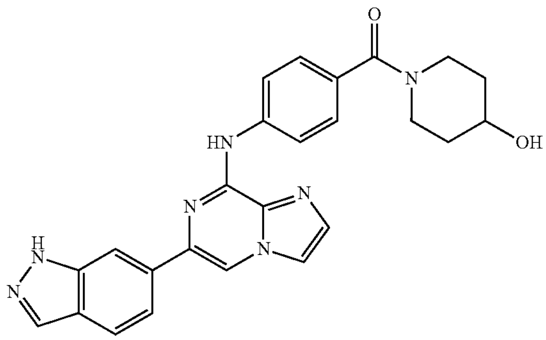 [SMILES: O=C(c1ccc(Nc2nc(-c3ccc4cn[nH]c4c3)cn3ccnc23)cc1)N1CCC(O)CC1] | 1-[(4-{[6-(1H-indazol-6-yl)imidazo[1,2-a]pyrazin-8-yl]amino}phenyl)carbonyl]piperidin-4-ol | 454.1 |
| 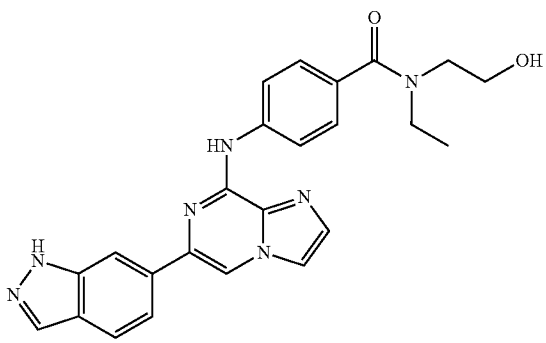 [SMILES: CCN(CCO)C(=O)c1ccc(Nc2nc(-c3ccc4cn[nH]c4c3)cn3ccnc23)cc1] | N-ethyl-N-(2-hydroxyethyl)-4-{[6-(1H-indazol-6-yl)imidazo[1,2-a]pyrazin-8-yl]amino}benzamide | 440.2 |
| 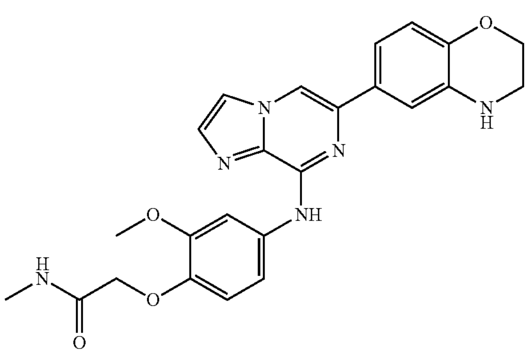 [SMILES: CNC(=O)COc1ccc(Nc2nc(-c3ccc4c(c3)NCCO4)cn3ccnc23)cc1OC] | 2-(4-{[6-(3,4-dihydro-2H-1,4-benzoxazin-6-yl)imidazo[1,2-a]pyrazin-8-yl]amino}-2-methoxyphenoxy)-N-methylacetamide | 461.4 |
| 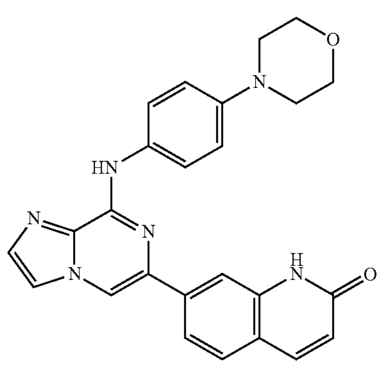 [SMILES: O=c1ccc2ccc(-c3cn4ccnc4c(Nc4ccc(N5CCOCC5)cc4)n3)cc2[nH]1] | 7-(8-{[4-(morpholin-4-yl)phenyl]amino}imidazo[1,2-a]pyrazin-6-yl)-1,2-dihydroquinolin-2-one | 439.5 |

-continued
| Structure | Name | [M + H]+ |
|---|---|---|
| 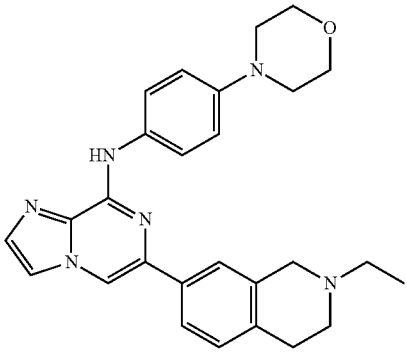 [SMILES: CCN1CCc2ccc(-c3cn4ccnc4c(Nc4ccc(N5CCOCC5)cc4)n3)cc2C1] | 6-(2-ethyl-1,2,3,4-tetrahydroisoquinolin-7-yl)-N-[4-(morpholin-4-yl)phenyl]imidazo[1,2-a]pyrazin-8-amine | 455.4 |
| 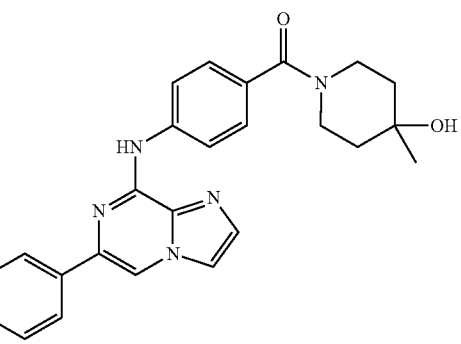 | 1-[(4-{[6-(1H-indazol-6-yl)imidazo[1,2-a]pyrazin-8-yl]amino}phenyl)carbonyl]-4-methylpiperidin-4-ol | 468.4 |
| 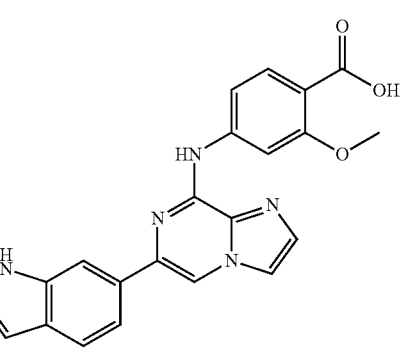 | 4-{[6-(1H-indazol-6-yl)imidazo[1,2-a]pyrazin-8-yl]amino}-2-methoxybenzoic acid | 401.1 |
| 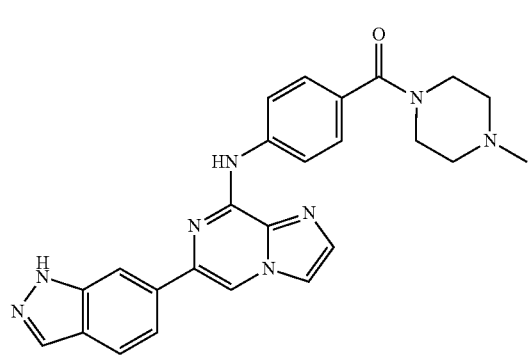 [SMILES: CN1CCN(C(=O)c2ccc(Nc3nc(-c4ccc5cn[nH]c5c4)cn4ccnc34)cc2)CC1] | 6-(1H-indazol-6-yl)-N-{4-[(4-methylpiperazin-1-yl)carbonyl]phenyl}imidazo[1,2-a]pyrazin-8-amine | 453.1 |

-continued

| Structure | Name | [M + H]+ |
|---|---|---|
| 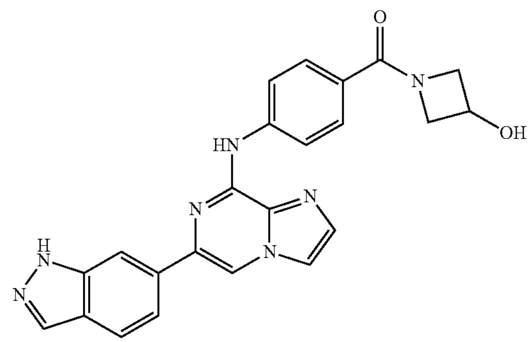 [SMILES: O=C(c1ccc(Nc2nc(-c3ccc4cn[nH]c4c3)cn3ccnc23)cc1)N1CC(O)C1] | 1-[(4-{[6-(1H-indazol-6-yl)imidazo[1,2-a]pyrazin-8-yl]amino}phenyl)carbonyl]azetidin-3-ol | 426.3 |
| 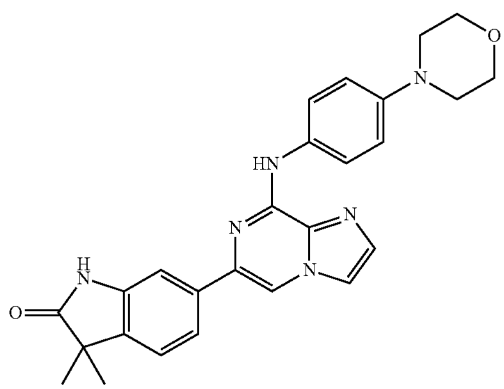 [SMILES: CC1(C)C(=O)Nc2cc(-c3cn4ccnc4c(Nc4ccc(N5CCOCC5)cc4)n3)ccc21] | 3,3-dimethyl-6-(8-{[4-(morpholin-4-yl)phenyl]amino}imidazo[1,2-a]pyrazin-6-yl)-2,3-dihydro-1H-indol-2-one | 455.4 |
| 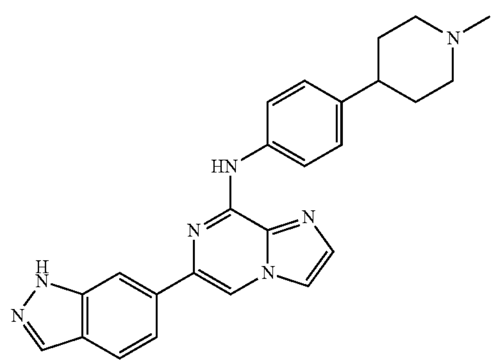 [SMILES: CN1CCC(c2ccc(Nc3nc(-c4ccc5cn[nH]c5c4)cn4ccnc34)cc2)CC1] | 6-(1H-indazol-6-yl)-N-[4-(1-methylpiperidin-4-yl)phenyl]imidazo[1,2-a]pyrazin-8-amine | 424.2 |
| 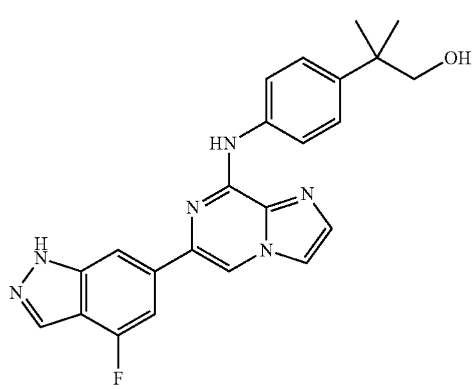 [SMILES: CC(C)(CO)c1ccc(Nc2nc(-c3cc(F)c4cn[nH]c4c3)cn3ccnc23)cc1] | 2-(4-{[6-(4-fluoro-1H-indazol-6-yl)imidazo[1,2-a]pyrazin-8-yl]amino}phenyl)-2-methylpropan-1-ol | 417.7 |

-continued

| Structure | Name | [M + H]+ |
|---|---|---|
| 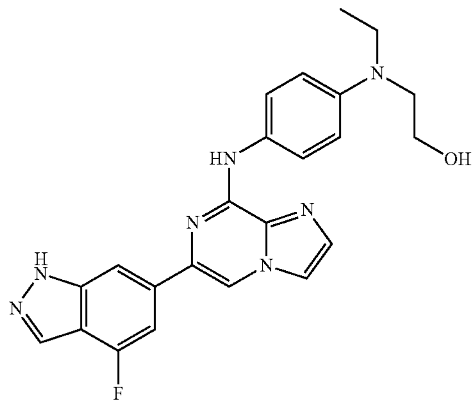 [SMILES: CCN(CCO)c1ccc(Nc2nc(-c3cc(F)c4cn[nH]c4c3)cn3ccnc23)cc1] | 2-[ethyl(4-{[6-(4-fluoro-1H-indazol-6-yl)imidazo[1,2-a]pyrazin-8-yl]amino}phenyl)amino]ethan-1-ol | 431.47 |
| 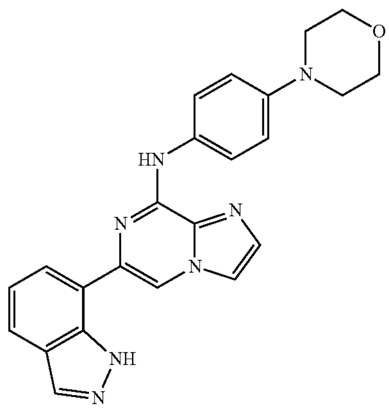 [SMILES: c1cc(-c2cn3ccnc3c(Nc3ccc(N4CCOCC4)cc3)n2)c2[nH]ncc2c1] | 6-(1H-indazol-7-yl)-N-[4-(morpholin-4-yl)phenyl]imidazo[1,2-a]pyrazin-8-amine | 412.2 |
| 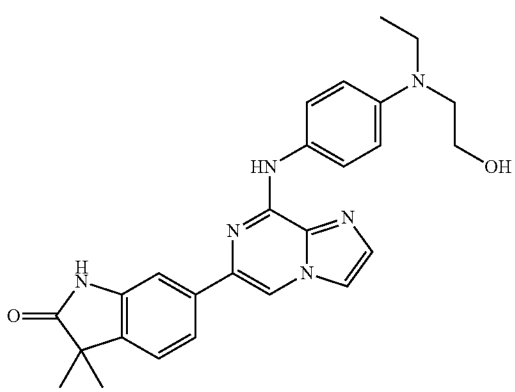 [SMILES: CCN(CCO)c1ccc(Nc2nc(-c3ccc4c(c3)NC(=O)C4(C)C)cn3ccnc23)cc1] | 6-[8-({4-[ethyl(2-hydroxyethyl)amino]phenyl}amino)imidazo[1,2-a]pyrazin-6-yl]-3,3-dimethyl-2,3-dihydro-1H-indol-2-one | 457.6 |
| 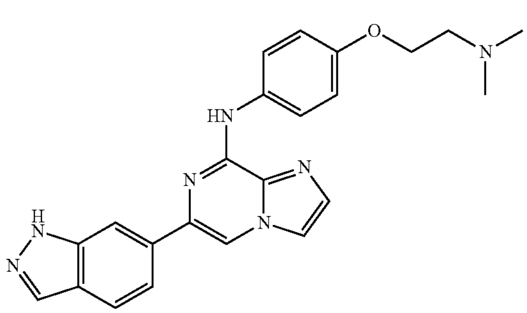 [SMILES: CN(C)CCOc1ccc(Nc2nc(-c3ccc4cn[nH]c4c3)cn3ccnc23)cc1] | N-{4-[2-(dimethylamino)ethoxy]phenyl}-6-(1H-indazol-6-yl)imidazo[1,2-a]pyrazin-8-amine | 414.6 |

-continued

| Structure | Name | [M + H]⁺ |
|---|---|---|
| 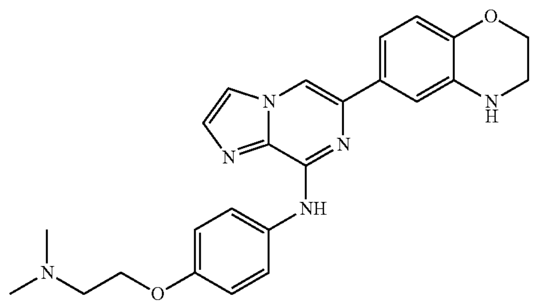 [SMILES: CN(C)CCOc1ccc(Nc2nc(-c3ccc4c(c3)NCCO4)cn3ccnc23)cc1] | 6-(3,4-dihydro-2H-1,4-benzoxazin-6-yl)-N-{4-[2-(dimethylamino)ethoxy]phenyl}imidazo[1,2-a]pyrazin-8-amine | 431.4 |
| 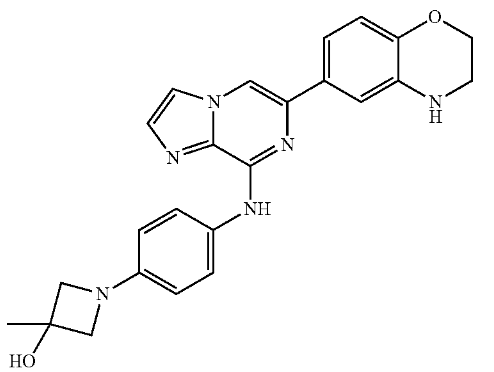 [SMILES: CC1(O)CN(c2ccc(Nc3nc(-c4ccc5c(c4)NCCO5)cn4ccnc34)cc2)C1] | 1-(4-{[6-(3,4-dihydro-2H-1,4-benzoxazin-6-yl)imidazo[1,2-a]pyrazin-8-yl]amino}phenyl)-3-methylazetidin-3-ol | 429.3 |
| 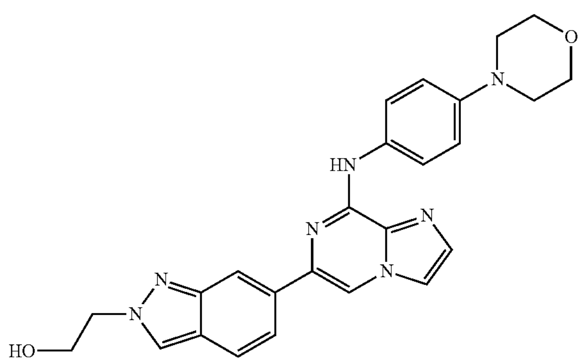 [SMILES: OCCn1cc2ccc(-c3cn4ccnc4c(Nc4ccc(N5CCOCC5)cc4)n3)cc2n1] | 2-[6-(8-{[4-(morpholin-4-yl)phenyl]amino}imidazo[1,2-a]pyrazin-6-yl)-2H-indazol-2-yl]ethan-1-ol | 456.3 |
| 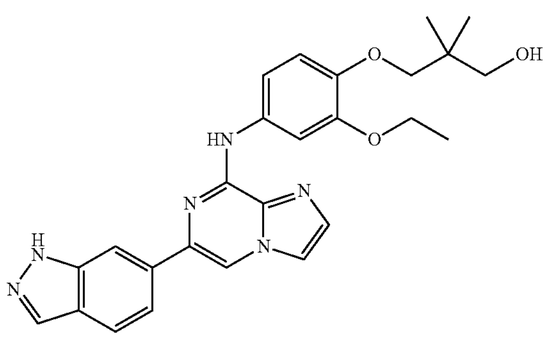 [SMILES: CCOc1cc(Nc2nc(-c3ccc4cn[nH]c4c3)cn3ccnc23)ccc1OCC(C)(C)CO] | 3-(2-ethoxy-4-{[6-(1H-indazol-6-yl)imidazo[1,2-a]pyrazin-8-yl]amino}phenoxy)-2,2-dimethylpropan-1-ol | 473.4 |

| Structure | Name | [M + H]+ |
|---|---|---|
| 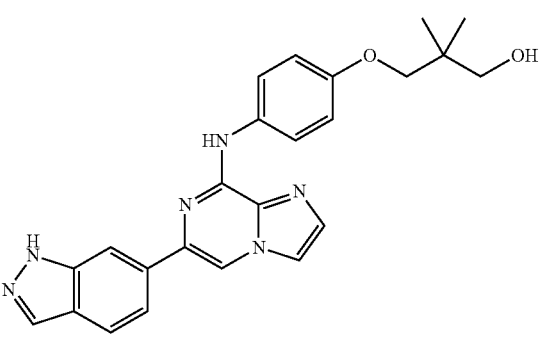 [SMILES: CC(C)(CO)COc1ccc(Nc2nc(-c3ccc4cn[nH]c4c3)cn3ccnc23)cc1] | 3-(4-{[6-(1H-indazol-6-yl)imidazo[1,2-a]pyrazin-8-yl]amino}phenoxy)-2,2-dimethylpropan-1-ol | 429.5 |
| 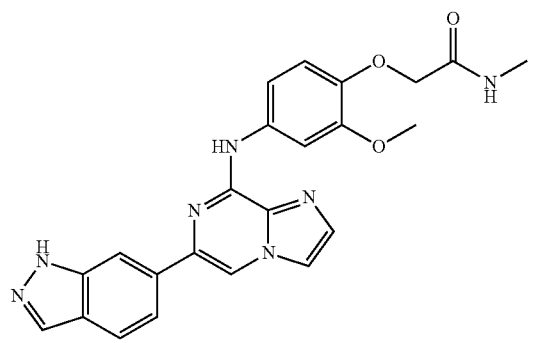 [SMILES: CNC(=O)COc1ccc(Nc2nc(-c3ccc4cn[nH]c4c3)cn3ccnc23)cc1OC] | 2-(4-{[6-(1H-indazol-6-yl)imidazo[1,2-a]pyrazin-8-yl]amino}-2-methoxyphenoxy)-N-methylacetamide | 444.8 |
| 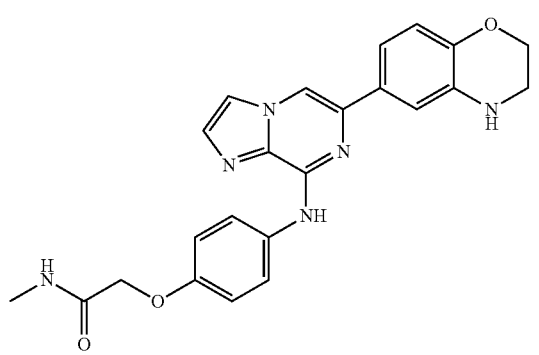 [SMILES: CNC(=O)COc1ccc(Nc2nc(-c3ccc4c(c3)NCCO4)cn3ccnc23)cc1] | 2-(4-{[6-(3,4-dihydro-2H-1,4-benzoxazin-6-yl)imidazo[1,2-a]pyrazin-8-yl]amino}phenoxy)-N-methylacetamide | 431.4 |
| 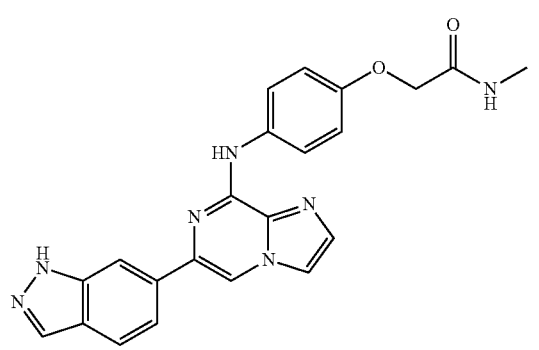 [SMILES: CNC(=O)COc1ccc(Nc2nc(-c3ccc4cn[nH]c4c3)cn3ccnc23)cc1] | 2-(4-{[6-(1H-indazol-6-yl)imidazo[1,2-a]pyrazin-8-yl]amino}phenoxy)-N-methylacetamide | 414.4 |

-continued

| Structure | Name | [M + H]+ |
|---|---|---|
| 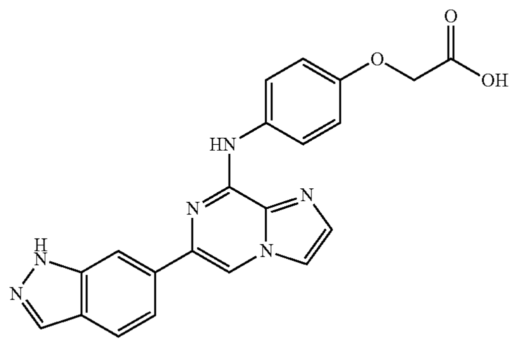 [SMILES: O=C(O)COc1ccc(Nc2nc(-c3ccc4cn[nH]c4c3)cn3ccnc23)cc1] | 2-(4-{[6-(1H-indazol-6-yl)imidazo[1,2-a]pyrazin-8-yl]amino}phenoxy)acetic acid | 401.1 |
| 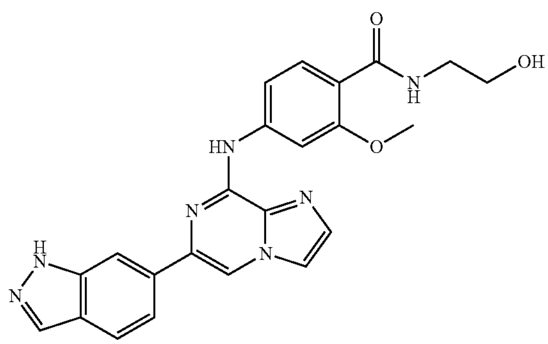 [SMILES: COc1cc(Nc2nc(-c3ccc4cn[nH]c4c3)cn3ccnc23)ccc1C(=O)NCCO] | N-(2-hydroxyethyl)-4-{[6-(1H-indazol-6-yl)imidazo[1,2-a]pyrazin-8-yl]amino}-2-methoxybenzamide | 442.1 |
| 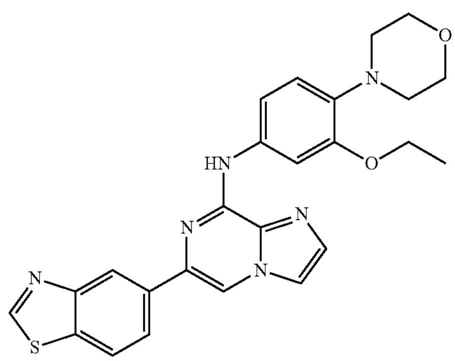 [SMILES: CCOc1cc(Nc2nc(-c3ccc4scnc4c3)cn3ccnc23)ccc1N1CCOCC1] | 6-(1,3-benzothiazol-5-yl)-N-[3-ethoxy-4-(morpholin-4-yl)phenyl]imidazo[1,2-a]pyrazin-8-amine | 473.2 |
| 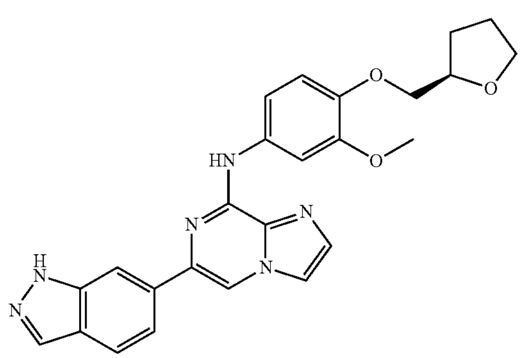 [SMILES: COc1cc(Nc2nc(-c3ccc4cn[nH]c4c3)cn3ccnc23)ccc1OC[C@H]1CCCO1] | 6-(1H-indazol-6-yl)-N-{3-methoxy-4-[(2R)-oxolan-2-ylmethoxy]phenyl}imidazo[1,2-a]pyrazin-8-amine | 457.4 |

-continued

| Structure | Name | [M + H]+ |
|---|---|---|
| 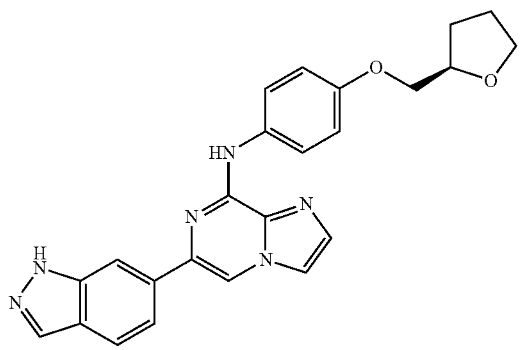 [SMILES: c1cn2cc(-c3ccc4cn[nH]c4c3)nc(Nc3ccc(OC[C@H]4CCCO4)cc3)c2n1] | 6-(1H-indazol-6-yl)-N-{4-[(2R)-oxolan-2-ylmethoxy]phenyl}imidazo[1,2-a]pyrazin-8-amine | 427 |
| 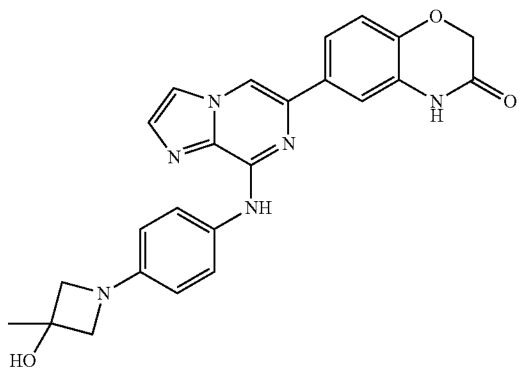 [SMILES: CC1(O)CN(c2ccc(Nc3nc(-c4ccc5c(c4)NC(=O)CO5)cn4ccnc34)cc2)C1] | 6-(8-{[4-(3-hydroxy-3-methylazetidin-1-yl)phenyl]amino}imidazo[1,2-a]pyrazin-6-yl)-3,4-dihydro-2H-1,4-benzoxazin-3-one | 443.2 |
| 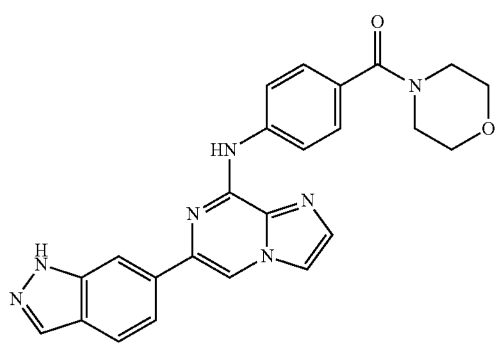 [SMILES: O=C(c1ccc(Nc2nc(-c3ccc4cn[nH]c4c3)cn3ccnc23)cc1)N1CCOCC1] | 6-(1H-indazol-6-yl)-N-[4-(morpholin-4-ylcarbonyl)phenyl]imidazo[1,2-a]pyrazin-8-amine | 440.3 |
| 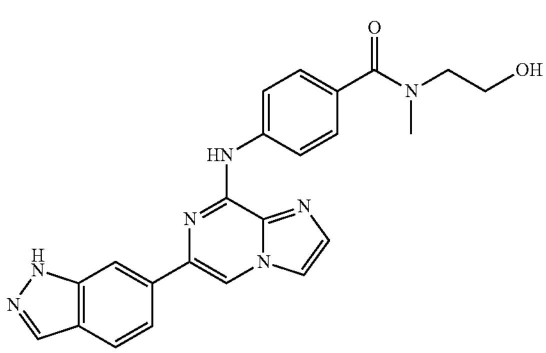 [SMILES: CN(CCO)C(=O)c1ccc(Nc2nc(-c3ccc4cn[nH]c4c3)cn3ccnc23)cc1] | N-(2-hydroxyethyl)-4-{[6-(1H-indazol-6-yl)imidazo[1,2-a]pyrazin-8-yl]amino}-N-methylbenzamide | 428.2 |

-continued
| Structure | Name | [M + H]+ |
|---|---|---|
| 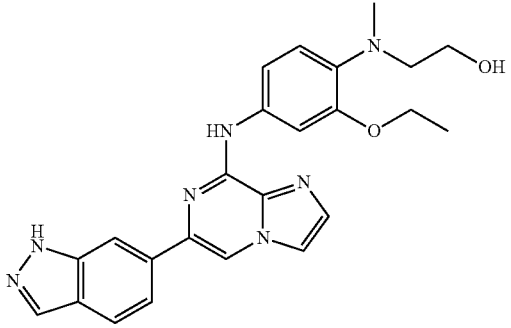 [SMILES: CCOc1cc(Nc2nc(-c3ccc4cn[nH]c4c3)cn3ccnc23)ccc1N(C)CCO] | 2-[(2-ethoxy-4-{[6-(1H-indazol-6-yl)imidazo[1,2-a]pyrazin-8-yl]amino}phenyl)(methyl)amino]ethan-1-ol | 444.6 |
| 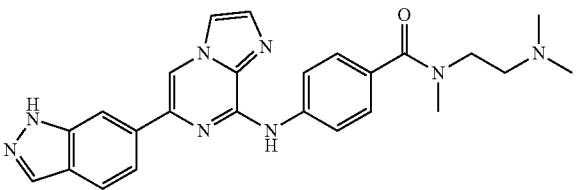 [SMILES: CN(C)CCN(C)C(=O)c1ccc(Nc2nc(-c3ccc4cn[nH]c4c3)cn3ccnc23)cc1] | N-[2-(dimethylamino)ethyl]-4-{[6-(1H-indazol-6-yl)imidazo[1,2-a]pyrazin-8-yl]amino}-N-methylbenzamide | 455.3 |
| 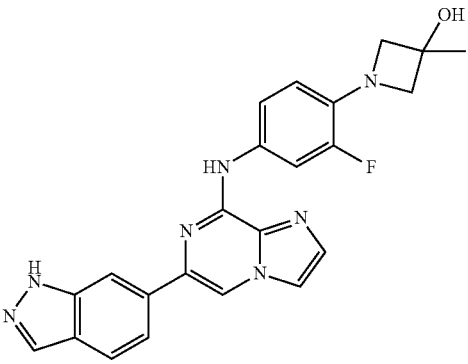 [SMILES: CC1(O)CN(c2ccc(Nc3nc(-c4ccc5cn[nH]c5c4)cn4ccnc34)cc2F)C1] | 1-(2-fluoro-4-{[6-(1H-indazol-6-yl)imidazo[1,2-a]pyrazin-8-yl]amino}phenyl)-3-methylazetidin-3-ol | 430.4 |
| 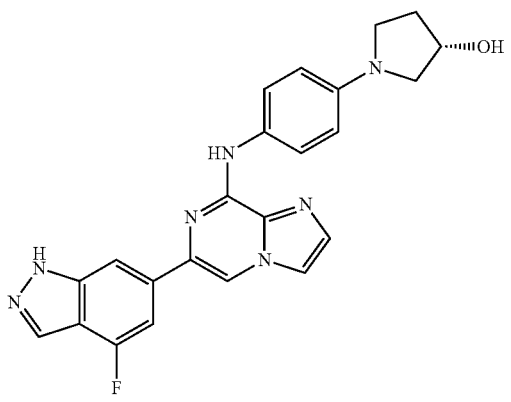 [SMILES: O[C@H]1CCN(c2ccc(Nc3nc(-c4cc(F)c5cn[nH]c5c4)cn4ccnc34)cc2)C1] | (3S)-1-(4-{[6-(4-fluoro-1H-indazol-6-yl)imidazo[1,2-a]pyrazin-8-yl]amino}phenyl)pyrrolidin-3-ol | 430.4 |

-continued

| Structure | Name | [M + H]+ |
|---|---|---|
| 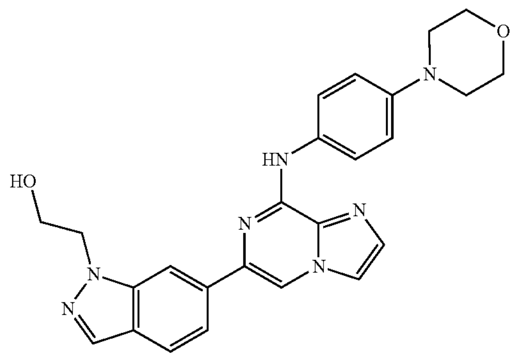 [SMILES: OCCn1ncc2ccc(-c3cn4ccnc4c(Nc4ccc(N5CCOCC5)cc4)n3)cc21] | 2-[6-(8-{[4-(morpholin-4-yl)phenyl]amino}imidazo[1,2-a]pyrazin-6-yl)-1H-indazol-1-yl]ethan-1-ol | 456.3 |
| 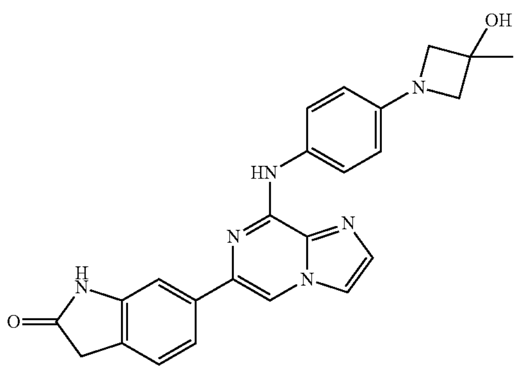 [SMILES: CC1(O)CN(c2ccc(Nc3nc(-c4ccc5c(c4)NC(=O)C5)cn4ccnc34)cc2)C1] | 6-(8-{[4-(3-hydroxy-3-methylazetidin-1-yl)phenyl]amino}imidazo[1,2-a]pyrazin-6-yl)-2,3-dihydro-1H-indol-2-one | 427.2 |
| 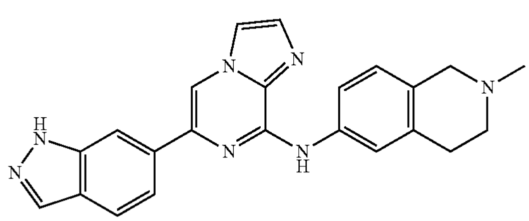 [SMILES: CN1CCc2cc(Nc3nc(-c4ccc5cn[nH]c5c4)cn4ccnc34)ccc2C1] | N-[6-(1H-indazol-6-yl)imidazo[1,2-a]pyrazin-8-yl]-2-methyl-1,2,3,4-tetrahydroisoquinolin-6-amine | 396.1 |
| 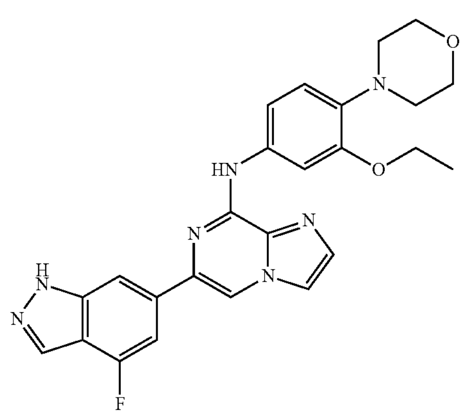 [SMILES: CCOc1cc(Nc2nc(-c3cc(F)c4cn[nH]c4c3)cn3ccnc23)ccc1N1CCOCC1] | N-[3-ethoxy-4-(morpholin-4-yl)phenyl]-6-(4-fluoro-1H-indazol-6-yl)imidazo[1,2-a]pyrazin-8-amine | 474.2 |

-continued
| Structure | Name | [M + H]+ |
|---|---|---|
| 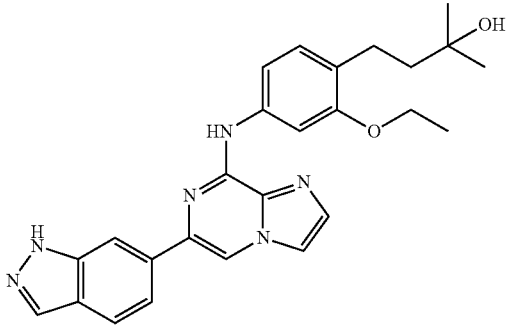 [SMILES: CCOc1cc(Nc2nc(-c3ccc4cn[nH]c4c3)cn3ccnc23)ccc1CCC(C)(C)O] | 1-(2-ethoxy-4-{[6-(1H-indazol-6-yl)imidazo[1,2-a]pyrazin-8-yl]amino}phenoxy)-2-methylpropan-2-ol | 459.4 |
| 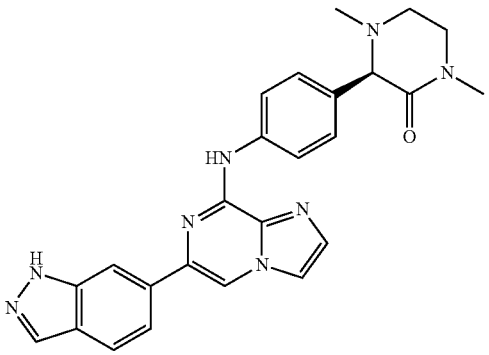 [SMILES: CN1CCN(C)[C@H](c2ccc(Nc3nc(-c4ccc5cn[nH]c5c4)cn4ccnc34)cc2)C1=O] | (3R)-3-(4-{[6-(1H-indazol-6-yl)imidazo[1,2-a]pyrazin-8-yl]amino}phenyl)-1,4-dimethylpiperazin-2-one | 453.4 |
| 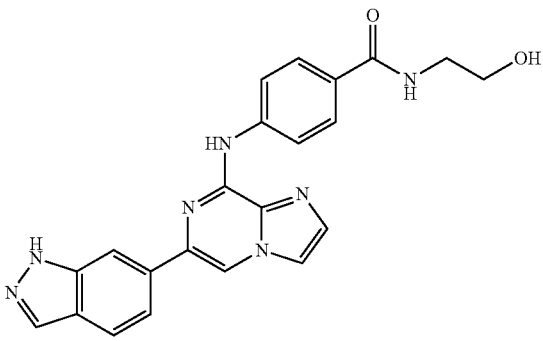 [SMILES: O=C(NCCO)c1ccc(Nc2nc(-c3ccc4cn[nH]c4c3)cn3ccnc23)cc1] | N-(2-hydroxyethyl)-4-{[6-(1H-indazol-6-yl)imidazo[1,2-a]pyrazin-8-yl]amino}benzamide | 414.5 |
| 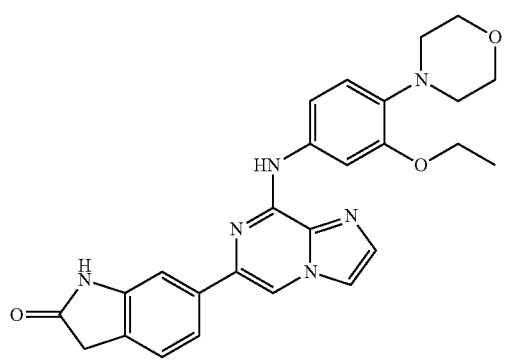 [SMILES: CCOc1cc(Nc2nc(-c3ccc4c(c3)NC(=O)C4)cn3ccnc23)ccc1N1CCOCC1] | 6-(8-{[3-ethoxy-4-(morpholin-4-yl)phenyl]amino}imidazo[1,2-a]pyrazin-6-yl)-2,3-dihydro-1H-indol-2-one | 471.7 |

-continued

| Structure | Name | [M + H]+ |
|---|---|---|
| 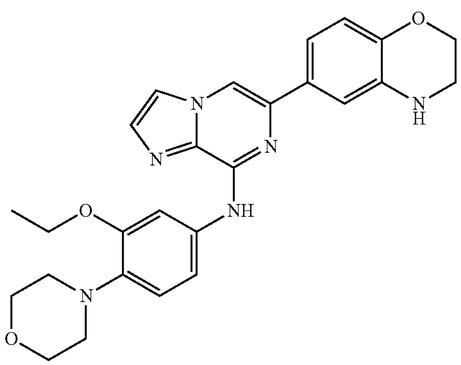 [SMILES: CCOc1cc(Nc2nc(-c3ccc4c(c3)NCCO4)cn3ccnc23)ccc1N1CCOCC1] | 6-(3,4-dihydro-2H-1,4-benzoxazin-6-yl)-N-[3-ethoxy-4-(morpholin-4-yl)phenyl]imidazo[1,2-a]pyrazin-8-amine | 473.2 |
| 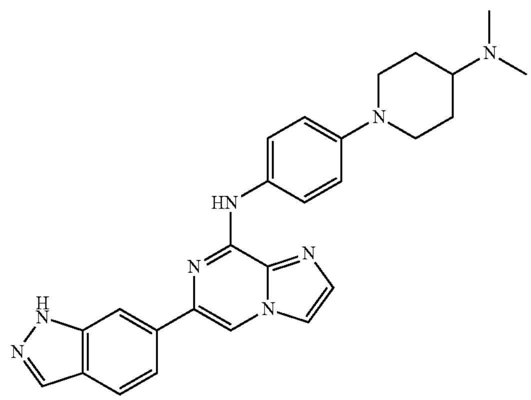 [SMILES: CN(C)C1CCN(c2ccc(Nc3nc(-c4ccc5cn[nH]c5c4)cn4ccnc34)cc2)CC1] | 1-(4-{[6-(1H-indazol-6-yl)imidazo[1,2-a]pyrazin-8-yl]amino}phenyl)-N,N-dimethylpiperidin-4-amine | 453.1 |
| 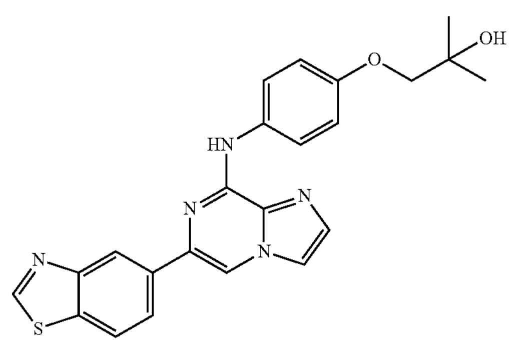 [SMILES: CC(C)(O)COc1ccc(Nc2nc(-c3ccc4scnc4c3)cn3ccnc23)cc1] | 1-(4-{[6-(1,3-benzothiazol-5-yl)imidazo[1,2-a]pyrazin-8-yl]amino}phenoxy)-2-methylpropan-2-ol | 432.4 |
| 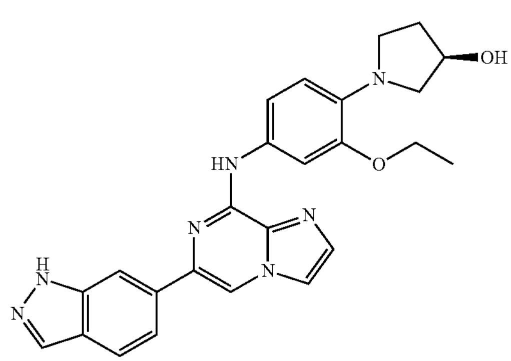 [SMILES: CCOc1cc(Nc2nc(-c3ccc4cn[nH]c4c3)cn3ccnc23)ccc1N1CC[C@@H](O)C1] | (3R)-1-(2-ethoxy-4-{[6-(1H-indazol-6-yl)imidazo[1,2-a]pyrazin-8-yl]amino}phenyl)pyrrolidin-3-ol | 456.4 |

-continued
| Structure | Name | [M + H]+ |
|---|---|---|
| 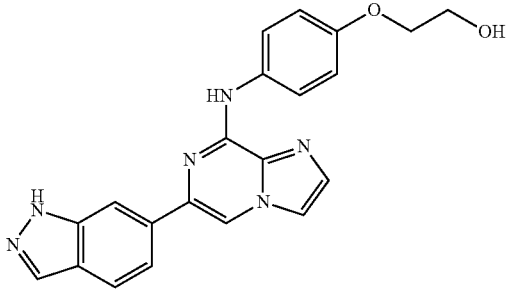 [SMILES: OCCOc1ccc(Nc2nc(-c3ccc4cn[nH]c4c3)cn3ccnc23)cc1] | 2-(4-{[6-(1H-indazol-6-yl)imidazo[1,2-a]pyrazin-8-yl]amino}phenoxy)ethan-1-ol | 387.3 |
| 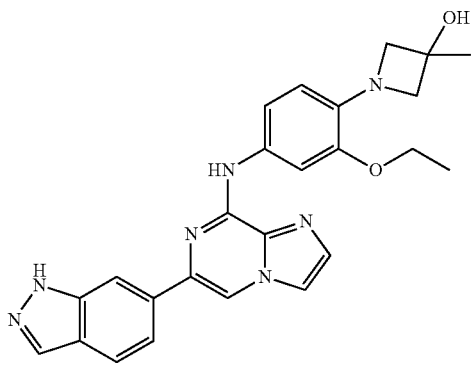 [SMILES: CCOc1cc(Nc2nc(-c3ccc4cn[nH]c4c3)cn3ccnc23)ccc1N1CC(C)(O)C1] | 1-(2-ethoxy-4-{[6-(1H-indazol-6-yl)imidazo[1,2-a]pyrazin-8-yl]amino}phenyl)-3-methylazetidin-3-ol | 456.2 |
| 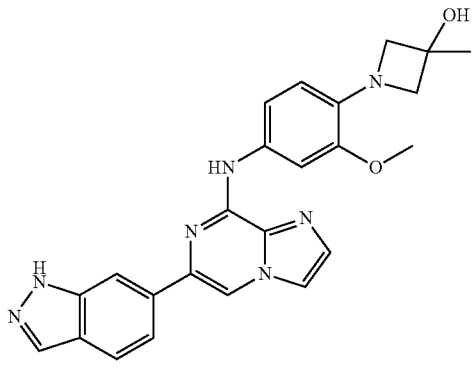 [SMILES: COc1cc(Nc2nc(-c3ccc4cn[nH]c4c3)cn3ccnc23)ccc1N1CC(C)(O)C1] | 1-(4-{[6-(1H-indazol-6-yl)imidazo[1,2-a]pyrazin-8-yl]amino}-2-methoxyphenyl)-3-methylazetidin-3-ol | 442.2 |
| 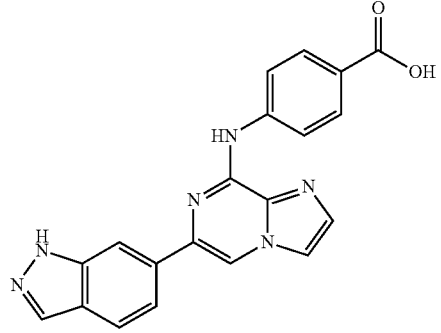 [SMILES: O=C(O)c1ccc(Nc2nc(-c3ccc4cn[nH]c4c3)cn3ccnc23)cc1] | 4-{[6-(1H-indazol-6-yl)imidazo[1,2-a]pyrazin-8-yl]amino}benzoic acid | 371 |

US 8,450,321 B2

213                                                                                      214

-continued

| Structure | Name | [M + H]⁺ |
|---|---|---|
| 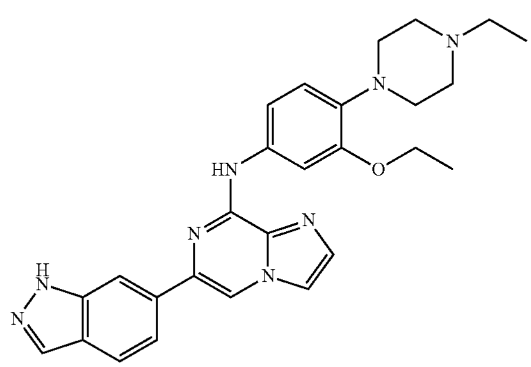 [SMILES: CCOc1cc(Nc2nc(-c3ccc4cn[nH]c4c3)cn3ccnc23)ccc1N1CCN(CC)CC1] | N-[3-ethoxy-4-(4-ethylpiperazin-1-yl)phenyl]-6-(1H-indazol-6-yl)imidazo[1,2-a]pyrazin-8-amine | 483.3 |
| 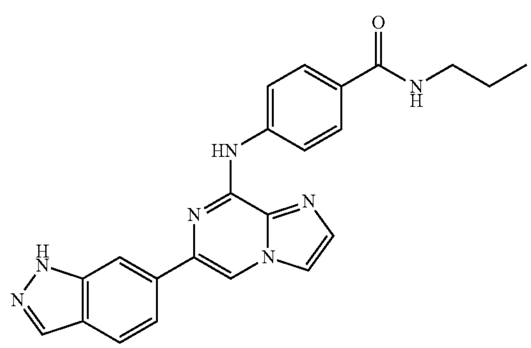 [SMILES: CCCNC(=O)c1ccc(Nc2nc(-c3ccc4cn[nH]c4c3)cn3ccnc23)cc1] | 4-{[6-(1H-indazol-6-yl)imidazo[1,2-a]pyrazin-8-yl]amino}-N-propylbenzamide | 412.1 |
| 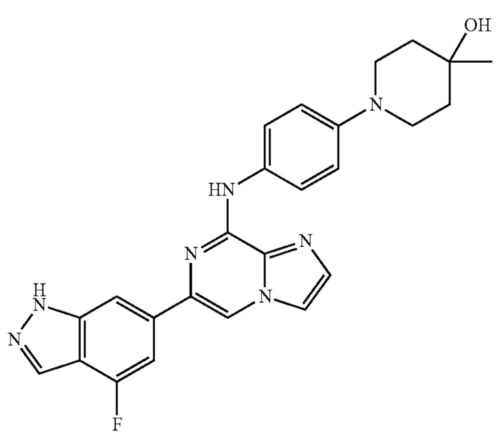 [SMILES: CC1(O)CCN(c2ccc(Nc3nc(-c4cc(F)c5cn[nH]c5c4)cn4ccnc34)cc2)CC1] | 1-(4-{[6-(4-fluoro-1H-indazol-6-yl)imidazo[1,2-a]pyrazin-8-yl]amino}phenyl)-4-methylpiperidin-4-ol | 458.6 |
| 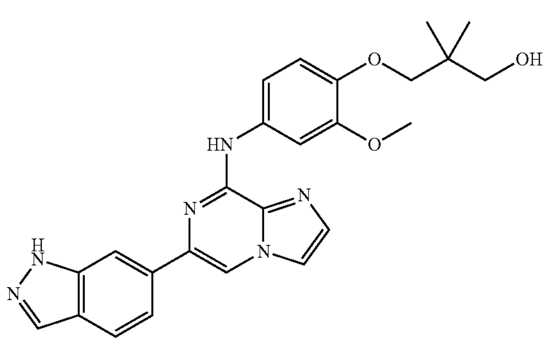 [SMILES: COc1cc(Nc2nc(-c3ccc4cn[nH]c4c3)cn3ccnc23)ccc1OCC(C)(C)CO] | 3-(4-{[6-(1H-indazol-6-yl)imidazo[1,2-a]pyrazin-8-yl]amino}-2-methoxyphenoxy)-2,2-dimethylpropan-1-ol | 459.5 |

-continued

| Structure | Name | [M + H]+ |
|---|---|---|
| 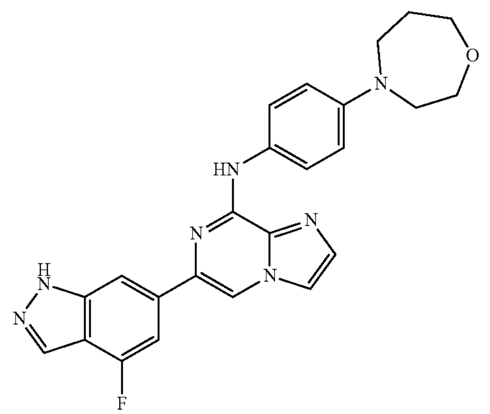 [SMILES: Fc1cc(-c2cn3ccnc3c(Nc3ccc(N4CCCOCC4)cc3)n2)cc2[nH]ncc12] | 6-(4-fluoro-1H-indazol-6-yl)-N-[4-(1,4-oxazepan-4-yl)phenyl]imidazo[1,2-a]pyrazin-8-amine | 444.7 |
| 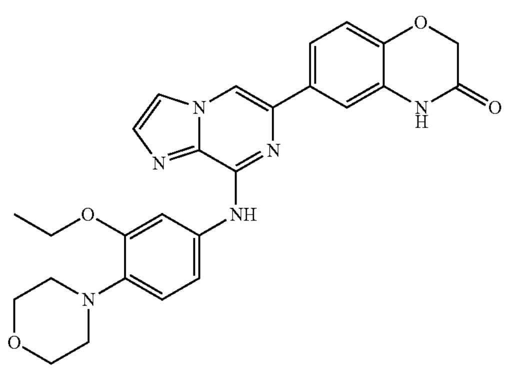 [SMILES: CCOc1cc(Nc2nc(-c3ccc4c(c3)NC(=O)CO4)cn3ccnc23)ccc1N1CCOCC1] | 6-(8-{[3-ethoxy-4-(morpholin-4-yl)phenyl]amino}imidazo[1,2-a]pyrazin-6-yl)-3,4-dihydro-2H-1,4-benzoxazin-3-one | 487.5 |
| 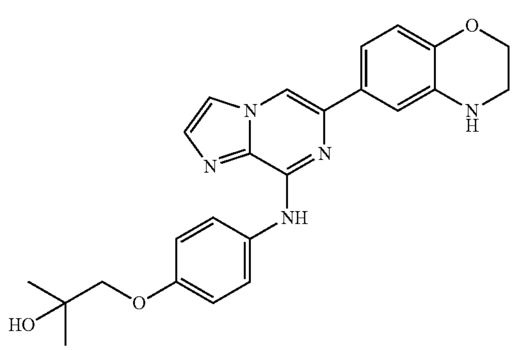 [SMILES: CC(C)(O)COc1ccc(Nc2nc(-c3ccc4c(c3)NCCO4)cn3ccnc23)cc1] | 1-(4-{[6-(3,4-dihydro-2H-1,4-benzoxazin-6-yl)imidazo[1,2-a]pyrazin-8-yl]amino}phenoxy)-2-methylpropan-2-ol | 432.4 |
| 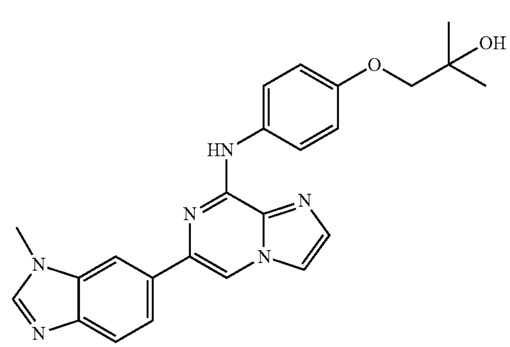 [SMILES: Cn1cnc2ccc(-c3cn4ccnc4c(Nc4ccc(OCC(C)(C)O)cc4)n3)cc21] | 2-methyl-1-(4-{[6-(1-methyl-1H-1,3-benzodiazol-6-yl)imidazo[1,2-a]pyrazin-8-yl]amino}phenoxy)propan-2-ol | 429.3 |

-continued

| Structure | Name | [M + H]⁺ |
|---|---|---|
| 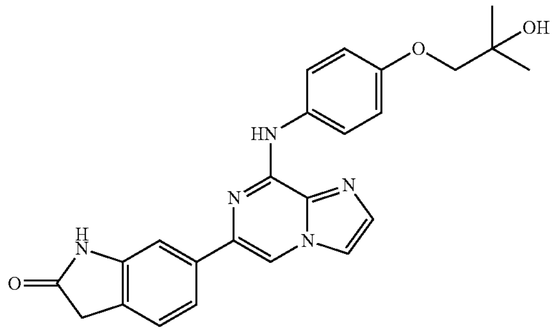 [SMILES: CC(C)(O)COc1ccc(Nc2nc(-c3ccc4c(c3)NC(=O)C4)cn3ccnc23)cc1] | 6-(8-{[4-(2-hydroxy-2-methylpropoxy)phenyl]amino}imidazo[1,2-a]pyrazin-6-yl)-2,3-dihydro-1H-indol-2-one | 430.2 |
| 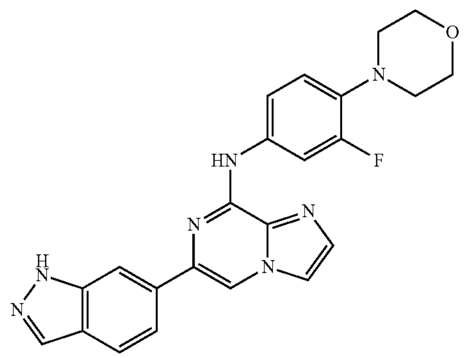 [SMILES: Fc1cc(Nc2nc(-c3ccc4cn[nH]c4c3)cn3ccnc23)ccc1N1CCOCC1] | N-[3-fluoro-4-(morpholin-4-yl)phenyl]-6-(1H-indazol-6-yl)imidazo[1,2-a]pyrazin-8-amine | 430.4 |
| 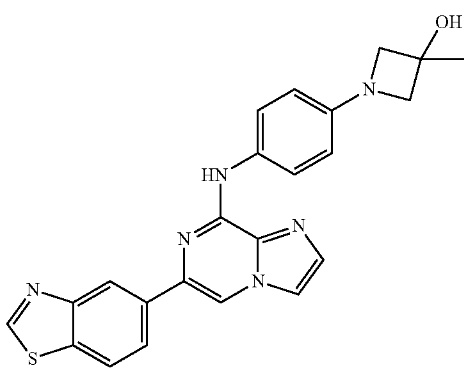 [SMILES: CC1(O)CN(c2ccc(Nc3nc(-c4ccc5scnc5c4)cn4ccnc34)cc2)C1] | 1-(4-{[6-(1,3-benzothiazol-5-yl)imidazo[1,2-a]pyrazin-8-yl]amino}phenyl)-3-methylazetidin-3-ol | 429.1 |
| 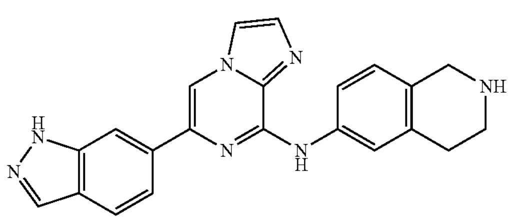 [SMILES: c1cn2cc(-c3ccc4cn[nH]c4c3)nc(Nc3ccc4c(c3)CCNC4)c2n1] | N-[6-(1H-indazol-6-yl)imidazo[1,2-a]pyrazin-8-yl]-1,2,3,4-tetrahydroisoquinolin-6-amine | 382.2 |
| 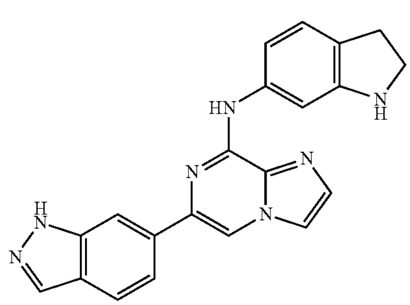 [SMILES: c1cn2cc(-c3ccc4cn[nH]c4c3)nc(Nc3ccc4c(c3)NCC4)c2n1] | N-[6-(1H-indazol-6-yl)imidazo[1,2-a]pyrazin-8-yl]-2,3-dihydro-1H-indol-6-amine | 368.2 |

-continued

| Structure | Name | [M + H]+ |
|---|---|---|
| 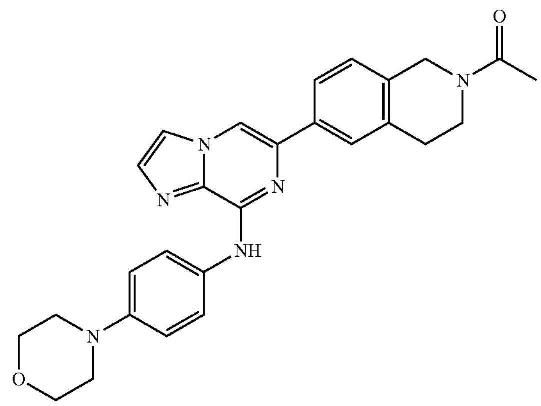 [SMILES: CC(=O)N1CCc2cc(-c3cn4ccnc4c(Nc4ccc(N5CCOCC5)cc4)n3)ccc2C1] | 1-[6-(8-{[4-(morpholin-4-yl)phenyl]amino}imidazo[1,2-a]pyrazin-6-yl)-1,2,3,4-tetrahydroisoquinolin-2-yl]ethan-1-one | 469.6 |
| 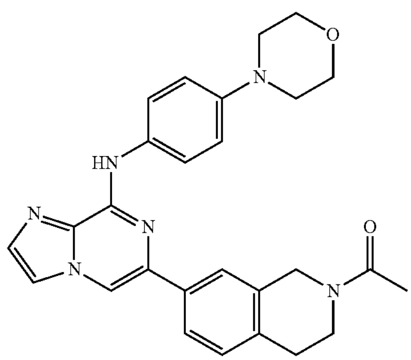 [SMILES: CC(=O)N1CCc2ccc(-c3cn4ccnc4c(Nc4ccc(N5CCOCC5)cc4)n3)cc2C1] | 1-[7-(8-{[4-(morpholin-4-yl)phenyl]amino}imidazo[1,2-a]pyrazin-6-yl)-1,2,3,4-tetrahydroisoquinolin-2-yl]ethan-1-one | 469.7 |
| 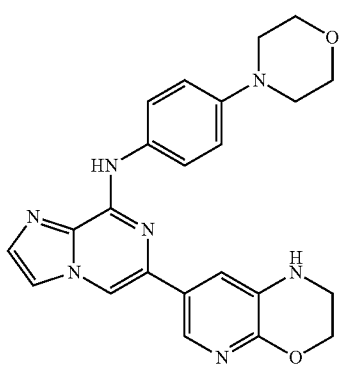 [SMILES: c1cn2cc(-c3cnc4c(c3)NCCO4)nc(Nc3ccc(N4CCOCC4)cc3)c2n1] | N-[4-(morpholin-4-yl)phenyl]-6-{1H,2H,3H-pyrido[2,3-b][1,4]oxazin-7-yl}imidazo[1,2-a]pyrazin-8-amine | 430.4 |
| 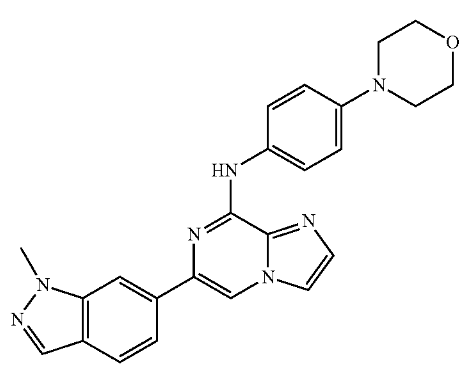 [SMILES: Cn1ncc2ccc(-c3cn4ccnc4c(Nc4ccc(N5CCOCC5)cc4)n3)cc21] | 6-(1-methyl-1H-indazol-6-yl)-N-[4-(morpholin-4-yl)phenyl]imidazo[1,2-a]pyrazin-8-amine | 426.1 |

-continued

| Structure | Name | [M + H]+ |
|---|---|---|
| 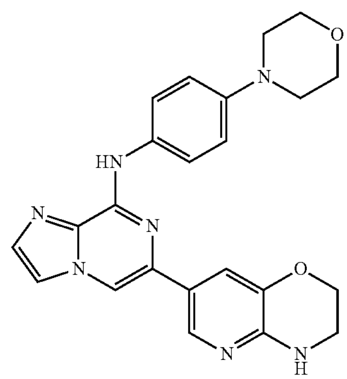 [SMILES: c1cn2cc(-c3cnc4c(c3)OCCN4)nc(Nc3ccc(N4CCOCC4)cc3)c2n1] | N-[4-(morpholin-4-yl)phenyl]-6-{2H,3H,4H-pyrido[3,2-b][1,4]oxazin-7-yl}imidazo[1,2-a]pyrazin-8-amine | 430.4 |
| 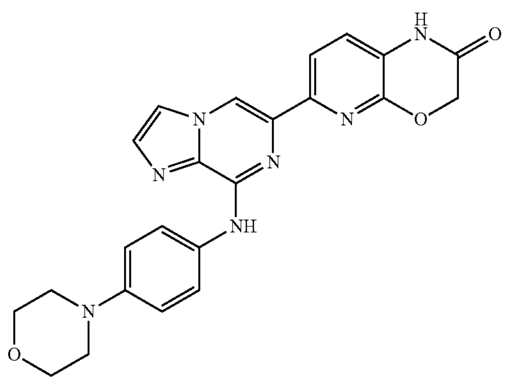 [SMILES: O=C1COc2nc(-c3cn4ccnc4c(Nc4ccc(N5CCOCC5)cc4)n3)ccc2N1] | 6-(8-{[4-(morpholin-4-yl)phenyl]amino}imidazo[1,2-a]pyrazin-6-yl)-1H,2H,3H-pyrido[2,3-b][1,4]oxazin-2-one | 444.2 |
| 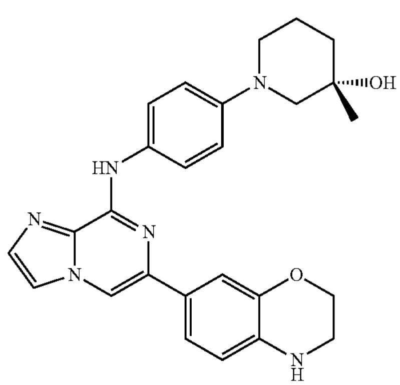 [SMILES: C[C@]1(O)CCCN(c2ccc(Nc3nc(-c4ccc5c(c4)OCCN5)cn4ccnc34)cc2)C1] | (3S)-1-(4-{[6-(3,4-dihydro-2H-1,4-benzoxazin-7-yl)imidazo[1,2-a]pyrazin-8-yl]amino}phenyl)-3-methylpiperidin-3-ol | 457.2 |
| 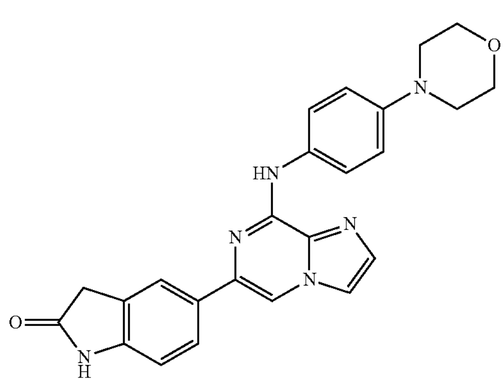 [SMILES: O=C1Cc2cc(-c3cn4ccnc4c(Nc4ccc(N5CCOCC5)cc4)n3)ccc2N1] | 5-(8-{[4-(morpholin-4-yl)phenyl]amino}imidazo[1,2-a]pyrazin-6-yl)-2,3-dihydro-1H-indol-2-one | 427 |

-continued

| Structure | Name | [M + H]+ |
|---|---|---|
| 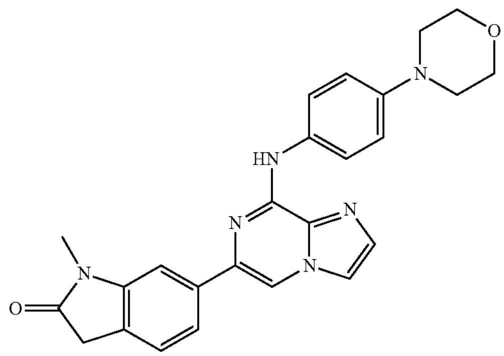 [SMILES: CN1C(=O)Cc2ccc(-c3cn4ccnc4c(Nc4ccc(N5CCOCC5)cc4)n3)cc21] | 1-methyl-6-(8-{[4-(morpholin-4-yl)phenyl]amino}imidazo[1,2-a]pyrazin-6-yl)-2,3-dihydro-1H-indol-2-one | 441.4 |
| 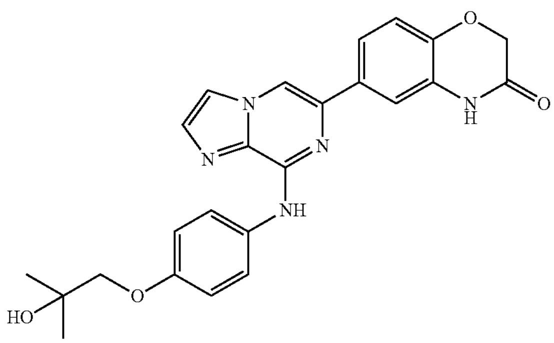 [SMILES: CC(C)(O)COc1ccc(Nc2nc(-c3ccc4c(c3)NC(=O)CO4)cn3ccnc23)cc1] | 6-(8-{[4-(2-hydroxy-2-methylpropoxy)phenyl]amino}imidazo[1,2-a]pyrazin-6-yl)-3,4-dihydro-2H-1,4-benzoxazin-3-one | 446.3 |
| 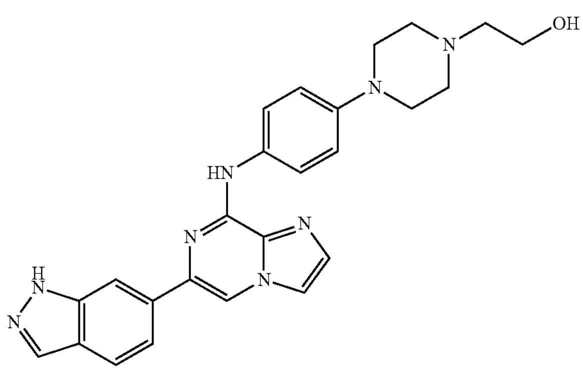 [SMILES: OCCN1CCN(c2ccc(Nc3nc(-c4ccc5cn[nH]c5c4)cn4ccnc34)cc2)CC1] | 2-[4-(4-{[6-(1H-indazol-6-yl)imidazo[1,2-a]pyrazin-8-yl]amino}phenyl)piperazin-1-yl]ethan-1-ol | 455.2 |
| 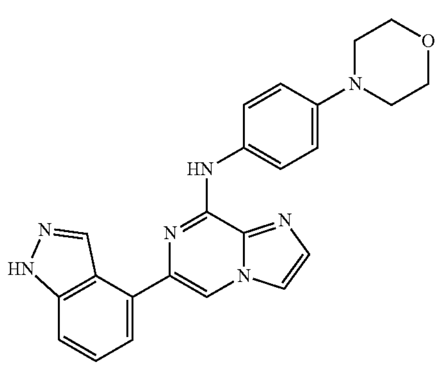 [SMILES: c1cc(-c2cn3ccnc3c(Nc3ccc(N4CCOCC4)cc3)n2)c2cn[nH]c2c1] | 6-(1H-indazol-4-yl)-N-[4-(morpholin-4-yl)phenyl]imidazo[1,2-a]pyrazin-8-amine | 412.2 |

| Structure | Name | [M + H]+ |
|---|---|---|
| 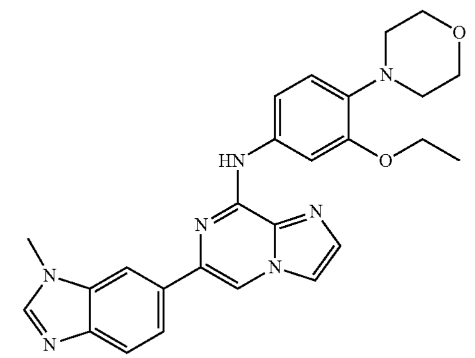 [SMILES: CCOc1cc(Nc2nc(-c3ccc4ncn(C)c4c3)cn3ccnc23)ccc1N1CCOCC1] | N-[3-ethoxy-4-(morpholin-4-yl)phenyl]-6-(1-methyl-1H-1,3-benzodiazol-6-yl)imidazo[1,2-a]pyrazin-8-amine | 470.2 |
| 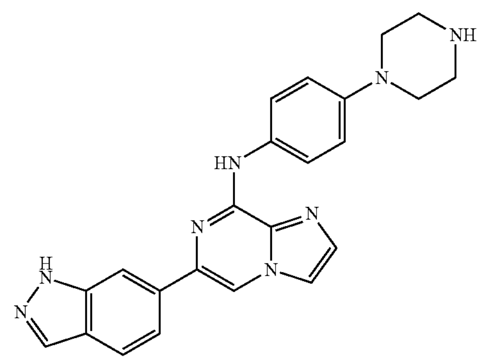 [SMILES: c1cn2cc(-c3ccc4cn[nH]c4c3)nc(Nc3ccc(N4CCNCC4)cc3)c2n1] | 6-(1H-indazol-6-yl)-N-[4-(piperazin-1-yl)phenyl]imidazo[1,2-a]pyrazin-8-amine | 411.2 |
| 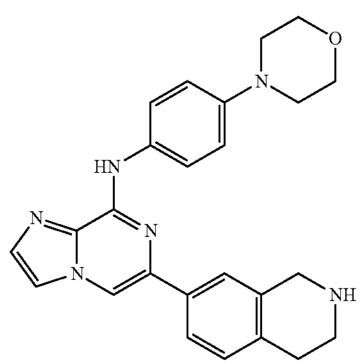 [SMILES: c1cn2cc(-c3ccc4c(c3)CNCC4)nc(Nc3ccc(N4CCOCC4)cc3)c2n1] | N-[4-(morpholin-4-yl)phenyl]-6-(1,2,3,4-tetrahydroisoquinolin-7-yl)imidazo[1,2-a]pyrazin-8-amine | 427.1 |
| 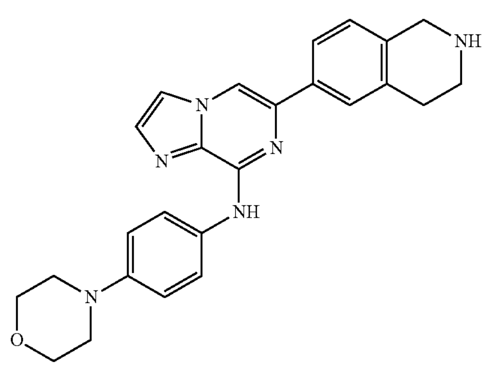 [SMILES: c1cn2cc(-c3ccc4c(c3)CCNC4)nc(Nc3ccc(N4CCOCC4)cc3)c2n1] | N-[4-(morpholin-4-yl)phenyl]-6-(1,2,3,4-tetrahydroisoquinolin-6-yl)imidazo[1,2-a]pyrazin-8-amine | 427 |

-continued
| Structure | Name | [M + H]+ |
|---|---|---|
| 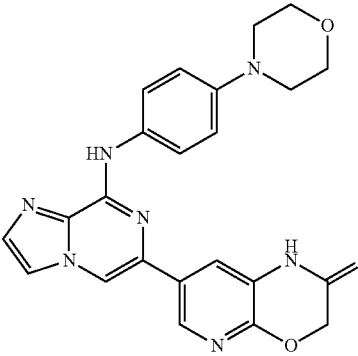 | 7-(8-{[4-(morpholin-4-yl)phenyl]amino}imidazo[1,2-a]pyrazin-6-yl)-1H,2H,3H-pyrido[2,3-b][1,4]oxazin-2-one | 444.8 |
| 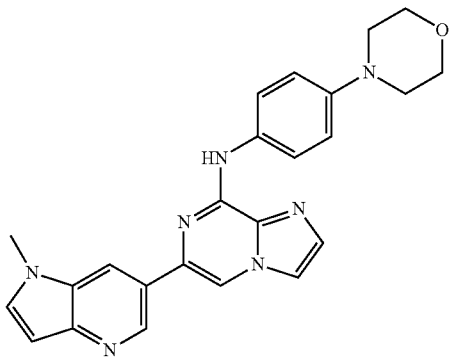 [SMILES: Cn1ccc2ncc(-c3cn4ccnc4c(Nc4ccc(N5CCOCC5)cc4)n3)cc21] | 6-{1-methyl-1H-pyrrolo[3,2-b]pyridin-6-yl}-N-[4-(morpholin-4-yl)phenyl]imidazo[1,2-a]pyrazin-8-amine | 426.2 |
| 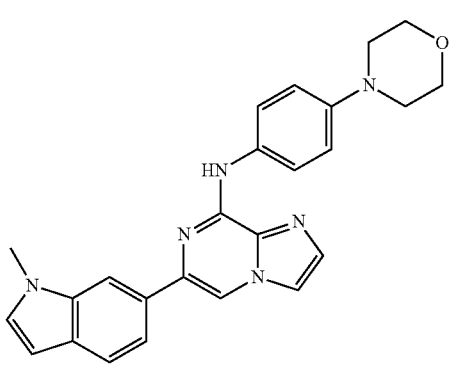 [SMILES: Cn1ccc2ccc(-c3cn4ccnc4c(Nc4ccc(N5CCOCC5)cc4)n3)cc21] | 6-(1-methyl-1H-indol-6-yl)-N-[4-(morpholin-4-yl)phenyl]imidazo[1,2-a]pyrazin-8-amine | 425.3 |
| 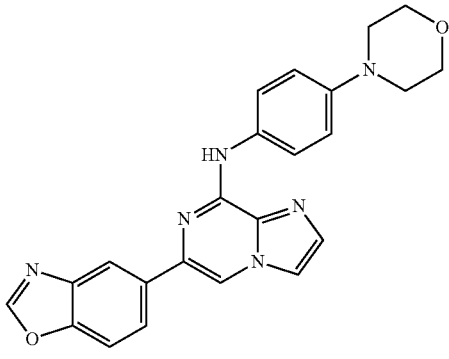 [SMILES: c1cn2cc(-c3ccc4ocnc4c3)nc(Nc3ccc(N4CCOCC4)cc3)c2n1] | 6-(1,3-benzoxazol-5-yl)-N-[4-(morpholin-4-yl)phenyl]imidazo[1,2-a]pyrazin-8-amine | 413.5 |

-continued

| Structure | Name | [M + H]⁺ |
|---|---|---|
| 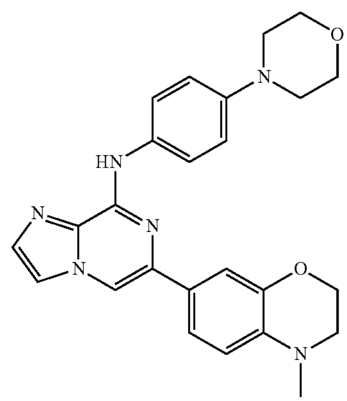 [SMILES: CN1CCOc2cc(-c3cn4ccnc4c(Nc4ccc(N5CCOCC5)cc4)n3)ccc21] | 6-(4-methyl-3,4-dihydro-2H-1,4-benzoxazin-7-yl)-N-[4-(morpholin-4-yl)phenyl]imidazo[1,2-a]pyrazin-8-amine | 443.6 |
| 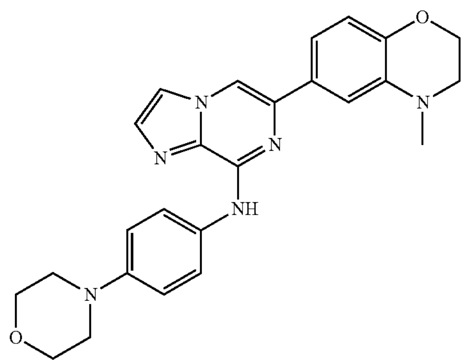 [SMILES: CN1CCOc2ccc(-c3cn4ccnc4c(Nc4ccc(N5CCOCC5)cc4)n3)cc21] | 6-(4-methyl-3,4-dihydro-2H-1,4-benzoxazin-6-yl)-N-[4-(morpholin-4-yl)phenyl]imidazo[1,2-a]pyrazin-8-amine | 443.9 |
| 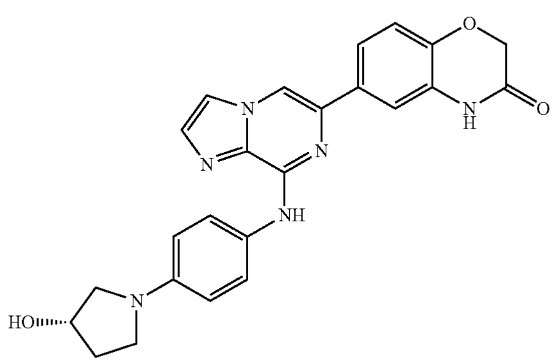 [SMILES: O=C1COc2ccc(-c3cn4ccnc4c(Nc4ccc(N5CC[C@H](O)C5)cc4)n3)cc2N1] | 6-[8-({4-[(3S)-3-hydroxypyrrolidin-1-yl]phenyl}amino)imidazo[1,2-a]pyrazin-6-yl]-3,4-dihydro-2H-1,4-benzoxazin-3-one | 443.7 |
| 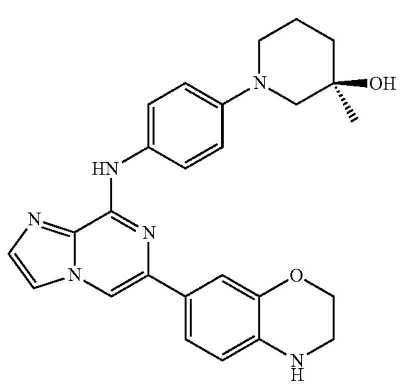 [SMILES: C[C@@]1(O)CCCN(c2ccc(Nc3nc(-c4ccc5c(c4)OCCN5)cn4ccnc34)cc2)C1] | (3R)-1-(4-{[6-(3,4-dihydro-2H-1,4-benzoxazin-7-yl)imidazo[1,2-a]pyrazin-8-yl]amino}phenyl)-3-methylpiperidin-3-ol | 457.2 |

| Structure | Name | [M + H]+ |
|---|---|---|
| 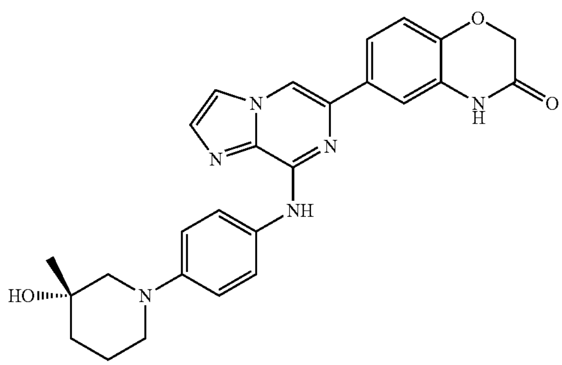 [SMILES: C[C@]1(O)CCCN(c2ccc(Nc3nc(-c4ccc5c(c4)NC(=O)CO5)cn4ccnc34)cc2)C1] | 6-[8-({4-[(3S)-3-hydroxy-3-methylpiperidin-1-yl]phenyl}amino)imidazo[1,2-a]pyrazin-6-yl]-3,4-dihydro-2H-1,4-benzoxazin-3-one | 471.7 |
| 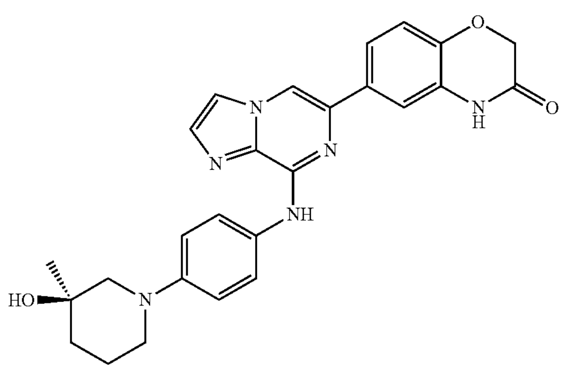 [SMILES: C[C@@]1(O)CCCN(c2ccc(Nc3nc(-c4ccc5c(c4)NC(=O)CO5)cn4ccnc34)cc2)C1] | 6-[8-({4-[(3R)-3-hydroxy-3-methylpiperidin-1-yl]phenyl}amino)imidazo[1,2-a]pyrazin-6-yl]-3,4-dihydro-2H-1,4-benzoxazin-3-one | 471.6 |
| 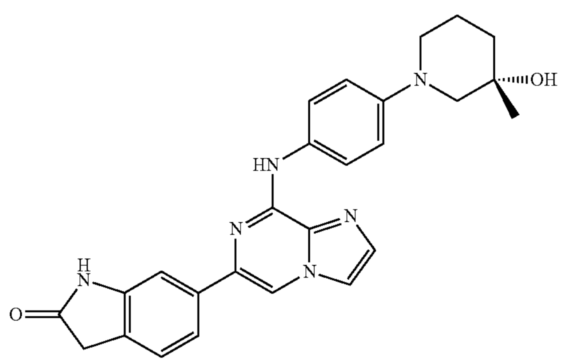 [SMILES: C[C@]1(O)CCCN(c2ccc(Nc3nc(-c4ccc5c(c4)NC(=O)C5)cn4ccnc34)cc2)C1] | 6-[8-({4-[(3S)-3-hydroxy-3-methylpiperidin-1-yl]phenyl}amino)imidazo[1,2-a]pyrazin-6-yl]-2,3-dihydro-1H-indol-2-one | 455.4 |
| 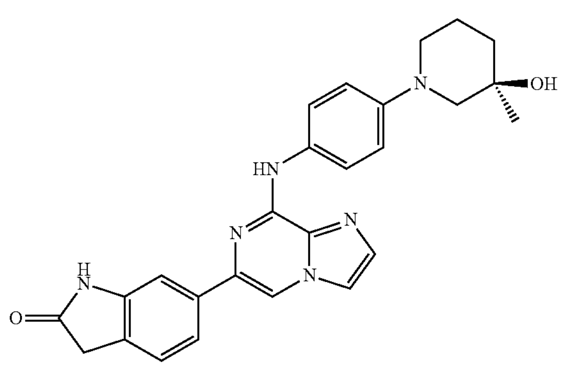 [SMILES: C[C@@]1(O)CCCN(c2ccc(Nc3nc(-c4ccc5c(c4)NC(=O)C5)cn4ccnc34)cc2)C1] | 6-[8-({4-[(3R)-3-hydroxy-3-methylpiperidin-1-yl]phenyl}amino)imidazo[1,2-a]pyrazin-6-yl]-2,3-dihydro-1H-indol-2-one | 455.2 |

-continued

| Structure | Name | [M + H]+ |
|---|---|---|
| 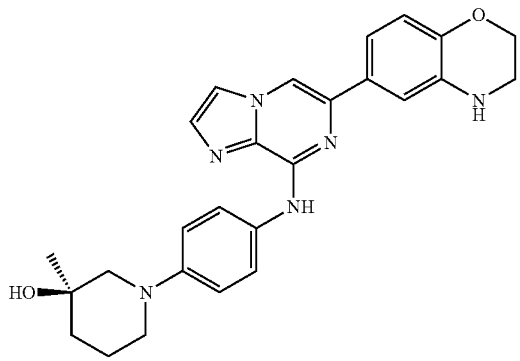 [SMILES: C[C@@]1(O)CCCN(c2ccc(Nc3nc(-c4ccc5c(c4)NCCO5)cn4ccnc34)cc2)C1] | (3R)-1-(4-{[6-(3,4-dihydro-2H-1,4-benzoxazin-6-yl)imidazo[1,2-a]pyrazin-8-yl]amino}phenyl)-3-methylpiperidin-3-ol | 457.2 |
| 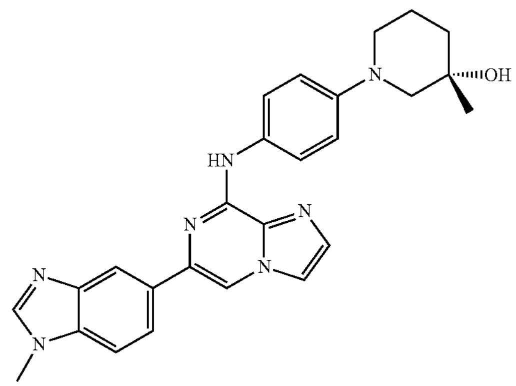 [SMILES: Cn1cnc2cc(-c3cn4ccnc4c(Nc4ccc(N5CCC[C@](C)(O)C5)cc4)n3)ccc21] | (3S)-3-methyl-1-(4-{[6-(1-methyl-1H-1,3-benzodiazol-5-yl)imidazo[1,2-a]pyrazin-8-yl]amino}phenyl)piperidin-3-ol | 454.6 |
| 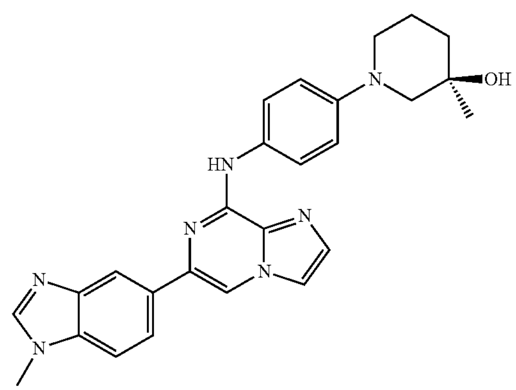 [SMILES: Cn1cnc2cc(-c3cn4ccnc4c(Nc4ccc(N5CCC[C@@](C)(O)C5)cc4)n3)ccc21] | (3R)-3-methyl-1-(4-{[6-(1-methyl-1H-1,3-benzodiazol-5-yl)imidazo[1,2-a]pyrazin-8-yl]amino}phenyl)piperidin-3-ol | 454.2 |
| 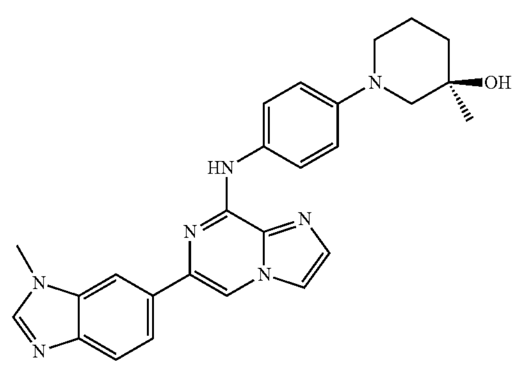 [SMILES: Cn1cnc2ccc(-c3cn4ccnc4c(Nc4ccc(N5CCC[C@@](C)(O)C5)cc4)n3)cc21] | (3R)-3-methyl-1-(4-{[6-(1-methyl-1H-1,3-benzodiazol-6-yl)imidazo[1,2-a]pyrazin-8-yl]amino}phenyl)piperidin-3-ol | 454.1 |

-continued
| Structure | Name | [M + H]+ |
|---|---|---|
| 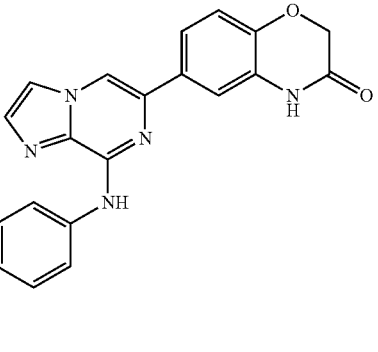 | 6-(8-{[4-(4-ethylpiperazin-1-yl)phenyl]amino}imidazo[1,2-a]pyrazin-6-yl)-3,4-dihydro-2H-1,4-benzoxazin-3-one | 470.8 |
| 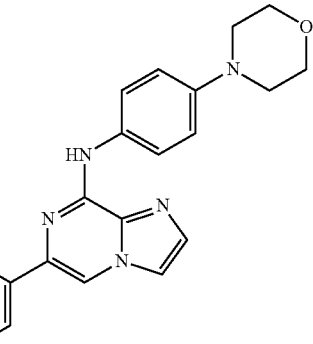 | 6-(1,3-benzothiazol-6-yl)-N-[4-(morpholin-4-yl)phenyl]imidazo[1,2-a]pyrazin-8-amine | 429.3 |
| 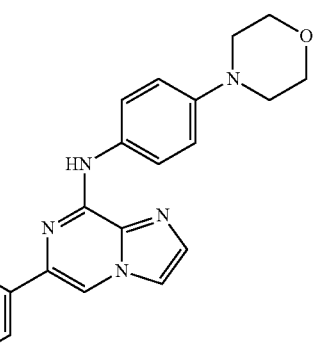 | 6-(1,3-benzothiazol-5-yl)-N-[4-(morpholin-4-yl)phenyl]imidazo[1,2-a]pyrazin-8-amine | 429.4 |
| 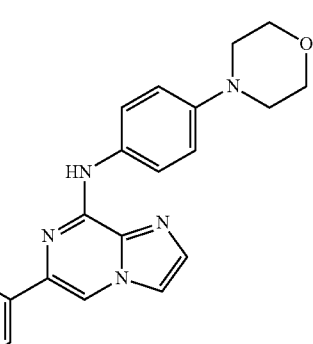 | 6-(1,3-benzoxazol-6-yl)-N-[4-(morpholin-4-yl)phenyl]imidazo[1,2-a]pyrazin-8-amine | 413.5 |

| Structure | Name | [M + H]+ |
|---|---|---|
| 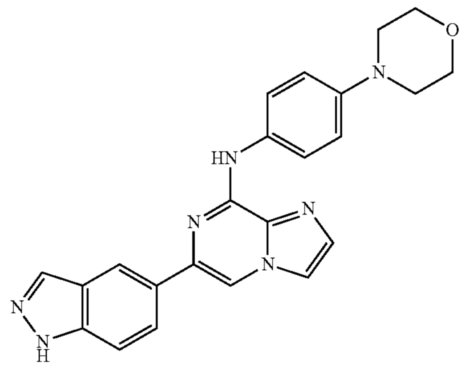 [SMILES: c1cn2cc(-c3ccc4[nH]ncc4c3)nc(Nc3ccc(N4CCOCC4)cc3)c2n1] | 6-(1H-indazol-5-yl)-N-[4-(morpholin-4-yl)phenyl]imidazo[1,2-a]pyrazin-8-amine | 412.3 |
| 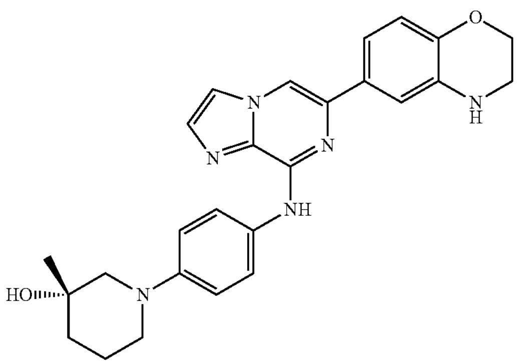 [SMILES: C[C@]1(O)CCCN(c2ccc(Nc3nc(-c4ccc5c(c4)NCCO5)cn4ccnc34)cc2)C1] | (3S)-1-(4-{[6-(3,4-dihydro-2H-1,4-benzoxazin-6-yl)imidazo[1,2-a]pyrazin-8-yl]amino}phenyl)-3-methylpiperidin-3-ol | 457.6 |
| 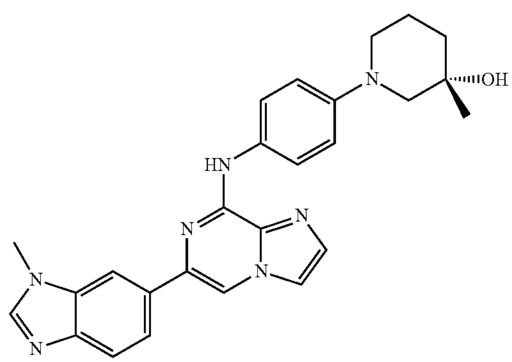 [SMILES: Cn1cnc2ccc(-c3cn4ccnc4c(Nc4ccc(N5CCC[C@](C)(O)C5)cc4)n3)cc21] | (3S)-3-methyl-1-(4-{[6-(1-methyl-1H-1,3-benzodiazol-6-yl)imidazo[1,2-a]pyrazin-8-yl]amino}phenyl)piperidin-3-ol | 450.4 |
| 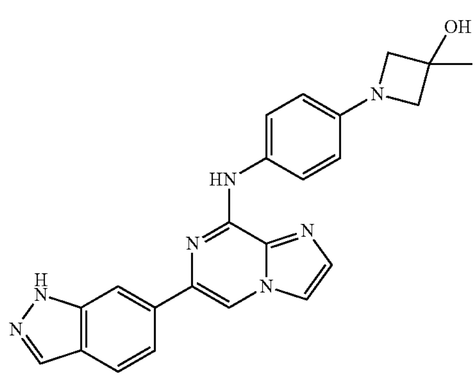 [SMILES: CC1(O)CN(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)-3-methylazetidin-3-ol | 412.3 |

-continued

| Structure | Name | [M + H]+ |
|---|---|---|
| 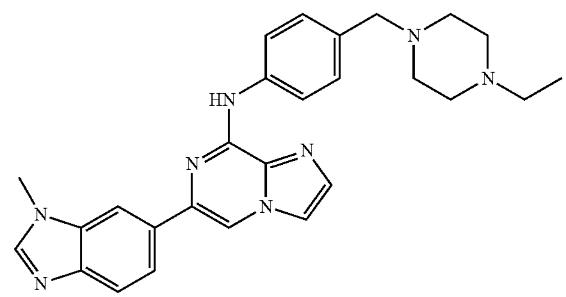 [SMILES: CCN1CCN(Cc2ccc(Nc3nc(-c4ccc5ncn(C)c5c4)cn4ccnc34)cc2)CC1] | N-{4-[(4-ethylpiperazin-1-yl)methyl]phenyl}-6-(1-methyl-1H-1,3-benzodiazol-6-yl)imidazo[1,2-a]pyrazin-8-amine | 467.5 |
| 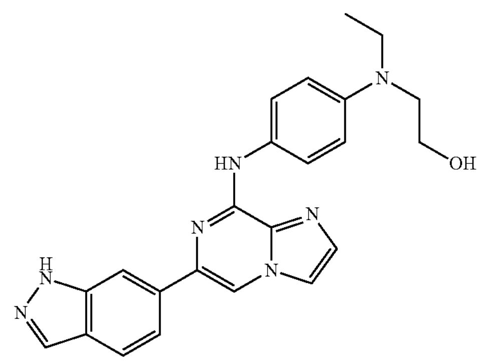 [SMILES: CCN(CCO)c1ccc(Nc2nc(-c3ccc4cn[nH]c4c3)cn3ccnc23)cc1] | 2-[ethyl(4-{[6-(1H-indazol-6-yl)imidazo[1,2-a]pyrazin-8-yl]amino}phenyl)amino]ethan-1-ol | 414.4 |
| 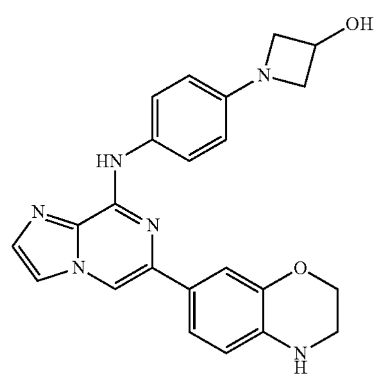 [SMILES: OC1CN(c2ccc(Nc3nc(-c4ccc5c(c4)OCCN5)cn4ccnc34)cc2)C1] | 1-(4-{[6-(3,4-dihydro-2H-1,4-benzoxazin-7-yl)imidazo[1,2-a]pyrazin-8-yl]amino}phenyl)azetidin-3-ol | 415.2 |
| 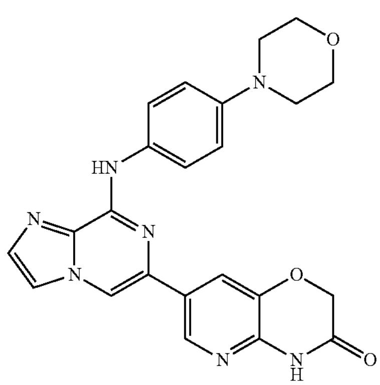 [SMILES: O=C1COc2cc(-c3cn4ccnc4c(Nc4ccc(N5CCOCC5)cc4)n3)cnc2N1] | 7-(8-{[4-(morpholin-4-yl)phenyl]amino}imidazo[1,2-a]pyrazin-6-yl)-2H,3H,4H-pyrido[3,2-b][1,4]oxazin-3-one | 444.8 |

| Structure | Name | [M + H]+ |
|---|---|---|
| 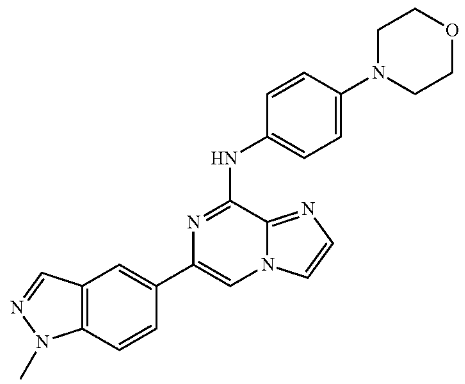 [SMILES: Cn1ncc2cc(-c3cn4ccnc4c(Nc4ccc(N5CCOCC5)cc4)n3)ccc21] | 6-(1-methyl-1H-indazol-5-yl)-N-[4-(morpholin-4-yl)phenyl]imidazo[1,2-a]pyrazin-8-amine | 426.1 |
| 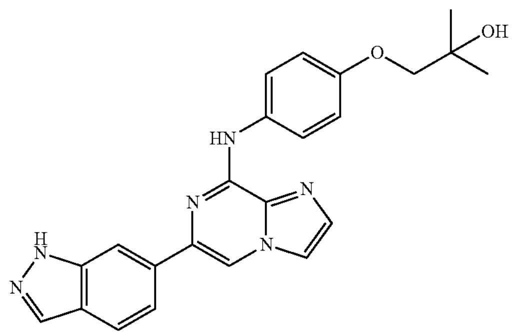 [SMILES: CC(C)(O)COc1ccc(Nc2nc(-c3ccc4cn[nH]c4c3)cn3ccnc23)cc1] | 1-(4-{[6-(1H-indazol-6-yl)imidazo[1,2-a]pyrazin-8-yl]amino}phenoxy)-2-methylpropan-2-ol | 415.4 |
| 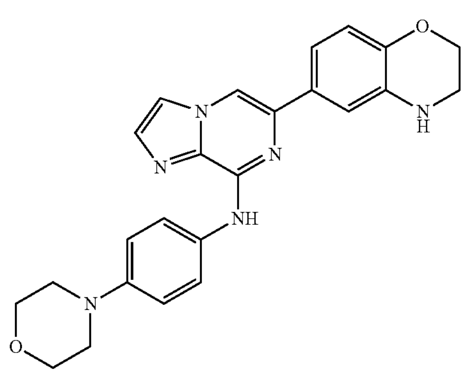 [SMILES: c1cn2cc(-c3ccc4c(c3)NCCO4)nc(Nc3ccc(N4CCOCC4)cc3)c2n1] | 6-(3,4-dihydro-2H-1,4-benzoxazin-6-yl)-N-[4-(morpholin-4-yl)phenyl]imidazo[1,2-a]pyrazin-8-amine | 429.3 |
| 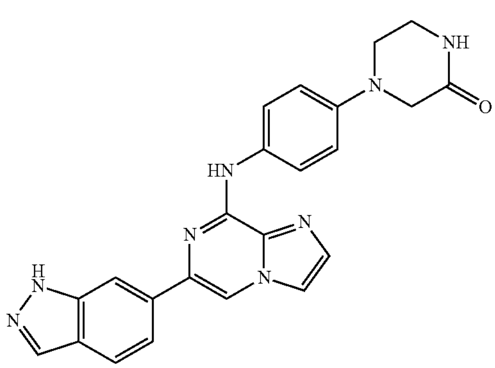 [SMILES: O=C1CN(c2ccc(Nc3nc(-c4ccc5cn[nH]c5c4)cn4ccnc34)cc2)CCN1] | 4-(4-{[6-(1H-indazol-6-yl)imidazo[1,2-a]pyrazin-8-yl]amino}phenyl)piperazin-2- | 425.1 |

-continued

| Structure | Name | [M + H]+ |
|---|---|---|
| 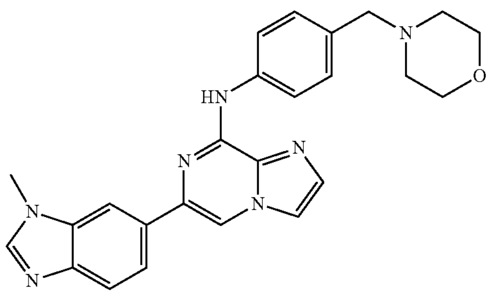 [SMILES: Cn1cnc2ccc(-c3cn4ccnc4c(Nc4ccc(CN5CCOCC5)cc4)n3)cc21] | 6-(1-methyl-1H-1,3-benzodiazol-6-yl)-N-[4-(morpholin-4-ylmethyl)phenyl]imidazo[1,2-a]pyrazin-8-amine | 440.4 |
| 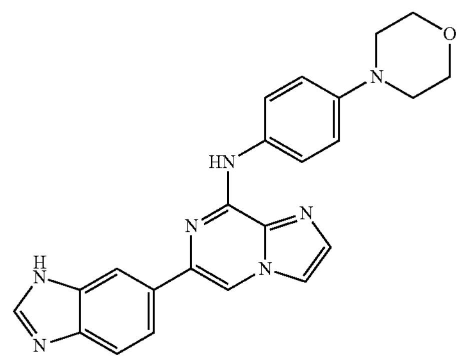 [SMILES: c1cn2cc(-c3ccc4nc[nH]c4c3)nc(Nc3ccc(N4CCOCC4)cc3)c2n1] | 6-(1H-1,3-benzodiazol-6-yl)-N-[4-(morpholin-4-yl)phenyl]imidazo[1,2-a]pyrazin-8-amine | 412.2 |
| 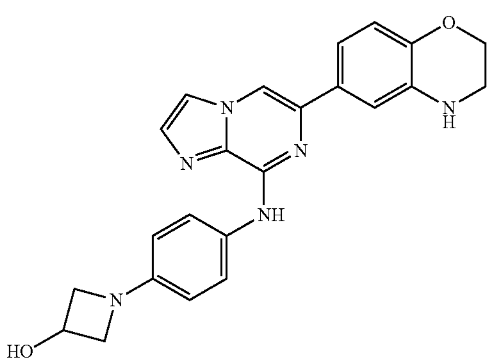 [SMILES: OC1CN(c2ccc(Nc3nc(-c4ccc5c(c4)NCCO5)cn4ccnc34)cc2)C1] | 1-(4-{[6-(3,4-dihydro-2H-1,4-benzoxazin-6-yl)imidazo[1,2-a]pyrazin-8-yl]amino}phenyl)azetidin-3-ol | 415.4 |
| 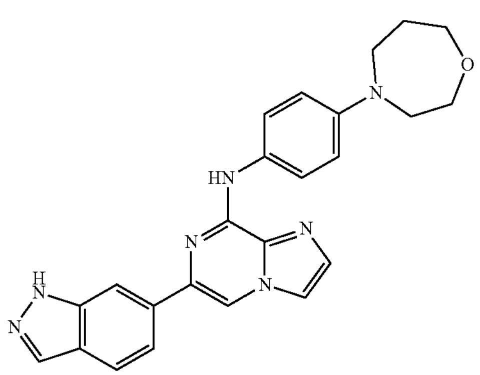 [SMILES: c1cn2cc(-c3ccc4cn[nH]c4c3)nc(Nc3ccc(N4CCCOCC4)cc3)c2n1] | 6-(1H-indazol-6-yl)-N-[4-(1,4-oxazepan-4-yl)phenyl]imidazo[1,2-a]pyrazin-8-amine | 426.1 |

| Structure | Name | [M + H]+ |
|---|---|---|
| 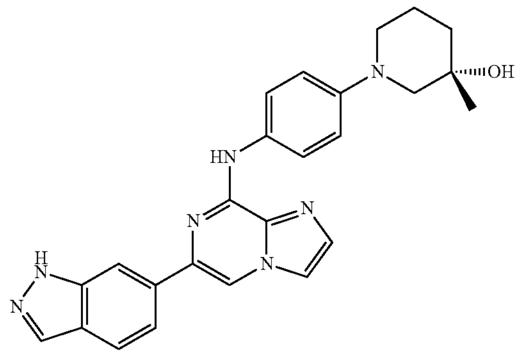 [SMILES: C[C@]1(O)CCCN(c2ccc(Nc3nc(-c4ccc5cn[nH]c5c4)cn4ccnc34)cc2)C1] | (3S)-1-(4-{[6-(1H-indazol-6-yl)imidazo[1,2-a]pyrazin-8-yl]amino}phenyl)-3-methylpiperidin-3-ol | 440.3 |
| 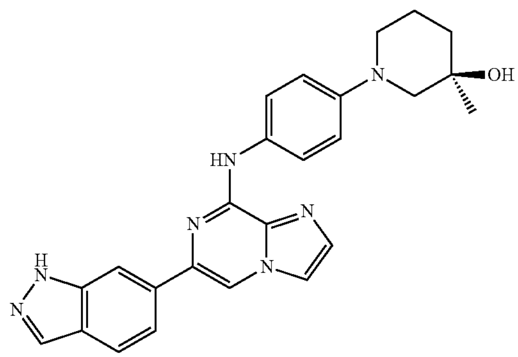 [SMILES: C[C@@]1(O)CCCN(c2ccc(Nc3nc(-c4ccc5cn[nH]c5c4)cn4ccnc34)cc2)C1] | (3R)-1-(4-{[6-(1H-indazol-6-yl)imidazo[1,2-a]pyrazin-8-yl]amino}phenyl)-3-methylpiperidin-3-ol | 440.3 |
| 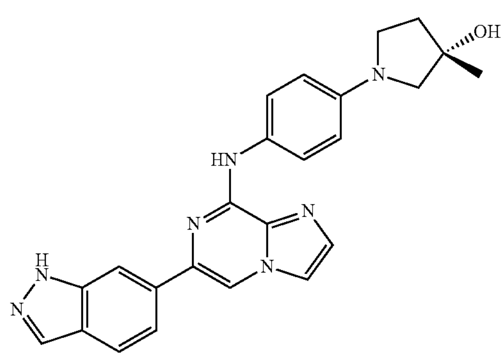 [SMILES: C[C@]1(O)CCN(c2ccc(Nc3nc(-c4ccc5cn[nH]c5c4)cn4ccnc34)cc2)C1] | (3S)-1-(4-{[6-(1H-indazol-6-yl)imidazo[1,2-a]pyrazin-8-yl]amino}phenyl)-3-methylpyrrolidin-3-ol | 426.1 |
| 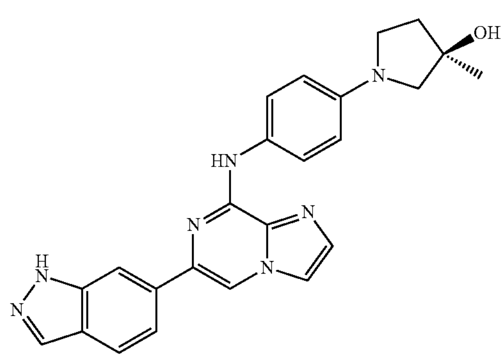 [SMILES: C[C@@]1(O)CCN(c2ccc(Nc3nc(-c4ccc5cn[nH]c5c4)cn4ccnc34)cc2)C1] | (3R)-1-(4-{[6-(1H-indazol-6-yl)imidazo[1,2-a]pyrazin-8-yl]amino}phenyl)-3-methylpyrrolidin-3-ol | 426.2 |

-continued

| Structure | Name | [M + H]+ |
|---|---|---|
| 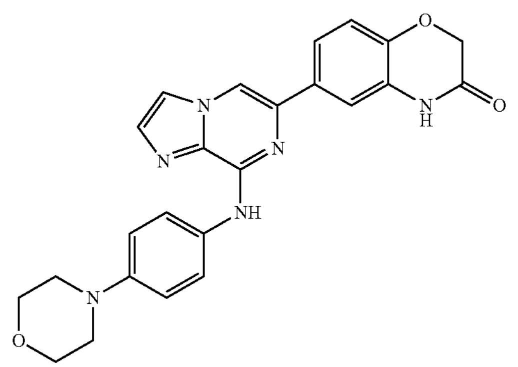 [SMILES: O=C1COc2ccc(-c3cn4ccnc4c(Nc4ccc(N5CCOCC5)cc4)n3)cc2N1] | 6-(8-{[4-(morpholin-4-yl)phenyl]amino}imidazo[1,2-a]pyrazin-6-yl)-3,4-dihydro-2H-1,4-benzoxazin-3-one | 443.7 |
| 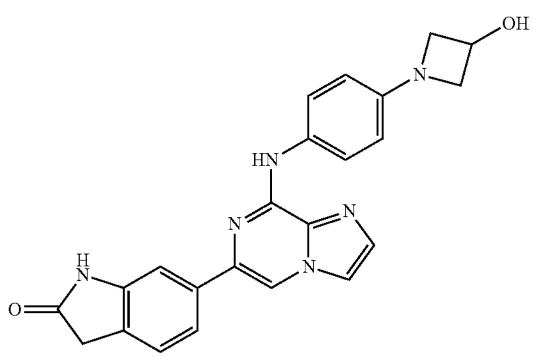 [SMILES: O=C1Cc2ccc(-c3cn4ccnc4c(Nc4ccc(N5CC(O)C5)cc4)n3)cc2N1] | 6-(8-{[4-(3-hydroxyazetidin-1-yl)phenyl]amino}imidazo[1,2-a]pyrazin-6-yl)-2,3-dihydro-1H-indol-2-one | 413.4 |
| 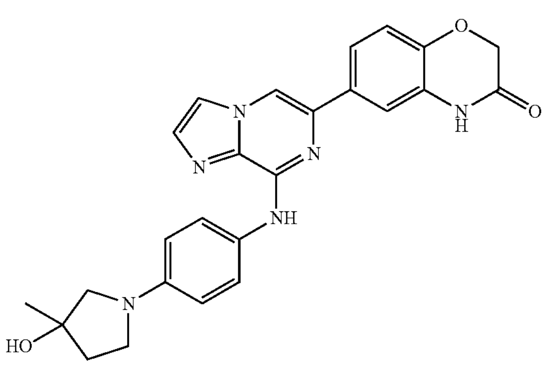 [SMILES: CC1(O)CCN(c2ccc(Nc3nc(-c4ccc5c(c4)NC(=O)CO5)cn4ccnc34)cc2)C1] | 6-(8-{[4-(3-hydroxy-3-methylpyrrolidin-1-yl)phenyl]amino}imidazo[1,2-a]pyrazin-6-yl)-3,4-dihydro-2H-1,4-benzoxazin-3-one | 457.6 |
| 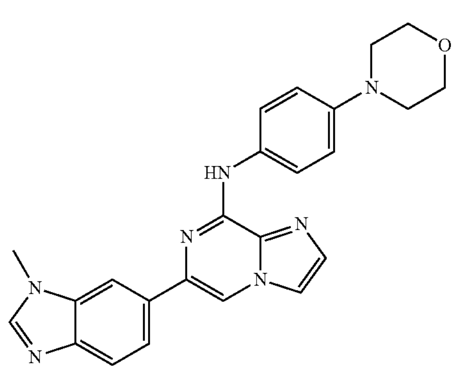 [SMILES: Cn1cnc2ccc(-c3cn4ccnc4c(Nc4ccc(N5CCOCC5)cc4)n3)cc21] | 6-(1-methyl-1H-1,3-benzodiazol-6-yl)-N-[4-(morpholin-4-yl)phenyl]imidazo[1,2-a]pyrazin-8-amine | 426.2 |

-continued

| Structure | Name | [M + H]+ |
|---|---|---|
| 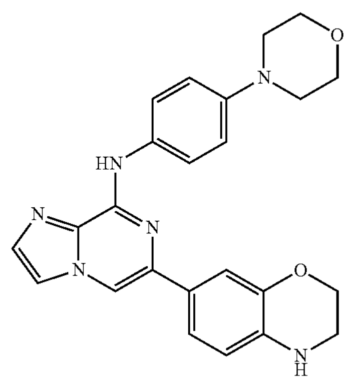 [SMILES: c1cn2cc(-c3ccc4c(c3)OCCN4)nc(Nc3ccc(N4CCOCC4)cc3)c2n1] | 6-(3,4-dihydro-2H-1,4-benzoxazin-7-yl)-N-[4-(morpholin-4-yl)phenyl]imidazo[1,2-a]pyrazin-8-amine | 429.2 |
| 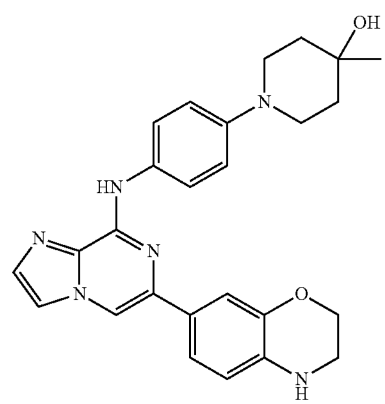 [SMILES: CC1(O)CCN(c2ccc(Nc3nc(-c4ccc5c(c4)OCCN5)cn4ccnc34)cc2)CC1] | 1-(4-{[6-(3,4-dihydro-2H-1,4-benzoxazin-7-yl)imidazo[1,2-a]pyrazin-8-yl]amino}phenyl)-4-methylpiperidin-4-ol | 457.2 |
| 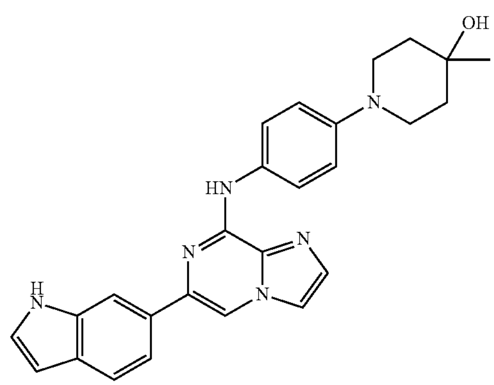 [SMILES: CC1(O)CCN(c2ccc(Nc3nc(-c4ccc5cc[nH]c5c4)cn4ccnc34)cc2)CC1] | 1-(4-{[6-(1H-indol-6-yl)imidazo[1,2-a]pyrazin-8-yl]amino}phenyl)-4-methylpiperidin-4-ol | 439.7 |
| 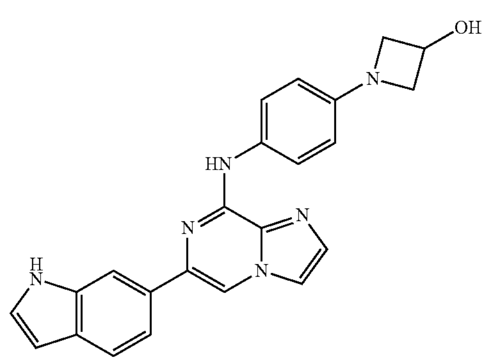 [SMILES: OC1CN(c2ccc(Nc3nc(-c4ccc5cc[nH]c5c4)cn4ccnc34)cc2)C1] | 1-(4-{[6-(1H-indol-6-yl)imidazo[1,2-a]pyrazin-8-yl]amino}phenyl)azetidin-3-ol | 397.1 |

| Structure | Name | [M + H]+ |
|---|---|---|
| 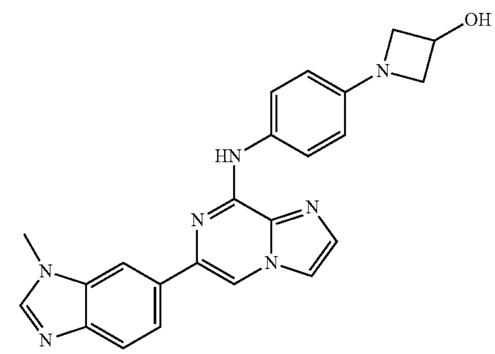 [SMILES: Cn1cnc2ccc(-c3cn4ccnc4c(Nc4ccc(N5CC(O)C5)cc4)n3)cc21] | 1-(4-{[6-(1-methyl-1H-1,3-benzodiazol-6-yl)imidazo[1,2-a]pyrazin-8-yl]amino}phenyl)azetidin-3-ol | 412.3 |
| 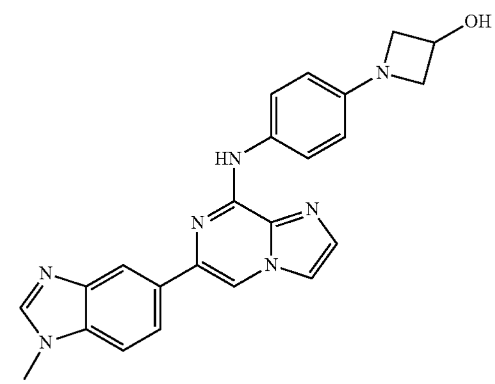 [SMILES: Cn1cnc2cc(-c3cn4ccnc4c(Nc4ccc(N5CC(O)C5)cc4)n3)ccc21] | 1-(4-{[6-(1-methyl-1H-1,3-benzodiazol-5-yl)imidazo[1,2-a]pyrazin-8-yl]amino}phenyl)azetidin-3-ol | 412.2 |
| 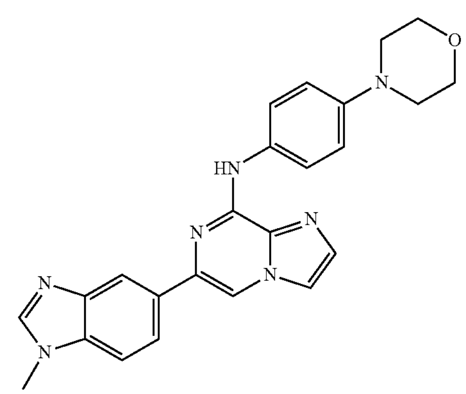 [SMILES: Cn1cnc2cc(-c3cn4ccnc4c(Nc4ccc(N5CCOCC5)cc4)n3)ccc21] | 6-(1-methyl-1H-1,3-benzodiazol-5-yl)-N-[4-(morpholin-4-yl)phenyl]imidazo[1,2-a]pyrazin-8-amine | 426.1 |
| 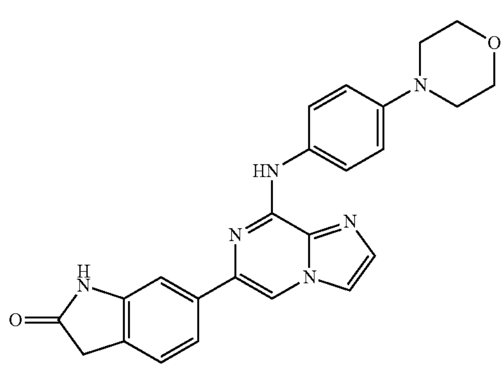 [SMILES: O=C1Cc2ccc(-c3cn4ccnc4c(Nc4ccc(N5CCOCC5)cc4)n3)cc2N1] | 6-(8-{[4-(morpholin-4-yl)phenyl]amino}imidazo[1,2-a]pyrazin-6-yl)-2,3-dihydro-1H-indol-2-one | 427.1 |

-continued
| Structure | Name | [M + H]+ |
|---|---|---|
| 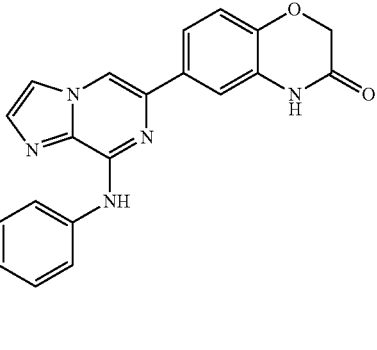 | 6-(8-{[4-(3-hydroxyazetidin-1-yl)phenyl]amino}imidazo[1,2-a]pyrazin-6-yl)-3,4-dihydro-2H-1,4-benzoxazin-3-one | 429.3 |
| 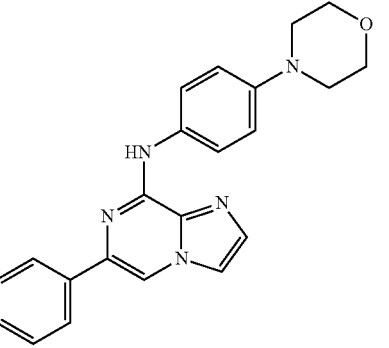 | 5-(8-{[4-(morpholin-4-yl)phenyl]amino}imidazo[1,2-a]pyrazin-6-yl)-2,3-dihydro-1,3-benzoxazol-2-one | 429.3 |
| 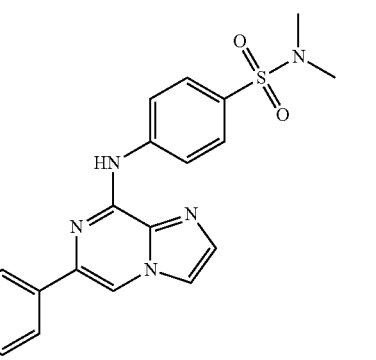 | 4-{[6-(1H-indazol-6-yl)imidazo[1,2-a]pyrazin-8-yl]amino}-N,N-dimethylbenzene-1-sulfonamide | 434.3 |
| 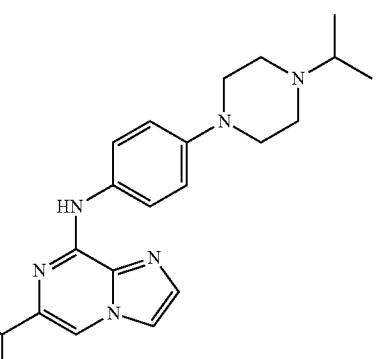 | 6-(1H-indazol-6-yl)-N-{4-[4-(propan-2-yl)piperazin-1-yl]phenyl}imidazo[1,2-a]pyrazin-8-amine | 453.9 |

| Structure | Name | [M + H]+ |
|---|---|---|
| 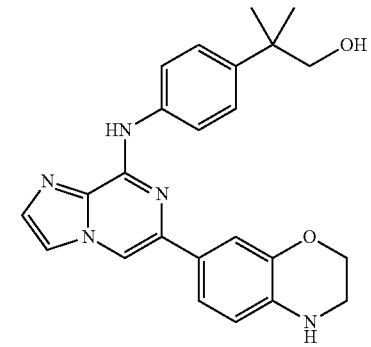 [SMILES: CC(C)(CO)c1ccc(Nc2nc(-c3ccc4c(c3)OCCN4)cn3ccnc23)cc1] | 2-(4-{[6-(3,4-dihydro-2H-1,4-benzoxazin-7-yl)imidazo[1,2-a]pyrazin-8-yl]amino}phenyl)-2-methylpropan-1-ol | 416.8 |
| 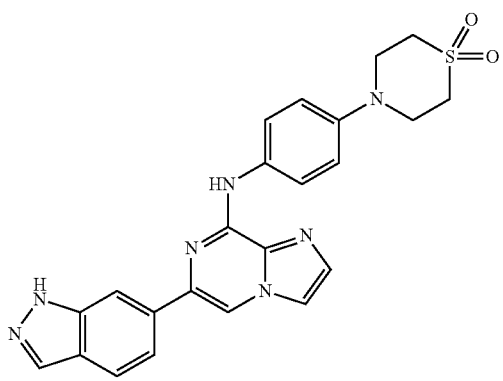 [SMILES: O=S1(=O)CCN(c2ccc(Nc3nc(-c4ccc5cn[nH]c5c4)cn4ccnc34)cc2)CC1] | 4-(4-{[6-(1H-indazol-6-yl)imidazo[1,2-a]pyrazin-8-yl]amino}phenyl)thiomorpholine-1,1-dione | 460.4 |
| 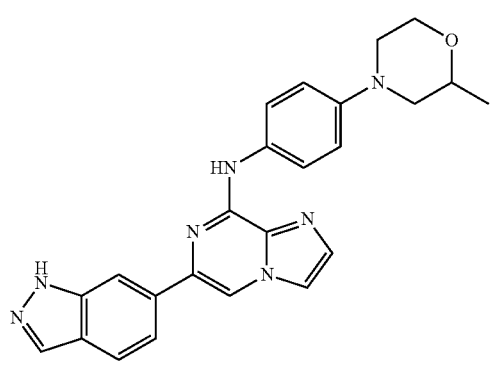 [SMILES: CC1CN(c2ccc(Nc3nc(-c4ccc5cn[nH]c5c4)cn4ccnc34)cc2)CCO1] | 6-(1H-indazol-6-yl)-N-[4-(2-methylmorpholin-4-yl)phenyl]imidazo[1,2-a]pyrazin-8-amine | 426.1 |
| 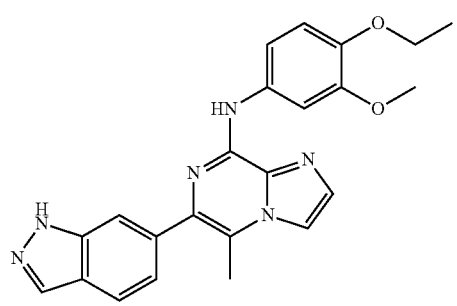 [SMILES: CCOc1ccc(Nc2nc(-c3ccc4cn[nH]c4c3)c(C)n3ccnc23)cc1OC] | N-(4-ethoxy-3-methoxyphenyl)-6-(1H-indazol-6-yl)-5-methylimidazo[1,2-a]pyrazin-8-amine | 415.3 |

| Structure | Name | [M + H]+ |
|---|---|---|
| 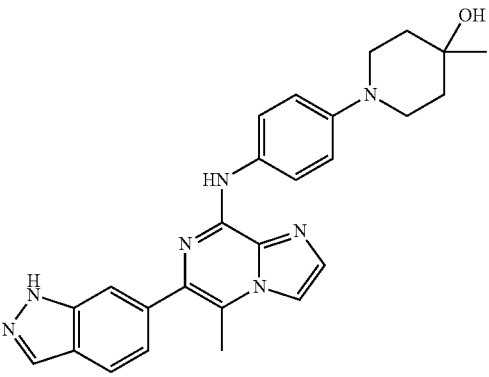 [SMILES: Cc1c(-c2ccc3cn[nH]c3c2)nc(Nc2ccc(N3CCC(C)(O)CC3)cc2)c2nccn12] | 1-(4-{[6-(1H-indazol-6-yl)-5-methylimidazo[1,2-a]pyrazin-8-yl]amino}phenyl)-4-methylpiperidin-4-ol | 454.2 |
| 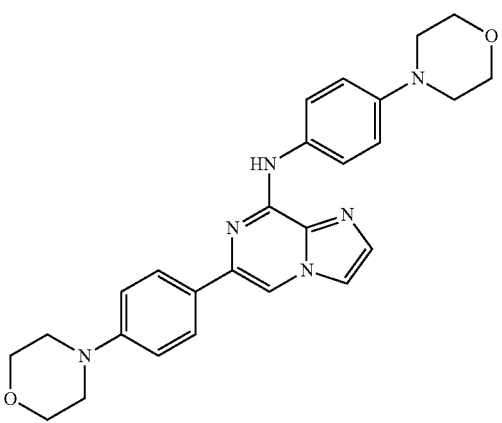 [SMILES: c1cn2cc(-c3ccc(N4CCOCC4)cc3)nc(Nc3ccc(N4CCOCC4)cc3)c2n1] | N,6-bis[4-(morpholin-4-yl)phenyl]imidazo[1,2-a]pyrazin-8-amine | 457.3 |
| 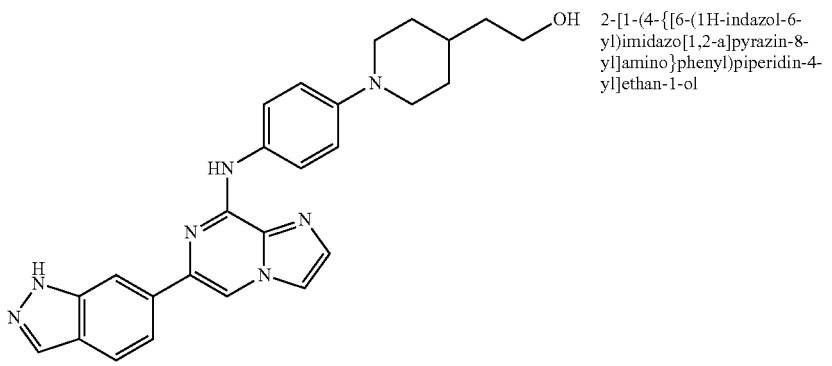 | 2-[1-(4-{[6-(1H-indazol-6-yl)imidazo[1,2-a]pyrazin-8-yl]amino}phenyl)piperidin-4-yl]ethan-1-ol | 454.1 |
| 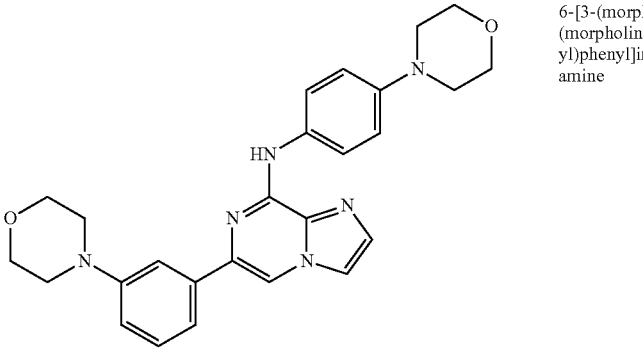 | 6-[3-(morpholin-4-yl)phenyl]-N-[4-(morpholin-4-yl)phenyl]imidazo[1,2-a]pyrazin-8-amine | 457.6 |

-continued
| Structure | Name | [M + H]+ |
|---|---|---|
| 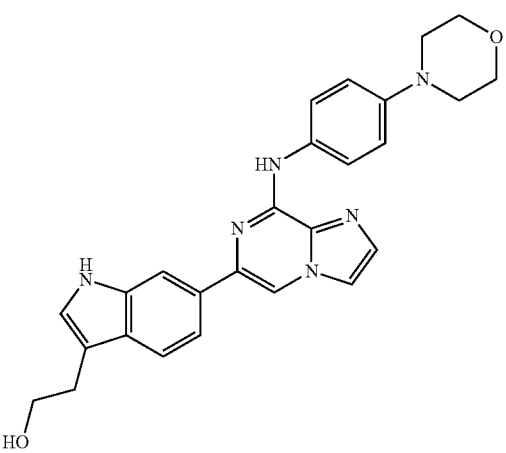 [SMILES: OCCc1c[nH]c2cc(-c3cn4ccnc4c(Nc4ccc(N5CCOCC5)cc4)n3)ccc12] | 2-[6-(8-{[4-(morpholin-4-yl)phenyl]amino}imidazo[1,2-a]pyrazin-6-yl)-1H-indol-3-yl]ethan-1-ol | 455.2 |
| 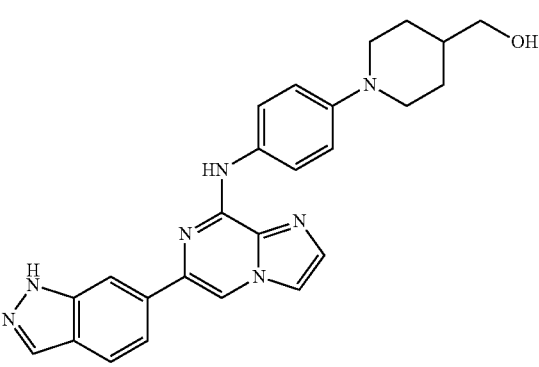 [SMILES: OCC1CCN(c2ccc(Nc3nc(-c4ccc5cn[nH]c5c4)cn4ccnc34)cc2)CC1] | [1-(4-{[6-(1H-indazol-6-yl)imidazo[1,2-a]pyrazin-8-yl]amino}phenyl)piperidin-4-yl]methanol | 440.4 |
| 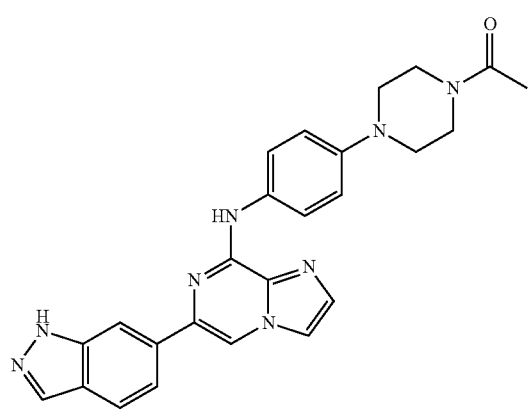 [SMILES: CC(=O)N1CCN(c2ccc(Nc3nc(-c4ccc5cn[nH]c5c4)cn4ccnc34)cc2)CC1] | 1-[4-(4-{[6-(1H-indazol-6-yl)imidazo[1,2-a]pyrazin-8-yl]amino}phenyl)piperazin-1-yl]ethan-1-one | 453 |
| 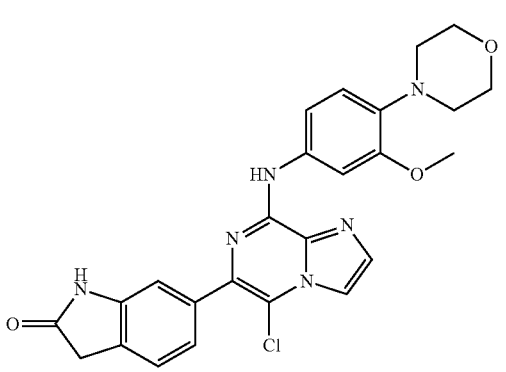 | 6-(5-chloro-8-{[3-methoxy-4-(morpholin-4-yl)phenyl]amino}imidazo[1,2-a]pyrazin-6-yl)-2,3-dihydro-1H-indol-2-one | 491.3 |

| Structure | Name | [M + H]+ |
|---|---|---|
| 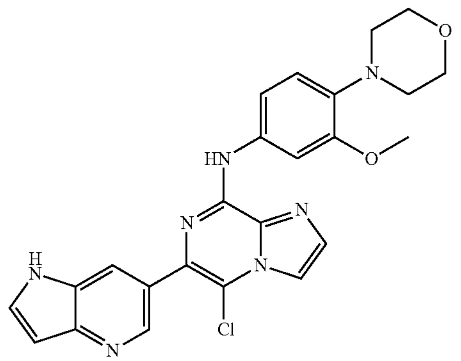 [SMILES: COc1cc(Nc2nc(-c3cnc4cc[nH]c4c3)c(Cl)n3ccnc23)ccc1N1CCOCC1] | 5-chloro-N-[3-methoxy-4-(morpholin-4-yl)phenyl]-6-{1H-pyrrolo[3,2-b]pyridin-6-yl}imidazo[1,2-a]pyrazin-8-amine | 476.4 |
| 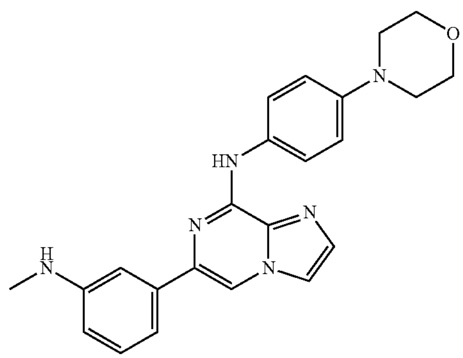 [SMILES: CNc1cccc(-c2cn3ccnc3c(Nc3ccc(N4CCOCC4)cc3)n2)c1] | N-methyl-5-(8-{[4-(morpholin-4-yl)phenyl]amino}imidazo[1,2-a]pyrazin-6-yl)pyridin-3-amine | 402.3 |
| 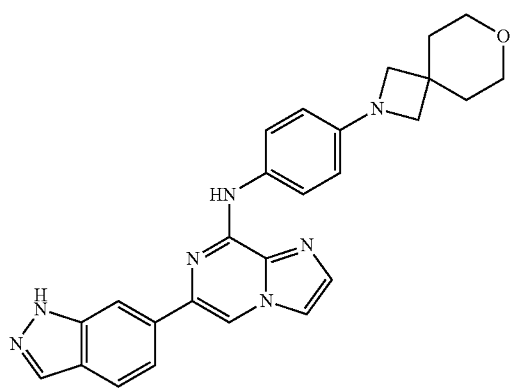 [SMILES: c1cn2cc(-c3ccc4cn[nH]c4c3)nc(Nc3ccc(N4CC5(CCOCC5)C4)cc3)c2n1] | 6-(1H-indazol-6-yl)-N-(4-{7-oxa-2-azaspiro[3.5]nonan-2-yl}phenyl)imidazo[1,2-a]pyrazin-8-amine | 452.3 |
| 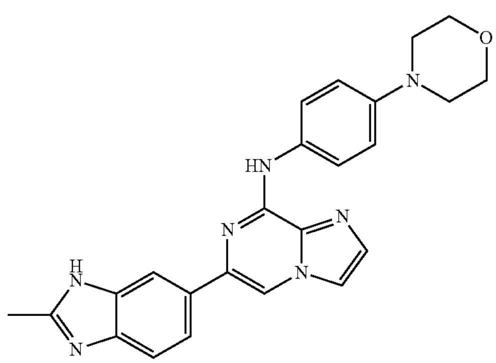 [SMILES: Cc1nc2ccc(-c3cn4ccnc4c(Nc4ccc(N5CCOCC5)cc4)n3)cc2[nH]1] | 6-(2-methyl-1H-1,3-benzodiazol-6-yl)-N-[4-(morpholin-4-yl)phenyl]imidazo[1,2-a]pyrazin-8-amine | 426.2 |

-continued

| Structure | Name | [M + H]+ |
|---|---|---|
| 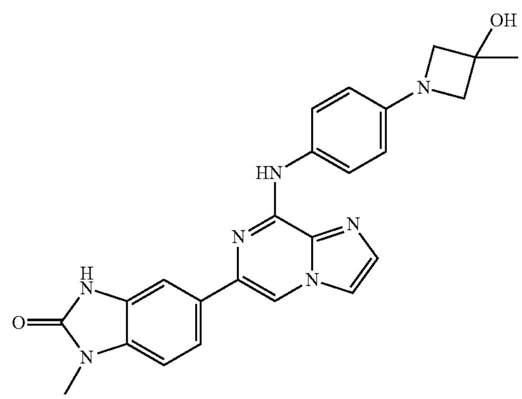 [SMILES: Cn1c(=O)[nH]c2cc(-c3cn4ccnc4c(Nc4ccc(N5CC(C)(O)C5)cc4)n3)ccc21] | 5-(8-{[4-(3-hydroxy-3-methylazetidin-1-yl)phenyl]amino}imidazo[1,2-a]pyrazin-6-yl)-1-methyl-2,3-dihydro-1H-1,3-benzodiazol-2-one | 442.7 |
| 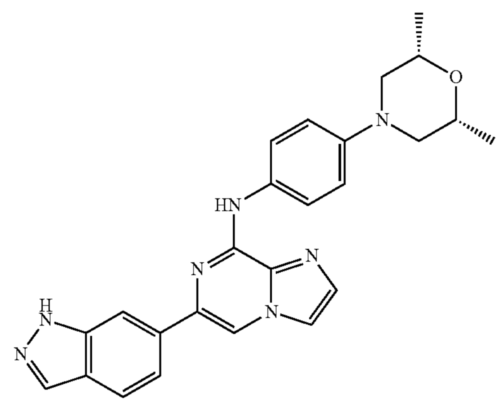 [SMILES: C[C@@H]1CN(c2ccc(Nc3nc(-c4ccc5cn[nH]c5c4)cn4ccnc34)cc2)C[C@H](C)O1] | N-{4-[(2R,6S)-2,6-dimethylmorpholin-4-yl]phenyl}-6-(1H-indazol-6-yl)imidazo[1,2-a]pyrazin-8-amine | 440.3 |
| 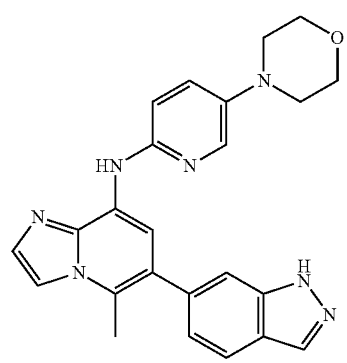 [SMILES: Cc1c(-c2ccc3cn[nH]c3c2)cc(Nc2ccc(N3CCOCC3)cn2)c2nccn12] | N-[6-(1H-indazol-6-yl)-5-methylimidazo[1,2-a]pyridin-8-yl]-5-(morpholin-4-yl)pyridin-2-amine | 426.2 |
| 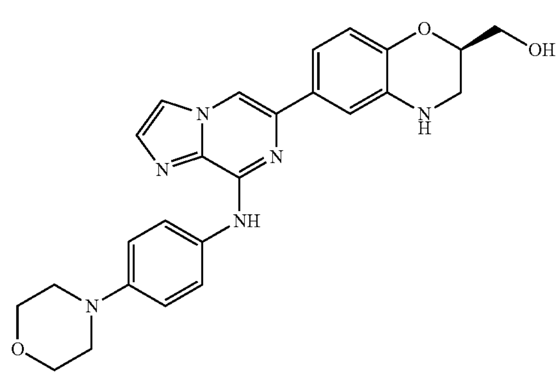 [SMILES: OC[C@H]1CNc2cc(-c3cn4ccnc4c(Nc4ccc(N5CCOCC5)cc4)n3)ccc2O1] | [(2R)-6-(8-{[4-(morpholin-4-yl)phenyl]amino}imidazo[1,2-a]pyrazin-6-yl)-3,4-dihydro-2H-1,4-benzoxazin-2-yl]methanol | 459.3 |

-continued

| Structure | Name | [M + H]+ |
|---|---|---|
| 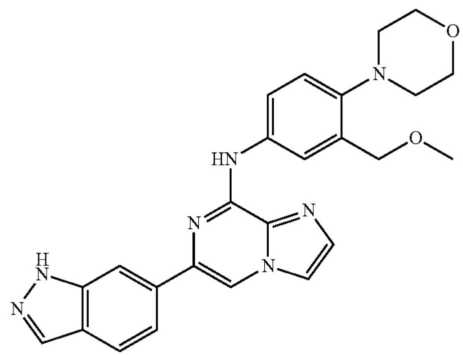 [SMILES: COCc1cc(Nc2nc(-c3ccc4cn[nH]c4c3)cn3ccnc23)ccc1N1CCOCC1] | 6-(1H-indazol-6-yl)-N-[3-(methoxymethyl)-4-(morpholin-4-yl)phenyl]imidazo[1,2-a]pyrazin-8-amine | 456.3 |
| 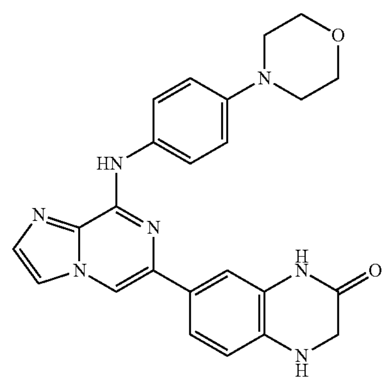 [SMILES: O=C1CNc2ccc(-c3cn4ccnc4c(Nc4ccc(N5CCOCC5)cc4)n3)cc2N1] | 7-(8-{[4-(morpholin-4-yl)phenyl]amino}imidazo[1,2-a]pyrazin-6-yl)-1,2,3,4-tetrahydroquinoxalin-2-one | 442.4 |
| 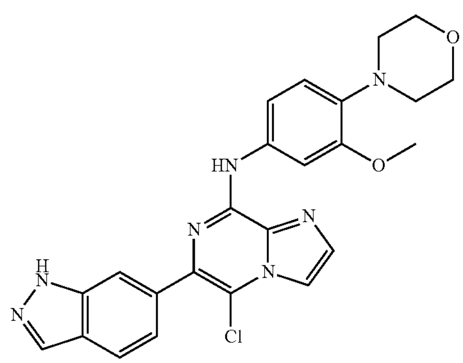 [SMILES: COc1cc(Nc2nc(-c3ccc4cn[nH]c4c3)c(Cl)n3ccnc23)ccc1N1CCOCC1] | 5-chloro-6-(1H-indazol-6-yl)-N-[3-methoxy-4-(morpholin-4-yl)phenyl]imidazo[1,2-a]pyrazin-8-amine | 476.1 |
| 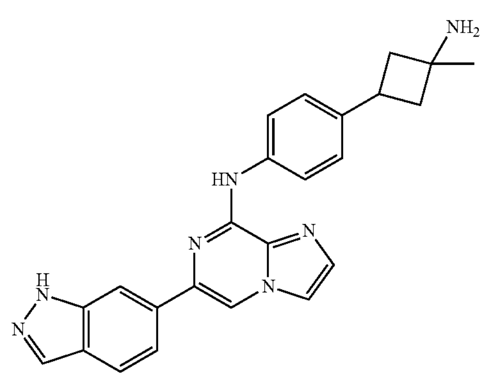 [SMILES: CC1(N)CC(c2ccc(Nc3nc(-c4ccc5cn[nH]c5c4)cn4ccnc34)cc2)C1] | 1-(4-{[6-(1H-indazol-6-yl)imidazo[1,2-a]pyrazin-8-yl]amino}phenyl)-3-methylazetidin-3-amine | 411.3 |

-continued

| Structure | Name | [M + H]+ |
|---|---|---|
| 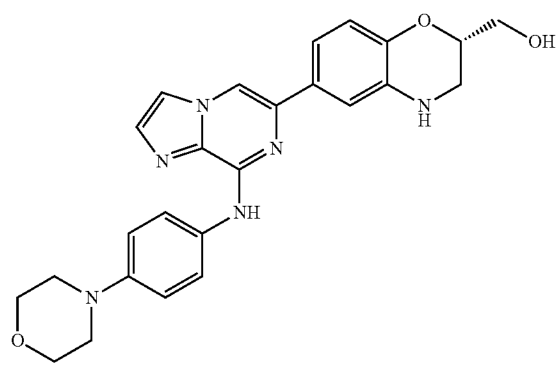 [SMILES: OC[C@@H]1CNc2cc(-c3cn4ccnc4c(Nc4ccc(N5CCOCC5)cc4)n3)ccc2O1] | [(2S)-6-(8-{[4-(morpholin-4-yl)phenyl]amino}imidazo[1,2-a]pyrazin-6-yl)-3,4-dihydro-2H-1,4-benzoxazin-2-yl]methanol | 459.3 |
| 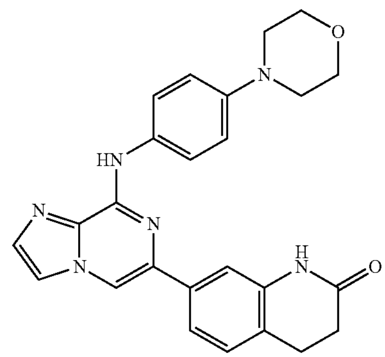 [SMILES: O=C1CCc2ccc(-c3cn4ccnc4c(Nc4ccc(N5CCOCC5)cc4)n3)cc2N1] | 7-(8-{[4-(morpholin-4-yl)phenyl]amino}imidazo[1,2-a]pyrazin-6-yl)-1,2,3,4-tetrahydroquinolin-2-one | 441.5 |
| 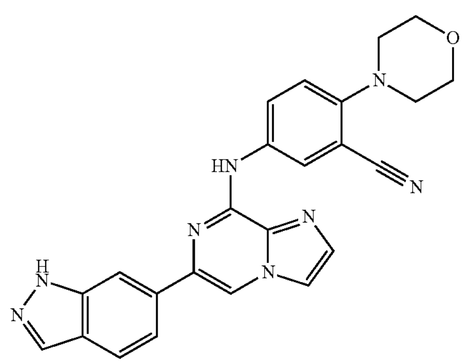 [SMILES: N#Cc1cc(Nc2nc(-c3ccc4cn[nH]c4c3)cn3ccnc23)ccc1N1CCOCC1] | 5-{[6-(1H-indazol-6-yl)imidazo[1,2-a]pyrazin-8-yl]amino}-2-(morpholin-4-yl)benzonitrile | 437.1 |
| 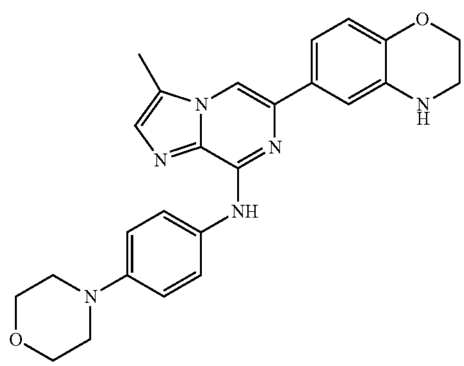 [SMILES: Cc1cnc2c(Nc3ccc(N4CCOCC4)cc3)nc(-c3ccc4c(c3)NCCO4)cn12] | 6-(3,4-dihydro-2H-1,4-benzoxazin-6-yl)-3-methyl-N-[4-(morpholin-4-yl)phenyl]imidazo[1,2-a]pyrazin-8-amine | 443.9 |

-continued

| Structure | Name | [M + H]+ |
|---|---|---|
| 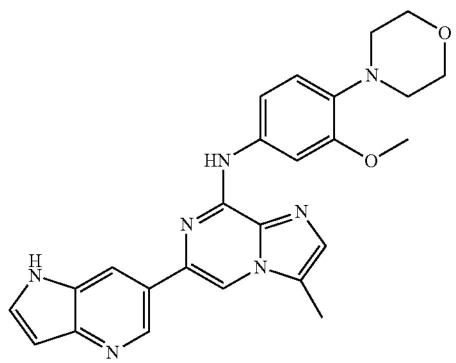 [SMILES: COc1cc(Nc2nc(-c3cnc4cc[nH]c4c3)cn3c(C)cnc23)ccc1N1CCOCC1] | N-[3-methoxy-4-(morpholin-4-yl)phenyl]-3-methyl-6-{1H-pyrrolo[3,2-b]pyridin-6-yl}imidazo[1,2-a]pyrazin-8-amine | 456.4 |
| 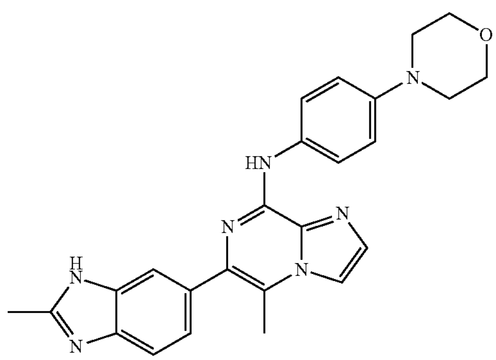 [SMILES: Cc1nc2ccc(-c3nc(Nc4ccc(N5CCOCC5)cc4)c4nccn4c3C)cc2[nH]1] | 5-methyl-6-(2-methyl-1H-1,3-benzodiazol-6-yl)-N-[4-(morpholin-4-yl)phenyl]imidazo[1,2-a]pyrazin-8-amine | 440.2 |
| 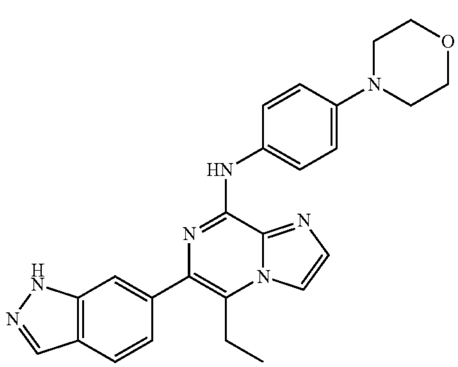 [SMILES: CCc1c(-c2ccc3cn[nH]c3c2)nc(Nc2ccc(N3CCOCC3)cc2)c2nccn12] | 5-ethyl-6-(1H-indazol-6-yl)-N-[4-(morpholin-4-yl)phenyl]imidazo[1,2-a]pyrazin-8-amine | 440.4 |
| 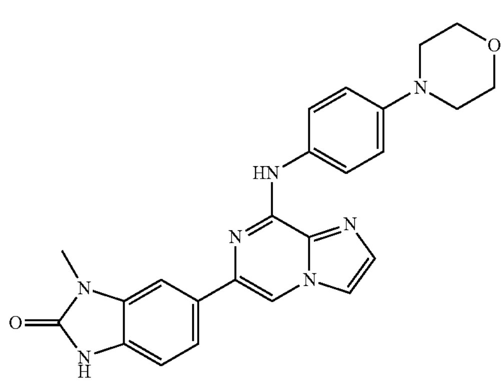 [SMILES: Cn1c(=O)[nH]c2ccc(-c3cn4ccnc4c(Nc4ccc(N5CCOCC5)cc4)n3)cc21] | 1-methyl-6-(8-{[4-(morpholin-4-yl)phenyl]amino}imidazo[1,2-a]pyrazin-6-yl)-2,3-dihydro-1H-1,3-benzodiazol-2-one | 442.7 |

-continued

| Structure | Name | [M + H]+ |
|---|---|---|
| 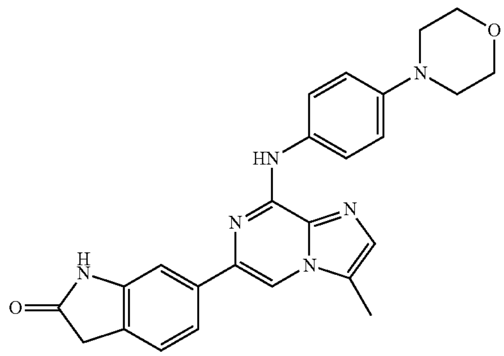 | 6-(3-methyl-8-{[4-(morpholin-4-yl)phenyl]amino}imidazo[1,2-a]pyrazin-6-yl)-2,3-dihydro-1H-indol-2-one | 441.3 |
| 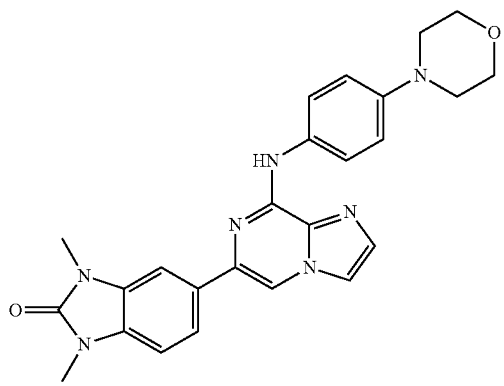 [SMILES: Cn1c(=O)n(C)c2cc(-c3cn4ccnc4c(Nc4ccc(N5CCOCC5)cc4)n3)ccc21] | 1,3-dimethyl-5-(8-{[4-(morpholin-4-yl)phenyl]amino}imidazo[1,2-a]pyrazin-6-yl)-2,3-dihydro-1H-1,3-benzodiazol-2-one | 456.2 |
| 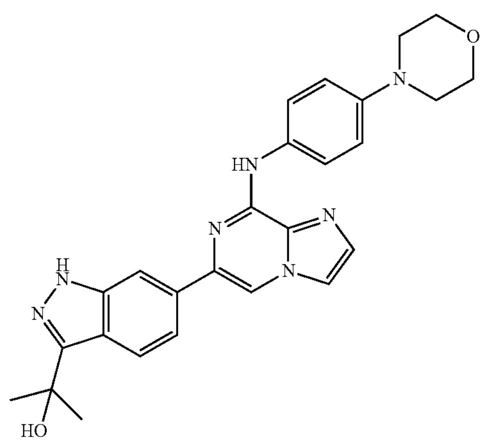 [SMILES: CC(C)(O)c1n[nH]c2cc(-c3cn4ccnc4c(Nc4ccc(N5CCOCC5)cc4)n3)ccc12] | 2-[6-(8-{[4-(morpholin-4-yl)phenyl]amino}imidazo[1,2-a]pyrazin-6-yl)-1H-indazol-3-yl]propan-2-ol | 470.8 |
| 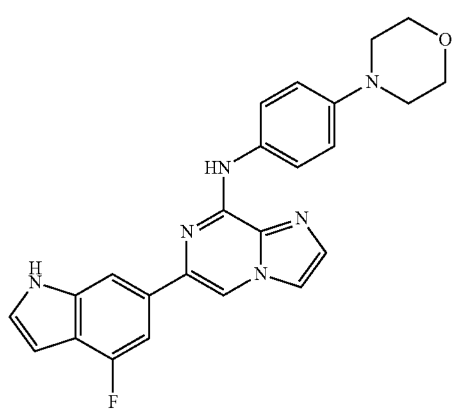 [SMILES: Fc1cc(-c2cn3ccnc3c(Nc3ccc(N4CCOCC4)cc3)n2)cc2[nH]ccc12] | 6-(4-fluoro-1H-indol-6-yl)-N-[4-(morpholin-4-yl)phenyl]imidazo[1,2-a]pyrazin-8-amine | 429.3 |

-continued

| Structure | Name | [M + H]+ |
|---|---|---|
| 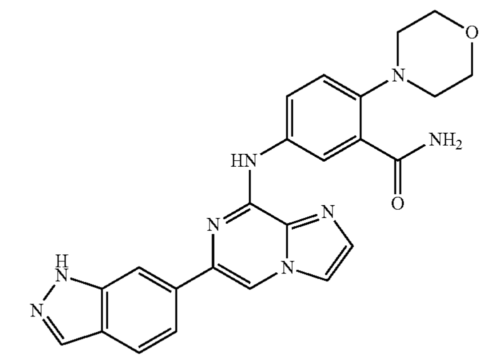 [SMILES: NC(=O)c1cc(Nc2nc(-c3ccc4cn[nH]c4c3)cn3ccnc23)ccc1N1CCOCC1] | 5-{[6-(1H-indazol-6-yl)imidazo[1,2-a]pyrazin-8-yl]amino}-2-(morpholin-4-yl)benzamide | 455.2 |
| 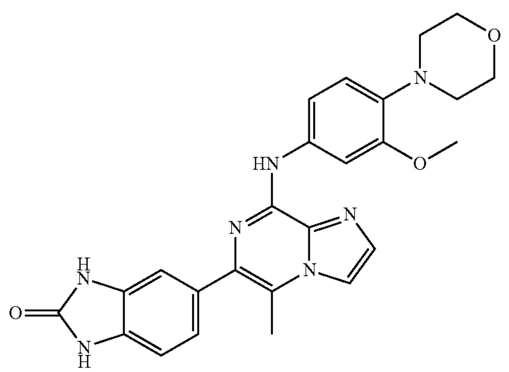 [SMILES: COc1cc(Nc2nc(-c3ccc4[nH]c(=O)[nH]c4c3)c(C)n3ccnc23)ccc1N1CCOCC1] | 5-(8-{[3-methoxy-4-(morpholin-4-yl)phenyl]amino}-5-methylimidazo[1,2-a]pyrazin-6-yl)-2,3-dihydro-1H-1,3-benzodiazol-2-one | 472.4 |
| 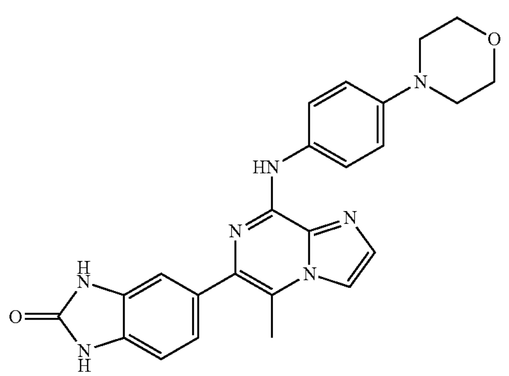 [SMILES: Cc1c(-c2ccc3[nH]c(=O)[nH]c3c2)nc(Nc2ccc(N3CCOCC3)cc2)c2nccn12] | 5-(5-methyl-8-{[4-(morpholin-4-yl)phenyl]amino}imidazo[1,2-a]pyrazin-6-yl)-2,3-dihydro-1H-1,3-benzodiazol-2-one | 442.4 |
| 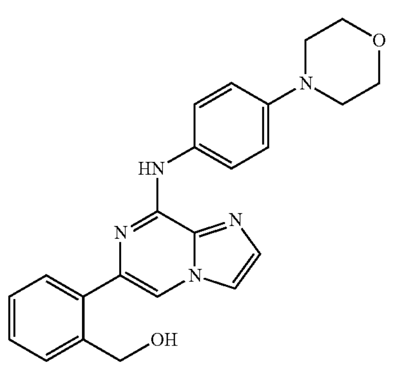 [SMILES: OCc1ccccc1-c1cn2ccnc2c(Nc2ccc(N3CCOCC3)cc2)n1] | [2-(8-{[4-(morpholin-4-yl)phenyl]amino}imidazo[1,2-a]pyrazin-6-yl)phenyl]methanol | 402.2 |

-continued

| Structure | Name | [M + H]+ |
|---|---|---|
| 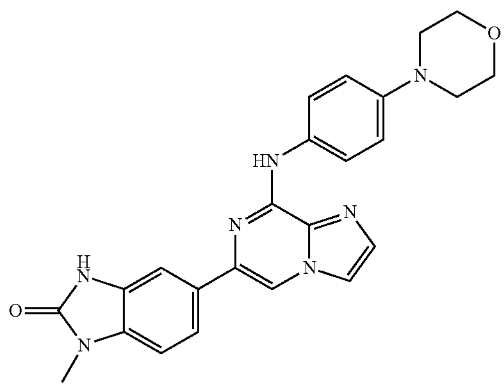 [SMILES: Cn1c(=O)[nH]c2cc(-c3cn4ccnc4c(Nc4ccc(N5CCOCC5)cc4)n3)ccc21] | 1-methyl-5-(8-{[4-(morpholin-4-yl)phenyl]amino}imidazo[1,2-a]pyrazin-6-yl)-2,3-dihydro-1H-1,3-benzodiazol-2-one | 442.7 |
| 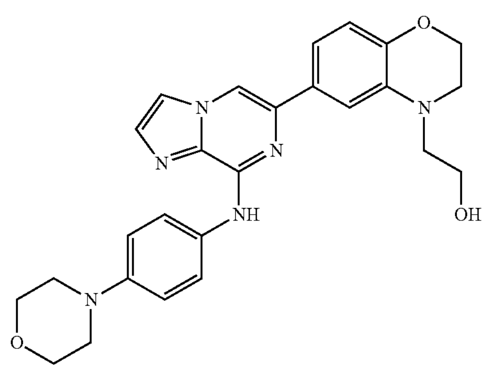 [SMILES: OCCN1CCOc2ccc(-c3cn4ccnc4c(Nc4ccc(N5CCOCC5)cc4)n3)cc21] | 2-[6-(8-{[4-(morpholin-4-yl)phenyl]amino}imidazo[1,2-a]pyrazin-6-yl)-3,4-dihydro-2H-1,4-benzoxazin-4-yl]ethan-1-ol | 473.2 |
| 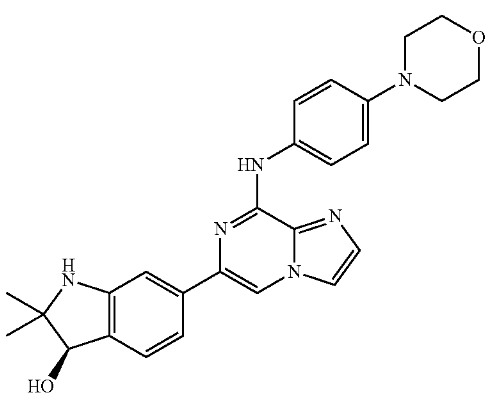 | (3R)-2,2-dimethyl-6-(8-{[4-(morpholin-4-yl)phenyl]amino}imidazo[1,2-a]pyrazin-6-yl)-2,3-dihydro-1H-indol-3-ol | 457.6 |
| | 6-(1H-indazol-6-yl)-N-{3-methoxy-4-[2-methoxyethyl)piperazin-1-yl]phenyl}imidazo[1,2-a]pyrazin-8-amine | 499.6 |

-continued

| Structure | Name | [M + H]+ |
|---|---|---|
| 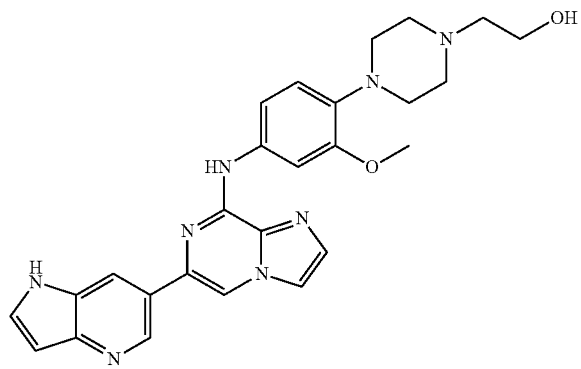 [SMILES: COc1cc(Nc2nc(-c3cnc4cc[nH]c4c3)cn3ccnc23)ccc1N1CCN(CCO)CC1] | 2-(4-{2-methoxy-4-[(6-{1H-pyrrolo[3,2-b]pyridin-6-yl}imidazo[1,2-a]pyrazin-8-yl)amino]phenyl}piperazin-1-yl)ethan-1-ol | 485.7 |
| 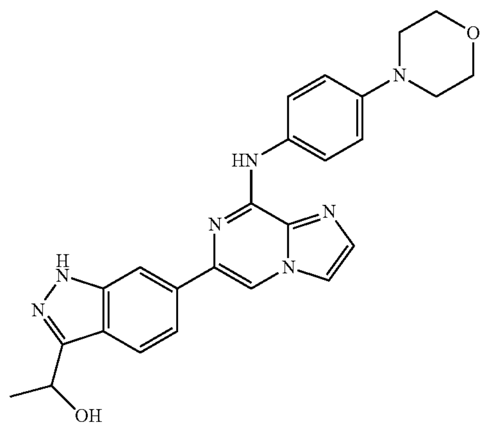 [SMILES: CC(O)c1n[nH]c2cc(-c3cn4ccnc4c(Nc4ccc(N5CCOCC5)cc4)n3)ccc12] | 1-[6-(8-{[4-(morpholin-4-yl)phenyl]amino}imidazo[1,2-a]pyrazin-6-yl)-1H-indazol-3-yl]ethan-1-ol | 456.5 |
| 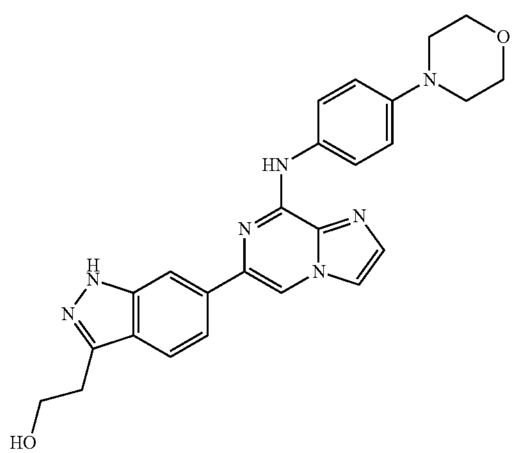 [SMILES: OCCc1n[nH]c2cc(-c3cn4ccnc4c(Nc4ccc(N5CCOCC5)cc4)n3)ccc12] | 2-[6-(8-{[4-(morpholin-4-yl)phenyl]amino}imidazo[1,2-a]pyrazin-6-yl)-1H-indazol-3-yl]ethan-1-ol | 456.5 |
| 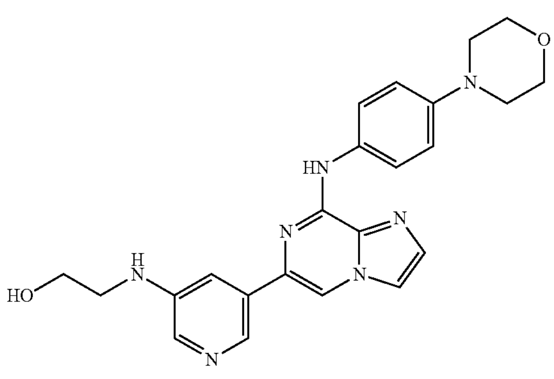 [SMILES: OCCNc1cncc(-c2cn3ccnc3c(Nc3ccc(N4CCOCC4)cc3)n2)c1] | 2-{[5-(8-{[4-(morpholin-4-yl)phenyl]amino}imidazo[1,2-a]pyrazin-6-yl)pyridin-3-yl]amino}ethan-1-ol | 432.6 |

-continued

| Structure | Name | [M + H]+ |
|---|---|---|
| 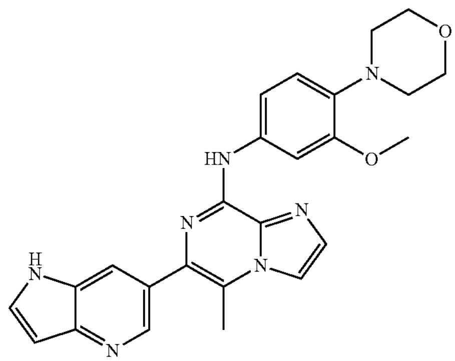 [SMILES: COc1cc(Nc2nc(-c3cnc4cc[nH]c4c3)c(C)n3ccnc23)ccc1N1CCOCC1] | N-[3-methoxy-4-(morpholin-4-yl)phenyl]-5-methyl-6-{1H-pyrrolo[3,2-b]pyridin-6-yl}imidazo[1,2-a]pyrazin-8-amine | 456.2 |
| 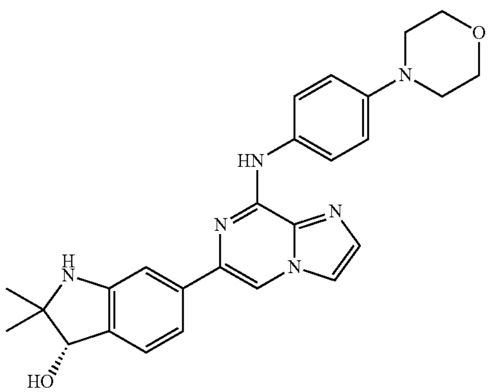 [SMILES: CC1(C)Nc2cc(-c3cn4ccnc4c(Nc4ccc(N5CCOCC5)cc4)n3)ccc2[C@@H]1O] | (3S)-2,2-dimethyl-6-(8-{[4-(morpholin-4-yl)phenyl]amino}imidazo[1,2-a]pyrazin-6-yl)-2,3-dihydro-1H-indol-3-ol | 457.8 |
| 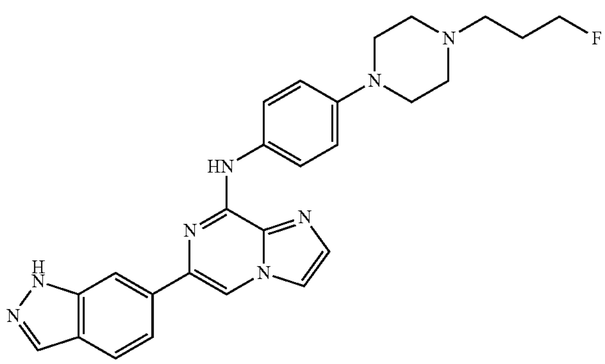 [SMILES: FCCCN1CCN(c2ccc(Nc3nc(-c4ccc5cn[nH]c5c4)cn4ccnc34)cc2)CC1] | N-{4-[4-(3-fluoropropyl)piperazin-1-yl]phenyl}-6-(1H-indazol-6-yl)imidazo[1,2-a]pyrazin-8-amine | 471.4 |
| 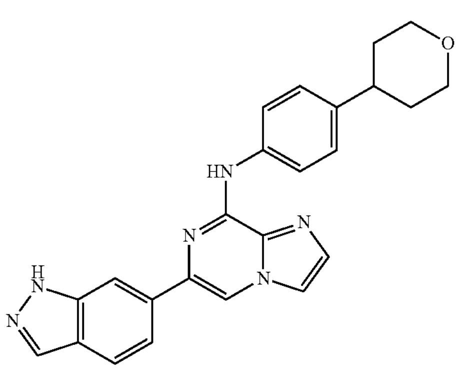 [SMILES: c1cn2cc(-c3ccc4cn[nH]c4c3)nc(Nc3ccc(C4CCOCC4)cc3)c2n1] | 6-(1H-indazol-6-yl)-N-[4-(oxan-4-yl)phenyl]imidazo[1,2-a]pyrazin-8-amine | 411.3 |

| Structure | Name | [M + H]+ |
|---|---|---|
| 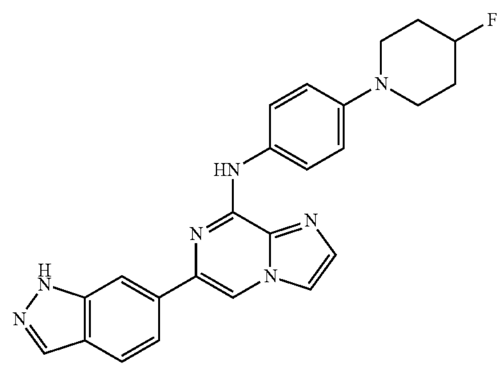 [SMILES: FC1CCN(c2ccc(Nc3nc(-c4ccc5cn[nH]c5c4)cn4ccnc34)cc2)CC1] | N-[4-(4-fluoropiperidin-1-yl)phenyl]-6-(1H-indazol-6-yl)imidazo[1,2-a]pyrazin-8-amine | 428.2 |
| 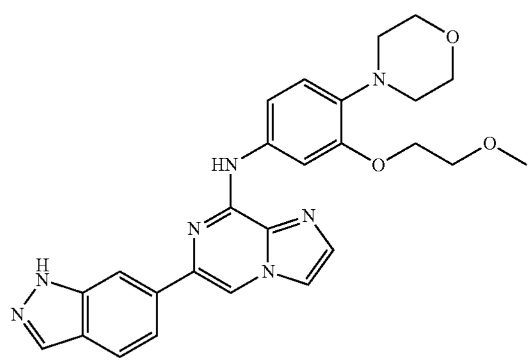 [SMILES: COCCOc1cc(Nc2nc(-c3ccc4cn[nH]c4c3)cn3ccnc23)ccc1N1CCOCC1] | 6-(1H-indazol-6-yl)-N-[3-(2-methoxyethoxy)-4-(morpholin-4-yl)phenyl]imidazo[1,2-a]pyrazin-8-amine | 486.6 |
| 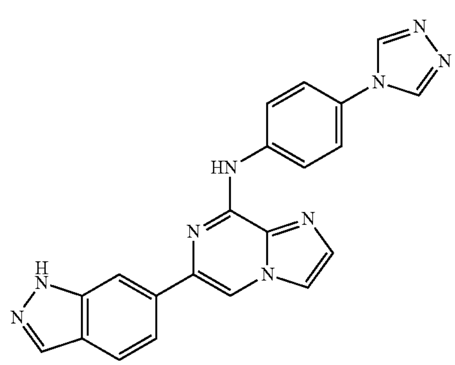 [SMILES: c1cn2cc(-c3ccc4cn[nH]c4c3)nc(Nc3ccc(-n4cnnc4)cc3)c2n1] | 6-(1H-indazol-6-yl)-N-[4-(4H-1,2,4-triazol-4-yl)phenyl]imidazo[1,2-a]pyrazin-8-amine | 394.3 |
| 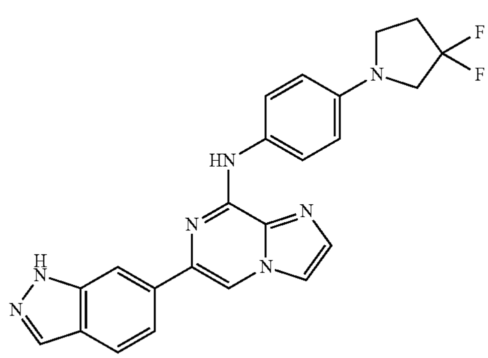 [SMILES: FC1(F)CCN(c2ccc(Nc3nc(-c4ccc5cn[nH]c5c4)cn4ccnc34)cc2)C1] | N-[4-(3,3-difluoropyrrolidin-1-yl)phenyl]-6-(1H-indazol-6-yl)imidazo[1,2-a]pyrazin-8-amine | 432.3 |

-continued

| Structure | Name | [M + H]+ |
|---|---|---|
| 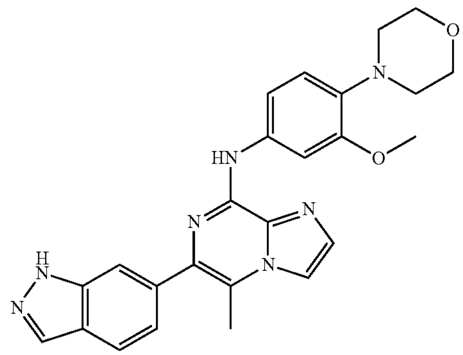 [SMILES: COc1cc(Nc2nc(-c3ccc4cn[nH]c4c3)c(C)n3ccnc23)ccc1N1CCOCC1] | 6-(1H-indazol-6-yl)-N-[3-methoxy-4-(morpholin-4-yl)phenyl]-5-methylimidazo[1,2-a]pyrazin-8-amine | 456.3 |
| 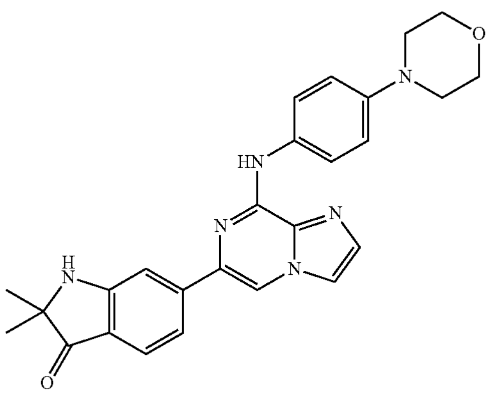 [SMILES: CC1(C)Nc2cc(-c3cn4ccnc4c(Nc4ccc(N5CCOCC5)cc4)n3)ccc2C1=O] | 2,2-dimethyl-6-(8-{[4-(morpholin-4-yl)phenyl]amino}imidazo[1,2-a]pyrazin-6-yl)-2,3-dihydro-1H-indol-3-one | 455.3 |
| 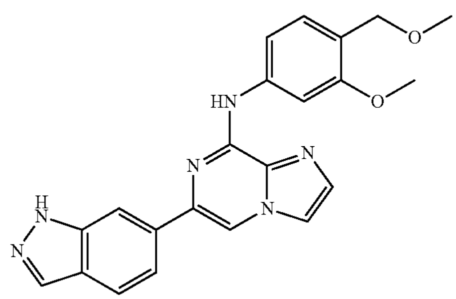 [SMILES: COCc1ccc(Nc2nc(-c3ccc4cn[nH]c4c3)cn3ccnc23)cc1OC] | 6-(1H-indazol-6-yl)-N-[3-methoxy-4-(methoxymethyl)phenyl]imidazo[1,2-a]pyrazin-8-amine | 401.2 |
| 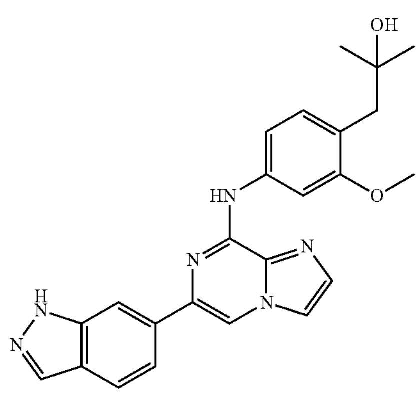 [SMILES: COc1cc(Nc2nc(-c3ccc4cn[nH]c4c3)cn3ccnc23)ccc1CC(C)(C)O] | 1-(4-{[6-(1H-indazol-6-yl)imidazo[1,2-a]pyrazin-8-yl]amino}-2-methoxyphenyl)-2-methylpropan-2-ol | 429.4 |

-continued

| Structure | Name | [M + H]+ |
|---|---|---|
| 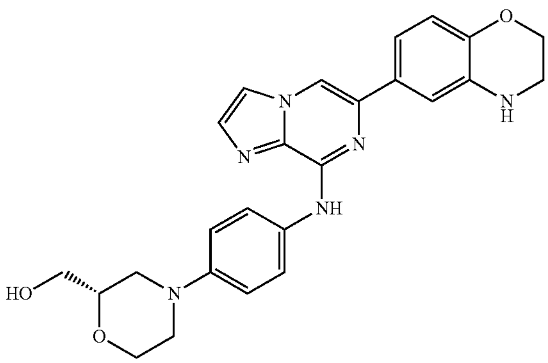 [SMILES: OC[C@@H]1CN(c2ccc(Nc3nc(-c4ccc5c(c4)NCCO5)cn4ccnc34)cc2)CCO1] | [(2S)-4-(4-{[6-(3,4-dihydro-2H-1,4-benzoxazin-6-yl)imidazo[1,2-a]pyrazin-8-yl]amino}phenyl)morpholin-2-yl]methanol | 459.3 |
| 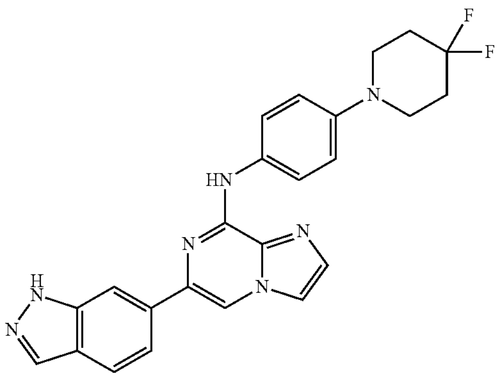 [SMILES: FC1(F)CCN(c2ccc(Nc3nc(-c4ccc5cn[nH]c5c4)cn4ccnc34)cc2)CC1] | N-[4-(4,4-difluoropiperidin-1-yl)phenyl]-6-(1H-indazol-6-yl)imidazo[1,2-a]pyrazin-8-amine | 446.3 |
| 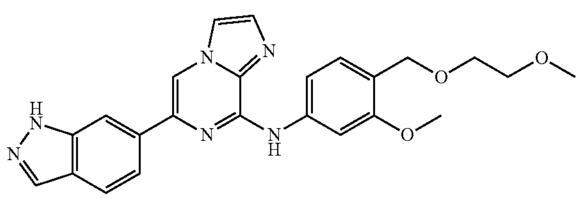 [SMILES: COCCOCc1ccc(Nc2nc(-c3ccc4cn[nH]c4c3)cn3ccnc23)cc1OC] | 6-(1H-indazol-6-yl)-N-{3-methoxy-4-[(2-methoxy-ethoxy)methyl]phenyl}imidazo[1,2-a]pyrazin-8-amine | 445.5 |
| 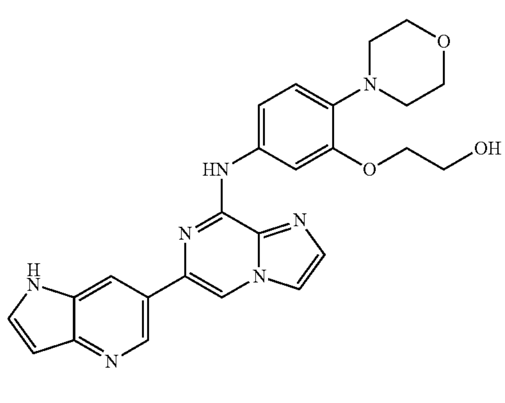 [SMILES: OCCOc1cc(Nc2nc(-c3cnc4cc[nH]c4c3)cn3ccnc23)ccc1N1CCOCC1] | 2-[2-(morpholin-4-yl)-5-[(6-{1H-pyrrolo[3,2-b]pyridin-6-yl}imidazo[1,2-a]pyrazin-8-yl)amino]phenoxy]ethan-1-ol | 472.4 |

-continued

| Structure | Name | [M + H]+ |
|---|---|---|
| 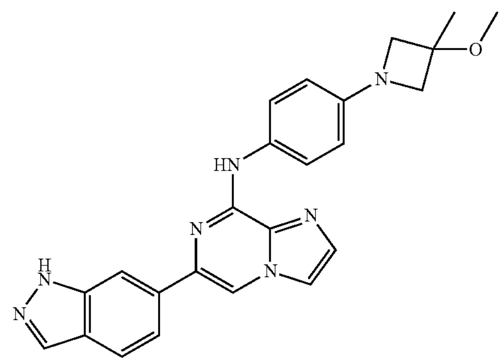 [SMILES: COC1(C)CN(c2ccc(Nc3nc(-c4ccc5cn[nH]c5c4)cn4ccnc34)cc2)C1] | 6-(1H-indazol-6-yl)-N-[4-(3-methoxy-3-methylazetidin-1-yl)phenyl]imidazo[1,2-a]pyrazin-8-amine | 426.2 |
| 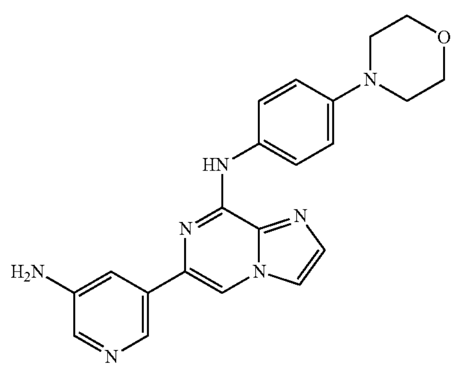 [SMILES: Nc1cncc(-c2cn3ccnc3c(Nc3ccc(N4CCOCC4)cc3)n2)c1] | 5-(8-{[4-(morpholin-4-yl)phenyl]amino}imidazo[1,2-a]pyrazin-6-yl)pyridin-3-amine | 388.8 |
| 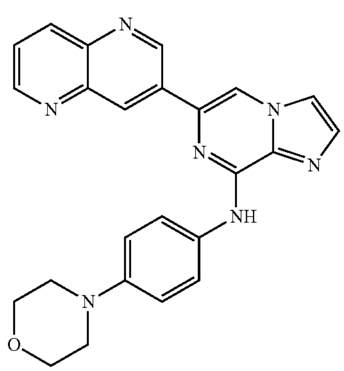 [SMILES: c1cnc2cc(-c3cn4ccnc4c(Nc4ccc(N5CCOCC5)cc4)n3)cnc2c1] | N-[4-(morpholin-4-yl)phenyl]-6-(1,5-naphthyridin-3-yl)imidazo[1,2-a]pyrazin-8-amine | 424.2 |
| 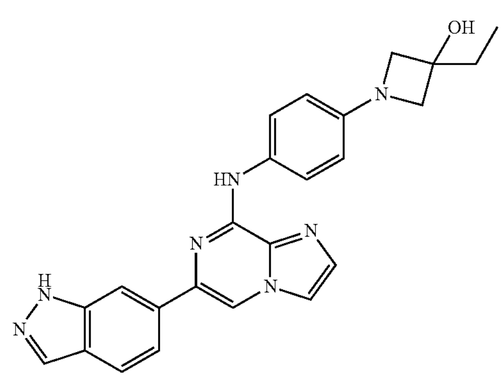 [SMILES: CCC1(O)CN(c2ccc(Nc3nc(-c4ccc5cn[nH]c5c4)cn4ccnc34)cc2)C1] | 3-ethyl-1-(4-{[6-(1H-indazol-6-yl)imidazo[1,2-a]pyrazin-8-yl]amino}phenyl)azetidin-3-ol | 426 |

| Structure | Name | [M + H]⁺ |
|---|---|---|
| 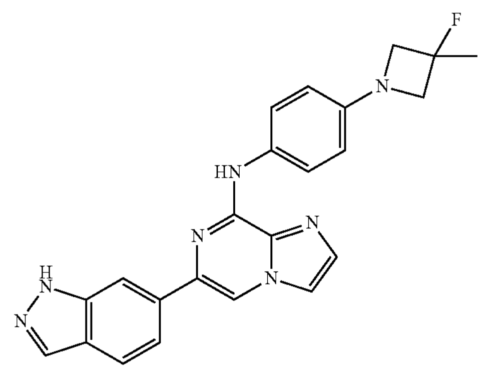 [SMILES: CC1(F)CN(c2ccc(Nc3nc(-c4ccc5cn[nH]c5c4)cn4ccnc34)cc2)C1] | N-[4-(3-fluoro-3-methylazetidin-1-yl)phenyl]-6-(1H-indazol-6-yl)imidazo[1,2-a]pyrazin-8-amine | 414.5 |
| 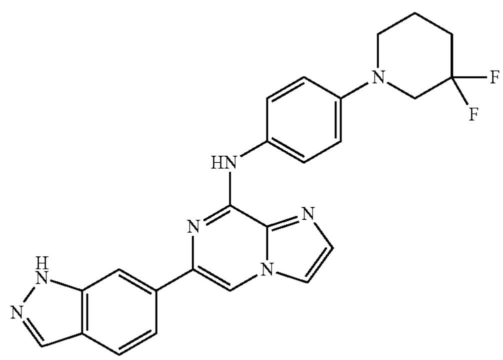 [SMILES: FC1(F)CCCN(c2ccc(Nc3nc(-c4ccc5cn[nH]c5c4)cn4ccnc34)cc2)C1] | N-[4-(3,3-difluoropiperidin-1-yl)phenyl]-6-(1H-indazol-6-yl)imidazo[1,2-a]pyrazin-8-amine | 446.2 |
| 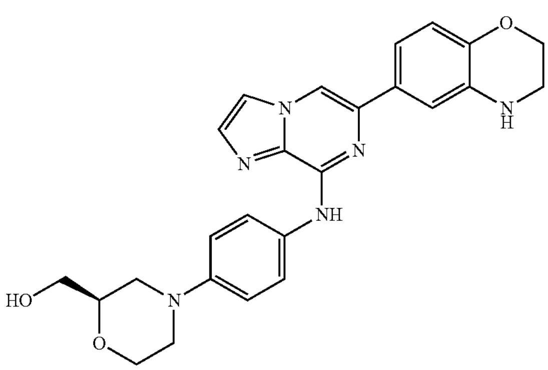 [SMILES: OC[C@H]1CN(c2ccc(Nc3nc(-c4ccc5c(c4)NCCO5)cn4ccnc34)cc2)CCO1] | [(2R)-4-(4-{[6-(3,4-dihydro-2H-1,4-benzoxazin-6-yl)imidazo[1,2-a]pyrazin-8-yl]amino}phenyl)morpholin-2-yl]methanol | 459.4 |
| 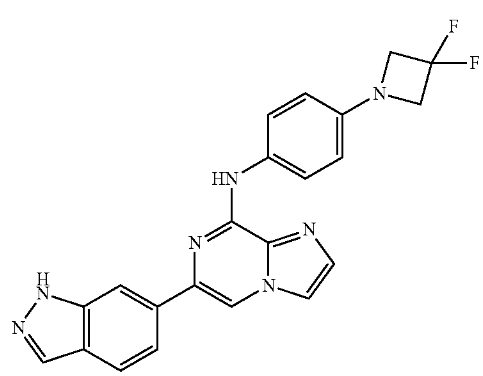 [SMILES: FC1(F)CN(c2ccc(Nc3nc(-c4ccc5cn[nH]c5c4)cn4ccnc34)cc2)C1] | N-[4-(3,3-difluoroazetidin-1-yl)phenyl]-6-(1H-indazol-6-yl)imidazo[1,2-a]pyrazin-8-amine | 418.6 |

| Structure | Name | [M + H]+ |
|---|---|---|
| 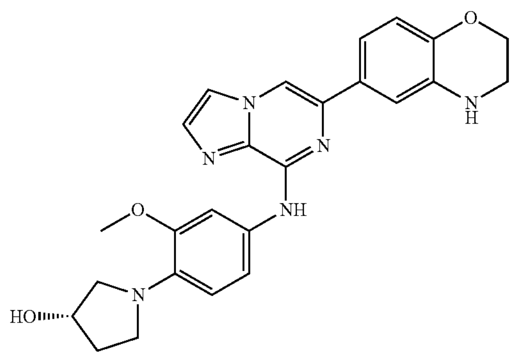 [SMILES: COc1cc(Nc2nc(-c3ccc4c(c3)NCCO4)cn3ccnc23)ccc1N1CC[C@H](O)C1] | (3S)-1-(4-{[6-(3,4-dihydro-2H-1,4-benzoxazin-6-yl)imidazo[1,2-a]pyrazin-8-yl]amino}-2-methoxyphenyl)pyrrolidin-3-ol | 459.5 |
| 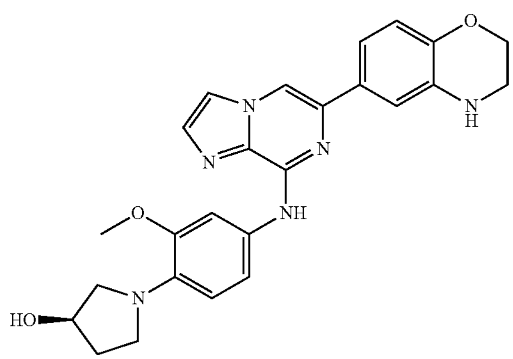 [SMILES: COc1cc(Nc2nc(-c3ccc4c(c3)NCCO4)cn3ccnc23)ccc1N1CC[C@@H](O)C1] | (3R)-1-(4-{[6-(3,4-dihydro-2H-1,4-benzoxazin-6-yl)imidazo[1,2-a]pyrazin-8-yl]amino}-2-methoxyphenyl)pyrrolidin-3-ol | 459.5 |
| 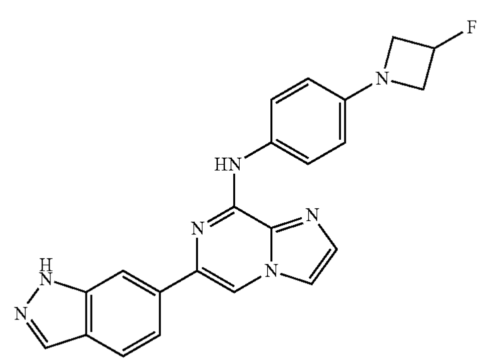 [SMILES: FC1CN(c2ccc(Nc3nc(-c4ccc5cn[nH]c5c4)cn4ccnc34)cc2)C1] | N-[4-(3-fluoroazetidin-1-yl)phenyl]-6-(1H-indazol-6-yl)imidazo[1,2-a]pyrazin-8-amine | 400.2 |
| 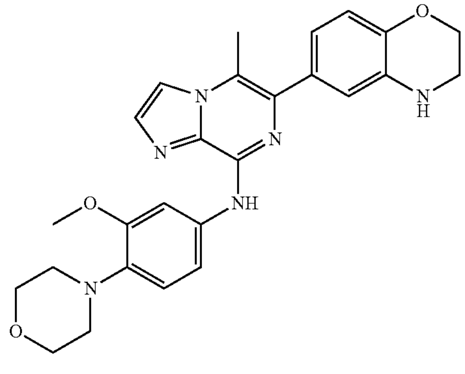 [SMILES: COc1cc(Nc2nc(-c3ccc4c(c3)NCCO4)c(C)n3ccnc23)ccc1N1CCOCC1] | 6-(3,4-dihydro-2H-1,4-benzoxazin-6-yl)-N-[3-methoxy-4-(morpholin-4-yl)phenyl]-5-methylimidazo[1,2-a]pyrazin-8-amine | 473.2 |

-continued

| Structure | Name | [M + H]+ |
|---|---|---|
| 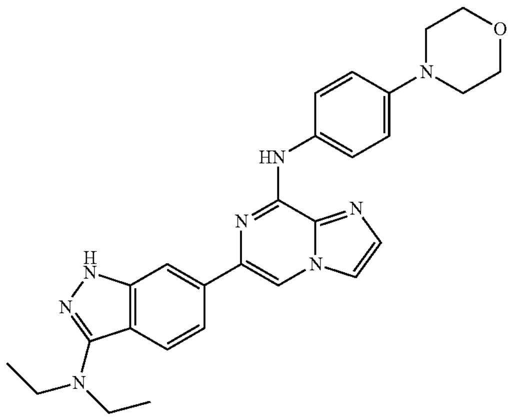 [SMILES: CCN(CC)c1n[nH]c2cc(-c3cn4ccnc4c(Nc4ccc(N5CCOCC5)cc4)n3)ccc12] | N,N-diethyl-6-(8-{[4-(morpholin-4-yl)phenyl]amino}imidazo[1,2-a]pyrazin-6-yl)-1H-indazol-3-amine | 483.6 |
| 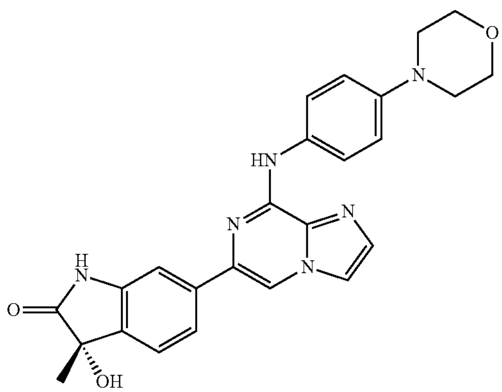 [SMILES: C[C@@]1(O)C(=O)Nc2cc(-c3cn4ccnc4c(Nc4ccc(N5CCOCC5)cc4)n3)ccc21] | (3S)-3-hydroxy-3-methyl-6-(8-{[4-(morpholin-4-yl)phenyl]amino}imidazo[1,2-a]pyrazin-6-yl)-2,3-dihydro-1H-indol-2-one | 457.6 |
| 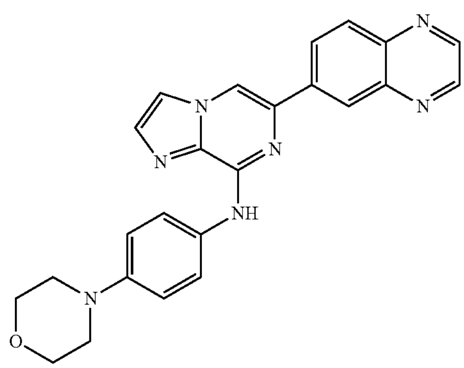 [SMILES: c1cnc2cc(-c3cn4ccnc4c(Nc4ccc(N5CCOCC5)cc4)n3)ccc2n1] | N-[4-(morpholin-4-yl)phenyl]-6-(quinoxalin-6-yl)imidazo[1,2-a]pyrazin-8-amine | 424.3 |
| 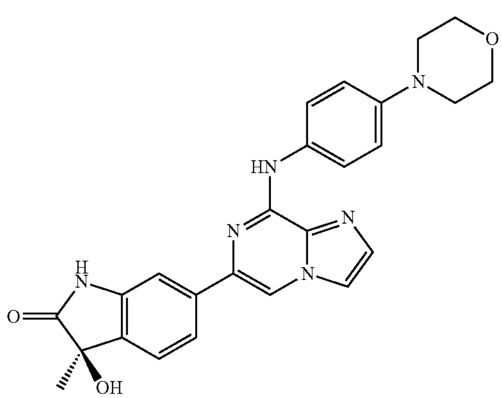 [SMILES: C[C@]1(O)C(=O)Nc2cc(-c3cn4ccnc4c(Nc4ccc(N5CCOCC5)cc4)n3)ccc21] | (3R)-3-hydroxy-3-methyl-6-(8-{[4-(morpholin-4-yl)phenyl]amino}imidazo[1,2-a]pyrazin-6-yl)-2,3-dihydro-1H-indol-2-one | 457.6 |

-continued

| Structure | Name | [M + H]+ |
|---|---|---|
| 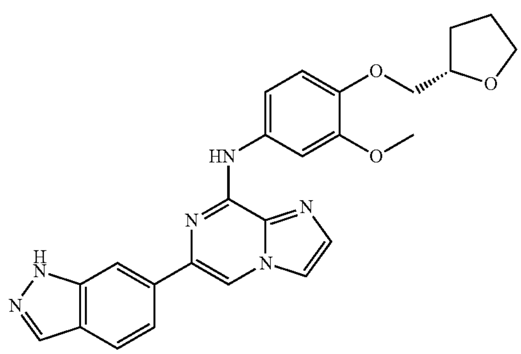 [SMILES: COc1cc(Nc2nc(-c3ccc4cn[nH]c4c3)cn3ccnc23)ccc1OC[C@@H]1CCCO1] | 6-(1H-indazol-6-yl)-N-{3-methoxy-4-[(2S)-oxolan-2-ylmethoxy]phenyl}imidazo[1,2-a]pyrazin-8-amine | 457.5 |
| 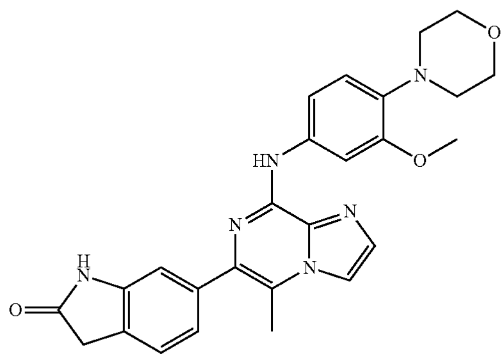 [SMILES: COc1cc(Nc2nc(-c3ccc4c(c3)NC(=O)C4)c(C)n3ccnc23)ccc1N1CCOCC1] | 6-(8-{[3-methoxy-4-(morpholin-4-yl)phenyl]amino}-5-methylimidazo[1,2-a]pyrazin-6-yl)-2,3-dihydro-1H-indol-2-one | 471.7 |
| 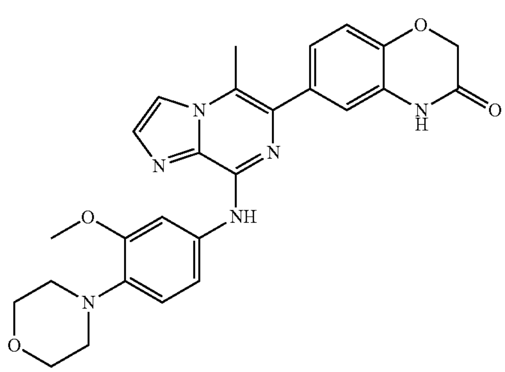 [SMILES: COc1cc(Nc2nc(-c3ccc4c(c3)NC(=O)CO4)c(C)n3ccnc23)ccc1N1CCOCC1] | 6-(8-{[3-methoxy-4-(morpholin-4-yl)phenyl]amino}-5-methylimidazo[1,2-a]pyrazin-6-yl)-3,4-dihydro-2H-1,4-benzoxazin-3-one | 487.5 |
| 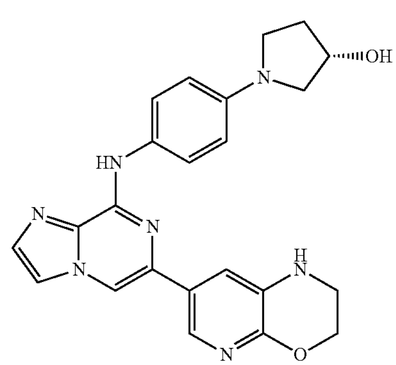 [SMILES: O[C@H]1CCN(c2ccc(Nc3nc(-c4cnc5c(c4)NCCO5)cn4ccnc34)cc2)C1] | (3S)-1-{4-[(6-{1H,2H,3H-pyrido[2,3-b][1,4]oxazin-7-yl}imidazo[1,2-a]pyrazin-8-yl)amino]phenyl}pyrrolidin-3-ol | 430.4 |

| Structure | Name | [M + H]+ |
|---|---|---|
| 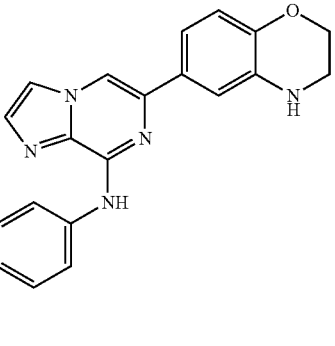 | (3R)-1-(4-{[6-(3,4-dihydro-2H-1,4-benzoxazin-6-yl)imidazo[1,2-a]pyrazin-8-yl]amino}phenyl)pyrrolidin-3-ol | 429.4 |
| 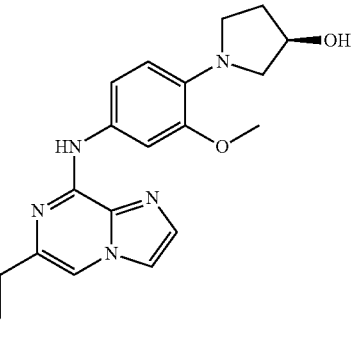 | 6-[8-({4-[(3R)-3-hydroxypyrrolidin-1-yl]-3-methoxyphenyl}amino)imidazo[1,2-a]pyrazin-6-yl]-2,3-dihydro-1H-indol-2-one | 457.3 |
| 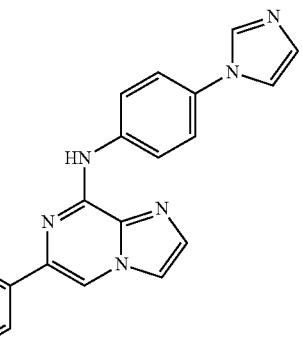 | N-[4-(1H-imidazol-1-yl)phenyl]-6-(1H-indazol-6-yl)imidazo[1,2-a]pyrazin-8-amine | 393.3 |
| 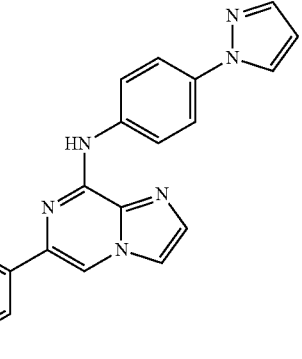 | 6-(1H-indazol-6-yl)-N-[4-(1H-pyrazol-1-yl)phenyl]imidazo[1,2-a]pyrazin-8-amine | 393.2 |

-continued

| Structure | Name | [M + H]+ |
|---|---|---|
| 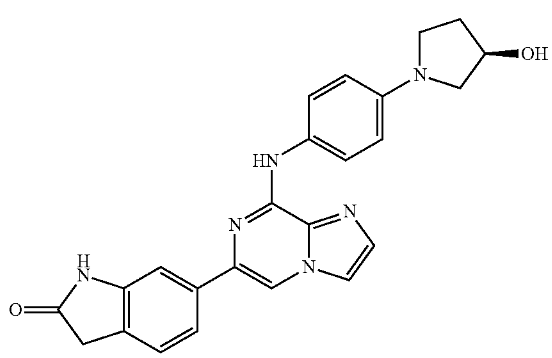 [SMILES: O=C1Cc2ccc(-c3cn4ccnc4c(Nc4ccc(N5CC[C@@H](O)C5)cc4)n3)cc2N1] | 6-[8-({4-[(3R)-3-hydroxypyrrolidin-1-yl]phenyl}amino)imidazo[1,2-a]pyrazin-6-yl]-2,3-dihydro-1H-indol-2-one | 427.1 |
| 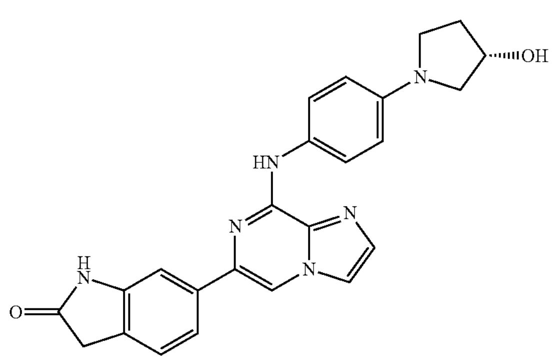 [SMILES: O=C1Cc2ccc(-c3cn4ccnc4c(Nc4ccc(N5CC[C@H](O)C5)cc4)n3)cc2N1] | 6-[8-({4-[(3S)-3-hydroxypyrrolidin-1-yl]phenyl}amino)imidazo[1,2-a]pyrazin-6-yl]-2,3-dihydro-1H-indol-2-one | 427 |
| 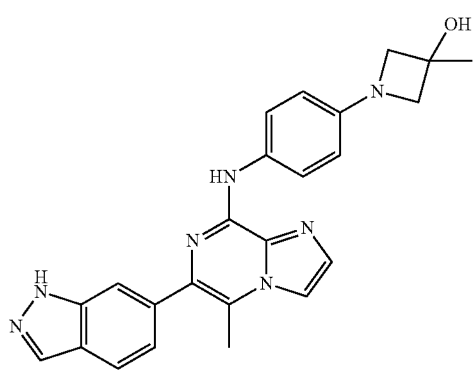 [SMILES: Cc1c(-c2ccc3cn[nH]c3c2)nc(Nc2ccc(N3CC(C)(O)C3)cc2)c2nccn12] | 1-(4-{[6-(1H-indazol-6-yl)-5-methylimidazo[1,2-a]pyrazin-8-yl]amino}phenyl)-3-methylazetidin-3-ol | 426.2 |
| 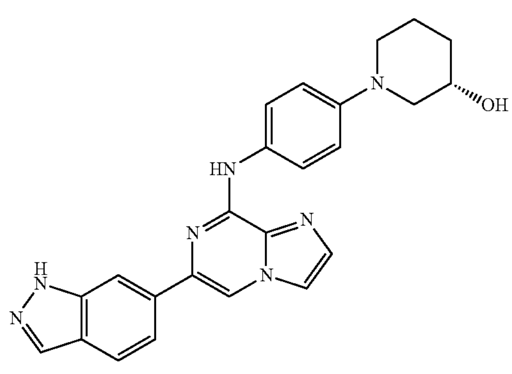 [SMILES: O[C@H]1CCCN(c2ccc(Nc3nc(-c4ccc5cn[nH]c5c4)cn4ccnc34)cc2)C1] | (3S)-1-(4-{[6-(1H-indazol-6-yl)imidazo[1,2-a]pyrazin-8-yl]amino}phenyl)piperidin-3-ol | 426.2 |

-continued

| Structure | Name | [M + H]⁺ |
|---|---|---|
| 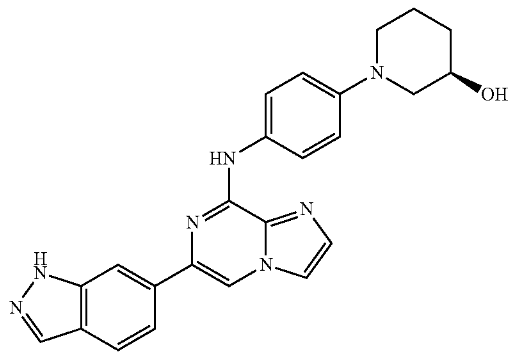 [SMILES: O[C@@H]1CCCN(c2ccc(Nc3nc(-c4ccc5cn[nH]c5c4)cn4ccnc34)cc2)C1] | (3R)-1-(4-{[6-(1H-indazol-6-yl)imidazo[1,2-a]pyrazin-8-yl]amino}phenyl)piperidin-3-ol | 426.2 |
| 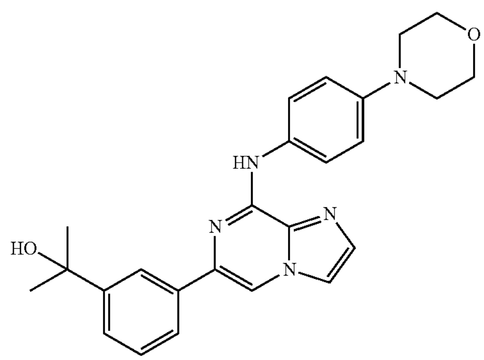 [SMILES: CC(C)(O)c1cccc(-c2cn3ccnc3c(Nc3ccc(N4CCOCC4)cc3)n2)c1] | 2-[3-(8-{[4-(morpholin-4-yl)phenyl]amino}imidazo[1,2-a]pyrazin-6-yl)phenyl]propan-2-ol | 430.2 |
| 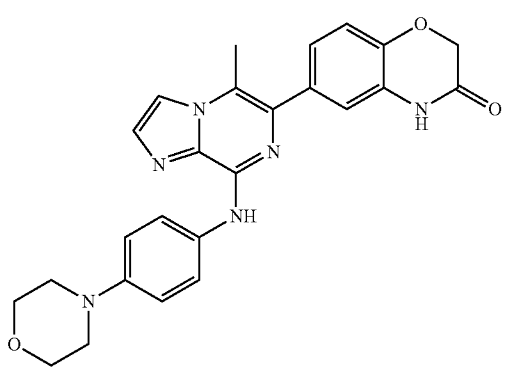 [SMILES: Cc1c(-c2ccc3c(c2)NC(=O)CO3)nc(Nc2ccc(N3CCOCC3)cc2)c2nccn12] | 6-(5-methyl-8-{[4-(morpholin-4-yl)phenyl]amino}imidazo[1,2-a]pyrazin-6-yl)-3,4-dihydro-2H-1,4-benzoxazin-3-one | 457.2 |
| | N-ethyl-6-(8-{[4-(morpholin-4-yl)phenyl]amino}imidazo[1,2-a]pyrazin-6-yl)-1H-indazol-3-amine | 455.2 |

| Structure | Name | [M + H]+ |
|---|---|---|
| 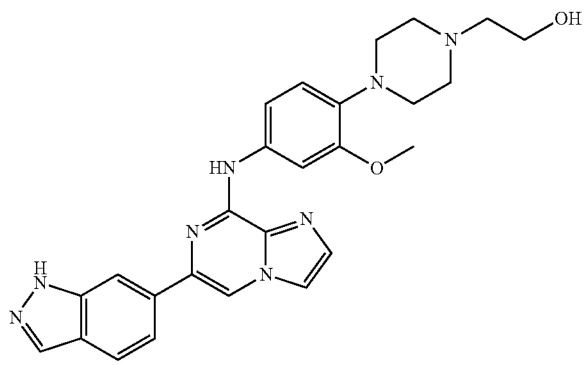 [SMILES: COc1cc(Nc2nc(-c3ccc4cn[nH]c4c3)cn3ccnc23)ccc1N1CCN(CCO)CC1] | 2-[4-(4-{[6-(1H-indazol-6-yl)imidazo[1,2-a]pyrazin-8-yl]amino}-2-methoxyphenyl)piperazin-1-yl]ethan-1-ol | 485.6 |
| 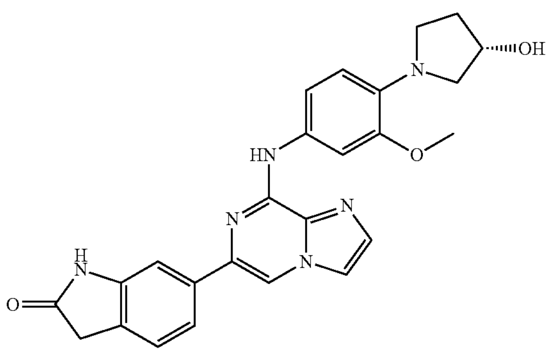 [SMILES: COc1cc(Nc2nc(-c3ccc4c(c3)NC(=O)C4)cn3ccnc23)ccc1N1CC[C@H](O)C1] | 6-[8-({4-[(3S)-3-hydroxypyrrolidin-1-yl]-3-methoxyphenyl}amino)imidazo[1,2-a]pyrazin-6-yl]-2,3-dihydro-1H-indol-2-one | 457.6 |
| 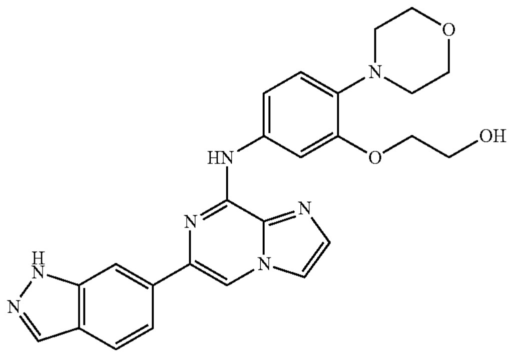 [SMILES: OCCOc1cc(Nc2nc(-c3ccc4cn[nH]c4c3)cn3ccnc23)ccc1N1CCOCC1] | 2-(5-{[6-(1H-indazol-6-yl)imidazo[1,2-a]pyrazin-8-yl]amino}-2-(morpholin-4-yl)phenoxy)ethan-1-ol | 472.4 |
| 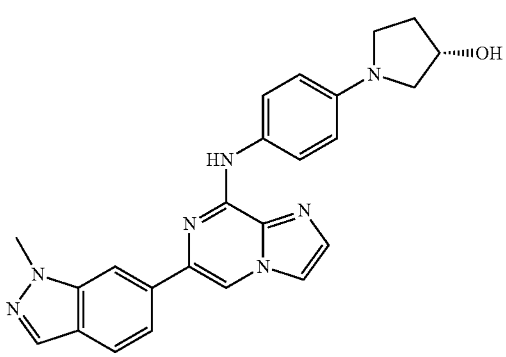 [SMILES: Cn1ncc2ccc(-c3cn4ccnc4c(Nc4ccc(N5CC[C@H](O)C5)cc4)n3)cc21] | (3S)-1-(4-{[6-(1-methyl-1H-indazol-6-yl)imidazo[1,2-a]pyrazin-8-yl]amino}phenyl)pyrrolidin-3-ol | 426.2 |

-continued

| Structure | Name | [M + H]+ |
|---|---|---|
| 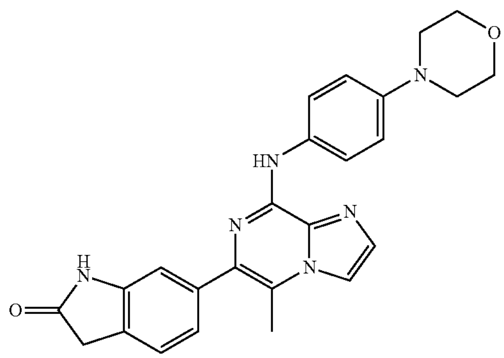 [SMILES: Cc1c(-c2ccc3c(c2)NC(=O)C3)nc(Nc2ccc(N3CCOCC3)cc2)c2nccn12] | 6-(5-methyl-8-{[4-(morpholin-4-yl)phenyl]amino}imidazo[1,2-a]pyrazin-6-yl)-2,3-dihydro-1H-indol-2-one | 441.3 |
| 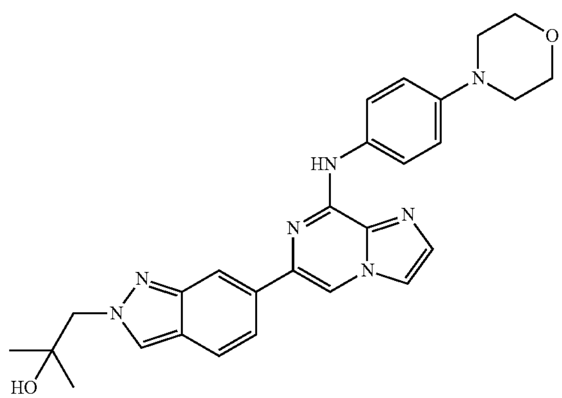 [SMILES: CC(C)(O)Cn1cc2ccc(-c3cn4ccnc4c(Nc4ccc(N5CCOCC5)cc4)n3)cc2n1] | 2-methyl-1-[6-(8-{[4-(morpholin-4-yl)phenyl]amino}imidazo[1,2-a]pyrazin-6-yl)-2H-indazol-2-yl]propan-2-ol | 484.6 |
| 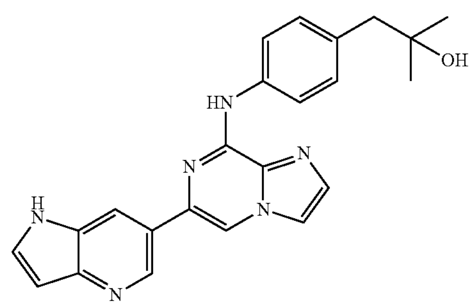 [SMILES: CC(C)(O)Cc1ccc(Nc2nc(-c3cnc4cc[nH]c4c3)cn3ccnc23)cc1] | 2-methyl-1-{4-[(6-{1H-pyrrolo[3,2-b]pyridin-6-yl}imidazo[1,2-a]pyrazin-8-yl)amino]phenyl}propan-2-ol | 399.2 |
| 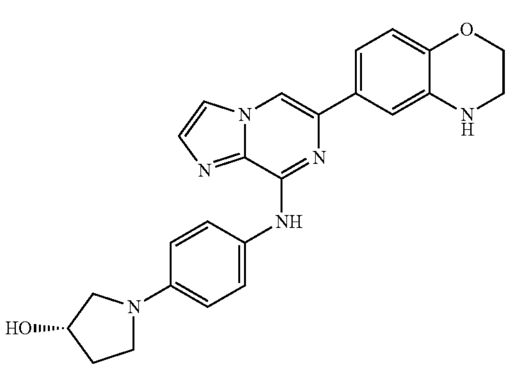 [SMILES: O[C@H]1CCN(c2ccc(Nc3nc(-c4ccc5c(c4)NCCO5)cn4ccnc34)cc2)C1] | (3S)-1-(4-{[6-(3,4-dihydro-2H-1,4-benzoxazin-6-yl)imidazo[1,2-a]pyrazin-8-yl]amino}phenyl)pyrrolidin-3-ol | 429.4 |

| Structure | Name | [M + H]+ |
|---|---|---|
| 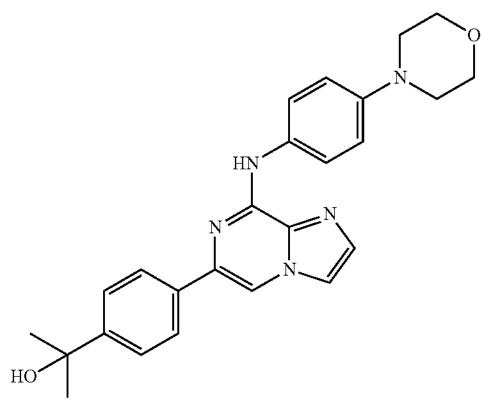 [SMILES: CC(C)(O)c1ccc(-c2cn3ccnc3c(Nc3ccc(N4CCOCC4)cc3)n2)cc1] | 2-[4-(8-{[4-(morpholin-4-yl)phenyl]amino}imidazo[1,2-a]pyrazin-6-yl)phenyl]propan-2-ol | 430.2 |
| 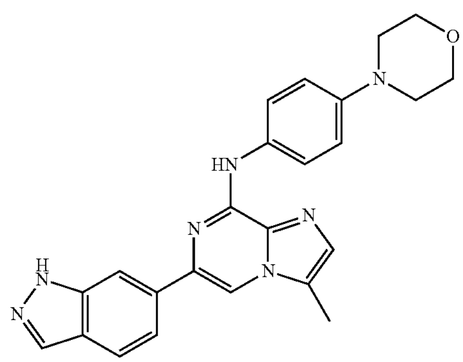 [SMILES: Cc1cnc2c(Nc3ccc(N4CCOCC4)cc3)nc(-c3ccc4cn[nH]c4c3)cn12] | 6-(1H-indazol-6-yl)-3-methyl-N-[4-(morpholin-4-yl)phenyl]imidazo[1,2-a]pyrazin-8-amine | 426.2 |
| 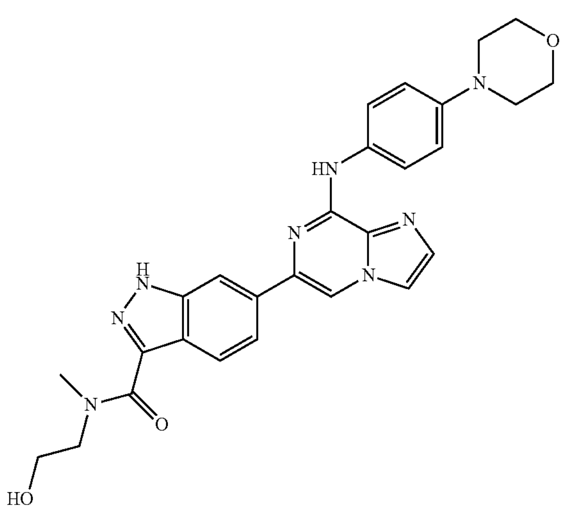 [SMILES: CN(CCO)C(=O)c1n[nH]c2cc(-c3cn4ccnc4c(Nc4ccc(N5CCOCC5)cc4)n3)ccc12] | N-(2-hydroxyethyl)-N-methyl-6-(8-{[4-(morpholin-4-yl)phenyl]amino}imidazo[1,2-a]pyrazin-6-yl)-1H-indazole-3-carboxamide | 513.6 |

-continued

| Structure | Name | [M + H]+ |
|---|---|---|
| 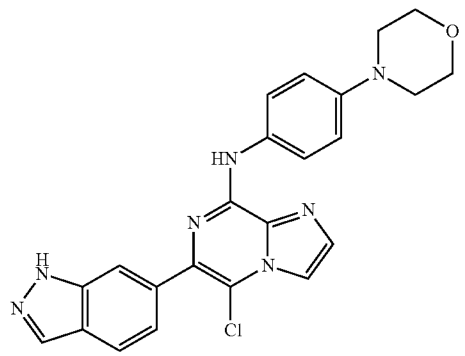 [SMILES: Clc1c(-c2ccc3cn[nH]c3c2)nc(Nc2ccc(N3CCOCC3)cc2)c2nccn12] | 5-chloro-6-(1H-indazol-6-yl)-N-[4-(morpholin-4-yl)phenyl]imidazo[1,2-a]pyrazin-8-amine | 446.4 |
| 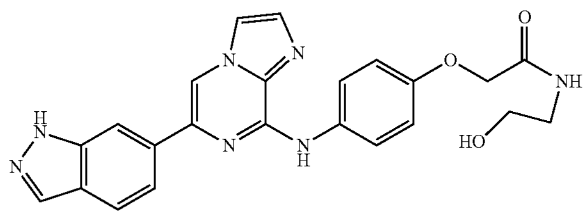 [SMILES: O=C(COc1ccc(Nc2nc(-c3ccc4cn[nH]c4c3)cn3ccnc23)cc1)NCCO] | N-(2-hydroxyethyl)-2-(4-{[6-(1H-indazol-6-yl)imidazo[1,2-a]pyrazin-8-yl]amino}phenoxy)acetamide | 444.8 |
| 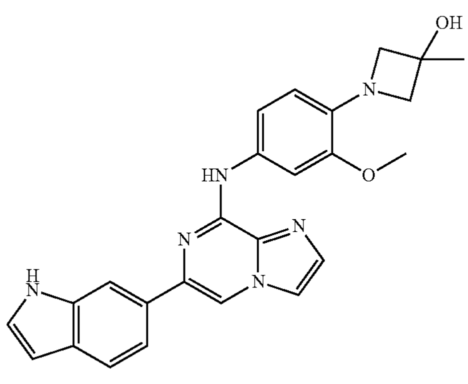 [SMILES: COc1cc(Nc2nc(-c3ccc4cc[nH]c4c3)cn3ccnc23)ccc1N1CC(C)(O)C1] | 1-(4-{[6-(1H-indol-6-yl)imidazo[1,2-a]pyrazin-8-yl]amino}-2-methoxyphenyl)-3-methylazetidin-3-ol | 441.4 |
| 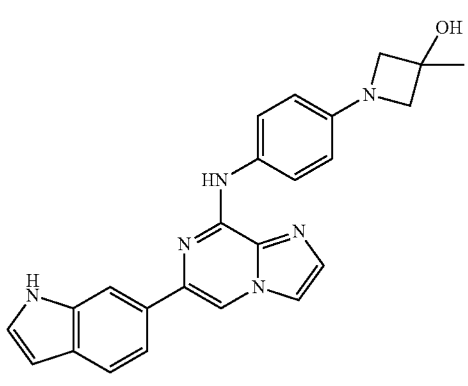 [SMILES: CC1(O)CN(c2ccc(Nc3nc(-c4ccc5cc[nH]c5c4)cn4ccnc34)cc2)C1] | 1-(4-{[6-(1H-indol-6-yl)imidazo[1,2-a]pyrazin-8-yl]amino}phenyl)-3-methylazetidin-3-ol | 411.4 |

-continued

| Structure | Name | [M + H]+ |
|---|---|---|
| 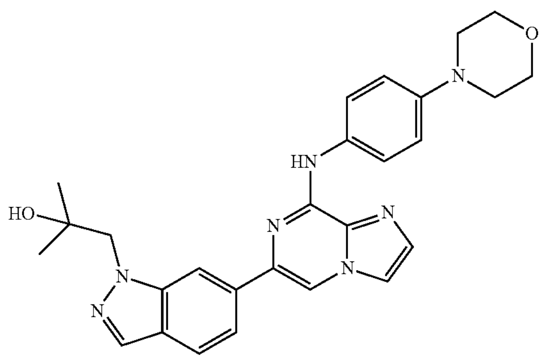 [SMILES: CC(C)(O)Cn1ncc2ccc(-c3cn4ccnc4c(Nc4ccc(N5CCOCC5)cc4)n3)cc21] | 2-methyl-1-[6-(8-{[4-(morpholin-4-yl)phenyl]amino}imidazo[1,2-a]pyrazin-6-yl)-1H-indazol-1-yl]propan-2-ol | 484.7 |
| 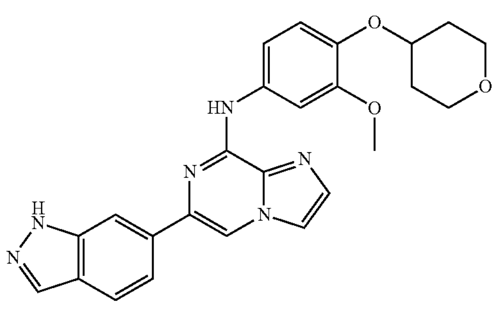 [SMILES: COc1cc(Nc2nc(-c3ccc4cn[nH]c4c3)cn3ccnc23)ccc1OC1CCOCC1] | 6-(1H-indazol-6-yl)-N-[3-methoxy-4-(oxan-4-yloxy)phenyl]imidazo[1,2-a]pyrazin-8-amine | 457.6 |
| 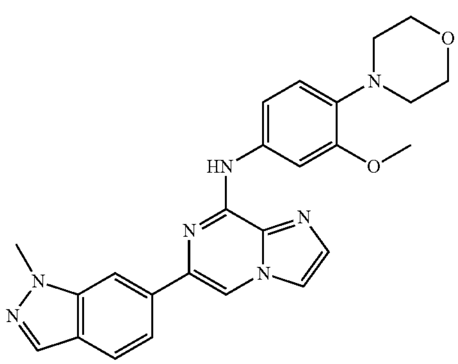 [SMILES: COc1cc(Nc2nc(-c3ccc4cnn(C)c4c3)cn3ccnc23)ccc1N1CCOCC1] | N-[3-methoxy-4-(morpholin-4-yl)phenyl]-6-(1-methyl-1H-indazol-6-yl)imidazo[1,2-a]pyrazin-8-amine | 456.2 |
| 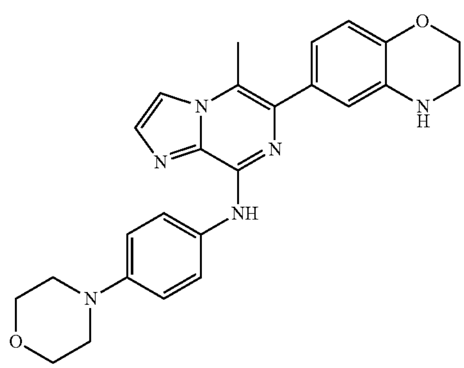 [SMILES: Cc1c(-c2ccc3c(c2)NCCO3)nc(Nc2ccc(N3CCOCC3)cc2)c2nccn12] | 6-(3,4-dihydro-2H-1,4-benzoxazin-6-yl)-5-methyl-N-[4-(morpholin-4-yl)phenyl]imidazo[1,2-a]pyrazin-8-amine | 443.3 |

-continued

| Structure | Name | [M + H]⁺ |
|---|---|---|
| 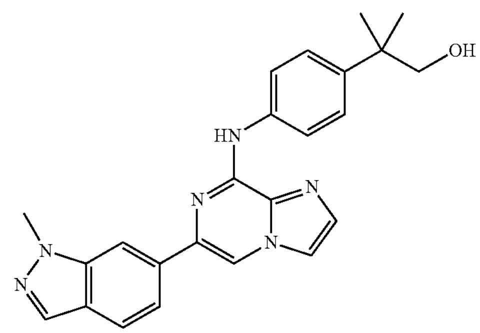 [SMILES: Cn1ncc2ccc(-c3cn4ccnc4c(Nc4ccc(C(C)(C)CO)cc4)n3)cc21] | 2-methyl-2-(4-{[6-(1-methyl-1H-indazol-6-yl)imidazo[1,2-a]pyrazin-8-yl]amino}phenyl)propan-1-ol | 413.5 |
| 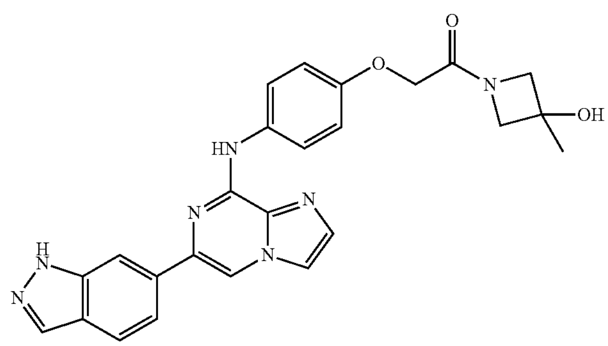 [SMILES: CC1(O)CN(C(=O)COc2ccc(Nc3nc(-c4ccc5cn[nH]c5c4)cn4ccnc34)cc2)C1] | 1-(3-hydroxy-3-methylazetidin-1-yl)-2-(4-{[6-(1H-indazol-6-yl)imidazo[1,2-a]pyrazin-8-yl]amino}phenoxy)ethan-1-one | 470.7 |
| 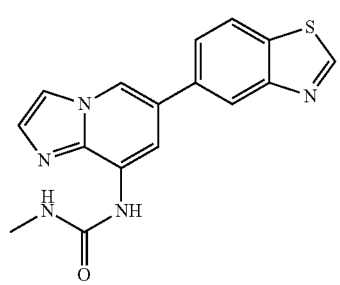 [SMILES: CNC(=O)Nc1cc(-c2ccc3scnc3c2)cn2ccnc12] | 1-[6-(1,3-benzothiazol-5-yl)imidazo[1,2-a]pyridin-3-methylurea | 324.2 |
| 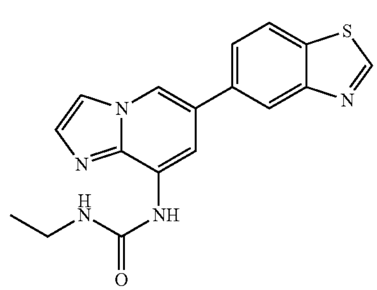 [SMILES: CCNC(=O)Nc1cc(-c2ccc3scnc3c2)cn2ccnc12] | 1-[6-(1,3-benzothiazol-5-yl)imidazo[1,2-a]pyridin-8-yl]-3-ethylurea | 338.3 |

| Structure | Name | [M + H]+ |
|---|---|---|
| 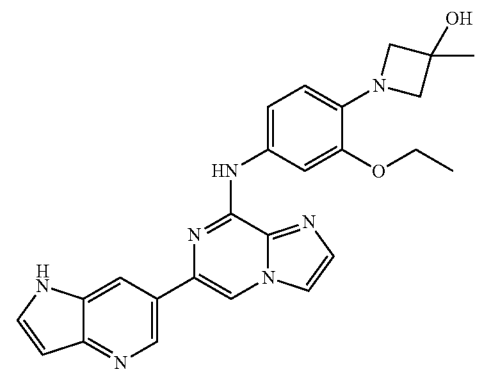 [SMILES: CCOc1cc(Nc2nc(-c3cnc4cc[nH]c4c3)cn3ccnc23)ccc1N1CC(C)(O)C1] | 1-{2-ethoxy-4-[(6-{1H-pyrrolo[3,2-b]pyridin-6-yl}imidazo[1,2-a]pyrazin-8-yl)amino]phenyl}-3-methylazetidin-3-ol | 456.4 |
| 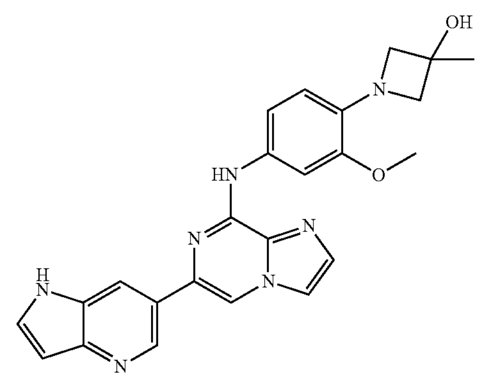 [SMILES: COc1cc(Nc2nc(-c3cnc4cc[nH]c4c3)cn3ccnc23)ccc1N1CC(C)(O)C1] | 1-{2-methoxy-4-[(6-{1H-pyrrolo[3,2-b]pyridin-6-yl}imidazo[1,2-a]pyrazin-8-yl)amino]phenyl}-3-methylazetidin-3-ol | 442.4 |
| 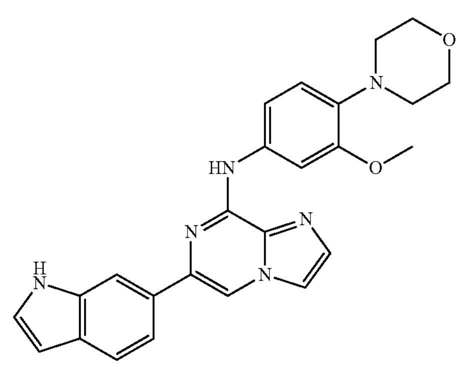 [SMILES: COc1cc(Nc2nc(-c3ccc4cc[nH]c4c3)cn3ccnc23)ccc1N1CCOCC1] | 6-(1H-indol-6-yl)-N-[3-methoxy-4-(morpholin-4-yl)phenyl]imidazo[1,2-a]pyrazin-8-amine | 441.5 |
| 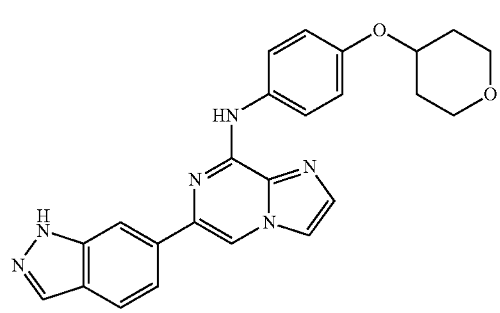 [SMILES: c1cn2cc(-c3ccc4cn[nH]c4c3)nc(Nc3ccc(OC4CCOCC4)cc3)c2n1] | 6-(1H-indazol-6-yl)-N-[4-(oxan-4-yloxy)phenyl]imidazo[1,2-a]pyrazin-8-amine | 427 |

-continued

| Structure | Name | [M + H]+ |
|---|---|---|
| 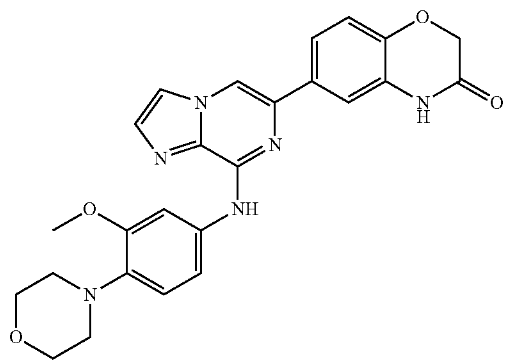 [SMILES: COc1cc(Nc2nc(-c3ccc4c(c3)NC(=O)CO4)cn3ccnc23)ccc1N1CCOCC1] | 6-(8-{[3-methoxy-4-(morpholin-4-yl)phenyl]amino}imidazo[1,2-a]pyrazin-6-yl)-3,4-dihydro-2H-1,4-benzoxazin-3-one | 473.2 |
| 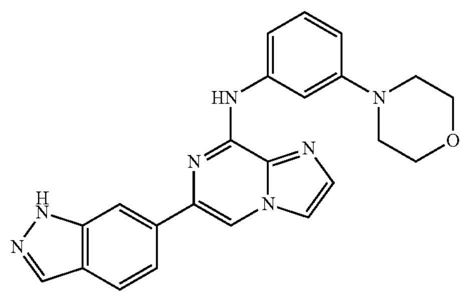 [SMILES: c1cc(Nc2nc(-c3ccc4cn[nH]c4c3)cn3ccnc23)cc(N2CCOCC2)c1] | 6-(1H-indazol-6-yl)-N-[3-(morpholin-4-yl)phenyl]imidazo[1,2-a]pyrazin-8-amine | 412.5 |
| 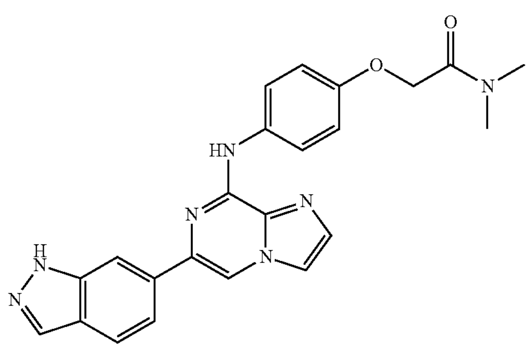 | 2-(4-{[6-(1H-indazol-6-yl)imidazo[1,2-a]pyrazin-8-yl]amino}phenoxy)-N,N-dimethylacetamide | 428.3 |
| 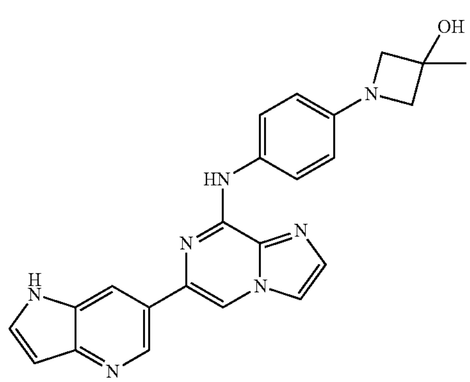 [SMILES: CC1(O)CN(c2ccc(Nc3nc(-c4cnc5cc[nH]c5c4)cn4ccnc34)cc2)C1] | 3-methyl-1-{4-[(6-{1H-pyrrolo[3,2-b]pyridin-6-yl}imidazo[1,2-a]pyrazin-8-yl)amino]phenyl}azetidin-3-ol | 412.3 |

| Structure | Name | [M + H]+ |
|---|---|---|
| 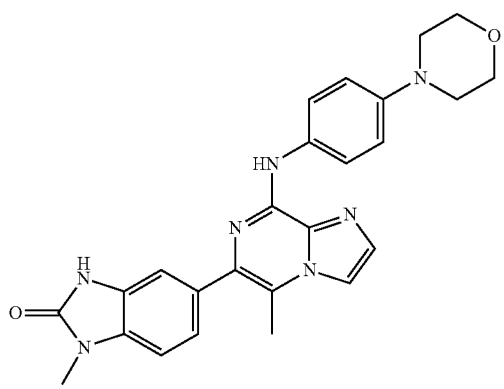 [SMILES: Cc1c(-c2ccc3c(c2)[nH]c(=O)n3C)nc(Nc2ccc(N3CCOCC3)cc2)c2nccn12] | 1-methyl-5-(5-methyl-8-{[4-(morpholin-4-yl)phenyl]amino}imidazo[1,2-a]pyrazin-6-yl)-2,3-dihydro-1H-1,3-benzodiazol-2-one | 456.5 |
| 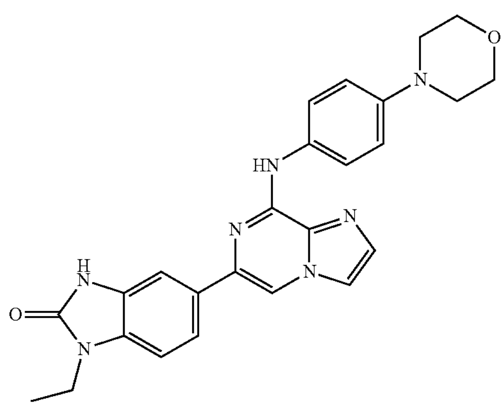 [SMILES: CCn1c(=O)[nH]c2cc(-c3cn4ccnc4c(Nc4ccc(N5CCOCC5)cc4)n3)ccc21] | 1-ethyl-5-(8-{[4-(morpholin-4-yl)phenyl]amino}imidazo[1,2-a]pyrazin-6-yl)-2,3-dihydro-1H-1,3-benzodiazol-2-one | 456.5 |
| 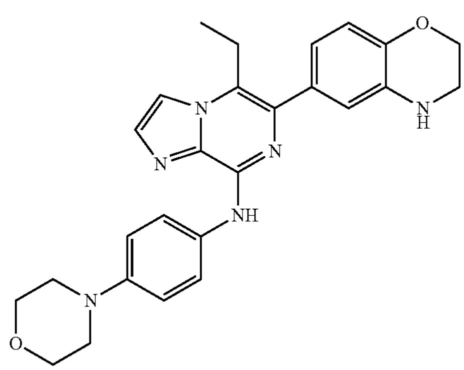 [SMILES: CCc1c(-c2ccc3c(c2)NCCO3)nc(Nc2ccc(N3CCOCC3)cc2)c2nccn12] | 6-(3,4-dihydro-2H-1,4-benzoxazin-6-yl)-5-ethyl-N-[4-(morpholin-4-yl)phenyl]imidazo[1,2-a]pyrazin-8-amine | 457.6 |
| 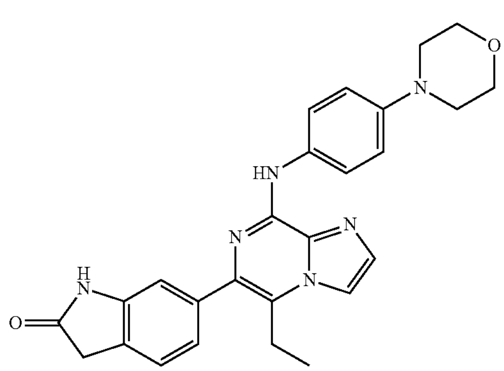 [SMILES: CCc1c(-c2ccc3c(c2)NC(=O)C3)nc(Nc2ccc(N3CCOCC3)cc2)c2nccn12] | 6-(5-ethyl-8-{[4-(morpholin-4-yl)phenyl]amino}imidazo[1,2-a]pyrazin-6-yl)-2,3-dihydro-1H-indol-2-one | 455.1 |

-continued

| Structure | Name | [M + H]+ |
|---|---|---|
| 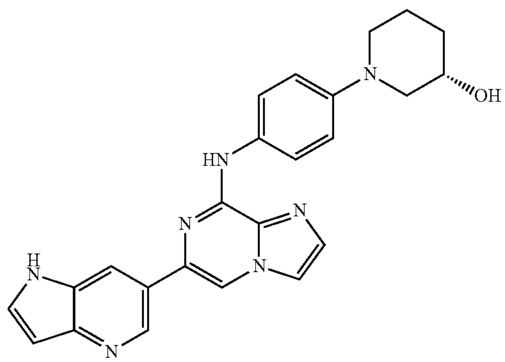 [SMILES: O[C@H]1CCCN(c2ccc(Nc3nc(-c4cnc5cc[nH]c5c4)cn4ccnc34)cc2)C1] | (3S)-1-{4-[(6-{1H-pyrrolo[3,2-b]pyridin-6-yl}imidazo[1,2-a]pyrazin-8-yl)amino]phenyl}piperidin-3-ol | 426.2 |
| 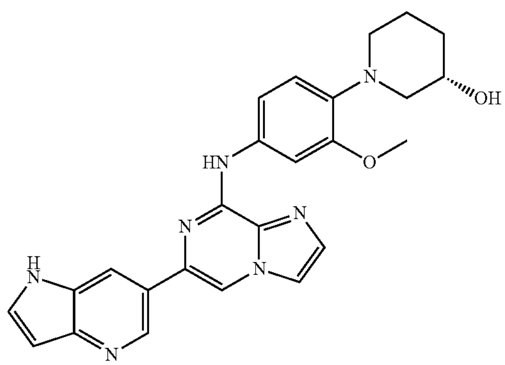 [SMILES: COc1cc(Nc2nc(-c3cnc4cc[nH]c4c3)cn3ccnc23)ccc1N1CCC[C@H](O)C1] | (3S)-1-{2-methoxy-4-[(6-{1H-pyrrolo[3,2-b]pyridin-6-yl}imidazo[1,2-a]pyrazin-8-yl)amino]phenyl}piperidin-3-ol | 456.2 |
| 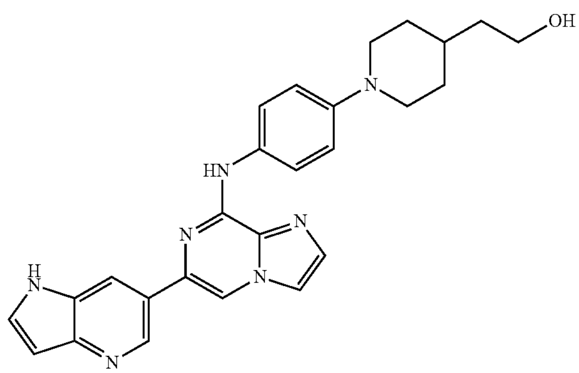 [SMILES: OCCC1CCN(c2ccc(Nc3nc(-c4cnc5cc[nH]c5c4)cn4ccnc34)cc2)CC1] | 2-(1-{4-[(6-{1H-pyrrolo[3,2-b]pyridin-6-yl}imidazo[1,2-a]pyrazin-8-yl)amino]phenyl}piperidin-4-yl)ethan-1-ol | 454.2 |
| 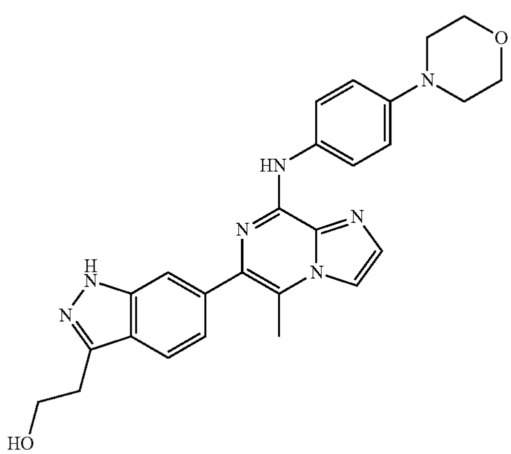 [SMILES: Cc1c(-c2ccc3c(CCO)n[nH]c3c2)nc(Nc2ccc(N3CCOCC3)cc2)c2nccn12] | 2-[6-(5-methyl-8-{[4-(morpholin-4-yl)phenyl]amino}imidazo[1,2-a]pyrazin-6-yl)-1H-indazol-3-yl]ethan-1-ol | 470.6 |

| Structure | Name | [M + H]+ |
|---|---|---|
| 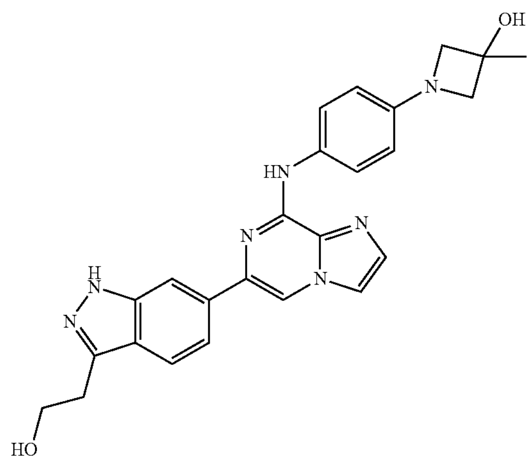 [SMILES: CC1(O)CN(c2ccc(Nc3nc(-c4ccc5c(CCO)n[nH]c5c4)cn4ccnc34)cc2)C1] | 1-[4-({6-[3-(2-hydroxyethyl)-1H-indazol-6-yl]imidazo[1,2-a]pyrazin-8-yl}amino)phenyl]-3-methylazetidin-3-ol | 456.4 |
| 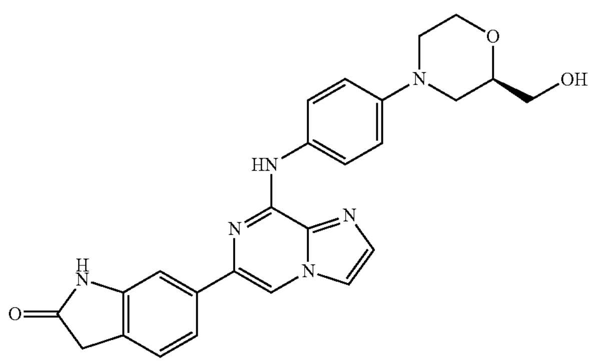 [SMILES: O=C1Cc2ccc(-c3cn4ccnc4c(Nc4ccc(N5CCO[C@@H](CO)C5)cc4)n3)cc2N1] | 6-[8-({4-[(2R)-2-(hydroxymethyl)morpholin-4-yl]phenyl}amino)imidazo[1,2-a]pyrazin-6-yl]-2,3-dihydro-1H-indol-2-one | 457.5 |
| 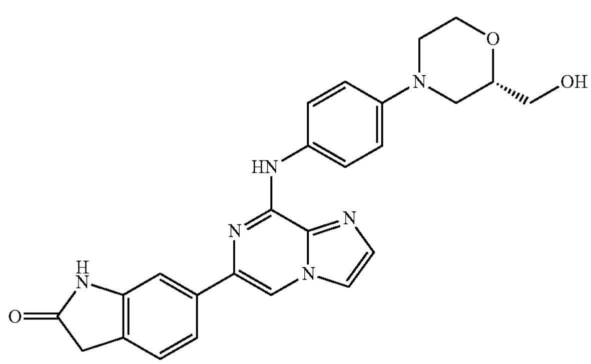 [SMILES: O=C1Cc2ccc(-c3cn4ccnc4c(Nc4ccc(N5CCO[C@H](CO)C5)cc4)n3)cc2N1] | 6-[8-({4-[(2S)-2-(hydroxymethyl)morpholin-4-yl]phenyl}amino)imidazo[1,2-a]pyrazin-6-yl]-2,3-dihydro-1H-indol-2-one | 457.6 |
| 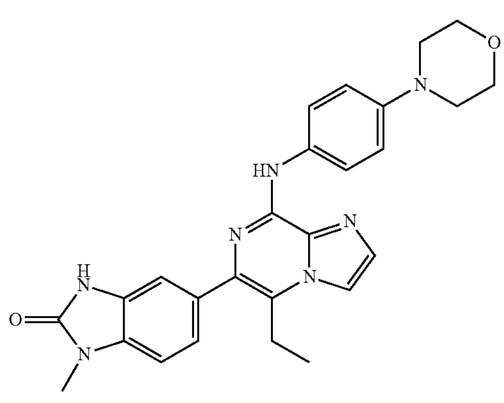 [SMILES: CCc1c(-c2ccc3c(c2)[nH]c(=O)n3C)nc(Nc2ccc(N3CCOCC3)cc2)c2nccn12] | 5-(5-ethyl-8-{[4-(morpholin-4-yl)phenyl]amino}imidazo[1,2-a]pyrazin-6-yl)-1-methyl-2,3-dihydro-1H-1,3-benzodiazol-2-one | 470.7 |

-continued
| Structure | Name | [M + H]+ |
|---|---|---|
| 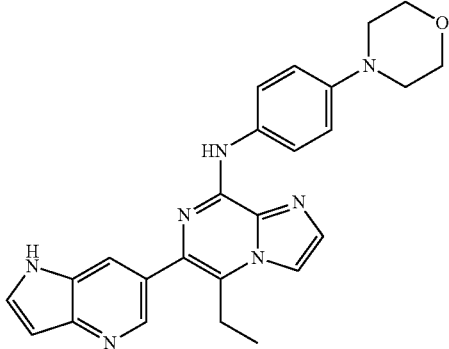 [SMILES: CCc1c(-c2cnc3cc[nH]c3c2)nc(Nc2ccc(N3CCOCC3)cc2)c2nccn12] | 5-ethyl-N-[4-(morpholin-4-yl)phenyl]-6-{1H-pyrrolo[3,2-b]pyridin-6-yl}imidazo[1,2-a]pyrazin-8-amine | 440.4 |
| 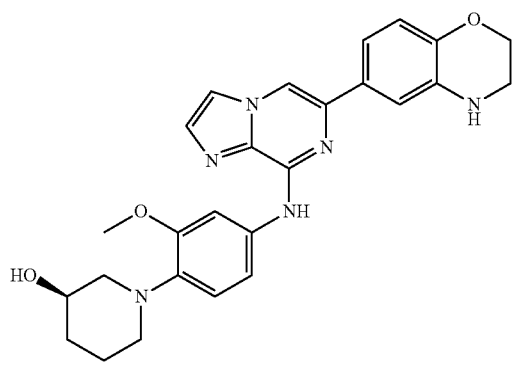 [SMILES: COc1cc(Nc2nc(-c3ccc4c(c3)NCCO4)cn3ccnc23)ccc1N1CCC[C@@H](O)C1] | (3R)-1-(4-{[6-(3,4-dihydro-2H-1,4-benzoxazin-6-yl)imidazo[1,2-a]pyrazin-8-yl]amino}-2-methoxyphenyl)piperidin-3-ol | 473.3 |
| 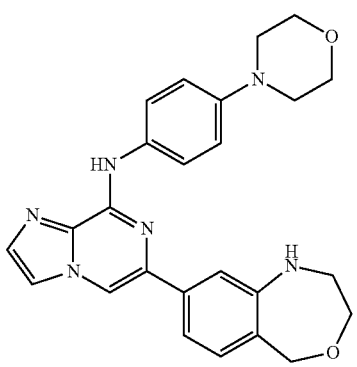 [SMILES: c1cn2cc(-c3ccc4c(c3)NCCOC4)nc(Nc3ccc(N4CCOCC4)cc3)c2n1] | N-[4-(morpholin-4-yl)phenyl]-6-(1,2,3,5-tetrahydro-4,1-benzoxazepin-8-yl)imidazo[1,2-a]pyrazin-8-amine | 443.4 |
| 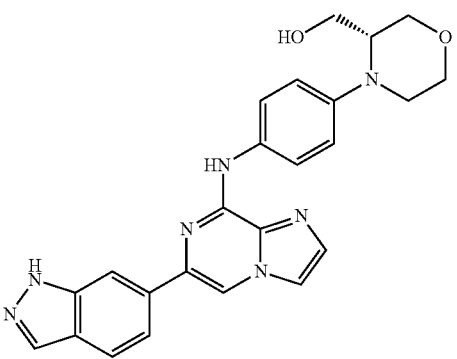 [SMILES: OC[C@@H]1COCCN1c1ccc(Nc2nc(-c3ccc4cn[nH]c4c3)cn3ccnc23)cc1] | [(3R)-4-(4-{[6-(1H-indazol-6-yl)imidazo[1,2-a]pyrazin-8-yl]amino}phenyl)morpholin-3-yl]methanol | 442.3 |

-continued

| Structure | Name | [M + H]⁺ |
|---|---|---|
| 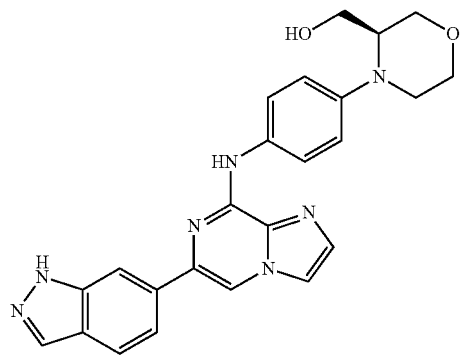 [SMILES: OC[C@H]1COCCN1c1ccc(Nc2nc(-c3ccc4cn[nH]c4c3)cn3ccnc23)cc1] | [(3S)-4-(4-{[6-(1H-indazol-6-yl)imidazo[1,2-a]pyrazin-8-yl]amino}phenyl)morpholin-3-yl]methanol | 442.2 |
| 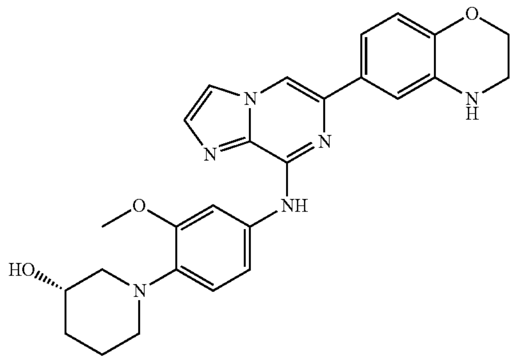 [SMILES: COc1cc(Nc2nc(-c3ccc4c(c3)NCCO4)cn3ccnc23)ccc1N1CCC[C@H](O)C1] | (3S)-1-(4-{[6-(3,4-dihydro-2H-1,4-benzoxazin-6-yl)imidazo[1,2-a]pyrazin-8-yl]amino}-2-methoxyphenyl)piperidin-3-ol | 473.2 |
| | (1-{4-[(6-{1H-pyrrolo[3,2-b]pyridin-6-yl}imidazo[1,2-a]pyrazin-8-yl)amino]phenyl}piperidin-4-yl)methanol | 440.3 |
| 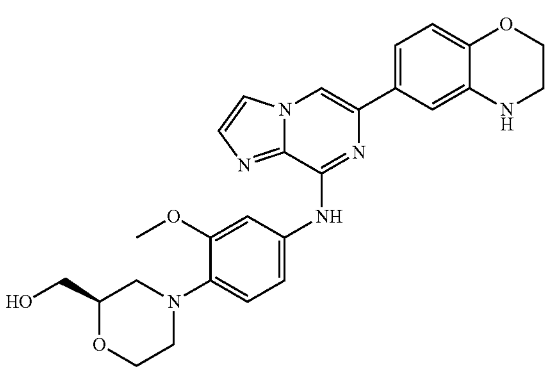 [SMILES: COc1cc(Nc2nc(-c3ccc4c(c3)NCCO4)cn3ccnc23)ccc1N1CCO[C@@H](CO)C1] | [(2R)-4-(4-{[6-(3,4-dihydro-2H-1,4-benzoxazin-6-yl)imidazo[1,2-a]pyrazin-8-yl]amino}-2-methoxyphenyl)morpholin-2-yl]methanol | 489.4 |

| Structure | Name | [M + H]⁺ |
|---|---|---|
| 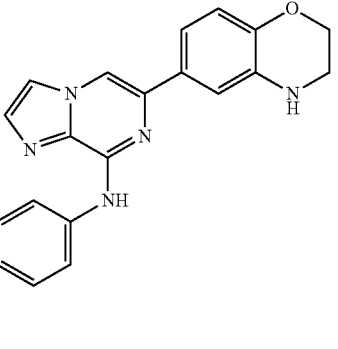 | [(2S)-4-(4-{[6-(3,4-dihydro-2H-1,4-benzoxazin-6-yl)imidazo[1,2-a]pyrazin-8-yl]amino}-2-methoxyphenyl)morpholin-2-yl]methanol | 489.4 |
| 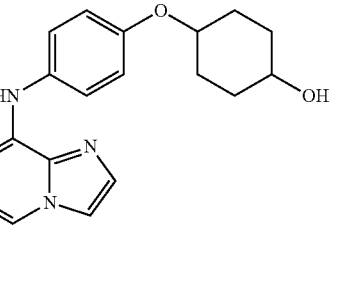 | 4-(4-{[6-(1H-indazol-6-yl)imidazo[1,2-a]pyrazin-8-yl]amino}phenoxy)cyclohexan-1-ol | 441.5 |
| 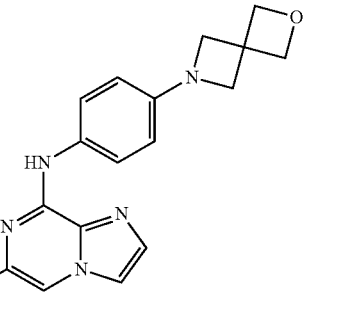 | 6-(1H-indazol-6-yl)-N-(4-{2-oxa-6-azaspiro[3.3]heptan-6-yl}phenyl)imidazo[1,2-a]pyrazin-8-amine | 424.2 |
| 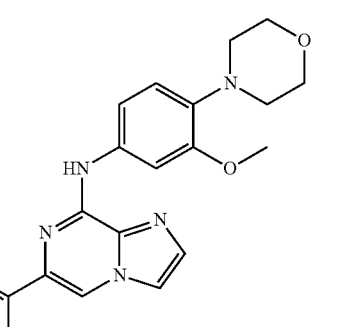 | 2-[6-(8-{[3-methoxy-4-(morpholin-4-yl)phenyl]amino}imidazo[1,2-a]pyrazin-6-yl)-1H-indazol-3-yl]ethan-1-ol | 486.6 |

-continued

| Structure | Name | [M + H]+ |
|---|---|---|
| 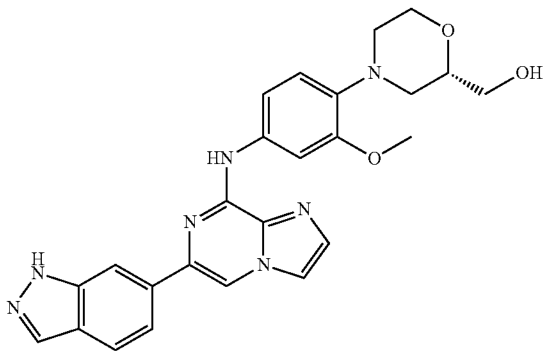 [SMILES: COc1cc(Nc2nc(-c3ccc4cn[nH]c4c3)cn3ccnc23)ccc1N1CCO[C@H](CO)C1] | [(2S)-4-(4-{[6-(1H-indazol-6-yl)imidazo[1,2-a]pyrazin-8-yl]amino}-2-methoxyphenyl)morpholin-2-yl]methanol | 472.4 |
| 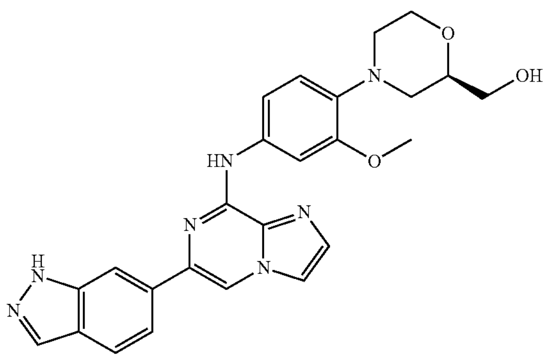 [SMILES: COc1cc(Nc2nc(-c3ccc4cn[nH]c4c3)cn3ccnc23)ccc1N1CCO[C@@H](CO)C1] | [(2R)-4-(4-{[6-(1H-indazol-6-yl)imidazo[1,2-a]pyrazin-8-yl]amino}-2-methoxyphenyl)morpholin-2-yl]methanol | 472.4 |
| 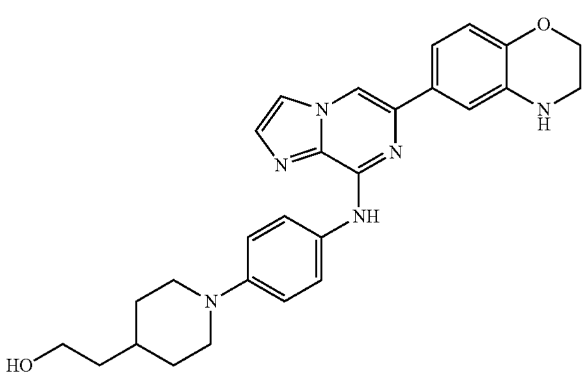 [SMILES: OCCC1CCN(c2ccc(Nc3nc(-c4ccc5c(c4)NCCO5)cn4ccnc34)cc2)CC1] | 2-[1-(4-{[6-(3,4-dihydro-2H-1,4-benzoxazin-6-yl)imidazo[1,2-a]pyrazin-8-yl]amino}phenyl)piperidin-4-yl]ethan-1-ol | 471.8 |
| 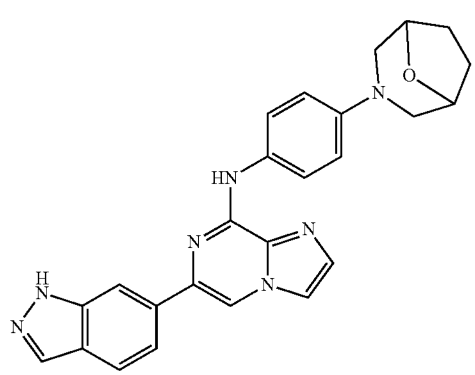 [SMILES: c1cn2cc(-c3ccc4cn[nH]c4c3)nc(Nc3ccc(N4CC5CCC(C4)O5)cc3)c2n1] | 6-(1H-indazol-6-yl)-N-(4-{8-oxa-3-azabicyclo[3.2.1]octan-3-yl}phenyl)imidazo[1,2-a]pyrazin-8-amine | 438.3 |

-continued

| Structure | Name | [M + H]+ |
|---|---|---|
| 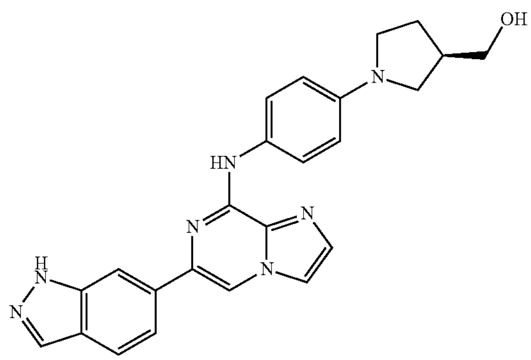 [SMILES: OC[C@@H]1CCN(c2ccc(Nc3nc(-c4ccc5cn[nH]c5c4)cn4ccnc34)cc2)C1] | [(3R)-1-(4-{[6-(1H-indazol-6-yl)imidazo[1,2-a]pyrazin-8-yl]amino}phenyl)pyrrolidin-3-yl]methanol | 426.2 |
| 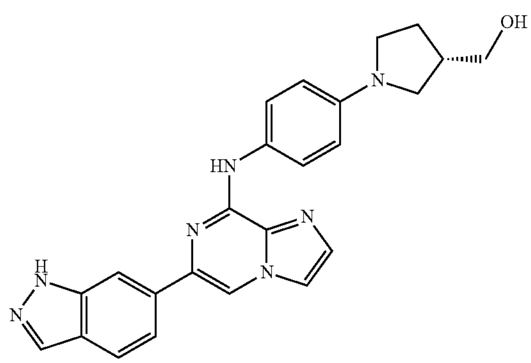 [SMILES: OC[C@H]1CCN(c2ccc(Nc3nc(-c4ccc5cn[nH]c5c4)cn4ccnc34)cc2)C1] | [(3S)-1-(4-{[6-(1H-indazol-6-yl)imidazo[1,2-a]pyrazin-8-yl]amino}phenyl)pyrrolidin-3-yl]methanol | 426.2 |
| 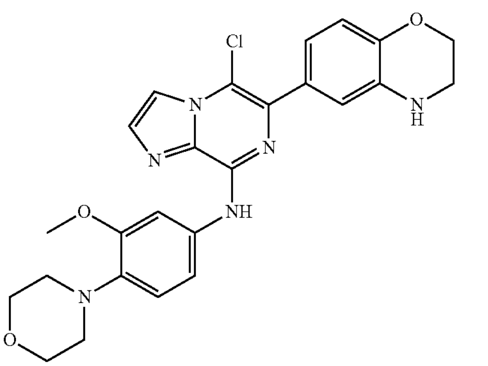 [SMILES: COc1cc(Nc2nc(-c3ccc4c(c3)NCCO4)c(Cl)n3ccnc23)ccc1N1CCOCC1] | 5-chloro-6-(3,4-dihydro-2H-1,4-benzoxazin-6-yl)-N-[3-methoxy-4-(morpholin-4-yl)phenyl]imidazo[1,2-a]pyrazin-8-amine | 493.5 |
| 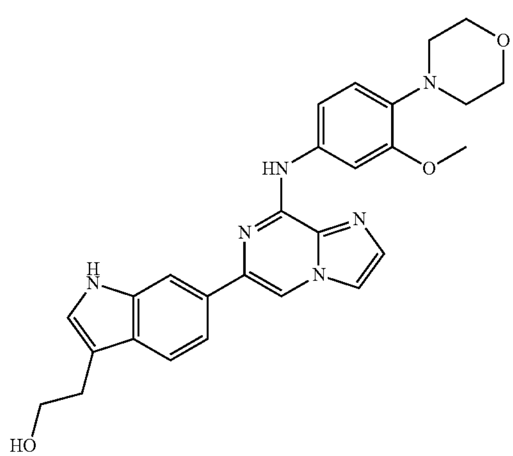 [SMILES: COc1cc(Nc2nc(-c3ccc4c(CCO)c[nH]c4c3)cn3ccnc23)ccc1N1CCOCC1] | 2-[6-(8-{[3-methoxy-4-(morpholin-4-yl)phenyl]amino}imidazo[1,2-a]pyrazin-6-yl)-1H-indol-3-yl]ethan-1-ol | 485.6 |

| Structure | Name | [M + H]+ |
|---|---|---|
| 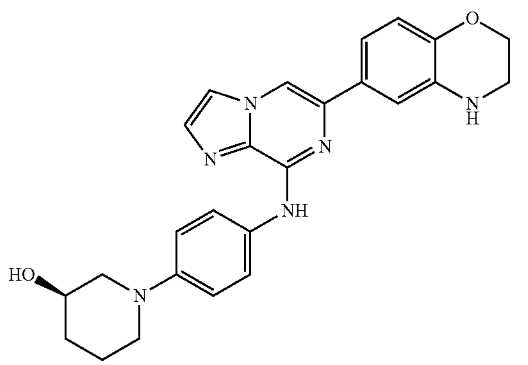 [SMILES: O[C@@H]1CCCN(c2ccc(Nc3nc(-c4ccc5c(c4)NCCO5)cn4ccnc34)cc2)C1] | (3R)-1-(4-{[6-(3,4-dihydro-2H-1,4-benzoxazin-6-yl)imidazo[1,2-a]pyrazin-8-yl]amino}phenyl)piperidin-3-ol | 443.8 |
| 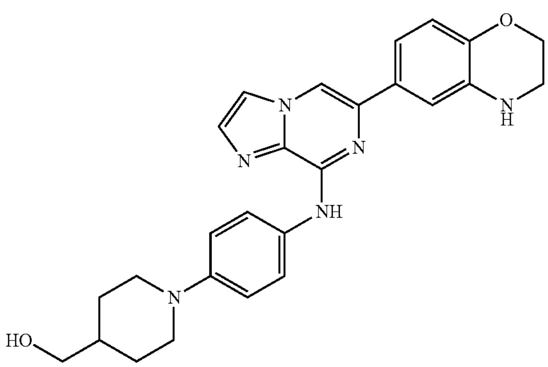 [SMILES: OCC1CCN(c2ccc(Nc3nc(-c4ccc5c(c4)NCCO5)cn4ccnc34)cc2)CC1] | [1-(4-{[6-(3,4-dihydro-2H-1,4-benzoxazin-6-yl)imidazo[1,2-a]pyrazin-8-yl]amino}phenyl)piperidin-4-yl]methanol | 457.5 |
| 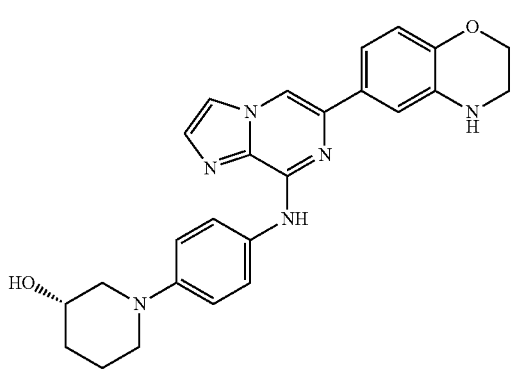 [SMILES: O[C@H]1CCCN(c2ccc(Nc3nc(-c4ccc5c(c4)NCCO5)cn4ccnc34)cc2)C1] | (3S)-1-(4-{[6-(3,4-dihydro-2H-1,4-benzoxazin-6-yl)imidazo[1,2-a]pyrazin-8-yl]amino}phenyl)piperidin-3-ol | 443.3 |
| 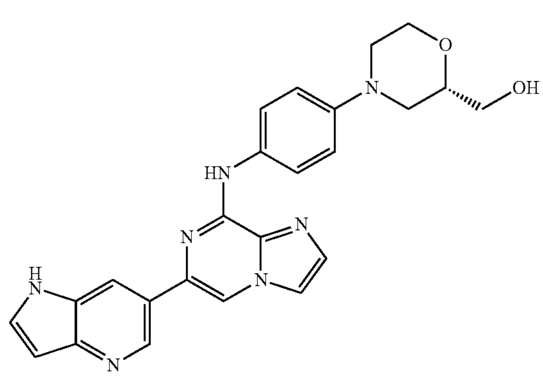 [SMILES: OC[C@@H]1CN(c2ccc(Nc3nc(-c4cnc5cc[nH]c5c4)cn4ccnc34)cc2)CCO1] | [(2S)-4-{4-[(6-{1H-pyrrolo[3,2-b]pyridin-6-yl}imidazo[1,2-a]pyrazin-8-yl)amino]phenyl}morpholin-2-yl]methanol | 442.7 |

-continued

| Structure | Name | [M + H]+ |
|---|---|---|
| 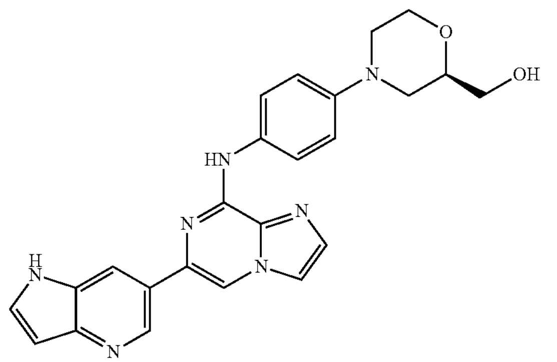 [SMILES: OC[C@H]1CN(c2ccc(Nc3nc(-c4cnc5cc[nH]c5c4)cn4ccnc34)cc2)CCO1] | [(2R)-4-{4-[(6-{1H-pyrrolo[3,2-b]pyridin-6-yl}imidazo[1,2-a]pyrazin-8-yl)amino]phenyl}morpholin-2-yl]methanol | 442.5 |
| 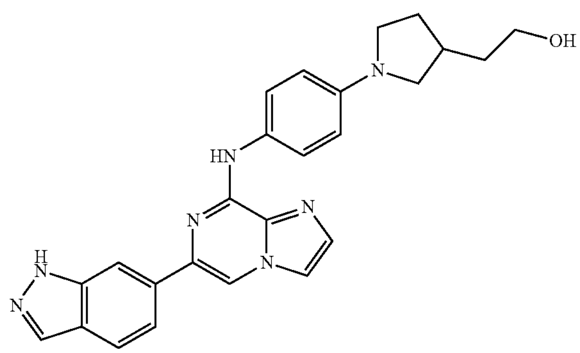 [SMILES: OCCC1CCN(c2ccc(Nc3nc(-c4ccc5cn[nH]c5c4)cn4ccnc34)cc2)C1] | 2-[1-(4-{[6-(1H-indazol-6-yl)imidazo[1,2-a]pyrazin-8-yl]amino}phenyl)pyrrolidin-3-yl]ethan-1-ol | 440.3 |
| 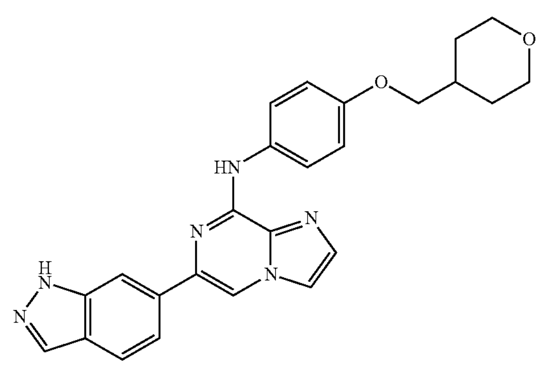 [SMILES: c1cn2cc(-c3ccc4cn[nH]c4c3)nc(Nc3ccc(OCC4CCOCC4)cc3)c2n1] | 6-(1H-indazol-6-yl)-N-[4-(oxan-4-ylmethoxy)phenyl]imidazo[1,2-a]pyrazin-8-amine | 441.4 |
| 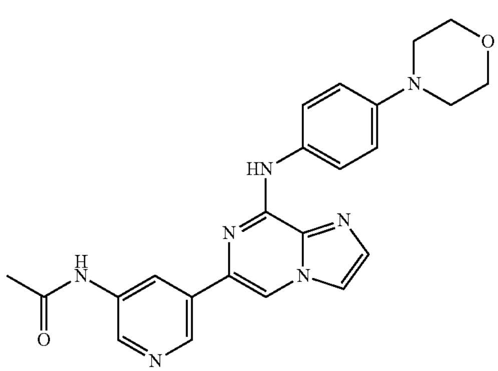 [SMILES: CC(=O)Nc1cncc(-c2cn3ccnc3c(Nc3ccc(N4CCOCC4)cc3)n2)c1] | N-[5-(8-{[4-(morpholin-4-yl)phenyl]amino}imidazo[1,2-a]pyrazin-6-yl)pyridin-3-yl]acetamide | 430.4 |

-continued

| Structure | Name | [M + H]+ |
|---|---|---|
| 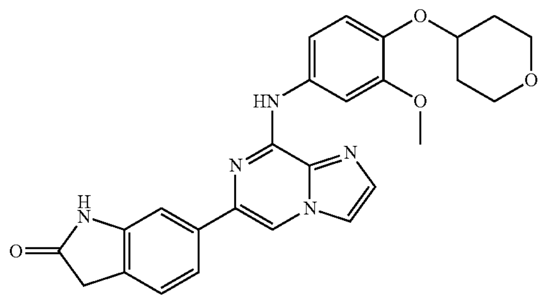 [SMILES: COc1cc(Nc2nc(-c3ccc4c(c3)NC(=O)C4)cn3ccnc23)ccc1OC1CCOCC1] | 6-(8-{[3-methoxy-4-(oxan-4-yloxy)phenyl]amino}imidazo[1,2-a]pyrazin-6-yl)-2,3-dihydro-1H-indol-2-one | 472.4 |
| 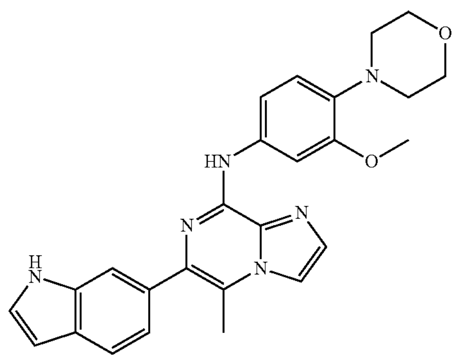 [SMILES: COc1cc(Nc2nc(-c3ccc4cc[nH]c4c3)c(C)n3ccnc23)ccc1N1CCOCC1] | 6-(1H-indol-6-yl)-N-[3-methoxy-4-(morpholin-4-yl)phenyl]-5-methylimidazo[1,2-a]pyrazin-8-amine | 455.2 |
| 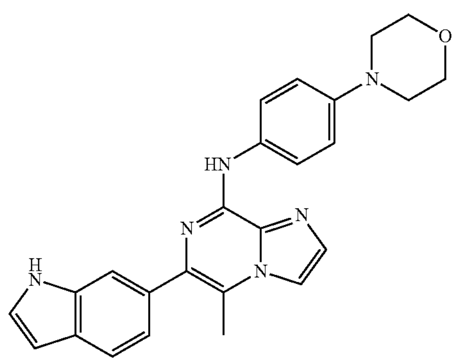 [SMILES: Cc1c(-c2ccc3cc[nH]c3c2)nc(Nc2ccc(N3CCOCC3)cc2)c2nccn12] | 6-(1H-indol-6-yl)-5-methyl-N-[4-(morpholin-4-yl)phenyl]imidazo[1,2-a]pyrazin-8-amine | 425.2 |
| 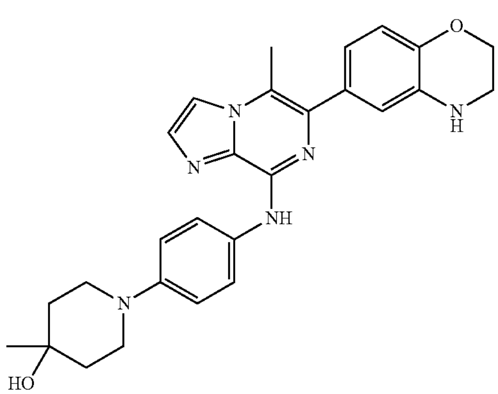 [SMILES: Cc1c(-c2ccc3c(c2)NCCO3)nc(Nc2ccc(N3CCC(C)(O)CC3)cc2)c2nccn12] | 1-(4-{[6-(3,4-dihydro-2H-1,4-benzoxazin-6-yl)-5-methylimidazo[1,2-a]pyrazin-8-yl]amino}phenyl)-4-methylpiperidin-4-ol | 471.8 |

-continued

| Structure | Name | [M + H]+ |
|---|---|---|
| 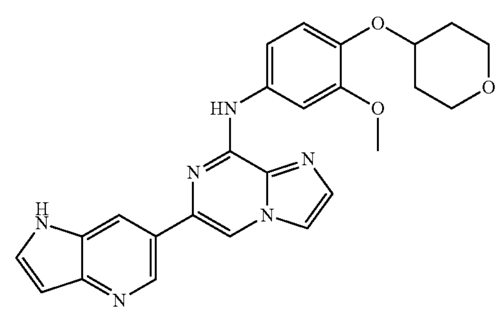 [SMILES: COc1cc(Nc2nc(-c3cnc4cc[nH]c4c3)cn3ccnc23)ccc1OC1CCOCC1] | N-[3-methoxy-4-(oxan-4-yloxy)phenyl]-6-{1H-pyrrolo[3,2-b]pyridin-6-yl}imidazo[1,2-a]pyrazin-8-amine | 457.4 |
| 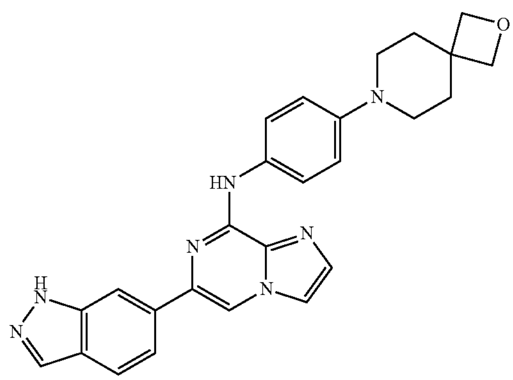 [SMILES: c1cn2cc(-c3ccc4cn[nH]c4c3)nc(Nc3ccc(N4CCC5(CC4)COC5)cc3)c2n1] | 6-(1H-indazol-6-yl)-N-(4-{2-oxa-7-azaspiro[3.5]nonan-7-yl}phenyl)imidazo[1,2-a]pyrazin-8-amine | 452.2 |
| 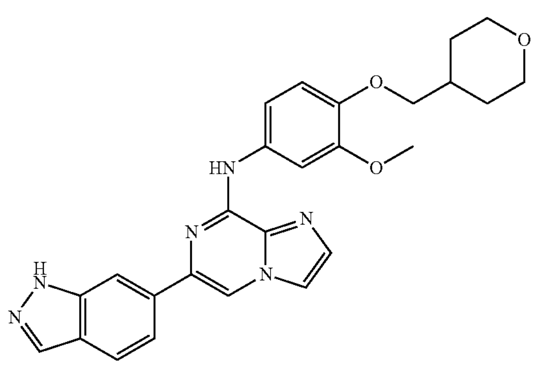 [SMILES: COc1cc(Nc2nc(-c3ccc4cn[nH]c4c3)cn3ccnc23)ccc1OCC1CCOCC1] | 6-(1H-indazol-6-yl)-N-[3-methoxy-4-(oxan-4-ylmethoxy)phenyl]imidazo[1,2-a]pyrazin-8-amine | 471.8 |
| 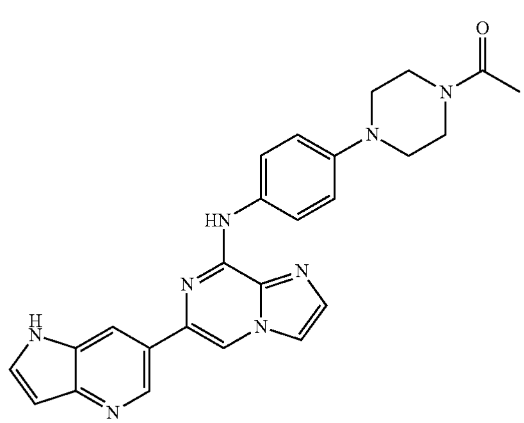 [SMILES: CC(=O)N1CCN(c2ccc(Nc3nc(-c4cnc5cc[nH]c5c4)cn4ccnc34)cc2)CC1] | 1-(4-{4-[(6-{1H-pyrrolo[3,2-b]pyridin-6-yl}imidazo[1,2-a]pyrazin-8-yl)amino]phenyl}piperazin-1-yl)ethan-1-one | 453.1 |

-continued

| Structure | Name | [M + H]+ |
|---|---|---|
| 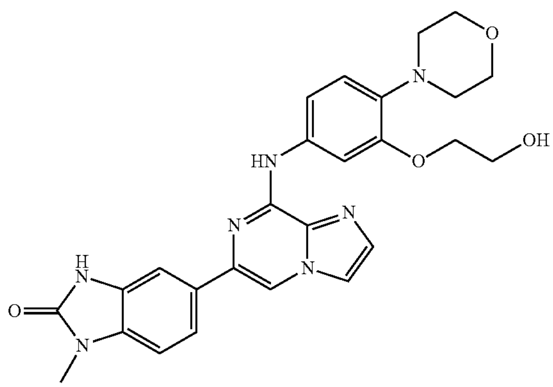 [SMILES: Cn1c(=O)[nH]c2cc(-c3cn4ccnc4c(Nc4ccc(N5CCOCC5)c(OCCO)c4)n3)ccc21] | 5-(8-{[3-(2-hydroxyethoxy)-4-(morpholin-4-yl)phenyl]amino}imidazo[1,2-a]pyrazin-6-yl)-1-methyl-2,3-dihydro-1H-1,3-benzodiazol-2-one | 502.2 |
| 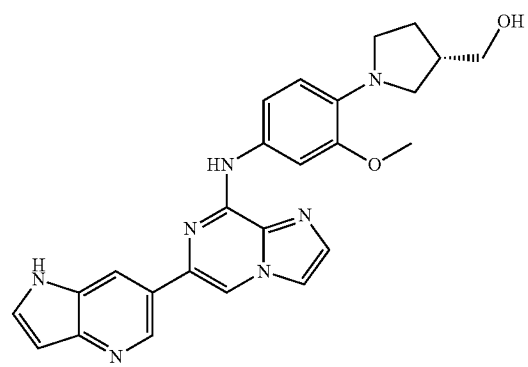 [SMILES: COc1cc(Nc2nc(-c3cnc4cc[nH]c4c3)cn3ccnc23)ccc1N1CC[C@H](CO)C1] | [(3S)-1-{2-methoxy-4-[(6-{1H-pyrrolo[3,2-b]pyridin-6-yl}imidazo[1,2-a]pyrazin-8-yl)amino]phenyl}pyrrolidin-3-yl]methanol | 456.5 |
| 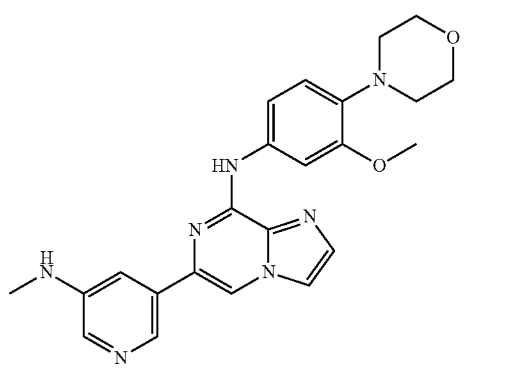 [SMILES: CNc1cncc(-c2cn3ccnc3c(Nc3ccc(N4CCOCC4)c(OC)c3)n2)c1] | 5-(8-{[3-methoxy-4-(morpholin-4-yl)phenyl]amino}imidazo[1,2-a]pyrazin-6-yl)-N-methylpyridin-3-amine | 432.5 |
| 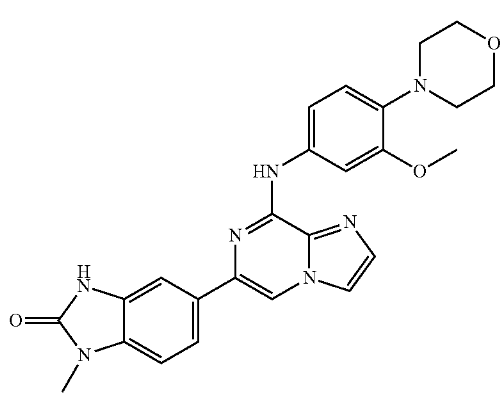 [SMILES: COc1cc(Nc2nc(-c3ccc4c(c3)[nH]c(=O)n4C)cn3ccnc23)ccc1N1CCOCC1] | 5-(8-{[3-methoxy-4-(morpholin-4-yl)phenyl]amino}imidazo[1,2-a]pyrazin-6-yl)-1-methyl-2,3-dihydro-1H-1,3-benzodiazol-2-one | 472.3 |

| Structure | Name | [M + H]+ |
|---|---|---|
| 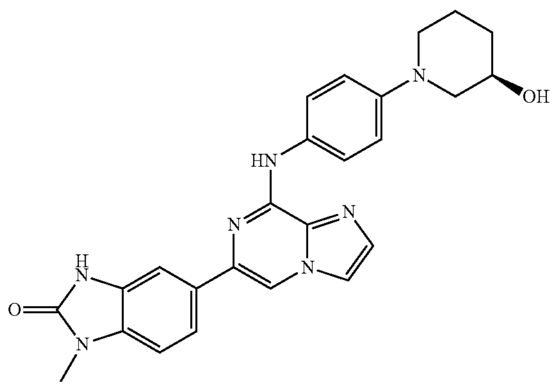 [SMILES: Cn1c(=O)[nH]c2cc(-c3cn4ccnc4c(Nc4ccc(N5CCC[C@@H](O)C5)cc4)n3)ccc21] | 5-[8-({4-[(3R)-3-hydroxypiperidin-1-yl]phenyl}amino)imidazo[1,2-a]pyrazin-6-yl]-1-methyl-2,3-dihydro-1H-1,3-benzodiazol-2-one | 456.2 |
| 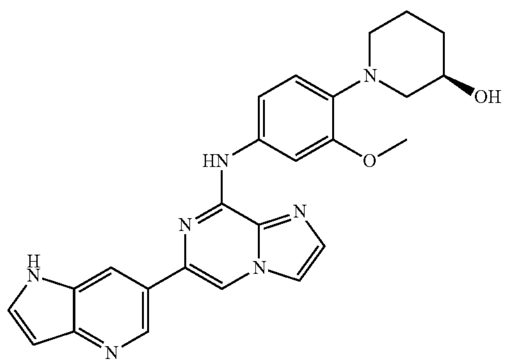 [SMILES: COc1cc(Nc2nc(-c3cnc4cc[nH]c4c3)cn3ccnc23)ccc1N1CCC[C@@H](O)C1] | (3R)-1-{2-methoxy-4-[(6-{1H-pyrrolo[3,2-b]pyridin-6-yl}imidazo[1,2-a]pyrazin-8-yl)amino]phenyl}piperidin-3-ol | 456.4 |
| 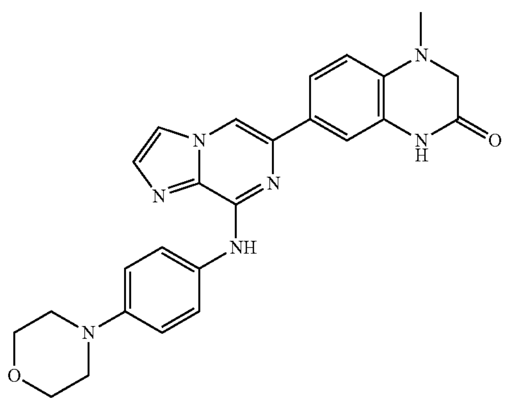 [SMILES: CN1CC(=O)Nc2cc(-c3cn4ccnc4c(Nc4ccc(N5CCOCC5)cc4)n3)ccc21] | 4-methyl-7-(8-{[4-(morpholin-4-yl)phenyl]amino}imidazo[1,2-a]pyrazin-6-yl)-1,2,3,4-tetrahydroquinoxalin-2-one | 456.5 |
| 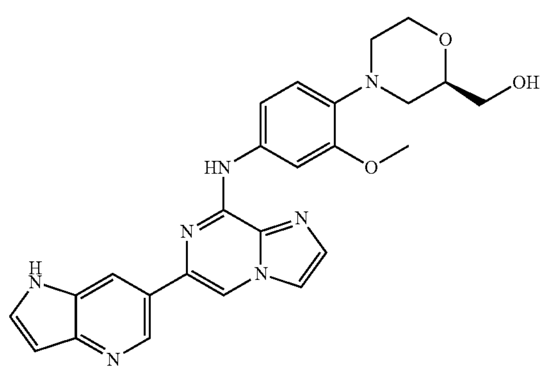 [SMILES: COc1cc(Nc2nc(-c3cnc4cc[nH]c4c3)cn3ccnc23)ccc1N1CCO[C@@H](CO)C1] | [(2R)-4-{2-methoxy-4-[(6-{1H-pyrrolo[3,2-b]pyridin-6-yl}imidazo[1,2-a]pyrazin-8-yl)amino]phenyl}morpholin-2-yl]methanol | 472.5 |

| Structure | Name | [M + H]+ |
|---|---|---|
| 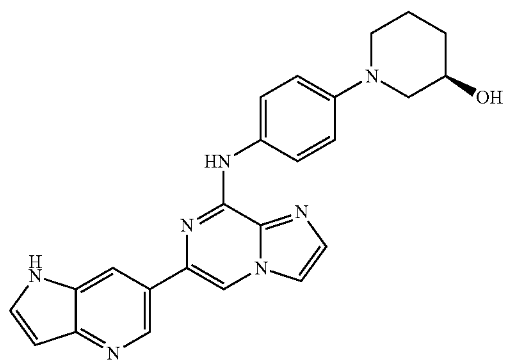 [SMILES: O[C@@H]1CCCN(c2ccc(Nc3nc(-c4cnc5cc[nH]c5c4)cn4ccnc34)cc2)C1] | (3R)-1-{4-[(6-{1H-pyrrolo[3,2-b]pyridin-6-yl}imidazo[1,2-a]pyrazin-8-yl)amino]phenyl}piperidin-3-ol | 426 |

Example 3

Biochemical Syk Assay

A generalized procedure for one standard biochemical Syk Kinase Assay that can be used to test compounds disclosed in this application is as follows.

A master mix minus Syk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 μM Promega PTK Biotinylated peptide substrate 1, 0.01% casein, 0.01% Triton-X100, and 0.25% glycerol. A master mix plus Syk enzyme is prepared containing 1× Cell Signaling kinase buffer, 0.5 μM PTK Biotinylated peptide substrate 1, 0.01% casein, 0.01% Triton-X100, 0.25% glycerol and 0.4 ng/well Syk enzyme. Syk enzyme is purchased from Cell Signaling Technologies, expressed in baculovirus and is an N-terminally GST-tagged full length human wildtype Syk (accession number NM-00377). The Syk protein was purified in one step using glutathione-agarose. The purity of the final protein preparation was assessed by SDS-PAGE and Coomassie staining. A solution of 200 μM ATP is prepared in water and adjusted to pH7.4 with 1N NaOH. A quantity of 1.25 μL of compounds in 5% DMSO is transferred to a 96-well ½ area Costar polystyrene plate Compounds are tested singly and with an 11-point dose-responsive curve (starting concentration is 10-1 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 80 nM SA-APC, and 4 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated using a linear regression algorithm.

Example 4

Ramos Cell pBLNK(Y96) Assay

Another generalized procedure for a standard cellular Syk Kinase Assay that can be used to test compounds disclosed in this application is as follows.

Ramos cells are serum starved at $2 \times 10^6$ cells/ml in serum-free RPMI for 1 hour in an upright T175 Falcon TC flask. Cells are centrifuged (1100 rpm×5 min) and incubated at a density of $0.5 \times 10^7$ cells/ml in the presence of test compound or DMSO controls for 1 hr at 37° C. Cells are then stimulated by incubating with 10 μg/ml anti-human IgM $F(ab)_2$ for 5 minutes at 37° C. Cells are pelleted, lysed in 40 ul cell lysis buffer, and mixed with Invitrogen SDS-PAGE loading buffer. 20 ul of cell lysate for each sample are subject to SDS-PAGE and western blotting with anti-phosphoBLNK(Tyr96) antibody (Cell Signaling Technology #3601) to assess Syk activity and anti-Syk antibody (BD Transduction Labs #611116) to control for total protein load in each lysate. The images are detected using fluorescent secondary detection systems and the LiCor Odyssey software.

Example 5

B-Cell Proliferation Assay

A generalized procedure for a standard cellular B-cell proliferation assay that can be used to test compounds disclosed in this application is as follows.

B-cells are purified from spleens of 8-16 week old Balb/c mice using a B-cell isolation kit (Miltenyi Biotech, Cat #130-090-862). Test compounds are diluted in 0.25% DMSO and incubated with $2.5 \times 10^5$ purified mouse splenic B-cells for 30 min prior to addition of 10 μg/ml of an anti-mouse IgM antibody (Southern Biotechnology Associates Cat #1022-01) in a final volume of 100 μl. Following 24 hr incubation, 1 μCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

Example 6

T Cell Proliferation Assay

A generalized procedure for a standard T cell proliferation assay that can be used to test compounds disclosed in this application is as follows.

T cells are purified from spleens of 8-16 week old Balb/c mice using a Pan T cell isolation kit (Miltenyi Biotech, Cat #130-090-861). Test compounds are diluted in 0.25% DMSO and incubated with 2.5×10⁵ purified mouse splenic T cells in a final volume of 100 μl in flat clear bottom plates precoated for 90 min at 37° C. with 10 μg/ml each of anti-CD3 (BD #553057) and anti-CD28 (BD #553294) antibodies. Following 24 hr incubation, 1 μCi $^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

Example 7

CD69 Inhibition Assay

A generalized procedure for a standard assay for the inhibition of B cell activity that can be used to test compounds disclosed in this application is as follows.

Total mouse splenocytes are purified from spleens of 8-16 week old Balb/c mice by red blood cell lysis (BD Pharmingen #555899). Testing compounds are diluted to 0.5% DMSO and incubated with 1.25×10⁶ splenocytes in a final volume of 200 μl in flat clear bottom plates (Falcon 353072) for 60 min at 37° C. Cells are then stimulated with the addition of 15 μg/ml IgM (Jackson ImmunoResearch 115-006-020), and incubated for 16 hr at 37° C., 5% $CO_2$. Following the 16 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD69-PE (BD Pharmingen #553237), and 7AAD (BD Pharmingen #51-68981E). Cells are sorted on a BD FACSCalibur and gated on the CD19$^{+/7}$AAD$^-$ population. The levels of CD69 surface expression on the gated population is measured versus test compound concentration.

Example 8

BMMC Degranulation

A generalized procedure for a standard assay for bone-marrow derived mouse mast cell (BMMC) degranulation that can be used to test compounds disclosed in this application is as follows.

Bone-marrow derived mast cells were cultured for >4 weeks with IL-3 (10 ng/ml) and SCF (10 ng/ml). The cells were determined to be >90% cKit$^+$/FceRI$^+$ by FACS analysis at the time of use. Cells (6×10⁷ cells/50 ml) were serum-starved in a T150 tissue culture flask for 16 h in the absence of IL-3 and SCF containing IgEα-DNP at 1 ug/ml. Overnight sensitized cells are washed twice in Tyrodes buffer and resuspended to 5×10⁶ cells/ml. 5×10⁵ cells (100 ul) are plated in a 96 well microtiter plate (Falcon 353072) and test compounds are serially diluted to a final concentration 0.25% DMSO in the plate for 1 hr at 37° C., 5% $CO_2$. Wells are treated with a DNP-BSA antigen challenge (50 ng/ml) and incubated for and additional 30 min at 37° C. Supernatants are assayed for hexosamimidase release versus control wells. Cell pellets are simultaneously lysed and assed for total hexosamimidase release to calculate specific release. Dose-response curves are generated using 4-parameter logistical fit and IC50s calculated.

Example 9

Passive Cutaneous Anaphylaxis (PCA)

The following is a procedure for a standard PCA model used for measuring in vivo IgE anti-DNP Ab sensitization and DNP-BSA antigen for triggering mast cell degranulation and release of immune regulators that cause acute vessel permeability monitored by Evan's blue dye into the inflamed area in the mouse ear.

Reagents: Anti-DNP IgE: is supplied as 1.2 mg/ml in a phosphate buffered solution with BSA for additional protein and azide for sterility. This is diluted 1:100 in sterile PBS as a 12 ug/ml working stock that can be further diluted in PBS to the appropriate concentration for injection. A further 1:5 dilution give a final 1:500 solution at 2.4 ng/ul. (10 ul/ear=24 ng). Sterile PBS alone will be used as a negative control. -DNP-BSA: will be made up at 4 mg/ml in sterile dd$H_2$O and stored at 40° C. solution. It is further diluted 1:1 with sterile saline prior to use. This solution or a further dilution in saline is diluted 1:1 with 2% Evan's Blue in sterile saline that has been filtered though 0.02 um filter and refiltered prior to injection. For these experiments a final solution of 0.5 mg/ml of DNP-BSA in 1% Evans blue can be used. Tail vein injections will be held constant at 200 ul=100 ug in 1% Evan's Blue. -Evan's blue dye: A 2% stock in saline will be sterile filtered and diluted 1:1 with DNP-BSA saline solution for final concentration of 1°/0 for injection.

General PCA Protocol Using Intradermal Ear Sensitization

1) On d0, animals, anesthetized with isofluorine, are passively sensitized by intradermal injections of IgE anti-DNP using a 29-gauge insulin syringe. By convention, the right ear receives 10 ul intradermal injection of anti-DNP IgE while the left ear receives PBS. 2) 20 hr post sensitization, antigen challenge is administered by tail i.v. injection of DNP-BSA in 200 ul of 1% Evan's blue dye solution in saline. Tails are immersed in warm water prior to iv injection to improve success. 3) 30 minutes to 2 hr prior to this antigen challenge, drug is delivered sc or po in 10% EtOH/20% cremaphor/70% saline. 4) Animals are sacrifice by $CO_2$ inhalation 30-60 min post antigen challenge and ears are removed for extraction of Evan's blue dye in 500 ul of formamide overnight at 65° C. 5) Blood is obtained by cardiac puncture just prior to final cervical dislocation and processed for plasma to provide PK analysis. 6) Evan's blue dye is quantified by reading absorbency of 200 ul of extracted solution in microtiter plates at 620 nm.

Study Design of Experiment

Each animal has one anti-DNP IgE sensitized ear (right ear by convention) and one PBS control ear (left ear by convention). Groups 1-8: represent the vehicle and compound testing arms; Group 9: represents the non-antigen negative control; Group 10: represents the non-sensitized challenged negative control; Group 11: represents the non-antigen challenged, non-sensitized negative control group (Groups 9-11 represent negative controls for background levels only and require only minimal number of animals per group.)

The compounds disclosed in the examples above were tested in the Syk biochemical assay described herein (Example 3) and certain of those compounds exhibited an $IC_{50}$ value less than or equal to 1 micromolar. Certain of those compounds exhibited an $IC_{50}$ value less than or equal to 100 nM. Certain of those compounds exhibited an $IC_{50}$ value less than or equal to 10 nM. Certain of those compounds exhibited an $IC_{50}$ value less than or equal to 1 nM.

Some of the compounds disclosed in Example 2 were tested in the B-cell proliferation assay (as described in Example 5) and exhibited an $IC_{50}$ value less than or equal to 10 micromolar. Certain of those compounds exhibited an $IC_{50}$ value less than or equal to 1 micromolar.

Certain of those compounds did not inhibit T-cell proliferation and had $IC_{50}$ values greater than or equal to 5 micromolar when assayed under conditions described herein (as described in Example 6).

Certain compounds described herein exhibited $IC_{50}$ values for inhibition of T-cell proliferation that were at least 3-fold, and in some instances 5-fold, greater than the $IC_{50}$ values of those compounds for inhibition of B-cell proliferation.

Some of the compounds described herein were tested in an assay for inhibition of B cell activity (under the conditions described in example 7), and exhibited an $IC_{50}$ value less than or equal to 10 micromolar. Certain of those compounds exhibited an $IC_{50}$ value less than or equal to 1 micromolar.

Some of the compounds disclosed in described herein exhibited both biochemical and cell-based activity. For example, some of the compounds described herein exhibited an $IC_{50}$ value less than or equal to 10 micromolar in the Syk biochemical assay described herein (Example 3) and an $IC_{50}$ value less than or equal to 10 micromolar in at least one of the cell-based assays (other than the T-cell assay) described herein (Examples 4, 5, 7 or 8). Certain of those compounds exhibited an $IC_{50}$ value less than or equal to 1 micromolar in the Syk biochemical assay described herein (Example 4) and an $IC_{50}$ value less than or equal to 10 micromolar in at least one of the cell-based assays (other than the T-cell assay) described herein (Examples 4, 5, 7 or 8). Certain of those compounds exhibited an $IC_{50}$ value less than or equal to 0.1 micromolar and an $IC_{50}$ value less than or equal to 10 micromolar in at least one of the cell-based assays (other than the T-cell assay) described herein (Examples 4, 5, 7 or 8).

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A compound having the structure:

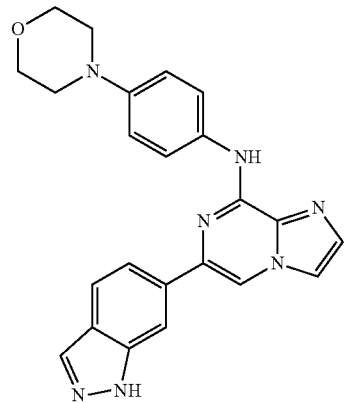 [SMILES: c1cn2cc(-c3ccc4cn[nH]c4c3)nc(Nc3ccc(N4CCOCC4)cc3)c2n1]

or a pharmaceutically acceptable salt thereof.

2. A pharmaceutical composition comprising
the compound of claim 1; and
at least one pharmaceutically acceptable vehicle selected from the group consisting of carriers, adjuvants, and excipients.

* * * * *